US012559732B2

(12) United States Patent
Bruno-Barcena et al.

(10) Patent No.: US 12,559,732 B2
(45) Date of Patent: Feb. 24, 2026

(54) COMPOSITIONS AND METHODS FOR PRODUCING HUMAN MILK OLIGOSACCHARIDES

(71) Applicant: NORTH CAROLINA STATE UNIVERSITY, Raleigh, NC (US)

(72) Inventors: Jose M. Bruno-Barcena, Raleigh, NC (US); Suzanne Dagher, Raleigh, NC (US); Maria Andrea Azcarate-Peril, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 448 days.

(21) Appl. No.: 17/999,017

(22) PCT Filed: May 18, 2021

(86) PCT No.: PCT/US2021/032998
§ 371 (c)(1),
(2) Date: Nov. 16, 2022

(87) PCT Pub. No.: WO2021/236664
PCT Pub. Date: Nov. 25, 2021

(65) Prior Publication Data
US 2023/0279368 A1 Sep. 7, 2023

Related U.S. Application Data

(60) Provisional application No. 63/030,054, filed on May 26, 2020, provisional application No. 63/026,776, filed on May 19, 2020.

(51) Int. Cl.
| | |
|---|---|
| *C12N 9/10* | (2006.01) |
| *A23L 33/125* | (2016.01) |
| *C12N 15/79* | (2006.01) |
| *C12P 19/18* | (2006.01) |
| *C12P 19/28* | (2006.01) |

(52) U.S. Cl.
CPC .......... *C12N 9/1051* (2013.01); *A23L 33/125* (2016.08); *C12N 15/79* (2013.01); *C12P 19/18* (2013.01); *C12P 19/28* (2013.01)

(58) Field of Classification Search
CPC ..... C12N 9/1051; C12N 15/79; A23L 33/125; C12P 19/18; C12P 19/28; C12R 2001/84
See application file for complete search history.

(56) References Cited

U.S. PATENT DOCUMENTS

| | | | |
|---|---|---|---|
| 5,011,912 | A | 4/1991 | Hopp et al. |
| 5,654,176 | A | 8/1997 | Smith |
| 6,653,109 | B1 | 11/2003 | Nilsson |
| 7,595,198 | B2 | 9/2009 | Olejnik et al. |
| 8,207,328 | B2 | 6/2012 | Dekany et al. |
| 9,783,789 | B2 | 10/2017 | Bruno-Barcena et al. |
| 10,513,695 | B2 | 12/2019 | Bruno-Barcena et al. |
| 2019/0119662 | A1 | 4/2019 | Hoshi et al. |

FOREIGN PATENT DOCUMENTS

| | | | | |
|---|---|---|---|---|
| EP | 0367566 | 5/1990 | | |
| WO | WO 91/18982 | 12/1991 | | |
| WO | WO 2014/089558 | 6/2014 | | |
| WO | WO2016/207343 | * 6/2016 | ......... | C07K 2319/70 |
| WO | WO-2021180702 A1 | 9/2021 | | |

OTHER PUBLICATIONS

International Preliminary Report on Patentability for PCT/US2021/032998. Mailed May 19, 2020. 6 pages.
International Search Report and Written Opinion for PCT/US21/32998. Mailed Sep. 24, 2021. 7 pages.
Ahmad et al., Protein expression in Pichia pastoris: recent achievements and perspectives for heterologous protein production. Appl Microbiol Biotechnol. Jun. 2014;98(12):5301-17.
Bode et al., Making Human Milk Oligosaccharides Available for Research and Application—Approaches, Challenges, and Future Opportunities. Human Milk. 2017. 251-293.
Chauhan et al., In silico Platform for Prediction of N-, O- and C-Glycosites in Eukaryotic Protein Sequences. PLOS One. 2013; 8, e67008. 10 pages.
Chong et al., Single-column purification of free recombinant proteins using a self-cleavable affinity tag derived from a protein splicing element. Gene. Jun. 19, 1997;192(2):271-81.
Cosman et al., Cloning, sequence and expression of human interleukin-2 receptor. Nature. 1984;312(5996):768-71.
Cosman et al., High level stable expression of human interleukin-2 receptors in mouse cells generates only low affinity interleukin-2 binding sites. Mol Immunol. Sep. 1986;23(9):935-41.
Dagher et al., A novel N-terminal region of the membrane β-hexosyltransferase: its role in secretion of soluble protein by Pichia pastoris. Microbiology. 2016; 162, 23-34.
Dagher et al., Heterologous expression of a bioactive β-hexosyltransferase, an enzyme producer of prebiotics, from Sporobolomyces singularis. Appl Environ Microbiol. Feb. 2013;79(4):1241-9.
De Giuseppe et al., Structural basis for glucose tolerance in GH1 β-glucosidases. Acta Crystallogr D Biol Crystallogr. Jun. 2014;70(Pt 6):1631-9.
Fischer et al., The pattern of protein synthesis in SV40-infected CV-1 cells. Int J Cancer. Jan. 15, 1970;5(1):21-7.
Florindo et al., Structural insights into β-glucosidase transglycosylation based on biochemical, structural and computational analysis of two GH1 enzymes from Trichoderma harzianum. N Biotechnol. Jan. 25, 2018;40(Pt B):218-227.

(Continued)

*Primary Examiner* — Ganapathirama Raghu
(74) *Attorney, Agent, or Firm* — Casimir Jones, S.C.; Peter J. Schlueter

(57) ABSTRACT

The present disclosure provides compositions and methods related to the production of human milk oligosaccharides (HMOs). In particular, the present disclosure provides compositions and methods for converting lactose and N-acetyl-glucosamine (GlcNAc) into N-acetyllactosamine (LacNAc)-enriched galactooligosaccharide (GOS) compositions using novel β-hexosyl-transferase (BHT) enzymes.

16 Claims, 9 Drawing Sheets
Specification includes a Sequence Listing.

(56)                References Cited

OTHER PUBLICATIONS

GenBank accession No. BAD95570.1. Jun. 28, 2008. Retrieved from the internet Feb. 3, 2023. 2 pages.

GenBAnk accession No. KIJ57308.1. Jan. 26, 2015. Retrieved from the internet Feb. 3, 2023. 2 pages.

GenBank accession No. KIK57390.1. Jan. 26, 2015. Retrieved from the internet Feb. 3, 2023. 2 pages.

GenBank accession No. PWN48553.1. May 23, 2018. Retrieved from the internet Feb. 3, 2023. 2 pages.

GenBank accession No. PWZ03736.1. Jun. 4, 2018. Retrieved from the internet Feb. 3, 2023. 2 pages.

GenBank accession No. XP_007881827.1. Dec. 10, 2021. Retrieved from the internet Feb. 3, 2023. 2 pages.

Gentz et al., Bioassay for trans-activation using purified human immunodeficiency virus tat-encoded protein: trans-activation requires mRNA synthesis. Proc Natl Acad Sci U S A. Feb. 1989;86(3):821-4.

Gluzman. SV40-transformed simian cells support the replication of early SV40 mutants. Cell. Jan. 1981;23(1):175-82.

Gyorgy et al., Bificus Factor. I. A Variant of Lactobacillus bifidus Requiring a Special Growth Factor. Archives of Biochemistry and Biophysics. 1954; 48(1): 193-201.

Hopp et al. A short polypeptide marker sequence useful for recombinant protein identification nad purification. 1988 Nat Biotech 6:1204-1210.

Intanon et al., Nature and biosynthesis of galacto-oligosaccharides related to oligosaccharides in human breast milk. FEMS Microbiol Lett. Apr. 2014;353(2):89-97.

Jeng et al., Structural and functional analysis of three β-glucosidases from bacterium *Clostridium cellulovorans*, fungus *Trichoderma reesei* and termite *Neotermes koshunensis*. J Struct Biol. Jan. 2011;173(1):46-56.

Kaneko et al., Development of hypoallergenic galacto-oligosaccharides on the basis of allergen analysis. Biosci Biotechnol Biochem. 2014;78(1):100-8.

Kao et al., Genetics of Somatic Mammalian Cells, VII. Induction and Isolation of Nutrintional Mutants in Chinese Hamster Cells. 1968 PNAS USA 60 1275-1281.

Knol et al., Unidirectional reconstitution into detergent-destabilized liposomes of the purified lactose transport system of *Streptococcus thermophilus*. J Biol Chem. Jun. 28, 1996;271(26):15358-66.

Lifran et al., Lactose derivatives: Turning waste into functional foods. Australian Journal of Dairy Technology; Melbourne. 2009; vol. 64, Iss. 1. 89-93.

Luckow et al., Trends in the Development of Baculovirus Expression Vectors. Bio/Technology. 1988; 6, 47-55.

Markets & Markets U.S. Digestive Health Ingredients Market Worth $495.3 million in 2015. Retrieved from internet Feb. 3, 2023. 4 pages.

Mcmahan et al., A novel IL-1 receptor, cloned from B cells by mammalian expression, is expressed in many cell types. EMBO J. Oct. 1991;10(10):2821-32.

Monteagudo-Mera et al., High purity galacto-oligosaccharides enhance specific *Biofidobacterium* species and their metabolic activity in the mouse gut microbiome. Beneficial Microbes. 2016; 7(2): 247-264.

Nielsen et al., Identification of prokaryotic and eukaryotic signal peptides and prediction of their cleavage sites. Protein Eng. Jan. 1997;10(1):1-6.

Nijikken et al., Crystal structure of intracellular family 1 beta-glucosidase BGL1A from the basidiomycete Phanerochaete chrysosporium. FEBS Lett. Apr. 3, 2007;581(7):1514-20.

Okayama et al., High-efficiency cloning of full-length cDNA. Mol Cell Biol. Feb. 1982;2(2):161-70.

Santos et al., Crystal structure and biochemical characterization of the recombinant ThBgl, a GH1 β-glucosidase overexpressed in Trichoderma harzianum under biomass degradation conditions. Biotechnology for Biofuels. 2016. 9(71) . 11 pages.

Sassenfeld. Engineering proteins for purification. Trends Biotechnol. Apr. 1990;8(4):88-93.

Von Heijne et al., Patterns of amino acids near signal-sequence cleavage sites. Eur J Biochem. Jun. 1, 1983;133(1):17-21.

Von Heijne et al., Signal sequences. The limits of variation. J Mol Biol. Jul. 5, 1985;184(1):99-105.

Wilson et al., The structure of an antigenic determinant in a protein. Cell. Jul. 1984;37(3):767-78.

Zilliken et al., Enzymatic synthesis of a growth factor for *Lactobacillus bifidus* var. *Penn*. J Biol Chem May 1954;208(1):299-305.

Dagher S.F., et al., "Structural Analysis and Functional Evaluation of the Disordered Beta-Hexosyltransferase Region from Hamamotoa Sporobolomyces) Singularis", Frontiers in Bioengineering and Biotechnology, Dec. 14, 2023, pp. 1-16.

* cited by examiner

6m4e – SEQ ID NO: 1
2E3Z – SEQ ID NO: 96
3AHY – SEQ ID NO: 97
5BWF – SEQ ID NO: 98
4MDO – SEQ ID NO: 99
5JBO – SEQ ID NO: 100

FIG. 6A (cont'd)

6m4e – SEQ ID NO: 1          5BWF – SEQ ID NO: 98

2E3Z – SEQ ID NO: 96          4MDO – SEQ ID NO: 99

3AHY – SEQ ID NO: 97          5JBO – SEQ ID NO: 100

FIGS. 6A-6C (cont'd)

COMPOSITIONS AND METHODS FOR PRODUCING HUMAN MILK OLIGOSACCHARIDES

CROSS REFERENCE TO RELATED APPLICATIONS

This application claims priority to and the benefit of U.S. Provisional Patent Application No. 63/026,776 filed May 19, 2020, and U.S. Provisional Patent Application No. 63/030,054 filed May 26, 2020, both of which are incorporated herein by reference in their entireties for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 273,190 Byte ASCII (Text) file named "NCSU_38389_253_SequenceListing_Corrected_ST25" created on Aug. 7, 2025.

FIELD

The present disclosure provides compositions and methods related to the production of human milk oligosaccharides (HMOs). In particular, the present disclosure provides compositions and methods for converting lactose and N-acetylglucosamine (GlcNAc) into N-acetyllactosamine (LacNAc)-enriched galactooligosaccharide (GOS) compositions using novel β-hexosyl-transferase (BHT) enzymes.

BACKGROUND

The complex interaction between diet, normal intestinal microbiota, and wellbeing has encouraged the development of strategies to promote the selective proliferation of beneficial microorganisms into the gastrointestinal track of humans. Probiotics are microorganisms that positively affect human health with attributed powerful antipathogenic and anti-inflammatory properties.

Also, years of probiotic research indicate that a selective modification of the intestinal microbiota and its associated biochemical activities can be promoted by the presence on the diet of selective prebiotics. Prebiotics added to infant or adult diets participate in prevention of allergies, disease such as symptoms of lactose intolerance, and food hypersensitivity. Prebiotics are non-digestible oligosaccharides (NDOs) that have a dual ability. First they reduce the intestinal colonizing efficiency of harmful bacteria and second they act as selective substrate to promote the growth and thereby increasing the number of specific probiotic bacteria. In addition, an increasing number of studies have shown that probiotics work best when combined with prebiotics.

Galactooligosaccharides (GOS) are considered one of the preferred choices of prebiotics and in the gastrointestinal tract, GOS are resistant to enzymes and transit though the small intestine without being digested, but in the large intestine GOS are fermented and can promote growth of intestinal bifidobacteria and Lactobacilli such as *Lactobacillus acidophilus* and *L. casei*, hence acting as a prebiotic. GOS are non-digestible oligosaccharides owing to the conformation of their anomeric C atom ($C_1$ or $C_2$), which allows their glycosidic bonds to evade hydrolysis by digestive enzymes in the stomach or small intestine. Free oligosaccharides are found in the milk of all placental mammals, providing a natural example of prebiotic feeding during infancy. The composition of human milk oligosaccharides (HMO) is very complex, which makes it unlikely to find alternative sources containing oligosaccharides of analogous composition. Improved colonic health among breastfed infants has been attributed to the presence of GOS in the mother's milk. In fact, infant formula with added GOS replicated the bifidogenic effect of the human milk with respect to metabolic activity of colonic microbiota and bacterial numbers. Among non-milk oligosaccharides, GOS are of special interest as their structure resembles the core molecules of HMOs. However, GOS concentration and composition vary with the method and the enzyme utilized for their generation, which in turn may influence their prebiotic effects and the proliferation of colonic probiotic strains. Traditionally, GOS have been produced using β-galactosidases from mesophilic or thermophilic microorganisms. β-galactosidases require high initial concentrations of lactose to drive the reaction away from lactose hydrolysis and towards GOS synthesis. Since lactose is more soluble at elevated temperatures, thermostable β-galactosidases exhibiting high initial velocities and increased half-lives have been utilized to reach a favorable equilibrium for the transgalactosylation reaction. However, competitive inhibition by glucose and/or galactose is another obstacle that remains and may be overcome by incorporating cells in the reaction.

The basidiomycete yeast *Hamamotoa* (Sporobolomyces) *singularis* (formerly *Bullera singularis*) cannot utilize galactose to grow but proliferates on lactose due to the activity of its β-hexosyl-transferase (BHT, EC 3.2.1.21). Studies have shown that the BHT has transgalactosylation activity even at low lactose concentrations and very limited lactose hydrolysis. In addition, the enzyme does not appear to be inhibited by lactose concentrations above 20% and has the potential for conversions into GOS close the maximum theoretical of 75%. Unlike β-galactosidases, the BHT from *Hamamotoa* (Sporobolomyces) *singularis* simultaneously carries out glycosyl-hydrolase and β-hexosyl-transferase activities, converting lactose to GOS without extracellular accumulation of galactose. Two molecules of lactose are required during the transgalactosylation event: one molecule is hydrolyzed and the second acts as galactose acceptor, generating the trisaccharide galactosyl-lactose (β-D-Gal(1-4)-β-D-Gal(1-4)-β-D-Glc) and residual glucose. Galactosyl-lactose can also act as acceptor of a new galactose to generate the tetrasaccharide galactosylgalactosyl-lactose (β-D-Gal(1-4)-β-D-Gal(1-4)-β-D-Gal(1-4)-β-D-Glc), and similarly for the pentasaccharide and subsequent products. The tri, tetra, and penta saccharides accumulating in *H. singularis* have been collectively designated GOS.

For practical interests, a recombinant secreted BHT could have several advantages over the native enzyme, including improved large-scale production and purification. Currently, purification of active enzyme from *Hamamotoa* (Sporobolomyces) *singularis* requires cell lysis followed by multiple chromatography steps. Previous attempts to express recombinant β-hexosyl-transferase in *E. coli* BL21 have resulted in high levels of production, but the enzyme was inactive and insoluble.

SUMMARY

Embodiments of the present disclosure include a functional, recombinant β-hexosyl-transferase (rBHT) polypeptide comprising at least 90% sequence identity with SEQ ID NO: 1 and an N-terminal truncation of at least one amino acid with reference to SEQ ID NO: 1.

In some embodiments, the polypeptide comprises at least 95% sequence identity with SEQ ID NO: 1. In some embodiments, the polypeptide further comprises at least one additional amino acid substitution. In some embodiments, the polypeptide comprises an N-terminal truncation that is from about 1 to about 81 amino acids in length. In some embodiments, the N-terminal truncation is from about 1 to about 56 amino acids in length. In some embodiments, the polypeptide comprises at least 90% sequence identity with any of SEQ ID NOs: 3, 5, 7, and 9.

In some embodiments, the polypeptide further comprises a signal sequence. In some embodiments, the signal sequence is non-native. In some embodiments, the signal sequence comprises an amino acid sequence derived from a yeast protein. In some embodiments, the signal sequence comprises an amino acid sequence from a protein from any one of *Komagataella (Pichia) pastoris, Saccharomyces cerevisiae, Yarrowia lipolytica, Hansenula (Ogataea) polymorpha*, or *Kluyveromyces lactis*. In some embodiments, the signal sequence comprises a polypeptide with at least 90% sequence identity to at least one of α-mating factor signal sequence from *Saccharomyces cerevisiae* (MFα) (SEQ ID NO: 29), Invertase (IV) signal sequence (SEQ ID NO: 30), Glucoamylase (GA) signal sequence (SEQ ID NO: 31), or Inulinase (IN) signal sequence (SEQ ID NO: 32). In some embodiments, the polypeptide comprises at least 90% sequence identity with any of SEQ ID NOs: 34, 36, 38, 40, 42, 44, 46, 48, 50, 52, 54, 56, 58, 60, 62, 64, 66, 68, or 70. In some embodiments, the polypeptide comprises at least one asparagine residue at position 289, 297, 431, and/or 569 with respect to SEQ ID NO: 1.

In some embodiments, the polypeptide is soluble or membrane-bound. In some embodiments, about 1% to about 50% of the polypeptide is soluble. In some embodiments, the polypeptide catalyzes the hydrolysis of lactose $\beta$-(1-4) glycosidic linkages. In some embodiments, the catalysis of the hydrolysis of lactose $\beta$-(1-4) glycosidic linkages by the polypeptide generates a composition comprising LacNAc-enriched GOS.

Embodiments of the present disclosure also include a nucleic acid molecule encoding any of the polypeptides described above. Embodiments of the present disclosure also include a vector comprising any one of these nucleic acid molecules.

Embodiments of the present disclosure also include a method of generating a GOS composition from lactose in a host cell using any of the polypeptides described above. In some embodiments, the GOS composition comprises LacNAc-enriched GOS and/or GOS lacking GlcNAc.

In some embodiments of the method, the host cell is one or more of a yeast cell, a fungal cell, a mammalian cell, an insect cell, a plant cell, or an algal cell. In some embodiments, the host cell includes any cell from the genus *Komagataella*.

In some embodiments of the method, the host cell comprises one or more cells from *Komagataella (Pichia) pastoris, Saccharomyces cerevisiae, Yarrowia lipolytica, Hansenula (Ogataea) polymorpha*, or *Kluyveromyces lactis, Aspergillus* spp., and *Trichoderma reesei*. In some embodiments, the method produces a LacNAc-enriched GOS yield of at least 10% of initial lactose concentration, and a total GOS concentration of at least 50% of initial lactose concentration.

Embodiments of the present disclosure also include a composition comprising any of the polypeptides described above, and/or one or more LacNAc-enriched GOS using any of the polypeptides described above.

In some embodiments, the composition is a food product. In some embodiments, the food product comprises one or more of infant formula, yogurt, dairy products, milk-based beverages, fruit beverages, hydration beverages, energy beverages, fruit preparations, and meal replacement beverages.

Other aspects and embodiments of the disclosure will be apparent in light of the following detailed description.

5 cates lane containing the molecular weight protein markers and (kDa) shown to the left of the panels.

Figure 4:
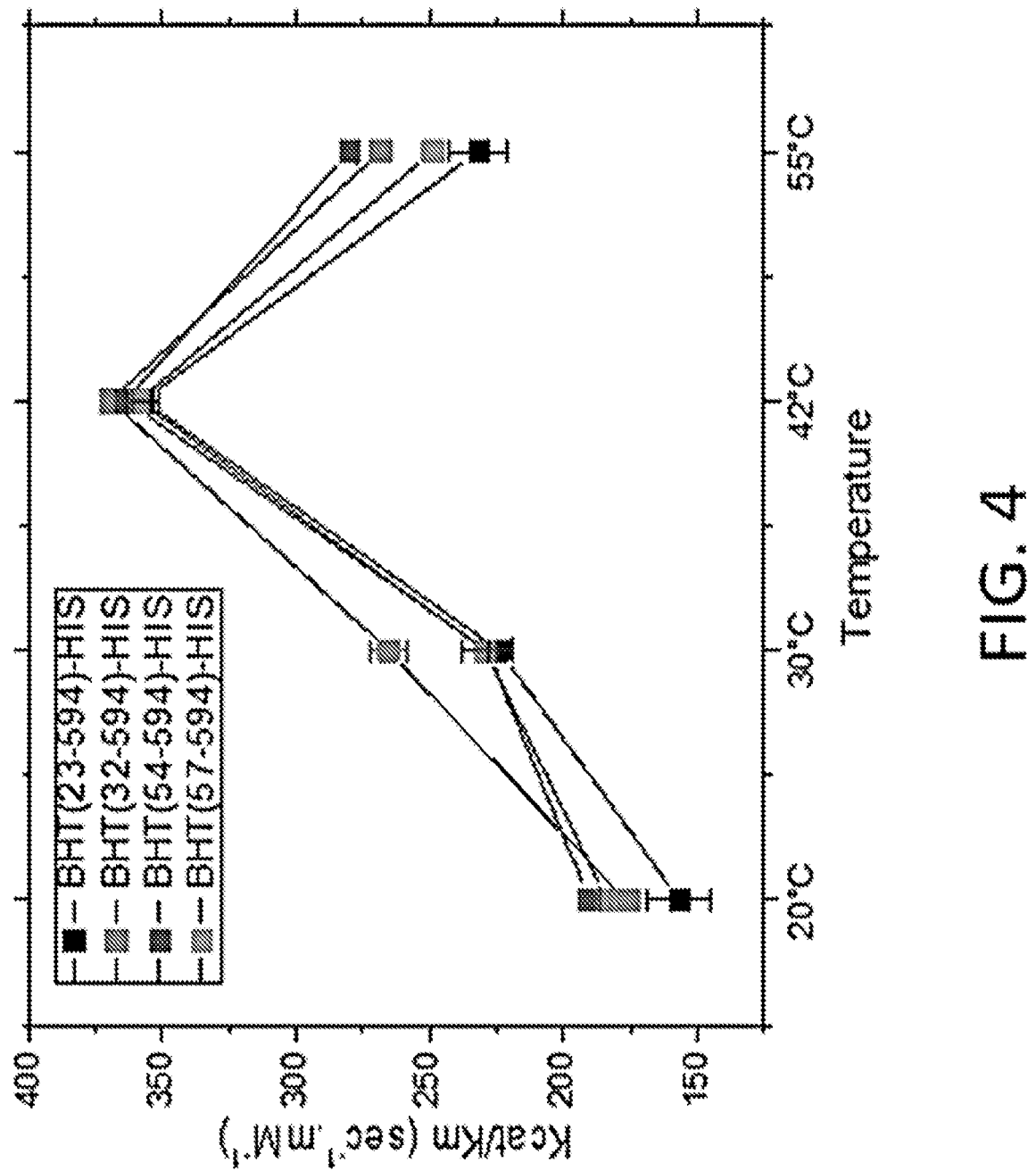

FIG. 4: Enzyme kinetic parameters for rBHT variants tested at 20° C., 30° C., 42° C. and 55° C. kcat/km versus temperature. Enzyme assays were carried out in the presence of 0.3 µg rBHT$_{(23-594)}$-HIS, rBHT$_{(32-594)}$-HIS, rBHT$_{(54-594)}$-HIS and rBHT$_{(57-594)}$-HIS over a range of ONP-Glu substrate concentrations (0.08-10.4 mM) as described under "Methods". Km and kcat were calculated from initial velocities of ONP-Glu cleavage using the Hill equation. The values are the average of three independent measurements±Standard Deviation (SD).

Figures 5A, 5B:
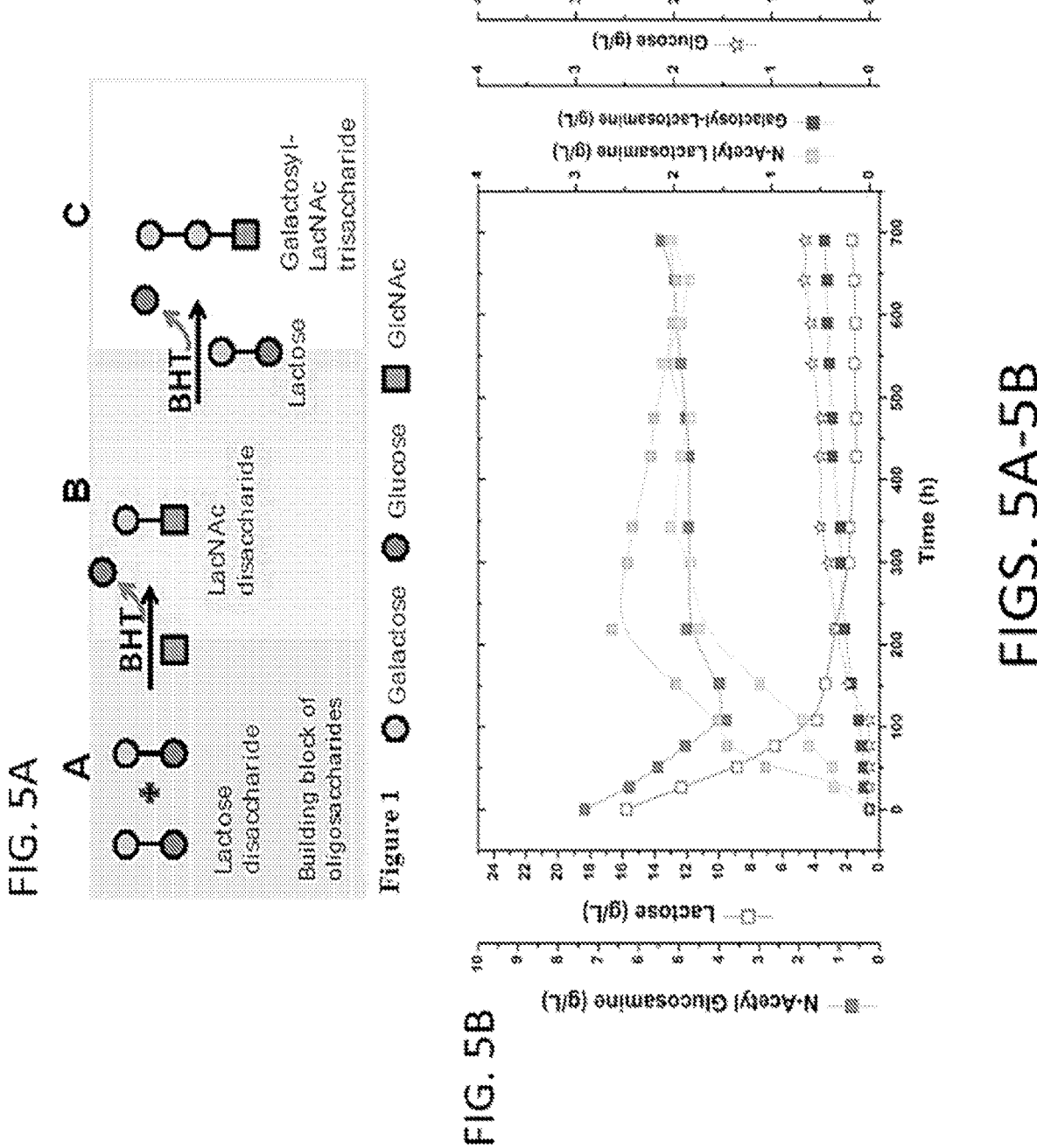

FIGS. 5A-5B: Example of production of N-acetyllactosamine (LacNAc) at a ratio lactose/N-acetylglucosamine 1:2. (A) The recombinant BHT (rBHT) polypeptides of the present disclosure are able to catalyze the repeated addition of galactose (Gal from lactose) to N-acetylglucosamine (GlcNAc). (B) Enzymatic reactions catalyzed by rBHT. An example of time course studies of galactosyl-lactose (Gal-lactose), galactosyl-N-acetallactosamine (Gal-LacNAc), and N-acetyllactosamine (LacNAc) synthesis were performed using whole cells membrane bound protein (1 U rBHT·g⁻¹ lactose). Assays contained ~20 g/L lactose; ~10 g/L N-acetylglucosamine (GlcNAc), in 5 mM sodium phosphate buffer (pH 5.0) and incubated at 30° C. Samples were removed periodically and analyzed by HPLC and detected by ELSD and PDA.

Figures 6A, 6B, 6C:
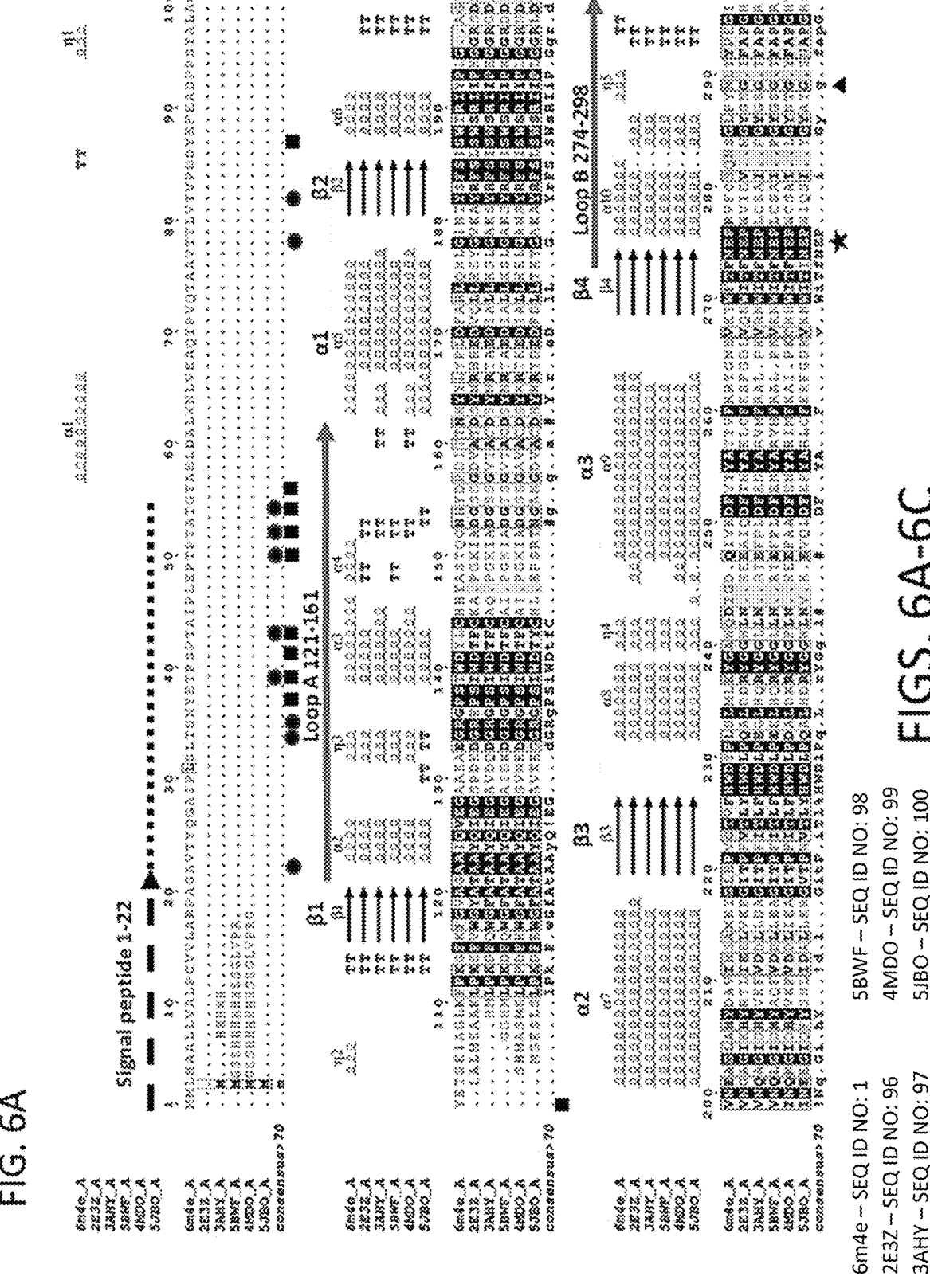

FIGS. 6A-6C: Multiple secondary structure alignment of 6m4e (HsBglA$_{(23-594)}$-HIS) with structurally GH1 homologous proteins. (A) The proteins found to be most structurally homologous from the PDB database include: 2E3ZA (BGL1A), 3AHYB (TrBgl2), 5BWFA (ThBgl), 4MDOA (HiBG), and 5JBOA (ThBgl2) (Tables 4A-4B). Primary sequence alignments are shown at the bottom. Secondary structure elements from rBHT$_{(23-594)}$-HIS and their designations are shown above the alignment. β-strands are shown by black arrows, α-helical structures by coils, strict α-turns (TTT letters), β-turns (TT letters) and η refers to 3₁₀ helix random coil. Numbering of the secondary structure elements for the (α/β)-Tim barrel structure are shown above the structural alignment as (α1-α8) and (β1-β8). For analysis of the HsBglA$_{(23-594)}$-HIS unstructured region, numbering of the amino acids for HsBglA from amino to carboxyl terminus includes the deleted signal sequence (residues 1-22) indicated with a dashed arrow and unstructured region missing from the crystal structure (residues 23-53) indicated with a dotted line. The amino acids were aligned with ClustalO based on % sequence similarities. Identical residues are white with black background and conservative changes are boxed with a gray background. Insertions are highlighted with a purple background. The catalytic acid/base and nucleophilic residues are indicated with stars. Glycosylation sites found on HsBglA$_{(23-594)}$-HIS are indicated with triangles. FIG. 6A shows predicted phosphorylation sites and potential O-glycosylation sites in the N-terminus shown in FIG. 1, indicated with squares and circles, respectively. The consensus sequence is shown at the bottom of the aligned sequences. The Image was generated using ENDscript 2.0 Webserver (endscript.ibcp.fr/ESPript/ENDscript/) (5) derived from the 3D crystal structure comparison based on HsBglA$_{(23-594)}$-HIS (PDB ID:M6E4) against those in the protein data bank using data obtained with Dali protein structure comparison server (ekhidna2.biocenter.helsinki.fi/dali/) (Holm, 2019). (B) HsBglA$_{(23-594)}$-HIS (PDB ID: M6E4) four extended loops A, B, C and D are colored in blue, green, yellow, and red and indicated as arrows in the same colors forming the substrate binding pocket entrance and are indicated above the secondary structures in (A). (C) The degree of conservation for HsBglA$_{(23-594)}$-HIS (PDB ID: M6E4) is represented by a red-to-blue color gradient. A deeper red color means a more conserved residue and a more variable residue is a deeper blue. (B) and (C) were produced using PyMOL (pymol.org/2/).

Figures 7A, 7B:

FIGS. 7A-7B: (A) SAXS data for BHT at 1 mg/ml (red) and 4 mg/ml (blue). SAXS data are shown on a log-log plot (left). I(Q) is in arbitrary units. (B) P(r) curve calculated from the SAXS data are normalized to a maximum height of 1.0.

DETAILED DESCRIPTION

The present disclosure provides compositions and methods related to the production of human milk oligosaccharides (HMOs). In particular, the present disclosure provides compositions and methods for converting lactose and N-acetylglucosamine (GlcNAc) into N-acetyllactosamine (LacNAc)-enriched galactooligosaccharide (GOS) compositions using novel β-hexosyl-transferase (BHT) enzymes.

*Hamamotoa (Sporobolomyces) singularis* codes for an industrially important inducible membrane bound β-hexosyltransferase (BHT), which is partially secreted soluble when heterologously expressed by *Komagataella (Pichia) pastoris*. BHT secretion is determined by a 22 amino acid signal sequence that is part of a novel amino terminal region (1-110 amino acids) and predicted to be glycosylated on four arginine positions of the catalytic glycosyl hydrolase (GH1) within the carboxyl terminal domain. To evaluate the role of each N-glycosylation site in the generation of biologically active soluble enzyme, the activity of N-glycosylated recombinant enzyme variants (e.g., N289Q, N297Q, N431Q and N569Q) produced by *Komagataella (Pichia)pastoris* were comparatively analyzed. Functional analysis of four deglycosylated soluble variants revealed a reduced total recombinant (rBHT) measurable activity (58-97% decrease) indicating that glycosylation at all four sites is critical for the generation of active enzyme. Additionally, in silico structural predictions show the presence of disordered segments within the novel amino terminal region (1-110 amino acids) preceding the catalytic C-terminal GH1 domain. Deletion analysis was performed targeting segments surrounding the putative disordered regions to generate eight truncated N-terminal domain enzyme variants. The impact of the enzyme truncations on the ratio of membrane bound to secreted soluble enzyme variants was assessed. Fusions of the truncated active soluble variants to the MFα signal sequence and modified MFα versions generated by *Komagataella (Pichia) pastoris* were compared for secretion titers, stability and enzyme kinetics. Surprisingly, N-terminal deletions up to 56 amino acids produced fully functional secreted soluble enzyme variants while ~65% of the total secreted active enzyme was membrane bound under the experimental conditions described herein.

*Hamamotoa (Sporobolomyces) singularis* (H *Singularis*) expresses, under inducible conditions, an extracellular membrane-bound glycosylated β-hexosyltransferase (BHT). BHT catalyzes the hydrolysis of cellobiose β-(1-4) glycosidic linkages and possesses appealing enzymatic transgalactosylation capabilities in the presence of lactose allowing for the synthesis of galacto-oligosaccharides (GOS), which are considered prebiotics and widely used as functional food additives. For this reason, the interest in the important role of this novel enzyme catalyzing transgalactosylation reactions has increased.

More recently, heterologous expression of biologically inactive rBHT by *Escherichia coli* (*E. coli*) suggested that post-translational modifications such as glycosylation were a requirement for obtaining an active enzyme. However, it remains unclear as to whether all the potential glycosylation sites within the carboxyl terminal domain and/or motifs on the N-terminal region are involved in the generation of biologically active rBHT. The novel N-terminal region has no known sequence homologs and has yet to be characterized. The carbohydrate moieties of glycoproteins are generally believed to facilitate protein folding, oligomerization, protection from proteolysis, secretion, intracellular trafficking, cell surface expression, and enzymatic activity.

*Komagataella* (*Pichia*)*pastoris* (*K. pastoris*) is commonly used as eukaryotic hosts for production of recombinant proteins due to its post-translational modifications and secretion capabilities. As would be recognized by one of ordinary skill in the art based on the present disclosure, *Komagataella* (*Pichia*) *pastoris* (*K. pastoris*) is also referred to as *Kamagataaella phaffi*. As described further herein, the various compositions and methods of the present disclosure are applicable to any host cell, including but not limited to, a yeast cell, a fungal cell, a mammalian cell, an insect cell, a plant cell, or an algal cell. In some embodiments, the host cell includes any cell from the genus *Komagataella*.

In *K. pastoris*, N-glycans form high-mannose-type heterogeneous oligosaccharides beginning with the addition of the core unit $Glc_3Man_9GlcNAc_2$ (Glc=glucose; GlcNAc=N-acetylglucosamine; Man=mannose) at asparagine in the recognition sequence Asn-X-Ser/Thr. Heterologous expression of rBHT by *K. pastoris* resulted in a glycosylated extracellular cell wall or membrane bound enzyme. Surprisingly, the native protein leader directed secretion of a small fraction of the enzyme into the culture broth as active soluble enzyme. Previous work demonstrated that *K. pastoris* was able to secrete soluble biologically active rBHT into the culture broth, which opened the possibility of a straightforward downstream recovery processes protocol. Thus, experiments were conducted to recover, purify, and evaluate the activity and stability of the soluble active enzyme and compare it with the membrane-bound rBHT.

The predicted protein includes 594 amino acids, contains an amino terminal region of 1-110 amino acids without known sequence homologs followed by a carboxyl terminal glycosyl hydrolase family 1 (GH1) catalytic domain. The N-terminus also possesses a secretory signal peptide consisting of 22 amino acids that limits its secretion when fused, upstream of the entire open reading frame, to the α-mating factor (MFα) signal sequence from *Saccharomyces cerevisiae*. Experiments demonstrated that this restriction could be partially released by replacing the native BHT signal sequence (1-22 aa) by the MFα signal sequence. The result was an unexpected 53-fold activity increase of the biologically active soluble enzyme in the culture broth and also an increase of the *K. pastoris* membrane associated form of the enzyme. These results demonstrated that the BHT signal sequence influences membrane bound localization versus secretion of soluble enzyme into the medium. While previous results did not address the role of N-terminal regions outside of the first 22 amino acid signal peptide, it did establish a system in which this question could be evaluated using deletion mutagenesis within the novel 1-110 N-terminal domain, as described further herein.

Secretion of soluble proteins by *K. pastoris* is highly protein dependent and remains a general bottleneck to production processes, as is well-recognized in the art. One of the reasons for this limitation is believed to come from improper folding, which can be remedied by overexpressing folding helper proteins. Alternative methods can include reengineered strains and mutagenesis as ways to improve secretion. Furthermore, a number of studies have shown increases in secretion of soluble recombinant proteins by altering glycosylation and cellular trafficking associated genes.

In this present disclosure, experiments were conducted (using site directed mutagenesis and progressive deletion analysis) to address whether secretion of soluble active rBHT is controlled by posttranslational N-glycosylation modifications buried within the C-terminal GH1 domain, and/or restricted by features contained within the novel 110 N-terminal region (amino acids 23 to 110). The overall analysis of rBHT expression of each altered or truncated enzyme variant was complemented by the analysis of enzyme activity, measured as the ratio of soluble versus membrane-associated enzyme. Finally, results of the present disclosure further demonstrate the uniqueness of the N-terminus by presenting a comparative sequence and structural analysis with homologous GH1 proteins, whose coordinates are available in the protein data bank (PDB) using the recently derived crystal structure of the BHT enzyme.

On the basis of BHT's industrial applications and importance, improving secretion efficiency of soluble active enzyme is highly desirable. Recently, structural information has become available for 90% of the BHT enzyme, and evidence was compared with other GH1 family members. The data obtained confirmed in silico structural predictions of the enzyme showing two distinct structural domains: a novel 110 N-terminal domain containing a signal sequence and probable disordered regions, and a conserved carboxyl GH1 domain. These data also predicted various glycosylation and phosphorylation sites. Thus, three general categories of protein structural modifications were performed: 1) site directed mutagenesis of four glycosylation sites; 2) truncations in the 110 N-terminal regions; and 3) replacement and modification of the secretion signals. The first group of modifications targeted the glycosylation sites by site directed mutagenesis and confirmed their importance for enzyme activity. The second group of modifications demonstrated that removal of up to 56 N-terminal amino acids does not impact enzyme activity, and that these residues do not play a critical role in secreting soluble active rBHT. The third group of modifications showed that altering MFα signal sequence allows for an increased ratio (0.67) of secreted soluble protein to membrane-associated protein (Table 1).

Examining the correlation between rBHT N-glycosylation and the corresponding enzymatic characteristics is an important step towards evaluating enzymatic stability, activity and even production. Post-translational modifications such as N-glycosylation are involved in protein folding in the ER and play an important role in heterologous protein secretion. However, not all predicted N-glycosylated sequons in polypeptides are glycosylated in vivo. A number of algorithms are available for predicting N- and O-glycosylation sites, although the effect of enhancing or removing a putative site on expression and secretion can only be confirmed in vivo. In silico analysis suggested that the BHT GH1 domain contains four N-glycosylation sites recently confirmed by the three-dimensional structure (HsBglA, PDB ID:M6E4). Importantly, single site replacement of asparagine by glutamine indicated a strong link to expression of the active enzyme. Though, surprisingly, the ratio of secreted soluble enzyme to cell membrane associated activity increased from 0.40 to 0.66 for $BHT_{(23-594)(N569Q)}$-HIS. In particular, the substitutions led to dramatic decreases in secreted soluble protein from 58% to 97%, and in cell membrane associated active protein from 75% to 95% compared to the parent strain, rBHT$_{(23-594)}$-HIS. This wide range in activities represented as a percentage of fully active enzyme shows that even the absence of one N-glycosylation site is sufficient to reduce titers of active enzyme, and a fully functional enzyme is only obtained when all four sites tested are glycosylated.

Experiments also examined whether secretion of soluble active protein is influenced by the presence of disordered N-terminal segments, and if their removal has a functional significance on catalytic activity of the truncated secreted soluble rBHT variants. Little is known about the novel 110 N-terminal region of BHT, a fragment that so far lacks homology with other known proteins. Based on the predicted disordered segments of the novel 110 N-terminal domain, deletion chimeras fused the MFα signal sequences were generated. Heterologous expression of N-terminal truncations comprising amino acids 1-56 generated comparable enzymatic kinetic parameter values for each secreted soluble, stable, and bioactive enzyme, whereas further N-terminal deletions of disordered segments abrogated the secretory process (FIG. 2; FIG. 3; Table 1). Therefore, BHT activity and stability is not dependent on the N-terminal 56 amino acids, although its impact on secretion can only be confirmed in vivo as was described for N-glycosylation sites. For example, the carboxyl-terminal boundary of the disordered region predicted by IUPRED2A at amino acid 56 can be removed but downstream-predicted disordered regions were required to obtain an active enzyme.

Intrinsically disordered proteins (IDPs) exist in inter-changing conformations rather than adapting well-defined structures. Disordered regions can be discriminated from ordered ones based on the amino acid sequence and in most cases, disordered proteins are less evolutionarily conserved but rather their disordered structure has been maintained. IDPs participate in a number of cellular functions, including transcription, translation, regulation, and signal transduction and are enriched in phosphorylation sites. Often IDPs are involved in binding DNA or RNA, and to other proteins, and can assist in the assembly of multi-protein complexes. Moreover, IDPs are less frequent in enzymes, and while different servers yield significant deviations as output within the GH1 domain, when using the more stringent server DISOPRED3 there is a lack of disordered regions in the GH1 domain.

Additionally, as described further herein, structural modifications were performed by replacing the secretion signal given that, previously, truncated active polypeptides of BHT at residues 17 or 22 were detected in protein cell extracts from cell membranes of *H. singularis*. This finding suggested that this fragment was cleaved to form the mature BHT. Using *K. pastoris*, results demonstrated that BHT amino acids 1-22 act as a functional native signal sequence. It was demonstrated that its replacement with the MFα signal sequence allowed for secretion of soluble active rBHT variants, though approximately an additional 71% of the secreted enzyme remained membrane associated (Table 1), in agreement with previous results.

It should be noted that the persistent partial localization of rBHT with the cell membrane following removal of the N-terminal disordered regions suggests that either impartial cleavage of the MFα or perhaps the 57-110 amino acids within the novel N-terminal region or the BHT GH1 domain may contain points of association with cell membrane. Most secreted proteins in eukaryotes contain N-terminal signal sequences that direct the protein to cellular or extracellular locations. The ability of peptide sequences with minimal sequence homology to function as signal peptides has allowed substitution of the original signal sequence with signal peptide sequences found in yeast. A comparison of four signal sequences revealed that the secreted BHT peptide continues to be associated with the cell membrane.

Cleavage of the signal peptide has been found to be important for the assembly and secretion of functional prolipoproteins across the *E. coli* membrane. In one study, unprocessed consensus MFα-α-interferon accumulated in the periplasmic space and cell wall, and secretion into the culture medium and cellular accumulation could be alleviated with Glu-Ala dipeptide between MFα and α-interferon. Furthermore, deletion of amino acids 57-70 in the pro-region of MFα has been shown to increase secretion of horseradish peroxidase and lipase by at least 50%. Thus, based on these results, cleavage of the signal peptide by signal peptidases may be required for the final assembly and secretion of soluble rBHT. The same modifications to MFα found in the variants GS115::MFα$_{(Δ57-70)}$-rBht$_{(23-594)}$-HIS and GS115::MFα$_{(Δ57-70)}$-rBht$_{(57-594)}$-HIS increased secretion compared to GS115::MFα-rBht$_{(23-594)}$-HIS by 58%, and as a result, increased the ratio of secreted soluble to membrane associated by 40% (Table 1).

The crystal structure of BHT is similar overall to GH1 family proteins; however, the N-terminus (residues 1-110) has no known homolog and residues 23-54 were not defined in the structure. It was previously proposed that this region is unstructured and structurally dynamic. As described further herein, deletion analysis was performed on the N-terminal unstructured domain based on in silico results. In light of these results, features within the first N-terminal 56 residues likely play a limited role in cell associated activity but are not required for enzyme folding, secretion or activity.

Figure 1:
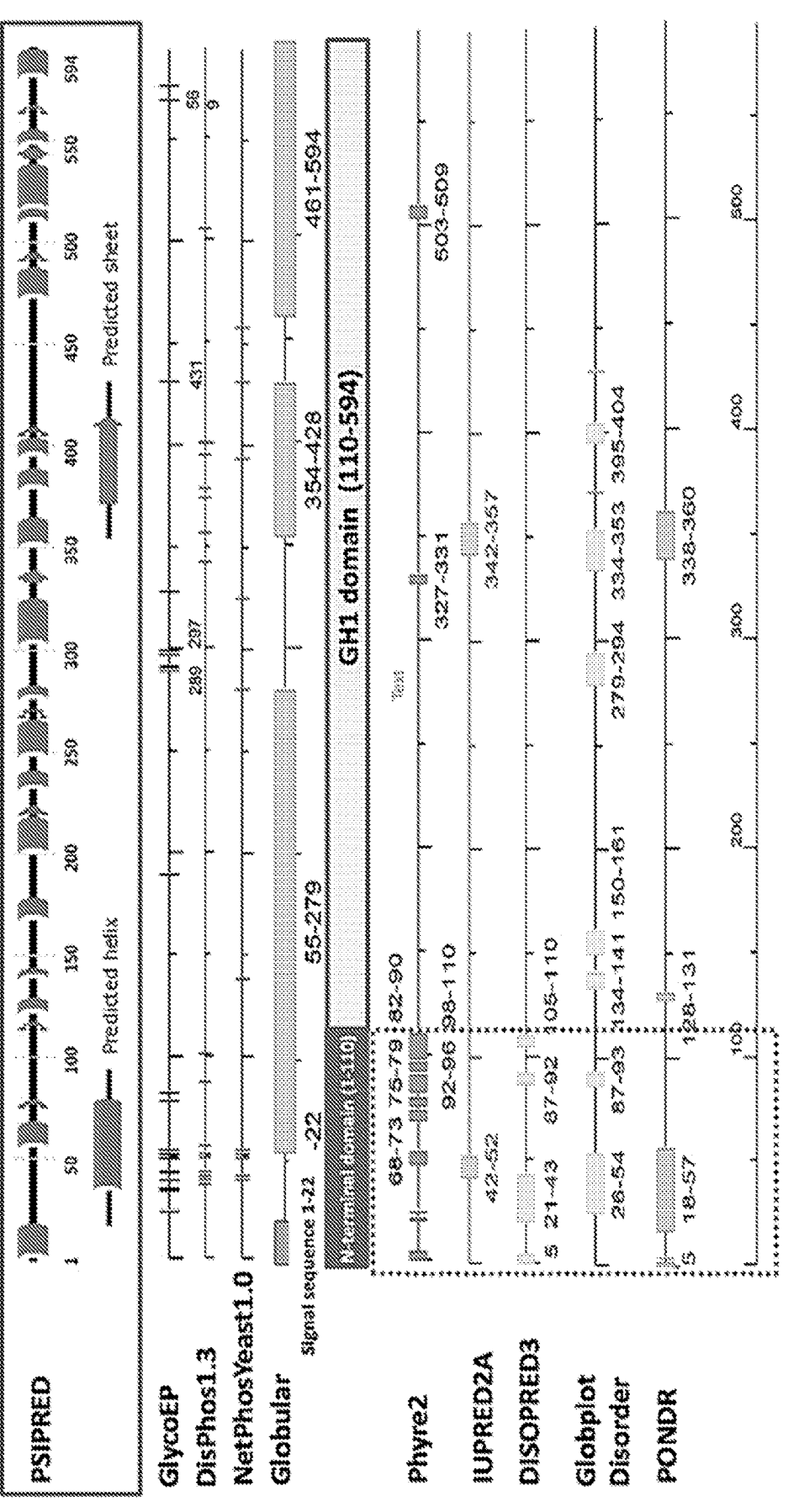
FIG. 1: Predicted structural posttranslational modifications and disordered vs. ordered secondary motifs of $\beta$-hexosyltransferase from *H. singularis*. BHT protein glycosylation, phosphorylation and secondary structures were predicted using various algorithms. Depicted are the structural elements, conserved regions, and functional domains of BHT using PSIPRED and Globplot Globular prediction tools. Disordered regions were predicted using algorithms Phyre2, IUPRED2A, DISOPRED3, Globplot Disorder, and PONDR. Phosphorylation servers DisPhos1.3 and NetPhosYeast1.0 display phosphorylation sites. GlycoEP display N-glycosylation (red lines) and O-glycosylation (black lines) while no C-mannosylation sites were predicted. Numbers below each prediction line indicate BHT amino acid residue number.
Figures 6A, 6B, 6C:
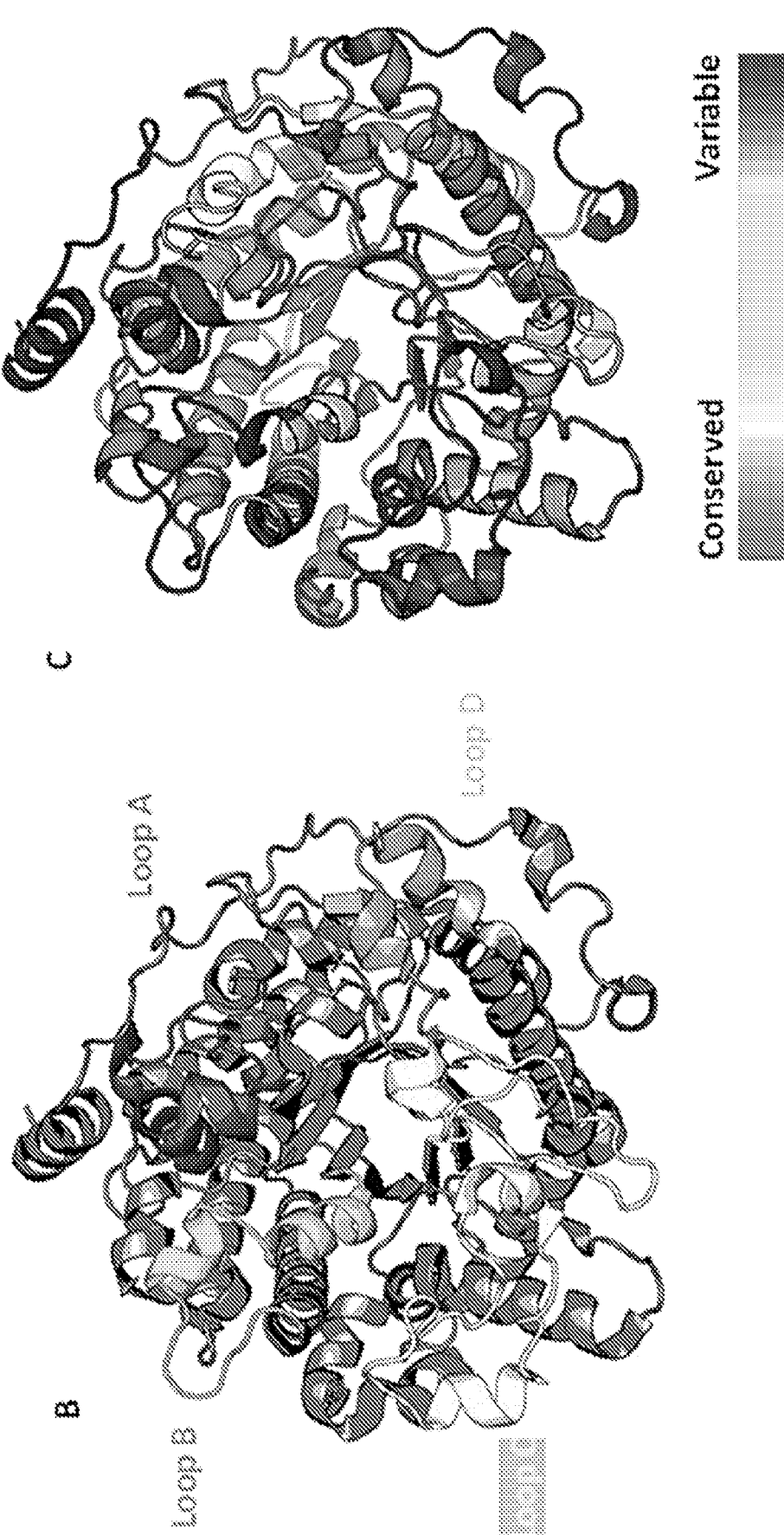

For rational enzyme redesign it is imperative to determine the possible regulatory mechanisms for the BHT N-terminal unstructured region. According to the results of the present disclosure, homologous structures include the conserved C-terminal catalytic domain but lack the highly intrinsically disordered N-terminal domain found in the BHT in silico analysis (FIG. 1). In agreement with the in silico predictions, the recently published three-dimensional structure of BHT$_{(23-594)}$-HIS resolved by X-ray crystallography (HsBglA, PDB: 6M4E) does not have a detectable electron density for residues 23-54 in the N-terminus, in agreement with the in silico predicted unstructured residues in this region (FIG. 1). The overall structure of the C-terminal catalytic domain is similar to the classical GH1 structure, also confirmed by the crystal structure. However, specific elements (FIG. 6) were found in addition to unique amino acids within the catalytic nucleophile which may provide a handle for the distinct catalytic characteristics of BHT for future studies.

All the above data further document the role of N-terminal disordered regions beyond residue 56 for sustaining active rBHT and attributes the basis for partial selective sequestration of cell wall bound rBHT to the inefficient processing of the signal secretion sequence. Overall, results of the present disclosure using *K. pastoris* improved secreted titers of soluble rBHT by removing the endogenous 56 N-terminal amino acids while fused to a truncated MFα version.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the present disclosure may be readily combined, without departing from the scope or spirit of the embodiments provided herein. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences for the production of a polypeptide, precursor, or RNA (e.g., rRNA, tRNA, sRNA, microRNA, lincRNA). The polypeptide can be encoded by a full-length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than about 300 residues long (e.g., between 15 and 100), however, as used herein, the term is also intended to encompass longer polynucleotide chains. Oligonucleotides are often referred to by their length. For example, a 24-residue oligonucleotide is referred to as a "24-mer." Oligonucleotides can form secondary and tertiary structures by self-hybridizing or by hybridizing to other polynucleotides. Such structures can include, but are not limited to, duplexes, hairpins, cruciforms, bends, and triplexes.

"Peptide" and "polypeptide" as used herein, and unless otherwise specified, refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

As used herein, the term "fragment" refers to a peptide or polypeptide that results from dissection or "fragmentation" of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or polypeptide that is not a subsequence of a preexisting whole protein is not a fragment (e.g., not a fragment of a preexisting protein).

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

In some embodiments the substitutions can be conservative amino acid substitutions. Examples of conservative amino acid substitutions, unlikely to affect biological activity, include the following: alanine for serine, valine for isoleucine, aspartate for glutamate, threonine for serine, alanine for glycine, alanine for threonine, serine for asparagine, alanine for valine, serine for glycine, tyrosine for phenylalanine, alanine for proline, lysine for arginine, aspartate for asparagine, leucine for isoleucine, leucine for valine, alanine for glutamate, aspartate for glycine, and these changes in the reverse. See e.g. Neurath et al., The Proteins, Academic Press, New York (1979), the relevant portions of which are incorporated herein by reference. Further, an exchange of one amino acid within a group for another amino acid within the same group is a conservative substitution, where the groups are the following: (1) alanine, valine, leucine, isoleucine, methionine, norleucine, and phenylalanine: (2) histidine, arginine, lysine, glutamine, and asparagine; (3) aspartate and glutamate; (4) serine, threonine, alanine, tyrosine, phenylalanine, tryptophan, and cysteine; and (5) glycine, proline, and alanine.

The term "homology" and "homologous" refers to a degree of identity. There may be partial homology or complete homology. A partially homologous sequence is one that is less than 100% identical to another sequence.

As used herein, the terms "complementary" or "complementarity" are used in reference to polynucleotides (e.g., a sequence of nucleotides such as an oligonucleotide or a target nucleic acid) related by the base-pairing rules. For example, for the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

In some contexts, the term "complementarity" and related terms (e.g., "complementary", "complement") refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. The percentage complementarity need not be calculated over the entire length of a nucleic acid sequence. The percentage of complementarity may be limited to a specific region of which the nucleic acid sequences that are base-paired, e.g., starting from a first base-paired nucleotide and ending at a last base-paired nucleotide. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present disclosure and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Thus, in some embodiments, "complementary" refers to a first nucleobase sequence that is at least 60%, 65%, 70%, 75%, 80%, 85%, 90%, 95%, 97%, 98%, or 99% identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases, or that the two sequences hybridize under stringent hybridization conditions. "Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleic acid has a nucleobase sequence that is identical to the complement of the nucleic acid over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases.

As used herein, a "double-stranded nucleic acid" may be a portion of a nucleic acid, a region of a longer nucleic acid, or an entire nucleic acid. A "double-stranded nucleic acid" may be, e.g., without limitation, a double-stranded DNA, a double-stranded RNA, a double-stranded DNA/RNA hybrid, etc. A single-stranded nucleic acid having secondary structure (e.g., base-paired secondary structure) and/or higher order structure comprises a "double-stranded nucleic acid". For example, triplex structures are considered to be "double-stranded". In some embodiments, any base-paired nucleic acid is a "double-stranded nucleic acid"

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

2. RECOMBINANT β-HEXOSYL-TRANSFERASE (RBHT) POLYPEPTIDES

Embodiments of the present disclosure provide compositions and methods related to the production of human milk oligosaccharides (HMOs). In particular, the present disclosure provides compositions and methods for converting lactose and N-acetylglucosamine (GlcNAc) into N-acetyl-lactosamine (LacNAc)-enriched galactooligosaccharide (GOS) compositions using novel β-hexosyl-transferase (BHT) enzymes.

As would be recognized by one of ordinary skill in the art based on the present disclosure, recombinant rBHT proteins, or rBHT proteins, includes full length rBHT proteins and any fragments and/or variants thereof, which includes proteins encoded by naturally-occurring allelic variants of the rBHT gene, as well as recombinantly-produced rBHT proteins, which may contain some sequence changes relative to naturally-occurring rBHT proteins. A recombinant protein can be a protein that results from the process of genetic engineering, which generally involves use of a corresponding recombinant nucleic acid molecule encoding the peptide that is inserted into an engineered host cell in order to express the nucleic acid molecule and the corresponding peptide. That is, the host cell has been transfected, transformed or transduced with a recombinant polynucleotide molecule, and thereby altered so as to cause the cell to express the desired polypeptide (e.g., rBHT).

In accordance with these embodiments, the present disclosure includes a functional, recombinant β-hexosyl-transferase (rBHT) polypeptide comprising at least 90% sequence identity with SEQ ID NO: 1 and an N-terminal truncation of at least one amino acid with reference to SEQ ID NO: 1. In some embodiments, the polypeptide comprises at least 95% sequence identity with SEQ ID NO: 1. In some embodiments, the polypeptide further comprises at least one additional amino acid substitution.

In some embodiments, the polypeptide comprises an N-terminal truncation that is from about 1 to about 81 amino acids in length. In some embodiments, the N-terminal truncation is from about 1 to about 56 amino acids in length. In some embodiments, the polypeptide comprises an N-terminal truncation that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 83, 74, 75, 76, 77, 78, 79, 80, or 81 amino acids in length.

In some embodiments, the polypeptide comprises at least 90% sequence identity with any of SEQ ID NOs: 3, 5, 7, and 9. In some embodiments, the polypeptide comprises at least 91% sequence identity with any of SEQ ID NOs: 3, 5, 7, and 9. In some embodiments, the polypeptide comprises at least 92% sequence identity with any of SEQ ID NOs: 3, 5, 7, and 9. In some embodiments, the polypeptide comprises at least 93% sequence identity with any of SEQ ID NOs: 3, 5, 7, and 9. In some embodiments, the polypeptide comprises at least 94% sequence identity with any of SEQ ID NOs: 3, 5, 7, and 9. In some embodiments, the polypeptide comprises at least 95% sequence identity with any of SEQ ID NOs: 3, 5, 7, and 9. In some embodiments, the polypeptide comprises at least 96% sequence identity with any of SEQ ID NOs: 3, 5, 7, and 9. In some embodiments, the polypeptide comprises at least 97% sequence identity with any of SEQ ID NOs: 3, 5, 7, and 9. In some embodiments, the polypeptide comprises at least 98% sequence identity with any of SEQ ID NOs: 3, 5, 7, and 9. In some embodiments, the polypeptide comprises at least 99% sequence identity with any of SEQ ID NOs: 3, 5, 7, and 9.

As would be recognized by one of ordinary skill in the art based on the present disclosure, soluble secreted proteins and proteins expressed on the cell surface can include an N-terminal signal sequence, which is generally a hydrophobic sequence that mediates insertion of the protein through the membrane of the endoplasmic reticulum (ER) in a eukaryotic cell. Type 1 transmembrane proteins also comprise signal sequences. Signal sequences, as used herein, can include amino-terminal hydrophobic sequences which are generally enzymatically removed following the insertion of part or all of the protein through the ER membrane into the lumen of the ER. Thus, a signal sequence can be present as part of a precursor form of a secreted or transmembrane protein, but will generally be absent from the mature form of the protein. When a protein is said to comprise a signal sequence, it is to be understood that, although a precursor form of the protein does contain the signal sequence, a mature form of the protein will likely not contain the signal sequence. Signal sequences may contain a residue adjacent to and immediately upstream from the cleavage site (position −1) and another residue at position −3, which are important for this enzymatic cleavage. (See, e.g., Nielsen et al. 1997 *Protein Eng* 10(1) 1-6; von Heijne 1983 *Eur J Biochem* 133(1) 7-21; von Heijne 1985 *J Mol Biol* 184 99-105, which describes signal sequences and how to identify them). In some embodiments, the rBHT polypeptides of the present disclosure can be soluble or membrane-bound. In some embodiments, about 1% to about 50% of the polypeptide is soluble. In some embodiments, about 1% to about 45% of the polypeptide is soluble. In some embodiments, about 1% to about 40% of the polypeptide is soluble. In some embodiments, about 1% to about 35% of the polypeptide is soluble. In some embodiments, about 1% to about 30% of the polypeptide is soluble. In some embodiments, about 1% to about 25% of the polypeptide is soluble. In some embodiments, about 1% to about 20% of the polypeptide is soluble. In some embodiments, about 10% to about 15% of the polypeptide is soluble. In some embodiments, about 10% to about 10% of the polypeptide is soluble.

In accordance with the embodiments of the present disclosure, any signal peptide(s) or signal sequence(s) can be included in the rBHT polypeptides of the present disclosure, including signal sequences derived from a peptide(s) or polypeptide(s) from a prokaryotic organism, a eukaryotic organism, a fungus, a mammal, an insect, a yeast, or a plant. In some embodiments, signal sequence(s) that can be included, without limitation, in the rBHT polypeptides of the present disclosure include those described in Ahmad, M., et. Al., (2014) "Protein expression in *Komagataella (Pichia) pastoris*: recent achievements and perspectives for heterologous protein production," Applied Microbiology and Biotechnology 98(12): 5301-5317.

In some embodiments, the rBHT polypeptides of the present disclosure include a signal sequence that is non-native or exogenous with reference to a host cell engineered to express the rBHT polypeptides. In some embodiments, the rBHT polypeptides of the present disclosure include a signal sequence that is native or endogenous with reference to a host cell engineered to express the rBHT polypeptides. In either case, the signal sequence can be in its native form/sequence, or truncated, and/or can include at least one amino acid substitution with reference to its native form/sequence.

In some embodiments, the signal sequence comprises an amino acid sequence derived from a yeast protein. In some embodiments, the signal sequence comprises an amino acid sequence from a protein from any one of *Komagataella (Pichia) pastoris, Saccharomyces cerevisiae, Yarrowia lipolytica, Hansenula (Ogataea) polymorpha,* or *Kluyvero-*

*myces lactis.* In some embodiments, the signal sequence comprises a polypeptide with at least 90% sequence identity to at least one of α-mating factor signal sequence from *Saccharomyces cerevisiae* (MFα) (SEQ ID NO: 29), Invertase (IV) signal sequence (SEQ ID NO: 30), Glucoamylase (GA) signal sequence (SEQ ID NO: 31), or Inulinase (IN) signal sequence (SEQ ID NO: 32). In some embodiments, the polypeptide comprises at least 91%, 92%, 93%, 94%, 95%, 96%, 97%, 98%, 99%, or 99.5% identity with any of SEQ ID NOs: 29, 30, 31, or 32. In some embodiments, the polypeptide comprises at least 91%, 92%, 93%, 94%, 95%, 96%, 97%, 98%, 99%, or 99.5% identity with any of SEQ ID NO: 29. In some embodiments, the polypeptide comprises at least 91%, 92%, 93%, 94%, 95%, 96%, 97%, 98%, 99%, or 99.5% identity with any of SEQ ID NO: 30. In some embodiments, the polypeptide comprises at least 91%, 92%, 93%, 94%, 95%, 96%, 97%, 98%, 99%, or 99.5% identity with any of SEQ ID NO: 31. In some embodiments, the polypeptide comprises at least 91%, 92%, 93%, 94%, 95%, 96%, 97%, 98%, 99%, or 99.5% identity with any of SEQ ID NO: 32.

As described further herein, the rBHT polypeptides of the present disclosure include a signal sequence (or functional fragment thereof) from any of SEQ ID NOs: 29, 30, 31, or 32. In accordance with these embodiments, the rBHT polypeptide can comprise at least 90% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 91% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 92% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 93% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 94% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 95% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 96% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 97% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 98% sequence identity with any of SEQ ID NOs: 34, 36, 38, 40, 42, 44, 46, 48, 50, 52, 54, 56, 58, 60, 62, 64, 66, 68, or 70. In some embodiments, the rBHT polypeptide can comprise at least 99% sequence identity with any of SEQ ID NOs: 34, 36, 38, 40, 42, 44, 46, 48, 50, 52, 54, 56, 58, 60, 62, 64, 66, 68, or 70.

The rBHT polypeptides of the present disclosure may be glycosylated to varying degrees or may not be glycosylated. For example, rBHT polypeptides of the present disclosure can comprise one or more N- or O-linked glycosylation sites in addition to those already found in a protein or polypeptide comprising any of SEQ ID NOs: 1, 3, 5, 7, 9, 11, 13, 15, 17, 19, 21, 23, 25, 34, 36, 38, 40, 42, 44, 46, 48, 50, 52, 54, 56, 58, 60, 62, 64, 66, 68, or 70. One of ordinary skill in the art would recognize based on the present disclosure that asparagine residues that are part of the sequence Asn Xxx Ser/Thr (where Xxx is any amino acid except proline) can serve as sites of addition for N-glycans. In addition, there are serine and threonine residues that may serve as O-linked glycosylation sites. Glycosylation may increase in vivo half-life or alter biological activity. Variants of rBHT proteins also include proteins comprising one, two, three, four, five, six, seven, eight, nine, or ten more N- and/or O-linked glycosylation sites than are present in a corresponding wildtype protein or polypeptide, as long as the resulting protein or polypeptide maintains its function as a glycosyl hydrolase and a β-hexosyl-transferase. Variant rBHT polypeptides also include those that have one, two, three, four, or five fewer N- and/or O-linked glycosylation sites than are present in a corresponding wildtype protein or polypeptide, as long as the resulting protein or polypeptide maintains its function as a glycosyl hydrolase and a β-hexosyl-transferase. In some embodiments, the rBHT polypeptides of the present disclosure comprise at least one asparagine residue at positions 289, 297, 431, and 569 with respect to SEQ ID NO: 1. In some embodiments, the rBHT polypeptides of the present disclosure comprise at least two asparagine residues at positions 289, 297, 431, and 569 with respect to SEQ ID NO: 1. In some embodiments, the rBHT polypeptides of the present disclosure comprise at least three asparagine residues at positions 289, 297, 431, and 569 with respect to SEQ ID NO: 1. In some embodiments, the rBHT polypeptides of the present disclosure comprise asparagine residues at positions 289, 297, 431, and 569 with respect to SEQ ID NO: 1.

Embodiments of the present disclosure include secreted, soluble variants of the rBHT polypeptides described herein, as well as variants that include a transmembrane domain that can be expressed on a cell surface. Such proteins can be isolated as part of a purified protein preparation in which the rBHT polypeptides constitute at least 80% or at least 90% of the protein present in the preparation. The rBHT polypeptides of the present disclosure encompass proteins and polypeptides comprising an amino acid sequence set forth in SEQ ID NOs: 1, 3, 5, 7, 9, 11, 13, 15, 17, 19, 21, 23, 25, 34, 36, 38, 40, 42, 44, 46, 48, 50, 52, 54, 56, 58, 60, 62, 64, 66, 68, or 70, as well as fragments, derivatives, and variants thereof, including fusion proteins.

The rBHT polypeptides of the present disclosure can be fusion proteins comprising at least one rBHT polypeptide, which can comprise an amino acid sequence that is a variant and/or a fragment of any of SEQ ID NOs: 1, 3, 5, 7, 9, 11, 13, 15, 17, 19, 21, 23, 25, 34, 36, 38, 40, 42, 44, 46, 48, 50, 52, 54, 56, 58, 60, 62, 64, 66, 68, or 70 (as explained above), and at least one other moiety. The other moiety can also be a non-protein moiety such as, for example, a polyethylene glycol (PEG) moiety or a cytotoxic, cytostatic, luminescent, and/or radioactive moiety. Attachment of PEG has been shown to increase the in vivo half-life of at least some proteins. Moreover, cytotoxic, cytostatic, luminescent, and/or radioactive moieties have been fused to antibodies for diagnostic or therapeutic purposes. A variety of polypeptides other than a rBHT polypeptide (or fragment thereof) can be fused to an rBHT polypeptide for a variety of purposes such as, for example, to increase in vivo half-life of the protein, to facilitate identification, isolation and/or purification of the protein, to increase the activity of the protein, and to promote oligomerization of the protein.

Many polypeptides can facilitate identification and/or purification of a recombinant fusion protein of which they are a part. Examples include polyarginine, polyhistidine, or HAT™ (Clontech), which is a naturally-occurring sequence of non-adjacent histidine residues that possess a high affinity for immobilized metal ions. rBHT proteins comprising these polypeptides can be purified by, for example, affinity chromatography using immobilized nickel or TALON™ resin (Clontech), which comprises immobilized cobalt tons. See e.g. Knol et al. 1996 *J Biol Chem* 27(26) 15358-15366. Polypeptides comprising polyarginine allow effective purification by ion exchange chromatography. Other useful polypeptides include, for example, the antigenic identification peptides described in U.S. Pat. No. 5,011,912 and in Hopp et al. 1988 *Bio/Technology* 6 1204. One such peptide is the FLAG™ peptide, which is highly antigenic and provides an epitope reversibly bound by a specific monoclonal antibody, enabling rapid assay and facile purification of expressed recombinant fusion protein. A murine hybridoma designated 4E11 produces a monoclonal antibody that binds the FLAG peptide in the presence of certain divalent metal cations, as described in U.S. Pat. No. 5,011,912. The 4E11 hybridoma cell line has been deposited with the American Type Culture Collection under Accession No. HB 9259. Monoclonal antibodies that bind the FLAG peptide can be used as affinity reagents to recover a polypeptide purification reagent that comprises the FLAG peptide. Other suitable protein tags and affinity reagents are: 1) those described in GST-Bind™ system (Novagen), which utilizes the affinity of glutathione-S-transferase fusion proteins for immobilized glutathione; 2) those described in the T7-TAG® affinity purification kit, which utilizes the affinity of the amino terminal 11 amino acids of the T7 gene 10 protein for a monoclonal antibody; or 3) those described in the STREP-TAG® system (Novagen), which utilizes the affinity of an engineered form of streptavidin for a protein tag. Some of the above-mentioned protein tags, as well as others, are described in Sassenfeld 1990 *TIBTECH* 8: 88-93, Brewer et al., in *Purification and Analysis of Recombinant Proteins, pp.* 239-266, Seetharam and Sharma (eds.), Marcel Dekker, Inc. (1991), and Brewer and Sassenfeld, in *Protein Purification Applications*, pp. 91-111, Harris and Angal (eds.), Press, Inc., Oxford England (1990). The portions of these references that describe protein tags are incorporated herein by reference. Further, fusions of two or more of the tags described herein, such as, for example, a fusion of a FLAG tag and a polyhistidine tag, can be fused to an rBHT polypeptide of the present disclosure.

In some embodiments, the rBHT polypeptides of the present disclosure also include an affinity tag that can be used as part of means for producing the polypeptides. In addition to the 6x-HIS tag described further herein, a variety of purification methods may be used such as affinity tags, such as antigenic tags (e.g., FLAG (Sigma-Aldrich, Hopp et al. 1988 *Nat Biotech* 6:1204-1210), hemagluttanin (HA) (Wilson et al., 1984 *Cell* 37:767), Intein fusion expression systems (New England Biolabs, USA) Chong et al. 1997 *Gene* 192(2), 271-281, or maltose-binding protein (MBP)), glutathione S transferase (GST)/glutathione, poly His/Ni or Co (Gentz et al., 1989 *PNAS USA* 86:821-824). Fusion proteins containing GST-tags at the N-terminus of the protein are also described in U.S. Pat. No. 5,654,176 (Smith). Magnetic separation techniques may also be used such as Strepavidin-DynaBeads® (Life Technologies, USA). Alternatively, photo-cleavable linkers may be used, e.g., U.S. Pat. No. 7,595,198 (Olejnik & Rothchild). Many other systems are known in the art and are suitable for use with the embodiments of the present disclosure.

3. NUCLEIC ACID CONSTRUCTS

Embodiments of the present disclosure also include a nucleic acid molecule encoding any of the rBHT polypeptides described herein. Embodiments of the present disclosure also include a vector comprising any one of these nucleic acid molecules. In some embodiments, isolated nucleic acids, including, for example DNA and RNA molecules, encode the rBHT polypeptides described herein, which include polypeptides comprising the amino acid sequence of SEQ ID NOs: 1, 3, 5, 7, 9, 11, 13, 15, 17, 19, 21, 23, 25, 34, 36, 38, 40, 42, 44, 46, 48, 50, 52, 54, 56, 58, 60, 62, 64, 66, 68, or 70 and fragments and/or variants thereof. In some embodiments, these nucleic acids are useful for producing recombinant proteins having glycosyl hydrolase and a β-hexosyl-transferase activity. Such nucleic acids can be modified genomic DNA or cDNA. In some cases, the nucleic acids can comprise an uninterrupted open reading frame encoding an rBHT protein. Nucleic acid molecules of the present disclosure include DNA and RNA in both single-stranded and double-stranded form, as well as the corresponding complementary sequences. An isolated nucleic acid is a nucleic acid that has been separated from adjacent genetic sequences present in the genome of the organism from which the nucleic acid was isolated, in the case of nucleic acids isolated from naturally-occurring sources, in the case of nucleic acids synthesized chemically, such as oligonucleotides, or enzymatically from a template, such as polymerase chain reaction (PCR) products or cDNAs, it is understood that the nucleic acids resulting from such processes are isolated nucleic acids. An isolated nucleic acid molecule refers to a nucleic acid molecule in the form of a separate fragment or as a component of a larger nucleic acid construct.

The present disclosure also includes nucleic acids comprising the sequence of SEQ ID NOs: 2, 4, 6, 7, 8, 10, 12, 14, 16, 18, 20, 22, 24, 26, 33, 35, 37, 39, 41, 43, 45, 47, 49, 51, 53, 55, 57, 59, 61, 63, 65, 67, and 69 or a fragment thereof or nucleic acids that hybridize under moderately stringent conditions, and optionally highly stringent conditions, to nucleic acids comprising the nucleotide sequence of SEQ ID NOs: 2, 4, 6, 7, 8, 10, 12, 14, 16, 18, 20, 22, 24, 26, 33, 35, 37, 39, 41, 43, 45, 47, 49, 51, 53, 55, 57, 59, 61, 63, 65, 67, and 69, which includes the nucleotide sequence of the full length rBHT cDNA (SEQ ID NO: 1), wherein the nucleic acid encodes a protein that can act as a glycosyl hydrolase and a β-hexosyl-transferase. Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, 1989) and *Current Protocols in Molecular Biology* (F. M. Ausubel et al., eds., John Wiley & Sons, Inc., sections 2.10 and 6.3-6.4 1995).

4. METHODS OF PRODUCTION

Embodiments of the present disclosure include methods of generating compositions comprising GOS ("GOS compositions") from lactose in a host cell using any of the rBHT polypeptides described herein. As described further herein, the rBHT polypeptides of the present disclosure are functional in that they exhibit the ability to catalyze the hydrolysis of β-(1-4) glycosidic linkages to generate any GOS composition(s) from lactose, including but not limited to, GOS with or without GlcNAc, as well as LacNAc-enriched GOS compositions. As would be recognized by one of ordinary skill in the art based on the present disclosure, GOS generally refers to a galactose-containing polysaccharide with two or more sugar units such as Gal-Gal or [Gal]$_n$-Glc (1≤n≤8), including β-D-Gal(1→4)-β-D-Gal(1→4)-β-D-

Glc, β-D-Gal(1→4)-β-D-Gal(1→4)-β-D-Gal(1→4)-β-D-Glc, and β-D-Gal(1→4)-β-D-Gal(1→4)-β-D-Gal(1→4)-β-D-Gal(1→4)-β-D-Glc.

In some embodiments, the GOS produced using the rBHT polypeptides of the present disclosure includes one or more N-acetyllactosamine (LacNAc) units. In one embodiment, GOS can be produced by incubating a host cell expressing the rBHT polypeptide in a medium that comprises a disaccharide substrate such as for example lactose. In one embodiment, the GOS is produced from lactose simultaneously with a glucose removal system. The glucose removal system may be a generally recognized as safe (GRAS) organism. In some embodiments, the host cell is one or more of a yeast cell, a fungal cell, a mammalian cell, an insect cell, a plant cell, or an algal cell. In some embodiments, the host cell comprises one or more cells from *Komagataella* (*Pichia*) *pastoris* (also referred to as *Kamagataaella phaffi*), *Saccharomyces cerevisiae, Yarrowia lipolytica, Hansenula* (*Ogataea*) *polymorpha*, or *Kluyveromyces lactis, Aspergillus* spp., and *Trichoderma reesei*. In some embodiments, the host cell includes any cell from the genus *Komagataella*. In some embodiments, the GOS comprises N-acetyllactosamine (LacNAc). In some embodiments, the method produces a LacNAc-enriched GOS yield of at least 10% of initial lactose concentration, and a total GOS concentration of at least 50% of initial lactose concentration. In some embodiments, the method produces a LacNAc-enriched GOS yield of at least 10% of initial lactose concentration, and a total GOS concentration of at least 60% of initial lactose concentration. In some embodiments, the method produces a LacNAc-enriched GOS yield of at least 10% of initial lactose concentration, and a total GOS concentration of at least 70% of initial lactose concentration. In some embodiments, the method produces a LacNAc-enriched GOS yield of at least 10% of initial lactose concentration, and a total GOS concentration of at least 75% of initial lactose concentration. For example, using an initial lactose-to-GlcNAc ratio of 1:8, the methods provided herein using the rBHT polypeptides (e.g., whole cells membrane bound enzyme) with about 200 g lactose and about 25 g GlcNAc) generate about 25 g of LacNAc and about 100 g GOS. Initial lactose-to-GlcNAc ratios can range from about 1:20 to about 20:1.

In some embodiments, the rBHT polypeptides of the present disclosure are useful for producing LacNAc and related compositions. The prebiotic LacNAc is regarded as one of the most important building blocks for higher order human milk oligosaccharide (HMO) generation. However, feasible industrial production routes by chemical synthesis suffer from low yields, thus favoring the biocatalysis of LacNAc. The major difference between other biosynthesis routes and the biological synthesis of LacNAc with the enzyme BHT, as described further herein, is lower cost and higher purity. Embodiments of the present disclosure demonstrate that LacNAc production by the rBHT polypeptides described herein is more suitable for industrial scale when compared with other processes. As shown in the example in FIG. 5, LacNAc is generated by mixing Lactose and GlcNAc with the rBHT polypeptides. Results of the present disclosure demonstrate a yield of at least about 25 g/L LacNAc from about 25 g/L of GlcNAc and about 200 g/L of lactose in a single synthesis step when the reaction ratio of about 1:8 of lactose-to-GlcNAc was initially present tin the reaction mixture.

In some embodiments, the rBHT polypeptides of the present disclosure can be used for producing GOS compositions that do not include N-acetylglucosamine (GlcNAc).

Embodiments of the present disclosure includes materials and methods for producing GOS compositions lacking GlcNAc, which include reacting lactose with rBHT polypeptides having the amino acid sequences provided herein under suitable conditions so as to produce GOS. Similar compositions and methods are described in related U.S. Pat. Nos. 10,513,695, and 9,783,789, both of which are herein incorporated by reference.

The rBHT polypeptides of the present disclosure can be made using various means known in the art. For example, a nucleic acid molecule that encodes an rBHT polypeptide, as described herein, can be introduced into a vector, which can be introduced into a host cell. Vectors and host cells comprising nucleic acids encoding an rBHT polypeptide are encompassed by the embodiments of the present disclosure. The host cell containing the nucleic acids encoding an rBHT polypeptide can be cultured under conditions such that the rBHT polypeptide can be expressed. The expressed rBHT polypeptide can then be obtained from the medium in which the cells are cultured or from the cells and purified by any of the many appropriate means known in the art. In addition, genetic engineering methods for the production of rBHT polypeptide include the expression of the polynucleotide molecules in cell free expression systems, in cellular hosts, in tissues, and in animal models, according to known methods.

The vector can include a selectable marker and an origin of replication, for propagation in a host. The vector can further include suitable transcriptional or translational regulatory sequences, such as those derived from mammalian, microbial, viral, or insect genes, operably linked to the nucleic acid encoding the rBHT polypeptide. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to an rBHT polypeptide sequence if the promoter nucleotide sequence directs the transcription of the rBHT protein-encoding sequence. If the rBHT polypeptide is a fusion protein, a nucleic acid sequence encoding a portion of the fusion protein, for example, a signal sequence, can be part of a vector, and a nucleic acid encoding an rBHT polypeptide can be inserted into the vector such that a protein comprising the added signal sequence plus the rBHT polypeptide is encoded by the vector.

Suitable host cells for expression of rBHT polypeptides include prokaryotic cells, yeast cells, plant cells, insect cells, and higher eukaryotic cells. The regulatory sequences in the vector will be chosen such that they are operable in the host cell. Suitable prokaryotic host cells include bacteria of the genera *Escherichia, Bacillus,* and *Salmonella,* as well as members of the genera *Pseudomonas, Streptomyces,* and *Staphylococcus.* For expression in prokaryotic cells, for example, in *E. coli* the polynucleotide molecule encoding an rBHT polypeptide includes an N-terminal methionine residue to facilitate expression of the recombinant polypeptide. The N-terminal methionine may optionally be cleaved from the expressed polypeptide. Suitable yeast host cells include cells from genera including, but not limited to, *Saccharomyces, Pichia (Komagataella),* and *Kluyveromyces.* In some embodiments, the host cell includes any cell from the genus *Pichia (Komagataella).* Preferred yeast hosts are *S. cerevisiae* and *P. pastoris* (also referred to as *Kamagataaella phaffi).* A suitable system for expression in an insect host cell is described, for example, in the review by Luckow and Summers (1988 *BioTechnology* 6 47-55), the relevant portions of which are incorporated herein by reference. Suitable mammalian host cells include the COS-7 line of monkey kidney cells (Gluzman et al. 1981 *Cell* 23 175-182), baby hamster kidney (BHK) cells, Chinese hamster ovary (CHO) cells (Puck et al. 1958 *PNAS USA* 60 1275-1281), CV-1 (Fischer et al. 1970 *Int J Cancer* 5 21-27), 293 cells from human kidney (American Type Culture Collection (ATCC®) catalog no. CRL-10852™), and human cervical carcinoma cells (HELA) (ATCC® CCL 2). The relevant portions of the references referred to in this paragraph are incorporated herein by reference.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM vectors (Promega), pSPORT vectors, and pPROEX vectors (InVitrogen, Life Technologies, Carlsbad, Calif), Bluescript vectors (Stratagene), and pQE vectors (Qiagen). Yeast vectors will often contain an origin of replication sequence from a yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli.* Direct secretion of the target polypeptides expressed in yeast hosts may be accomplished by the inclusion of nucleotide sequence encoding the yeast α-factor leader sequence at the 5' end of the rBHT-encoding nucleotide sequence. Brake 1989 *Biotechnology* 13 269-280.

Examples of suitable expression vectors for use in mammalian host cells include pcD A3.1/Hygro (Invitrogen), pDC409 (McMahan et al. 1991 *EMBO J* 10: 2821-2832), and pSVL (Pharmacia Biotech). Expression vectors for use in mammalian host cells can include transcriptional and translational control sequences derived from viral genomes. Commonly used promoter sequences and enhancer sequences that can be used to express rBHT RNA include, but are not limited to, those derived from human cytomegalovirus (CMV). Adenovirus 2, Polyomavirus, and Simian virus 40 (SV40). Methods for the construction of mammalian expression vectors are disclosed, for example, in Okayama and Berg (1982 *Mol Cell Biol* 2: 161-170), Cosman et al. (1986 *Mol Immunol* 23:935-941), Cosman et al. (1984 *Nature* 312: 768-771), EP-A-0367566, and WO 91/18982. The relevant portions of these references are incorporated herein by reference. Additionally, any spray drying or lyophilization or other concentration methods can be used to render the reaction mixture as a final product, as would be recognized by one of ordinary skill in the art based on the present disclosure. Cell separation techniques may be required when whole cells are used instead of pure enzymes.

5. COMPOSITIONS

Embodiments of the present disclosure include a composition comprising any of the polypeptides described herein and/or one or more GOS generated using any of the polypeptides described herein (e.g., GOS with or without GlcNAc, as well as LacNAc-enriched GOS). In some embodiments, the composition is a food product. In some embodiments, the food product includes, but is not limited to, infant formula, yogurt, dairy products, milk-based beverages, fruit beverages, hydration beverages, energy beverages, fruit preparations, and meal replacement beverages.

As would be recognized by one of ordinary skill in the art based on the present disclosure, GOS compositions, including GOS with or without GlcNAc and LacNAc-enriched GOS compositions, are widely used as prebiotic supplements in foods and beverages around the world. These highly prized non-digestible sugars are able to mimic Human Milk Oligosaccharides (HMOs) by having a positive influence on the growth and metabolism of gastrointestinal (GI) bacteria (probiotics). Addition of prebiotics to the diet has shown a substantiated improvement in overall health of the host by reducing GI discomfort, managing the immune system and reducing pathogenic and opportunistic bacteria and viruses. Embodiments of the present disclosure demonstrate novel materials and methods for the development of prebiotics to generate LacNAc from pure lactose and GlcNAc and to significantly increase the concentration of secreted soluble rBHT.

In some embodiments, the present disclosure includes use of the rBHT protein or cells expressing rBHT to produce a foodstuff or a dietary supplement containing LacNAc-enriched GOS compositions. The foodstuff may be diary foodstuff such as yogurt, cheese or fermented dairy products. The rBHT or cell expressing rBHT may be part added to the foodstuff or dietary supplements. The rBHT may be dried using Spray Dry; a quick and gentle method of obtaining even the smallest quantities of temperature sensitive substances in powder form. The dried rBHT also may be encapsulated form using the Spray dryer's ability to coat particles, immobilize solid material in a matrix and manufacture microcapsules (buchi.com/Mini_Spray_Dryer_B-290.179.0). Other drug delivery applications using functional GRAS encapsulating agents and technologies may be used. The dried rBHT tablet and powder forms may be analyzed for rBHT rate of activity once rehydrated in buffer containing lactose and in milk products.

Any of the rBHT polypeptides described herein may be delivered in the form of a composition, that is, with one or more additional components such as a physiologically acceptable carrier, excipient, or diluent. For example, a composition may comprise a soluble rBHT polypeptides as described herein plus a buffer, an antioxidant such as ascorbic acid, a low molecular weight polypeptide (such as those having less than 10 amino acids), a protein, amino acids, carbohydrates such as glucose, sucrose, or dextrin, chelating agent such as EDTA, glutathione, and/or other stabilizers, excipients, and/or preservatives. The composition may be formulated as a liquid or a freeze-dried powder. Further examples of components that may be employed in pharmaceutical formulations are presented in *Remington's Pharmaceutical Sciences,* 16th Ed., Mack Publishing Company, Easton, Pa., (1980), the relevant portions of which are incorporated herein by reference.

Compositions comprising therapeutic molecules described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. Other alternatives include eye drops, oral preparations such as pills, lozenges, syrups, and chewing gum, and topical preparations such as lotions, gels, sprays, and ointments. In most cases, therapeutic molecules that are polypeptides can be administered topically or by injection or inhalation.

The therapeutic molecules described above can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. The periodicity of treatment may or may not be constant throughout the duration of the treatment. For example, treatment may initially occur at weekly intervals and later occur every other week. Treatments having durations of days, weeks, months, or years are encompassed by the embodiments of the present disclosure. Treatment may be discontinued and then restarted.

Maintenance doses may be administered after an initial treatment. Dosage may be measured as milligrams per kilogram of body weight (mg/kg) or as milligrams per square meter of skin surface (mg/m$^2$) or as a fixed dose, irrespective of height or weight. These are standard dosage units in the art. A person's skin surface area is calculated from her height and weight using a standard formula. For example, a therapeutic rBHT protein can be administered at a dose of from about 0.05 mg/kg to about 10 mg/kg or from about 0.1 mg/kg to about 1.0 mg/kg. Alternatively, a dose of from about 1 mg to about 500 mg can be administered. Or a dose of about 5 mg, 10 mg, 15 mg, 20 mg, 25 mg, 30 mg, 35 mg, 40, mg, 45, mg, 50 mg, 55 mg, 60 mg, 100 mg, 200 mg, or 300 mg can be administered.

6. MATERIALS AND METHODS

Strains and media. Growth and maintenance of the strain GS115 (Invitrogen Life Technologies, Thermo Fisher Scientific) and media has been described previously. *E. coli* XL1-Blue was used as the cloning host (Agilent Technologies, Thermo Fisher Scientific). The plasmid pPIC9 (Invitrogen Life Technologies, Thermo Fisher Scientific) was used to construct expression vectors containing codon optimized Bht (rBht variants) (GenBank accession number JF29828).

Plasmid constructions, Expression and Purification of rBHT-truncated variants. All molecular biology protocols were carried out as those described previously. Briefly, plasmids constructed for expression of rBHT variants in *K. pastoris* coding for truncation mutations were generated by PCR amplification of the codon optimized rBht open reading frame in pPIC9-MFα-rBht$_{(1-594)}$-HIS using primers purchased from Integrated DNA Technologies (IDT Coralville, IA, USA) (listed in Table 5). The bacterial strains and *K. pastoris* strains used in this study are shown in Tables 4A-4B. Bacteria were grown at 37° C. in Luria-Bertani (LB) Medium with antibiotic ampicillin (100 μg/ml) (Thermo Fisher Scientific).

Mutagenesis and Cloning. Plasmids coding for the truncated rBHT variants were generated by PCR amplification using HotStar® Taq (Qiagen, Hilden, Germany) and pJB110 (pPIC9-MFα-rBht$_{(1-594)}$-HIS) as template. Primers were purchased from Integrated DNA Technologies (IDT Coralville, IA, USA). When appropriate, the primers included restriction sites to facilitate cloning (listed in Table 5). Briefly, primer pairs for sequences coding for the truncated rBHT variants encoding amino acids 32-594 (primers: JBB21/JBB5), 54-594 (primers: JBB22/JBB5), 57-594 (primers: JBB23/JBB5), 82-594 (primers: JBB24/JBB5), 95-594 (primers: JBB25/JBB5) and 103-594 (primers: JBB26/JBB5). The amplicons were digested with XhoI-NotI and cloned into pPIC9 (Invitrogen Life Technologies, Thermo Fisher Scientific) generating pJB123 (pPIC9-MFα-rBht$_{(32-594)}$-HIS), pJB124 (pPIC9-MFα-rBht$_{(54-594)}$-HIS), pJB125 (pPIC9-MFα-rBht$_{(57-594)}$-HIS), pJB126 (pPIC9-MFα-rBht$_{(82-594)}$-HIS), pJB127 (pPIC9-MFα-rBht$_{(95-594)}$-HIS) and pJB128 (pPIC9-MFα-rBht$_{(103-594)}$-HIS) respectively.

Plasmids coding for pJB134 (pPIC9-IV-rBht$_{(54-594)}$-HIS), pJB135 (pPIC9-GA-rBht$_{(54-594)}$-HIS) and pJB136 (pPIC9-IN-rBht$_{(54-594)}$-HIS) were generated using pJB124 (pPIC9-MFα-rBht$_{(54-594)}$-HIS) as the template and primer sets JBB37/JBB5, JBB38/JBB5 and JBB39/JBB5, respectively. The amplicons were digested with XhoI-NotI and cloned into pPIC9 (Invitrogen Life Technologies, Thermo Fisher Scientific).

Site directed mutagenesis was performed using complementary oligonucleotides designed to incorporate the desired base changes using QuickChange site directed mutagenesis kit (Agilent Technologies Santa Clara, CA, USA) according to manufacturer's instructions to generate constructions containing single amino acid exchanges from asparagine to glutamine (N289Q (primers: JBB27/JBB28), N297Q (primers: JBB29/JBB30), N431Q (primers: JBB31/JBB32), and N569Q (primers: JBB33/JBB34)) in putative N-glycosylation sites using (pJB112, pPIC9-MFα-rBht$_{(23-594)}$-HIS) as the template and oligonucleotide primers with substituted nucleotides (Table 5). Site directed mutagenesis was also used to remove amino acids 57-70 from MFα using primer set JBB35/JBB36 (Table 5) to generate pJB133 (pPIC9-MFα$_{(Δ57-70)}$-rBht$_{(23-594)}$-HIS) and pJB137(pPIC9-MFα$_{(Δ57-70)}$-rBht$_{(57-594)}$-HIS) (Tables 4A-4B). DNA fragments from restriction enzyme digests were purified from agarose gels using QIAquick gel extraction kit (Qiagen, Hilden, Germany). All mutations were confirmed with restriction digests for detecting restriction sites in primers and by Sanger sequencing performed by the NC State University Genomic Sciences Laboratory (Raleigh, NC, USA) using primers JBB3, JBB4, 5' AOX1, 3' AOX1 and α-factor (Table 1).

K. pastoris Transformation and Expression. K. pastoris was transformed with linearized plasmids as per the Invitrogen Pichia Expression Kit manual (Invitrogen, USA). Plasmid integration and Mut$^{+}$ phenotype in histidine positive colonies was confirmed by sequencing PCR products generated by primers 5' AOX1 and 3' AOX1 (Invitrogen Pichia expression kit). Single copy integration was confirmed as previously described. Expression and purification have been described previously. Briefly, filtered culture media was purified using the ÅKTApurifier and HISTrap™ HP Nickel column (GE Healthcare, Life sciences). The purified proteins were quantified by Bradford protein assay (Thermo Fisher Scientific).

SDS-PAGE and Western Immunoblot Analysis. Proteins were analyzed by SDS-PAGE using 10% resolving gels and visualized by Coomassie and silver stain (Bio-Rad, Hercules, CA). Immunoblots were probed with 1:10,000 dilution of anti-HIS antibody (GenScript, Piscataway, NJ) followed by 1:10,000 dilution of alkaline phosphatase conjugated goat anti-mouse antibody (GenScript, Piscataway, NJ).

Detection was carried out with 1-Step™ NBT/BCIP Substrate Solution according to manufacturer's instructions (Thermo Fisher Scientific).

Enzyme Assays. The ONP-Glu activities were measured using the methods described previously (see, e.g., Dagher, S. F., and Bruno-Bircena, J. M. (2016) A novel N-terminal region of the membrane β-hexosyltransferase: its role in secretion of soluble protein by Pichia pastoris. Microbiology 162, 23-34.)

Sequence Analysis. Alignments were generated using ClustalX algorithm (www.clustal.org) and Jalview algorithm. The sequences of the top five homologous proteins were selected using NCBI blastp (blast.ncbi.nlm.nih.gov/): glycoside hydrolase family 1 protein glycoside hydrolase family 1 protein [Sphaerobolus stellatus SS14], accession number BAD95570.1, glycoside hydrolase [Violaceomyces palustris], accession number KIJ57308.1, glycoside hydrolase [Violaceomyces palustris], accession number PWN48553.1, hypothetical protein PFL1_06098 [Anthracocystis flocculosa PF-1], accession number XP_007881827.1, glycoside hydrolase [Testicularia cyperi], accession number PWZ03736.1 and glycoside hydrolase family 1 protein [Gymnopus luxurians FD-317 M1] accession number KIK57390.1.

Secondary Structure Prediction. Secondary structure consensus prediction of BHT was performed at the PSIPRED server (protein structure prediction) and at the NPS@server (network protein sequence analysis). The signal sequence was predicted using the SignalP 5.0 algorithm. Protein disorder was predicted using the consensus of six methods, Dispred3, Phyre2, IUPred2A, PONDR-VSL2 and GlobPlot (prediction of protein disorder and globularity), PHYRE2. Domain boundaries were predicted using the DomPred server and Pfam version 32.0.

N-glycosylation Prediction. BHT N- and O-glycosylation site prediction was performed at the GlycoEP server (see, e.g., Chauhan, J. S., Rao, A., and Raghava, G. P. S. (2013) In silico Platform for Prediction of N-, O- and C-Glycosites in Eukaryotic Protein Sequences. PLOS ONE 8, e67008).

Phosphorylation Site Prediction. BHT phosphorylation site prediction was performed using DEPP (Disorder enhanced phosphorylation predictor), also known as DisPhos1.3 (www.dabi.temple.edu/disphos/) and NetPhos-Yeast1.0 (www.cbs.dtu.dk/services/NetPhosYeast/).

Structural Modeling Programs. Structural figures and structural superimpositions were generated in PyMOL (www.schrodinger.com/pymol/). A dimer is present in the crystal asymmetric unit; however, the monomer was considered for structural analysis. Structural comparisons between BHT$_{(23-594)}$-HIS and other known structures were executed with Dali (ekhidna2.biocenter.helsinki.fi/dali/) Dali Server against PDB90 database was used for the protein structure alignment. The alignment was visualized with the ESPript/ENDscript program (espript.ibcp.fr/ESPript/ESPript/). Protein sequences were obtained from the UniProt database (www.uniprot.org/) and aligned using Clustal Omega tool.

Size Exclusion Chromatography. To determine molecular mass, NTA purified samples were subjected to size exclusion chromatography (Superdex 200 10/300 GL, GE Healthcare) equilibrated with SEC buffer (100 mM Tris pH7.5, 200 mM sodium chloride). The protein sample equilibrated in SEC buffer was applied to the column. The mass of BHT$_{(23-594)}$-HIS was calculated based on the standards in the high molecular weight gel calibration kit (Cytiva Life Sciences®).

Small angle X-ray scattering: Data Collection and Analysis. rBHT$_{(23-594)}$-HIS samples at 1 mg/ml and 4 mg/ml 5 mM in sodium phosphate buffer at pH 5 were measured on a Rigaku Bio-SAXS 2000. The instrument uses Cu K$_\alpha$ radiation ($\lambda$=1.54 Å) and was collimated to provide a sufficient Q-range of 0.01-0.67 Å$^{-1}$. Measurements were performed at ambient temperature. Samples were measured for a total of 40 min in 5 min scans. Data were corrected for transmission and sample background. Reduction, averaging, and buffer subtraction were performed with Rigaku SAX-SLab 3.1.0b14 (FIG. 7A).

7. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

In silico analysis of BHT. Following translation, proteins can be altered by a variety of post-translation modifications (PTMs). This can include, for example, glycosylation and phosphorylation. The PTMs can alter protein conformation, thereby impacting stability, activity, subcellular distribution, and secretion. The crystal structure for BHT$_{(23-594)}$-HIS (6M4E) has recently been solved; however, the initial portion of the novel N-terminal region (residues 23-54) was not modeled and still lacks a known structure. To achieve an accurate prediction for the BHT N-terminus structure and PTMs, comprehensive in silico predictions were conducted using different comparative methods (FIG. 1).

Example 2

Site directed mutagenesis of the predicted N-glycosylation sites within the conserved BHT GH1 domain. Gly-cosylation is one of the central post-translational modifications of proteins mainly occurring by binding glycans to the nitrogen atom of asparagine residues (N-linked) or to the hydroxyl oxygen of serine, threonine, or tyrosine residues (O-linked), but also by C-mannosylation, phospho-serine glycosylation and glypiation (formation of GPI anchors). N-glycosylation has been shown to influence enzymatic activity, stability, and cell surface expression as previously reviewed. Thus, extensive search and alignment analysis performed to identify BHT homologs predicted 25 potential N-linked glycosylation sites. Four of them were located within the GH1 domain with predicted highly conserved glycosylation consensus sites (Asn-X-Ser/Thr), suggesting a high probability of functionally relevant glycosylation at positions; N289LTY, N297STS, N431QSD and N569QSD (FIG. 1; GlycoEP analysis) and recently confirmed in the crystal structure of rBht$_{(23-594)}$-HIS(HsBglA, PDB: 6M4E). Of them, N431QSD was predicted to be both N-glycosylated (FIG. 1; GlycoEP) and phosphorylated at serine 433 within N431QSD (NetPhosYeast 1.0). Therefore, to help narrow down putative regions responsible for membrane associated rBHT and to determine whether these sites have functional significance, the four N-glycosylation sites of BHT were analyzed. The asparagine residues (N289, N297, N431, and N569) were independently mutated to glutamine residues by site-directed mutagenesis using rBht$_{(23-594)}$-HIS as template, to abrogate glycosylation as described in Materials and Methods.

The results showed significant reductions of secreted soluble enzyme activities (90%, 95% and 97%) from three variants GS115::MFα-rBht$_{(23-594)(N431Q)}$-HIS, GS115::MFα-rBht$_{(23-594)(N289Q)}$-HIS and GS115::MFα-rBht$_{(23-594)(N297Q)}$-HIS when compared to non-mutated variant GS115::MFα-rBht$_{(23-594)}$-HIS activity, respectively. The GS115::MFα-rBht$_{(23-594)(N569Q)}$-HIS variant showed a less severe activity reduction of 58% compared to the GS115::MFα-rBht$_{(23-594)}$-HIS (FIG. 2; Table 1). Cell membrane associated activity, when compared to the parent strain GS115: MFα-rBht$_{(23-594)}$-HIS, also decreased by 81%, 95%, 84% and 75% for GS115::MFα-rBht$_{(23-594)(N289Q)}$-HIS, GS115::MFα-rBht$_{(23-594)(N297Q)}$-HIS, GS115::MFα-rBht$_{(23-594)(N431Q)}$-HIS, and GS115::MFα-rBht$_{(23-594)(N569Q)}$-HIS, respectively (FIG. 2 and Table 1). Notably, membrane bound associated activity was significantly reduced but not completely abolished, increasing the ratio of secreted to cell membrane associated activity from 0.40 to 0.66 for GS115::MFα-rBht$_{(23-594)(N569Q)}$-HIS (Table 1), suggesting that glycosylation influences catalytic activity but does not fully determine cell membrane localization.

TABLE 1

| | | Mean values of secreted activity $(mU \cdot OD_{600\ nm}) \pm SD^a$ | | Ratio Secreted Soluble/ |
|---|---|---|---|---|
| Normalized enzyme activity comparison of soluble versus membrane bound secreted protein variants. | | | | |
| Enzyme Source | | Soluble ± SD | Membrane Bound ± SD | Membrane Bound |
| 1 | GS115::rBht$_{(1-594)}$-HIS | 0.69 ± 0.01 | 10.63 ± 0.31 | 0.06 |
| 2 | GS115::MFα-rBht$_{(1-594)}$-HIS | ND | ND | |
| 3 | GS115::MFα-rBht$_{(23-594)}$-HIS | 9.62 ± 0.20 | 24.04 ± 0.53 | 0.40 |
| 4 | GS115::MFα-rBht$_{(23-594)(N289Q)}$-HIS | 0.48 ± 0.02 | 4.51 ± 0.20 | 0.11 |
| 5 | GS115::MFα-rBht$_{(23-594)(N297Q)}$-HIS | 0.27 ± 0.04 | 1.12 ± 0.26 | 0.24 |
| 6 | GS115::MFα-rBht$_{(23-594)(N431Q)}$-HIS | 0.95 ± 0.09 | 3.94 ± 0.51 | 0.24 |
| 7 | GS115::MFα-rBht$_{(23-594)(N569Q)}$-HIS | 4.02 ± 0.25 | 6.06 ± 0.43 | 0.66 |

TABLE 1-continued

Normalized enzyme activity comparison of soluble
versus membrane bound secreted protein variants.

| Enzyme Source | Mean values of secreted activity $(mU \cdot OD_{600\ nm}) \pm SD^a$ | | Ratio Secreted Soluble/ Membrane Bound |
|---|---|---|---|
| | Soluble ± SD | Membrane Bound ± SD | |
| 8  GS115::MFα-rBht$_{(32-594)}$-HIS | 8.24 ± 0.12 | 25.84 ± 0.86 | 0.32 |
| 9  GS115::MFα-rBht$_{(54-594)}$-HIS | 10.87 ± 0.30 | 30.23 ± 1.08 | 0.36 |
| 10  GS115::MFα-rBht$_{(57-594)}$-HIS | 15.60 ± 0.66 | 29.52 ± 1.28 | 0.53 |
| 11  GS115::MFα-rBht$_{(82-594)}$-HIS | ND | ND | |
| 12  GS115::MFα-rBht$_{(95-594)}$-HIS | ND | ND | |
| 13  GS115::MFα-rBht$_{(103-594)}$-HIS | ND | ND | |
| 14  GS115::MFα-rBht$_{(111-594)}$-HIS | ND | ND | |
| 15  GS115::IV-rBht$_{(54-594)}$-HIS | 3.51 ± 0.00 | 14.29 ± 0.39 | 0.25 |
| 16  GS115::GA-rBht$_{(54-594)}$-HIS | 0.39 ± 0.02 | 3.85 ± 0.42 | 0.10 |
| 17  GS115::IN-rBht$_{(54-594)}$-HIS | 7.13 ± 0.20 | 17.14 ± 0.59 | 0.42 |
| 18  GS115::MFα$_{(Δ57-70)}$-rBht$_{(23-594)}$-HIS | 22.96 ± 0.54 | 34.11 ± 1.18 | 0.67 |
| 19  GS115::MFα$_{(Δ57-70)}$-rBht$_{(57-594)}$-HIS | 22.62 ± 0.13 | 42.11 ± 0.31 | 0.54 |
| 20  GS115 control | ND | ND | |

$^a$The value of cell density ($OD_{600\ nm}$) reached by the recombinant strains after methanol induction was used to normalize the secreted soluble and membrane-bound activities. The maximum cell densities obtained were between 60 and 75 $OD_{600\ nm}$. The results are mean values for three measurements of enzyme activity and standard deviation (SD).
"ND" indicates enzyme activity was not detected.

Example 3

Expression and secretion by *K. pastoris* of truncated N-terminal rBHT variants. The novel BHT N-terminal 110 region lacks homology with known proteins; thus, in this region, in silico structural predictions were performed, which showed predominantly large proportions of disordered fragments using five available predictions tools (FIG. 1). Known PSIPRED and Globplot methods were employed to predict secondary structure and globular domains. Upon comparison, the disorder datasets derived from Phyre2, IUPRED2A, DISOPRED3, Globplot Disorder and PONDR (FIG. 1), indicate probable disorder boundaries between 18-42, 43-57, 87-96, and 96-110 residues. Combining different disorder predictors reinforces the reliability of the predicted regions since they use different definitions of disorder.

Figures 2A, 2B, 2C:
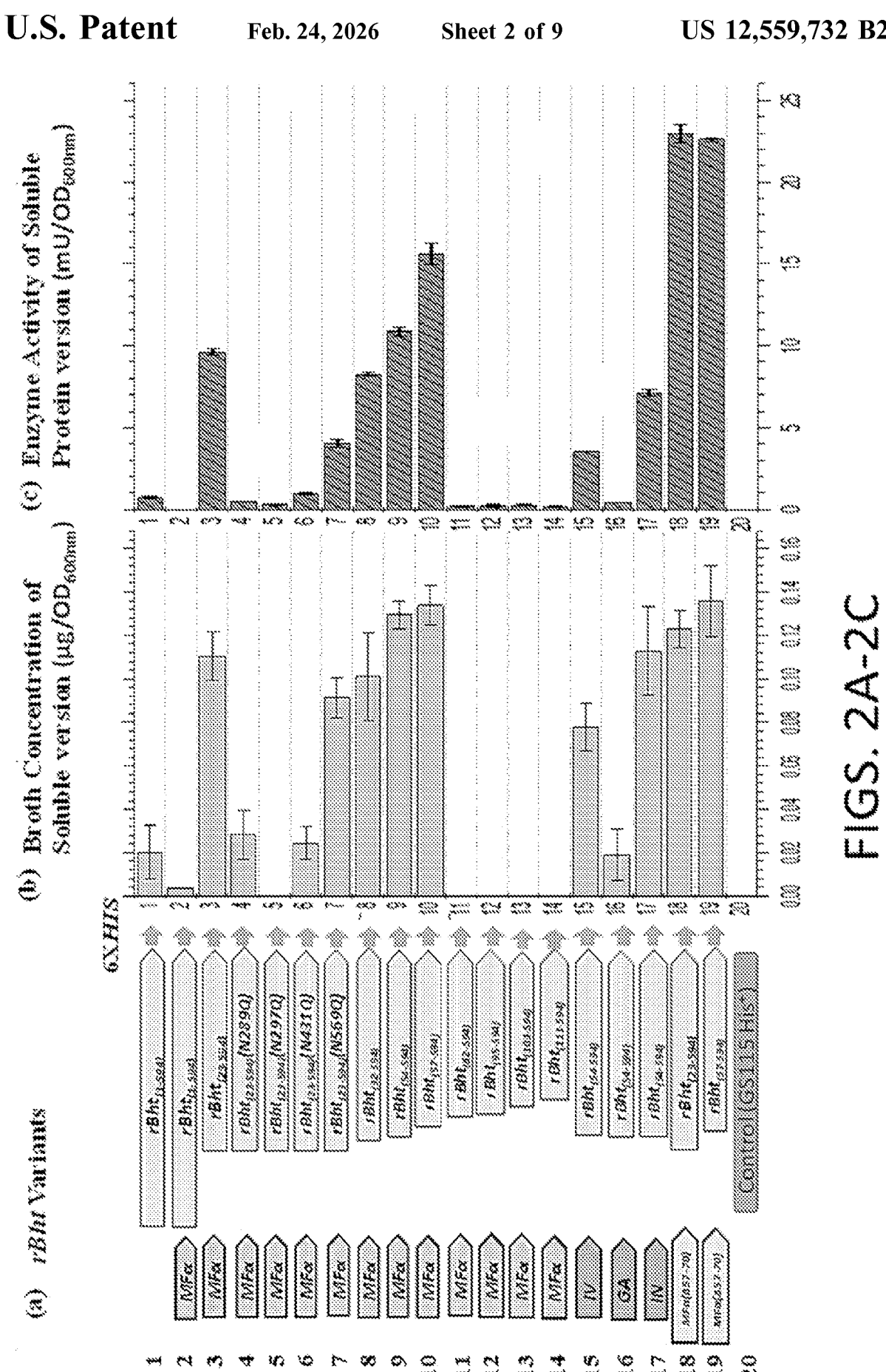
FIGS. 2A-2C: Enzyme activity comparisons of rBHT variants, secreted soluble protein amounts (normalized for the final culture ($OD_{600\ nm}$)) generated by recombinant *K. pastoris* strains carrying truncated variants of rBht-HIS under AOX1 promoter control. (A) Graphic representations of chimeric genes generated containing combinations of leader domains and ORFs of rBht variants. Specific tags, mutations and deletions are indicated. Protein concentration of soluble secreted protein (B) and enzymatic activity (C) secreted by the following recombinant strains was compared: row 1, GS115::rBht$_{(1-594)}$-HIS; row 2, GS115::MFα-rBht$_{(1-594)}$-HIS; row 3, GS115: MFα-rBht$_{(23-594)}$-HIS; row 4, GS115::MFα-rBht$_{(23-594)(N289Q)}$-HIS; row 5, GS115::MFα-rBht$_{(23-594)(N297Q)}$-HIS; row 6, GS115::MFα-rBht$_{(23-594)(N431Q)}$-HIS; row 7, GS115::MFα-rBht$_{(23-594)(N569Q)}$-HIS; row 8, GS115::MFα-rBht$_{(32-594)}$-HIS; row 9, GS115::MFα-rBht$_{(54-594)}$-HIS; row 10, GS115::MFα-rBht$_{(57-594)}$-HIS; row 11, GS115::MFα-rBht$_{(82-594)}$-HIS; row 12, GS115::MFα-rBht$_{(95-594)}$-HIS; row 13, GS115::MFα-rBht$_{(103-594)}$-HIS; row 14, GS115::MFα-rBht$_{(111-594)}$-HIS, row 15, GS115::IV-rBht$_{(54-594)}$-HIS; row 16, GS115::GA-rBht$_{(54-594)}$-HIS; row 17, GS115::IN-rBht$_{(54-594)}$-HIS; row 18, GS115::MFα$_{(\Delta57-70)}$-rBht$_{(23-594)}$-HIS; row 19, GS115::MFα$_{(\Delta57-70)}$-rBht$_{(57-594)}$-HIS; row 20, GS115 (His$^+$) control.

A major function of disordered regions is thought to be their ability to fold upon contact with the membrane and upon specific ligand binding. The approach of the present disclosure was to utilize this information to perform progressive and selective deletions of the predicted disordered fragments to determine if they have an impact on restricting secretion of soluble active rBHT. A schematic representation of the complete rBHT and eight rBHT-truncated variants of the enzyme generated and tested in the present disclosure are shown in FIG. 2A. These rBHT variants were created by removing N-terminal amino-acid block groups progressively from the rBHT$_{(1-594)}$-HIS parent sequence and included; 1 to 22 rBHT$_{(23-594)}$-HIS, 1 to 31 rBHT$_{(32-594)}$-HIS, 1 to 53 rBHT$_{(54-594)}$-HIS, 1 to 56 rBHT$_{(57-594)}$-HIS, 1 to 81 rBHT$_{(82-594)}$-HIS, 1 to 94 rBHT$_{(95-594)}$-HIS, 1 to 102 rBHT$_{(103-594)}$-HIS and 1 to 110 rBHT$_{(111-594)}$-HIS as illustrated in FIG. 2A. *K. pastoris* secreted membrane associated and soluble active enzymes were evaluated for each truncated variant following methanol induction as previously described.

Figures 3A, 3B:
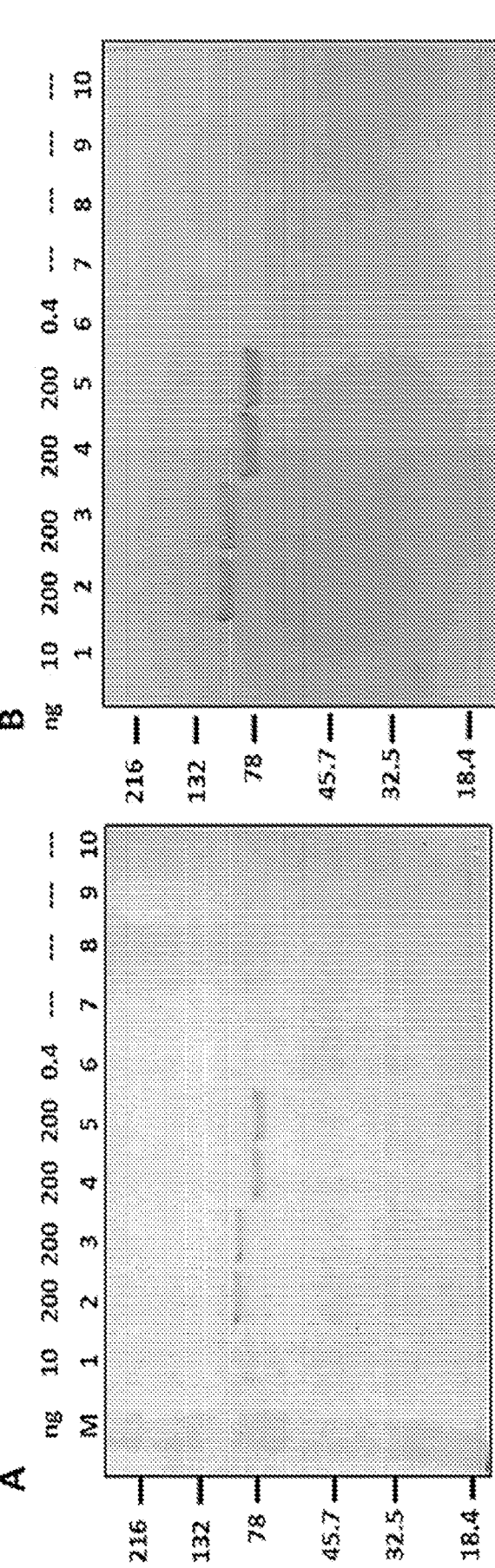
FIGS. 3A-3B: Coomassie stained SDS-PAGE (10%) separation and Western blot. The figures show protein cell free extracts (soluble secreted proteins) expressed by different recombinants of *K. pastoris* GS115. (A) SDS-PAGE and (B) Western blot exposed to anti-HIS antiserum of separated proteins generated by; lane 1, GS115::MFα-rBht-HIS; lane 2, GS115::MFα-rBht$_{(23-594)}$-HIS; lane 3, GS115::MFα-rBht$_{(32-594)}$-HIS; lane 4, GS115::αMF-rBhts$_{(54-594)}$-HIS; lane 5, GS115::αMF-rBht$_{(57-594)}$-HIS; lane 6, GS115::αMF-rBht$_{(82-594)}$-HIS; lane 7, GS115::αMF-rBht$_{(95-594)}$-HIS; lane 8, GS115::MFα-rBht$_{(103-594)}$-HIS; lane 9, GS115::MFα-rBht$_{(111-594)}$-HIS; lane 10, GS115 control containing empty pPIC9 vector. Equal volumes were loaded in each lane to aid in the comparison. Total protein (ng) loaded in each well is indicated above (A) and (B). "---" indicates concentration could not be determined. M indi-

To investigate for the presence of secreted soluble rBHT truncated protein variants, the medium broth was initially inspected by Coomassie stained SDS-PAGE (FIG. 3A) followed by Western blot analysis (FIG. 3B). Secreted soluble rBHT$_{(23-594)}$-HIS, rBHT$_{(32-594)}$-HIS, rBHT$_{(54-594)}$-HIS and rBHT$_{(57-594)}$-HIS were clearly detectable by Coomassie stain (FIG. 3A) and Western blot (FIG. 3B). The rBHT$_{(82-594)}$-HIS, rBHT$_{(95-594)}$-HIS, rBHT$_{(103-594)}$-HIS, rBHT$_{(111-594)}$-HIS protein bands were not detectable by Western blot (FIG. 2B) or Silver stain (data not shown but can be made available upon request), indicating residues downstream of 57 were important for processing secreted protein. In agreement with previous results, rBHT$_{(1-594)}$-HIS variant was barely visible by Western blot (FIG. 3B) (8). No protein band was detected when broth medium from induced GS115 transformed with empty pPIC9 vector was used as a negative control.

Most notable finding was an approximately 30 kDa mobility shift on SDS-PAGE between rBHT$_{(32-594)}$-HIS and rBHT$_{(54-594)}$-HIS, possibly due to the deletion of predicted phosphorylation sites and surrounding acidic residues (Y37 (LTSNYETPS), T39 (SNYETPSPT), S41 (YETPSPTAI), T43 (TPSPTAIPL), T50 (PLEPTPTAT), T52 (EPTPTATGT)) (FIG. 1; DisPhos3.1), known to retard proteins on SDS-PAGE. The algorithm DisPhos1.3 (DEPP) uses disorder information to help improve and discriminate between phosphorylation and non-phosphorylation sites (www.pondr.com/pondr-tut2.html). In addition, the accuracy of DEPP reaches 76.0+/−0.3%, 81.3+/−0.3% and 83.3+/−0.3% for seine, threonine, and tyrosine respectively. The observation that characteristics of amino acids in regions adjacent to phosphorylation sites are intrinsically similar to disordered regions has suggested that disorder in and around the potential phosphorylation site may be a prerequisite for phosphorylation. Furthermore, transmembrane disordered proteins were enriched in phosphorylated residues and interact with more partners than structured counterparts.

Following the above results, the concentration of soluble proteins and activity normalized to cell concentration ($OD_{600\ nm}$) when assayed at 42° C. using ONP-Glu as the substrate were compared (FIG. 2). No significant differences in enzyme activities were detected between truncated protein variants rBHT$_{(23-594)}$-HIS, rBHT$_{(32-594)}$-HIS and rBHT$_{(54-594)}$-HIS. While the truncated variant rBHT$_{(57-594)}$-

HIS showed a 38% increase in enzyme activity in the medium compared to rBHT$_{(23-594)}$-HIS.

An additional feature tested was the ability to drive secretion from predominantly membrane associated to soluble form. The secreted enzymatic activity associated with the membrane remained constant for rBHT$_{(23-594)}$-HIS, rBHT$_{(32-594)}$-HIS and rBHT$_{(54-594)}$-HIS and rBHT$_{(57-594)}$-HIS and no significant differences in ratio of soluble secreted versus membrane associated enzyme activity were observed for variants rBHT$_{(23-594)}$-HIS, rBHT$_{(32-594)}$-HIS and rBHT$_{(54-594)}$-HIS. However, while the activity found associated with the membrane remained relatively constant, rBHT$_{(57-594)}$-HIS variant's ratio of secreted versus membrane associated enzyme activity increased between 25 to 38% (Table 1) when compared to variants rBHT$_{(23-594)}$-HIS, rBHT$_{(32-594)}$-HIS and rBHT$_{(54-594)}$-HIS. To further evaluate whether bioactive rBHT$_{(82-594)}$-HIS, rBHT$_{(95-594)}$-HIS and rBHT$_{(103-594)}$-HIS variants, albeit in low amounts, were produced and secreted, inductions of the corresponding cell lines were performed, and culture broth was concentrated 100-fold followed by affinity chromatography with nickel resin. Yet, no protein could be eluted and/or activity was detected from either soluble or cell associated rBHT from those deletion variants (data not shown but can be made available upon request). The results of the activity assays indicated that amino acid residues 1 to 56 were not required for expression and secretion of active enzyme. This finding is consistent with SDS-PAGE and Western blot data (FIG. 3).

Example 4

Evaluation of alternative signal sequences. Testing alternative signal sequences other than the popularly used MFα seemed daunting considering the ever-increasing choices. Thus, chimeras were generated merging the rBht$_{(54-594)}$ variant to signal sequences from the following open reading frames (ORF): Glucoamylase (GA), Invertase (IV), and Inulinase (IN). Under the experimental conditions, the results showed lower amounts of soluble, and membrane associated active protein compared to the MFα signal sequence routinely used throughout this the present disclosure (Table 1). Therefore, it was decided to concentrate the investigation on MFα. It has previously been shown that deletion of amino acids 57-70 of MFα pro region enhances secretion of reporter proteins by at least 50%. A 58% and 31% increase in secretion of soluble enzyme was obtained by removing amino acids 57-70 from MFα for expression GS115::MFα$_{(Δ57-70)}$-rBht$_{(23-594)}$-HIS and GS115::MFα$_{(Δ57-70)}$-rBht$_{(57-594)}$-HIS variants compared to expression from GS115::MFα-rBht$_{(23-594)}$-HIS and GS115::MFα-rBht$_{(57-594)}$-HIS, respectively (Table 1).

It was inferred from these experiments that maintaining BHT amino acids 57-110 from the BHT N-terminal domain was necessary for enzymatic activity, secretion, and stability. These findings also underline an unbalanced secretion of soluble versus cell associated rBHT, with the balance shifting to the active soluble secreted form either when 56 amino terminal amino acids are deleted or when the MFα signal sequence is altered (Table 1).

Kinetic parameters of secreted soluble rBHT variants. After purification to homogeneity using a carboxy 6×Histidine epitope and Nickel affinity chromatography purification, active soluble secreted rBHT variants were functionally characterized by standard kinetic assays. SDS-PAGE separation followed by detection using anti-HIS monoclonal antibody under reducing conditions indicated that the isolated proteins were essentially homogeneous (FIGS.

3A-3B). The kinetic parameters characterizing each active secreted soluble variant including rBHT$_{(23-594)}$-HIS, rBHT$_{(32-594)}$-HIS, rBHT$_{(54-594)}$-HIS, rBHT$_{(57-594)}$-HIS were examined. To obtain a full kinetic picture, an important parameter to evaluate is the impact of temperature on enzymatic activity. Therefore, assays were performed at the optimum temperature for rBHT$_{(23-594)}$-HIS of 42° C. (8), below (20 and 30° C.) and above (55° C.) using ONP-Glu as substrate. The results of the respective kcat/km for all four truncated enzyme variants indicate a temperature optimum. Surprisingly, all enzyme-truncated variants retain similar affinity for the substrate ONP-Glu (Km) and turnover activity (kcat) indicating that truncations do not affect the catalytic integrity of the enzyme (FIG. 4).

Example 5

Production of N-acetyllactosamine (LacNAc). As shown in FIG. 5A, rBHT polypeptides of the present disclosure are able to catalyze the repeated addition of galactose (Gal from lactose) to N-acetylglucosamine (GlcNAc). FIG. 5B includes representative results demonstrating the enzymatic reactions catalyzed by rBHT. Time course studies of galactosyl-lactose and N-acetylglucosamine (LacNAc) synthesis were performed using whole cells membrane bound protein (1 U rBHT.g$^{-1}$ lactose). Assays contained ~20 g/L lactose; ~10 g/L N-acetylglucosamine (GlcNAc), in 5 mM sodium phosphate buffer (pH 5.0) and incubated at 30° C. Samples were removed periodically and analyzed by HPLC and detected by ELSD and PDA.

The data provided herein provide an efficient solution to generate LacNAc at cost-competitive industrial scale. The capability of rBHT polypeptides of the present disclosure to synthesize LacNAc using lactose as a donor and N-acetylglucosamine as acceptor was demonstrated (FIG. 5). These data provide evidence that this enzyme is an essential and novel tool to achieve, at above gram concentrations, of the synthesis of LacNAc (Galβ1-4GlcNAc), considered a Human Milk Oligosaccharide (HMO)-like sugar. These catalyzed reactions were very regioselective, forming the beta-galactosyl linkage at the 4-position of GlcNAc and also at the 1-position of D-galactose, synthesizing various glycoconjugates directly from soluble GlcNAc. The obtained products included Galβ(1,4)GlcNAc (LacNAc, FIG. 5A, panel B) disaccharides and Galβ(1,4)Galβ(1,4)GlcNAc (Galactosyl-LacNAc, FIG. 5A, panel C) trisaccharides which were produced by two sequential transgalactosylations (FIGS. 5A-5B).

Example 6

Sequence and Structural BHT homologs. Beta-glucosidases GH1 family members consist of a single domain with (a/0)$_8$ TIM barrel topology in the CaZy classification (www.cazy.org/GH1_characterized.html). However, BHT folds into two domains (FIG. 1). The main domain is a (α/β)$_8$ TIM barrel that starts at residue 116 and extends to residue 547 (HsBglA, PDB: 6M4E) (17). This domain has eight parallel β-strands that form the central barrel connected by eight external α-helices that is common to GH1 family members (www.cazypedia.org/index.php/Glycoside_Hydrolase_Family_1). To identify similar structures, heuristic PDB searches were carried out using the Dali server using the structure of rBHT$_{(23-594)}$-HIS (HsBglA, PDB: 6M4E) as a query to search against all the deposits in the Protein Data Bank. Structures in the Dali server PDB90 database revealed beta-glucosidase BGL1A from the basidiomycete *Phanerochaete chrysosporium* (PDB: 2B3Z-A) as the closest structural match to the C-domain of rBHT$_{(23-594)}$-HIS with the highest Z score of 49.3 (Table 2). In this case 450 amino acids Cα out of 460 were superimposable with the rBHT$_{(23-594)}$-HIS structure and 34% and sequence identity. The top ranking 5 structures were chosen, which have a Z-score larger than 46.5 and r.m.s.d. less than 1.8 Å to directly compare structural similarities and differences with rBHT$_{(23-594)}$-HIS. Interestingly, the top 5 structural matches are also fungal Beta-glucosidases, and the alignment is specific to the C-terminal domain of rBHT$_{(23-594)}$-HIS for all 5 (Table 2).

Aside from *Phanerochaete chrysosporium* BGL1A (PDB: 2B3Z-A), the list includes Beta-glucosidase from *Trichoderma reesei* (PDB: 3AHY-B), Beta-1,4-Glucosidase from *Trichoderma harzianum* (PDB:5BWF-A), Beta-Glucosidase from *Humicola insolens* (PDB: 4MDO-A) and Beta-Glucosidase from *Trichoderma harzianum* (PDB:5JBO-A). Primary sequence alignment of these top 5 structures with the rBHT$_{(23-594)}$-HIS shows that, while the core GH1 structure is shared, its N-terminus is distinct and unique (FIG. 6A). While the sequence identity varied little from 31% to 34%, (α/β)$_8$ TIM barrel β8 in Loop C and β9 in Loop D are much longer than the found in HsBglA (PDB: 6M4E) and the 3$^{rd}$ β-sheet has is replaced with α17 in Loop C (FIG. 6A). Also notable is the absence of N-glycosylation residues at all 4 established N-glycosylation sites (N289, N297, N431 and N569) (FIG. 6A).

The CaZy database indicates that GenBank contains over 40,000 GH1 proteins and over 270 PDB structures are available. The GH1 protein sequences from the RCSB PDB database (rcsb.org) were extracted using SANSparallel (ekhidna2.biocenter.helsinki.fi/cgi-bin/sans/sans.cgi) and aligned with the Clustal Omega program. The amino acid sequence of 60 GH1 genes structurally homologous to the C-terminal domain of BHT and with Z scores above 40 showed 60% sequence identity with each other and 27-33% identity to BHT and no matches to the N-terminus. Additionally, Blast analysis of the N-terminal domain amino acid sequence did not locate a match. From this sequence and structure comparison data, it was concluded that the structure of the BHT N-terminus found in the 6M4E structure is novel to the GH1 proteins and does not presently have a close structural homolog in the PDB database.

TABLE 2

| | | | | | | |
|---|---|---|---|---|---|---|
| | | | | Protein structural similarity results using Dali server. | | |
| No. | Accession number | Z-score[a] | Identity (%)[b] | RMSD Å[c] | Superimposed[d] | Protein/ Organism | Reference |
| 1 | 2E3Z-A | 49.3 | 34 | 1.3 | 450 from 460 | Beta-Glucosidase (BGL1A) from *Phanerochaete chrysosporium* | Nijikken, et al. 2007 |
| 2 | 3AHY-B | 48.1 | 32 | 1.7 | 458 from 466 | Beta-Glucosidase (TrBg12) from *Trichoderma reesei* | Jeng, et al. 2011 |
| 3 | 5BWF-A | 47.7 | 32 | 1.6 | 458 from 471 | Beta-1,4-Glucosidase (ThBg1) from *Trichoderma harzianum* | Santos, et al. 2016 |
| 4 | 4MDO-A | 47.3 | 33 | 1.7 | 461 from 477 | Beta-Glucosidase (HiBG) from *Humicola insolens* | de Giuseppe, et al. 2014 |
| 5 | 5JBO-A | 46.8 | 31 | 1.7 | 459 from 475 | Beta-Glucosidase (ThBg12) from *Trichoderma harzianum* | Florindo, et al. 2018 |

Monomeric HsBgl A(23-594)-HIS (PDB: 6M4E) was used as the query.
The top 5 closest structures from the PDB90 database results are shown.
[a]Z-score used to select top 5 similar structures.
[b]Sequence identity.
[c]Average distance between superimposed residues.
[d]Number of superimposed residues from total residues.

the nucleophile and general acid/base residues in the enzyme sequences aligned well. Superposition of these structures with rBHT$_{(23-594)}$-HIS (HsBglA, PDB: 6M4E) structure shows the C-terminal core of rBHT$_{(23-594)}$-HIS is nearly identical with other GH1 structures with the exception of the variability found in Loops A-D contouring the catalytic pocket that is located at the center of the barrel (FIGS. 6A-6B), typical of GH1 proteins. The most outstanding feature is a long insertion in Loop C (residues 423-433, NGIANCIRNQS) as well as smaller insertions in loop A (Y147), Loop B (Q282, N283, L290), loop C (S460 and A461) and Loop D (L510, Y511, Q512) and T244, G245, G327, T328, G374, K489 and P573 insertions (FIG. 6A). The inserted residues reside on the surface of the structure (FIG. 6B). Interestingly, in all 5 structural homologs, non- Example 7

Influence of N-terminal deletions on rBHT dimerization. rBHT$_{(23-594)}$-HIS exists as a dimeric form in solution as determined by size exclusion chromatography (SEC) column packed with Sephacryl S-200 that showed rBHT$_{(23-594)}$-HIS eluted as a single peak having a retention time of 12.5 min with calculated M. 150 kDa corresponding the dimeric state (data not shown but can be made available upon request). The dimer conformation was further validated in solution by small X-ray scattering (SAXS) (FIG. 7A). Guinier and P(r) analysis was performed using PRI-MUS and GNOM, respectively. D$_{max}$ values were manually chosen in GNOM to optimize the P(r) calculation (FIG. 7B). These D$_{max}$ values are approximate to ~±2-3 Å. Molecular mass were calculated using the method described by Rambo and Tamer. The data are presented in Table 3. The molecular mass determined from SAXS (~169 KDa) confirmed that BHT forms a dimer in solution Table 3. The $R_g$ and $D_{max}$ of the dimer in solution are 39 Å and 124 Å, respectively. The deposited X-ray crystallographic structures (6M4E, 6M4F and 6M55) also suggest that BHT forms a dimer. The $R_g$ and $D_{max}$ of the 6M4F crystallographic dimer (molecule A and molecule C) calculated using Crysol are 34 Å and 110 Å, respectively. These values are in good agreement with the experimental SAXS data. The disordered N-terminus led to a more expanded dimer in solution, and it was concluded that $rBHT_{(23-594)}$-HIS likely functions as a dimer. Similarly, SEC analysis of $rBHT_{(32-594)}$-HIS, $rBHT_{(54-594)}$-HIS, and $rBHT_{(57-594)}$-HIS also indicate dimer formation (data not shown but can be made available upon request), suggesting that the unstructured regions spanning residues 23-56 are not involved in dimerization.

TABLE 3

Solution scattering parameters zero-angle intensity $I_0$, radius of gyration $R_g$, and maximum dimension $D_{max}$ and SAXS-calculated molecular weight for BHT at 1 mg/ml and 4 mg/ml.

| Sample (concentration) | $I_0$ (arbitrary unit) | $R_g$ (Å) | $D_{max}$ (Å) | Mass (Da) |
|---|---|---|---|---|
| $rBHT_{(23-594)}$-HIS (1 mg/ml) | 5.07 ± 0.02 | 39.07 ± 0.15 | 124 | 169400 ± 1600 |
| $rBHT_{(23-594)}$-HIS (4 mg/ml) | 20.27 ± 0.05 | 38.29 ± 0.08 | 125 | 169300 ± 900 |

8. SEQUENCES

Sequences relevant to the various embodiments of the present disclosure are provided in the tables below.

TABLE 4A

Sequence information.

| SEQ ID NO: | Name | aMF | Size amino acid | HIS tag |
|---|---|---|---|---|
| 1 protein | β-hexosyl transferase (BHT; GenBank: F298281.1) | no | 594 | no |
| 2 DNA | β-hexosyl transferase (BHT; GenBank: F298281.1) | no | | no |
| 3 protein | Synthetic β-hexosyl transferase (23-594) | no | 572 | no |
| 4 DNA | Synthetic β-hexosyl transferase (23-594) | no | | no |
| 5 protein | Synthetic β-hexosyl transferase (32-594) | no | 563 | no |
| 6 DNA | Synthetic β-hexosyl transferase (32-594) | no | | no |
| 7 protein | Synthetic β-hexosyl transferase (54-594) | no | 541 | no |
| 8 DNA | Synthetic β-hexosyl transferase (54-594) | no | | no |
| 9 protein | Synthetic β-hexosyl transferase (57-594) | no | 538 | no |
| 10 DNA | Synthetic β-hexosyl transferase (57-594) | no | | no |
| 11 protein | Synthetic β-hexosyl transferase (82-594) | no | 513 | no |
| 12 DNA | Synthetic β-hexosyl transferase (82-594) | no | | no |
| 13 protein | Synthetic β-hexosyl transferase (95-594) | no | 500 | no |
| 14 DNA | Synthetic β-hexosyl transferase (95-594) | no | | no |
| 15 protein | Synthetic β-hexosyl transferase (103-594) | no | 492 | no |
| 16 DNA | Synthetic β-hexosyl transferase (103-594) | no | | no |
| 17 protein | Synthetic β-hexosyl transferase (111-594) | no | 484 | no |
| 18 DNA | Synthetic β-hexosyl transferase (111-594) | no | | no |
| 19 protein | Synthetic β-hexosyl transferase (23-594) (N289Q) | no | 572 | no |
| 20 DNA | Synthetic β-hexosyl transferase (23-594) (N289Q) | no | | no |
| 21 protein | Synthetic β-hexosyl transferase (23-594) (N297Q) | no | 572 | no |
| 22 DNA | Synthetic β-hexosyl transferase (23-594) (N297Q) | no | | no |
| 23 protein | Synthetic β-hexosyl transferase (23-594) (N431Q) | no | 572 | no |
| 24 DNA | Synthetic β-hexosyl transferase (23-594) (N431Q) | no | | no |
| 25 protein | Synthetic β-hexosyl transferase (23-594) (N569Q) | no | 572 | no |
| 26 DNA | Synthetic β-hexosyl transferase (23-594) (N569Q) | no | | no |
| 27 protein | α-mating factor signal sequence from *Saccharomyces cerevisiae* (MFα) | yes | 89 | no |
| 28 DNA | α-mating factor signal sequence from *Saccharomyces cerevisiae* (MFα) | yes | | no |
| 29 protein | α-mating factor signal sequence from *Saccharomyces cerevisiae* (MFα) (Δ57-70) | Partial | 67 | no |
| 30 protein | Invertase (IV) signal sequence | no | 19 | no |
| 31 protein | Glucoamylase (GA) signal sequence | no | 8 | no |

TABLE 4A-continued

Sequence information.

| SEQ ID NO: | Name | aMF | Size amino acid | HIS tag |
|---|---|---|---|---|
| 32 protein | Inulinase (IN) signal sequence | no | 15 | no |
| 33 DNA | MFα-rBht(1-594)-HIS (nucleic acid) | yes | | yes |
| 34 protein | MFα-rBht(1-594)-HIS (protein) | yes | 689 | yes |
| 35 DNA | rBht(1-594)-HIS (nucleic acid) | no | | yes |
| 36 protein | rBht(1-594)-HIS (protein) | no | 600 | yes |
| 37 DNA | MFα-rBht(23-594)-HIS (nucleic acid) | yes | | yes |
| 38 protein | MFα-rBht(23-594)-HIS (protein) | yes | 667 | yes |
| 39 DNA | MFα-rBht(23-594)(N289Q)-HIS (nucleic acid) | yes | | yes |
| 40 protein | MFα-rBht(23-594)(N289Q)-HIS (protein) | yes | 667 | yes |
| 41 DNA | MFα-rBht(23-594)(N297Q)-HIS (nucleic acid) | yes | | yes |
| 42 protein | MFα-rBht(23-594)(N297Q)-HIS (protein) | yes | 667 | yes |
| 43 DNA | MFα-rBht(23-594)(N431Q)-HIS (nucleic acid) | yes | | yes |
| 44 protein | MFα-rBht(23-594)(N431Q)-HIS (protein) | yes | 667 | yes |
| 45 DNA | MFα-rBht(23-594)(N569Q)-HIS (nucleic acid) | yes | | yes |
| 46 protein | MFα-rBht(23-594)(N569Q)-HIS (protein) | yes | 667 | yes |
| 47 DNA | MFα-rBht(32-594)-HIS (nucleic acid) | yes | | yes |
| 48 protein | MFα-rBht(32-594)-HIS (protein) | yes | 658 | yes |
| 49 DNA | MFα-rBht(54-594)-HIS (nucleic acid) | yes | | yes |
| 50 protein | MFα-rBht(54-594)-HIS (protein) | yes | 636 | yes |
| 51 DNA | MFα-rBht(57-594)-HIS (nucleic acid) | yes | | yes |
| 52 protein | MFα-rBht(57-594)-HIS (protein) | yes | 633 | yes |
| 53 DNA | MFα-rBht(82-594)-HIS (nucleic acid) | yes | | yes |
| 54 protein | MFα-rBht(82-594)-HIS (protein) | yes | 608 | yes |
| 55 DNA | MFα-rBht(95-594)-HIS (nucleic acid) | yes | | yes |
| 56 protein | MFα-rBht(95-594)-HIS (protein) | yes | 595 | yes |
| 57 DNA | MFα-rBht(103-594)-HIS (nucleic acid) | yes | | yes |
| 58 protein | MFα-rBht(103-594)-HIS (protein) | yes | 587 | yes |
| 59 DNA | MFα-rBht(111-594)-HIS (nucleic acid) | yes | | yes |
| 60 protein | MFα-rBht(111-594)-HIS (protein) | yes | 584 | yes |
| 61 DNA | IV-rBht(54-594)-HIS (nucleic acid) | no | | yes |
| 62 protein | IV-rBht(54-594)-HIS (protein) | no | 566 | yes |
| 63 DNA | GA-rBht(54-594)-HIS (nucleic acid) | no | | yes |
| 64 protein | GA-rBht(54-594)-HIS (protein) | no | 565 | yes |
| 65 DNA | IN-rBht(54-594)-HIS (nucleic acid) | no | | yes |
| 66 protein | IN-rBht(54-594)-HIS (protein) | no | 563 | yes |
| 67 DNA | MFα(Δ57-70)-rBht(23-594)-HIS (nucleic acid) | yes | | yes |
| 68 protein | MFα(Δ57-70)-rBht(23-594)-HIS (protein) | yes | 653 | yes |
| 69 DNA | MFα(Δ57-70)-rBht(57-594)-HIS (nucleic acid) | yes | | yes |
| 70 protein | MFα(Δ57-70)-rBht(57-594)-HIS (protein) | yes | 619 | yes |

TABLE 5

Sequences.

| SEQ ID NO: | Name | Sequence |
|---|---|---|
| 1 | β-hexosyl transferase BHT; GenBank: F298281.1) | MMLHAALLVALPCVVLARPAGAVTYPGAIPLSLTSNYETPSPTAI<br>PLEPTPTATGTAELDALWNLVEAQYPVQTAAVTTLVTVPDDYKF<br>EADPPSYALAGYETSEIAGLKFPKGFKFGVAGAAIQVEGAAKAEG<br>RGPSTWDYLCHHYASTQCNNYDPDITTNHYYLYPLDFARLQHLG<br>INTYSFSISWTRIYPLGAGYVNEAGLAHYDAVIHSAKKYGLEPVG<br>TVFHWDTPLSLMLKYGAWQDTGDQIVKDFVTYATTVFKRYGNE<br>VKTWFTFNEPRVFCSQNSGLPYNLTYPEGINSTSAVFRCTYNVLK<br>AHGHAVKVYRDLVASGTIAAGEIGFKSDDNYPIPARPGNADDEES<br>AKRHEAFRIGIFAQPVYGNGDYPDVVKETVGDMLPALTDEDKGY<br>IKGSGDIFAIDGYRTDISHAALNGIANCIRNQSDPNWPVCEEGSDP<br>FAHVYPSGFAIGQSADPLSSWLVNSAPFIRDQLKFLTQTYPAKGGI<br>YFSEFGWAEDAEYDRQLLYQITWDGLRTQYLTDYLSQLLLAVHK<br>DGINLRGALTWSFVDNWEWGLGMQQKFGFQFVNQSDPDLTRTF<br>KLSAHAYAQFGRNHL |
| 2 | β-hexosyl transferase (BHT; GenBank: | atgatgctgcatgctgcactgctagtagcgctgccatgtgttgttttttggcgcgcccggccggagcggtta<br>cttatccgggagccattcctctgtccctgacgagcaattacgaaacccaagtccgacagcaatcccgct<br>ggagccaacaccgacggctaccggtacagcagaattagatgcgctgtgtgg aacttagtcgaagctcag<br>tac ccagttcaaactgctgcagtgacaactttggtgacagtgcccgatgattataagtttgaggcagatc |

TABLE 5-continued

Sequences.

| SEQ ID NO: | Name | Sequence |
|---|---|---|
| | F298281.1) | cac cgagttatgcattagcagggtatgaaacaagcgagattgccggactgaagtttccaaaggggttta agtt tggtggttgcggggcagccattcaagttgaaggtgcagcaaaagccgaagggcggggcccaa gtacctgg gattatctgtgtcatcactatgccagcacgcagtgtaacaattatgatcccgatattacaacc aaccatt actacctgtacccattggactttgcgcgcctgcaacacctaggcattaacacttactcgttttca atttc atggacgcgtatttatccattgggcgcaggctatgttaatgaagcagggttagcccactatgatgc cgta atccatagtgccaagaagtatggtctggaaccagtgggcaccgttttcactgggatacgccact gtctc tgatgctgaaatacggtgcctggcaagatactggtgaccaaattgttaaggactttgttacctatg ccac aactgtgtttaagcgttatggtaatgaagtcaagacgtggtttactttcaatgaaccacgggttttct gt tcacaaaatagtggtctgccatacaatctgacgtatccagaaggtattaacagcacctccgctgtattt c gttgcacctacaatgttctgaaagctcatggtcatgctgttaaagtgtatcgggatctagttgcctccgg gaccattgcggcaggtgaaatcggctttaaatccgatgataactacccaatcccggcccgtccaggaa c gccgatgacgaggaatcagccaagcgtcacgaggcttttcgcattgggattttttgcgcaaccggtttat g gtaatggcgattatccagatgttgttaaagaaactgttggagatatgctgccggccctgacggatgaa ga taaaggatacattaaaggtagcggagatattttgcgattgacgggtatcgtaccgatatttcccatgc g gctctgaacgggatcgcgaattgtattcgcaaccaaagtgacccgaattggccagtgtgtgaagaag ggt cagatccttttgctcatgtttacccatccgggtttgctattggtcaatcagccgatccactgtcttcatg gttagtcaactcagccccgtttatccgcgatcaactgaagtttctgacacaaacctaccctgctaaggt ggtatttatttctcggaatttggttgggctgaagacgccgaatatgatcgtcaactgctgtatcaaatta cct gggatggtctgcgtacgcaatacctgacggactatctgagccagctgctgttggctgtgcacaaaga c gggattaatctgcgaggcgcgctgacgtggagttttgtcgataattgggagtgggggtttagggatgcaa cagaaattcggatttcagtttgttaatcaatcagatcccgatctgacacgcacgtttaaactgagcgctc a cgcttacgcccaatttgggcgtaatcatctg |
| 3 | Synthetic β-hexosyl transferase (23-594) | VTYPGAIPLSLTSNYETPSPTAIPLEPTPTATGTAELDALWNLVEA QYPVQTAAVTTLVTVPDDYKFEADPPSYALAGYETSEIAGLKFPK GFKFGVAGAAIQVEGAAKAEGRGPSTWDYLCHHYASTQCNNYD PDITTNHYYLYPLDFARLQHLGINTYSFSISWTRIYPLGAGYVNEA GLAHYDAVIHSAKKYGLEPVGTVFHWDTPLSLMLKYGAWQDTG DQIVKDFVTYATTVFKRYGNEVKTWFTFNEPRVFCSQNSGLPYN LTYPEGINSTSAVFRCTYNVLKAHGHAVKVYRDLVASGTIAAGEI GFKSDDNYPIPARPGNADDEESAKRHEAFRIGIFAQPVYGNGDYP DVVKETVGDMLPALTDEDKGYIKGSGDIFAIDGYRTDISHAALNG IANCIRNQSDPNWPVCEEGSDPFAHVYPSGFAIGQSADPLSSWLV NSAPFIRDQLKFLTQTYPAKGGIYFSEFGWAEDAEYDRQLLYQIT WDGLRTQYLTDYLSQLLLAVHKDGINLRGALTWSFVDNWEWGL GMQQKFGFQFVNQSDPDLTRTFKLSAHAYAQFGRNHL |
| 4 | Synthetic β-hexosyl transferase (23-594) | gttacttatccgggagccattcctctgtccctgacgagcaattacgaaaccccaagtccgacagcaatcc cgctggagccaacaccgacggctaccggtacagcagaattagatgcgctgtggaacttagtcgaagct cagtacccagttcaaactgctgcagtgacaacttttggtgacagtgcccgatgattataagtttgaggcaga tccaccgagttatgcattagcagggtatgaaacaagcgagattgccggactgaagtttccaaaggggtttt aagtttggtgttgcggggcagccattcaagttgaaggtgcagcaaaagccgaagggcggggcccaa gtacctgggattatctgtgtcatcactatgccagcacgcagtgtaacaattatgatcccgatattacaacca accattactacctgtacccattggactttgcgcgcctgcaacacctaggcattaacacttactcgttttcaat ttcatggacgcgtatttatccattgggcgcaggctatgttaatgaagcagggttagcccactatgatgccg taatccatagtgccaagaagtatggtctggaaccagtgggcaccgtttttcactgggatacgccactgtct ctgatgctgaaatacggtgcctggcaagatactggtgaccaaattgttaaggactttgttacctatgccac aactgtgtttaagcgttatggtaatgaagtcaagacgtggtttactttcaatgaaccacgggtttttctgttcac aaaatagtggtctgccatacaatctgacgtatccagaaggtattaacagcacctccgctgtatttcgttgca cctacaatgttctgaaagctcatggtcatgctgttaaagtgtatcgggatctagttgcctccgggaccattg cggcaggtgaaatcggctttaaatccgatgataactacccaatcccggcccgtccaggaacgccgat gacgaggaatcagccaagcgtcacgaggcttttcgcattgggattttttgcgcaaccggtttatggtaatg gcgattatccagatgttgttaaagaaactgttggagatatgctgccggccctgacggatgaagataaagg atacattaaaggtagcggagatattttgcgattgacgggtatcgtaccgatatttcccatgcggctctgaa cgggatcgcgaattgtattcgcaaccaaagtgacccgaattggccagtgtgtgaagaagggtcagatcc ttttgctcatgtttacccatccgggtttgctattggtcaatcagccgatccactgtcttcatggttagtcaactc agccccgtttatccgcgatcaactgaagtttctgacacaaacctaccctgctaaggtggtatttatttctcg gaatttggttgggctgaagacgccgaatatgatcgtcaactgctgtatcaaattacctgggatggtctgcg tacgcaatacctgacggactatctgagccagctgctgttggctgtgcacaaagacgggattaatctgcga ggcgcgctgacgtggagttttgtcgataattgggagtgggggtttagggatgcaacagaaattcggatttc agtttgttaatcaatcagatcccgatctgacacgcacgtttaaactgagcgctcacgcttacgcccaatttg ggcgtaatcatctg |
| 5 | Synthetic β-hexosyl transferase (32-594) | SLTSNYETPSPTAIPLEPTPTATGTAELDALWNLVEAQYPVQTAA VTTLVTVPDDYKFEADPPSYALAGYETSEIAGLKFPKGFKFGVAG AAIQVEGAAKAEGRGPSTWDYLCHHYASTQCNNYDPDITTNHY YLYPLDFARLQHLGINTYSFSISWTRIYPLGAGYVNEAGLAHYDA VIHSAKKYGLEPVGTVFHWDTPLSLMLKYGAWQDTGDQIVKDF VTYATTVFKRYGNEVKTWFTFNEPRVFCSQNSGLPYNLTYPEGIN STSAVFRCTYNVLKAHGHAVKVYRDLVASGTIAAGEIGFKSDDN YPIPARPGNADDEESAKRHEAFRIGIFAQPVYGNGDYPDVVKETV GDMLPALTDEDKGYIKGSGDIFAIDGYRTDISHAALNGIANCIRN |

TABLE 5-continued

Sequences.

| SEQ ID NO: | Name | Sequence |
|---|---|---|
| | | QSDPNWPVCEEGSDPFAHVYPSGFAIGQSADPLSSWLVNSAPFIR DQLKFLTQTYPAKGGIYFSEFGWAEDAEYDRQLLYQITWDGLRT QYLTDYLSQLLLAVHKDGINLRGALTWSFVDNWEWGLGMQQK FGFQFVNQSDPDLTRTFKLSAHAYAQFGRNHL |
| 6 | Synthetic β-hexosyl transferase (32-594) | tccctgacgagcaattacgaaaccccaagtccgacagcaatcccgctggagccaacaccgacggcta ccggtacagcagaattagatgcgctgtggaacttagtcgaagctcagtacccagttcaaactgctgcagt gacaactttggtgacagtgcccgatgattataagtttgaggcagatccaccgagttatgcattagcagggt atgaaacaagcgagattgccggactgaagtttccaaaggggtttaagtttggtgttgcgggggcagcca ttcaagttgaaggtgcagcaaaagccgaagggcggggcccaagtacctgggattatctgtgtcatcact atgccagcacgcagtgtaacaattatgatcccgatattacaaccaaccattactacctgtacccattggact ttgcgcgcctgcaacacctaggcattaacacttactcgttttcaatttcatggacgcgtatttatccattggg cgcaggctatgttaatgaagcagggttagcccactatgatgccgtaatccatagtgccaagaagtatggt ctggaaccagtgggcaccgttttttcactgggatacgccactgtctctgatgctgaaatacggtgcctggc aagatactggtgaccaaattgttaaggactttgttacctatgccacaactgtgtttaagcgttatggtaatga agtcaagacgtggtttacttttcaatgaaccacgggtttctgttcacaaaatagtggtctgccatacaatctg acgtatccagaaggtattaacagcacctccgctgtatttcgttgcacctacaatgttctgaaagctcatggt catgctgttaaagtgtatcgggatctagttgcctccgggaccattgcggcaggtgaaatcggctttaaatc cgatgataactacccaatcccggcccgtccaggaacgccgatgacgaggaatcagccaagcgtcac gaggcttttcgcattgggattttttgcgcaaccggtttatggtaatggcgattatccagatgttgttaaagaa ctgttggagatatgctgccggccctgacggatgaagataaaggatacattaaaggtagcggagatattttt gcgattgacgggtatcgtaccgatatttcccatgcggctctgaacgggatcgcgaattgtattcgcaacc aaagtgacccgaattggccagtgtgtgaagaagggtcagatcctttgctcatgtttacccatccgggttt gctattggtcaatcagccgatccactgtcttcatggttagtcaactcagccccgtttatccgcgatcaactg aagtttctgacacaaacctaccctgctaaggtggtatttatttctcggaatttggttgggctgaagacgcc gaatatgatcgtcaactgctgtatcaaattacctgggatggtctgcgtacgcaatacctgacggactatct gagccagctgctgttggctgtgcacaaagacgggattaatctgcgaggcgcgctgacgtggagttttgt cgataattgggagtggggtttagggatgcaacagaaattcggatttcagttgttaatcaatcagatcccg atctgacacgcacgtttaaactgagcgctcacgcttacgcccaatttgggcgtaatcatctg |
| 7 | Synthetic β-hexosyl transferase (54-594) | TGTAELDALWNLVEAQYPVQTAAVTTLVTVPDDYKFEADPPSY ALAGYETSEIAGLKFPKGFKFGVAGAAIQVEGAAKAEGRGPSTW DYLCHHYASTQCNNYDPDITTNHYYLYPLDFARLQHLGINTYSFS ISWTRIYPLGAGYVNEAGLAHYDAVIHSAKKYGLEPVGTVFHWD TPLSLMLKYGAWQDTGDQIVKDFVTYATTVFKRYGNEVKTWFT FNEPRVFCSQNSGLPYNLTYPEGINSTSAVFRCTYNVLKAHGHAV KVYRDLVASGTIAAGEIGFKSDDNYPIPARPGNADDEESAKRHEA FRIGIFAQPVYGNGDYPDVVKETVGDMLPALTDEDKGYIKGSGDI FAIDGYRTDISHAALNGIANCIRNQSDPNWPVCEEGSDPFAHVYP SGFAIGQSADPLSSWLVNSAPFIRDQLKFLTQTYPAKGGIYFSEFG WAEDAEYDRQLLYQITWDGLRTQYLTDYLSQLLLAVHKDGINL RGALTWSFVDNWEWGLGMQQKFGFQFVNQSDPDLTRTFKLSAH AYAQFGRNHL |
| 8 | Synthetic β-hexosyl transferase (54-594) | accggtacagcagaattagatgcgctgtggaacttagtcgaagctcagtacccagttcaaactgctgca gtgacaactttggtgacagtgcccgatgattataagtttgaggcagatccaccgagttatgcattagcagg gtatgaaacaagcgagattgccggactgaagtttccaaaggggtttaagtttggtgttgcgggggcagc cattcaagttgaaggtgcagcaaaagccgaagggcggggcccaagtacctgggattatctgtgtcatca ctatgccagcacgcagtgtaacaattatgatcccgatattacaaccaaccattactacctgtacccattgga ctttgcgcgcctgcaacacctaggcattaacacttactcgttttcaatttcatgacgcgtatttatccattgg gcgcaggctatgttaatgaagcagggttagcccactatgatgccgtaatccatagtgccaagaagtatgg tctggaaccagtgggcaccgttttttcactgggatacgccactgtctctgatgctgaaatacggtgcctggc aagatactggtgaccaaattgttaaggactttgttacctatgccacaactgtgtttaagcgttatggtaatga agtcaagacgtggtttacttttcaatgaaccacgggtttctgttcacaaaatagtggtctgccatacaatctg acgtatccagaaggtattaacagcacctccgctgtatttcgttgcacctacaatgttctgaaagctcatggt catgctgttaaagtgtatcgggatctagttgcctccgggaccattgcggcaggtgaaatcggctttaaatc cgatgataactacccaatcccggcccgtccaggaacgccgatgacgaggaatcagccaagcgtcac gaggcttttcgcattgggattttttgcgcaaccggtttatggtaatggcgattatccagatgttgttaaagaa ctgttggagatatgctgccggccctgacggatgaagataaaggatacattaaaggtagcggagatattttt gcgattgacgggtatcgtaccgatatttcccatgcggctctgaacgggatcgcgaattgtattcgcaacc aaagtgacccgaattggccagtgtgtgaagaagggtcagatcctttgctcatgtttacccatccgggttt gctattggtcaatcagccgatccactgtcttcatggttagtcaactcagccccgtttatccgcgatcaactg aagtttctgacacaaacctaccctgctaaggtggtatttatttctcggaatttggttgggctgaagacgcc gaatatgatcgtcaactgctgtatcaaattacctgggatggtctgcgtacgcaatacctgacggactatct gagccagctgctgttggctgtgcacaaagacgggattaatctgcgaggcgcgctgacgtggagttttgt cgataattgggagtggggtttagggatgcaacagaaattcggatttcagttgttaatcaatcagatcccg atctgacacgcacgtttaaactgagcgctcacgcttacgcccaatttgggcgtaatcatctg |
| 9 | Synthetic β-hexosyl transferase (57-594) | AELDALWNLVEAQYPVQTAAVTTLVTVPDDYKFEADPPSYALA GYETSEIAGLKFPKGFKFGVAGAAIQVEGAAKAEGRGPSTWDYL CHHYASTQCNNYDPDITTNHYYLYPLDFARLQHLGINTYSFSISW TRIYPLGAGYVNEAGLAHYDAVIHSAKKYGLEPVGTVFHWDTPL SLMLKYGAWQDTGDQIVKDFVTYATTVFKRYGNEVKTWFTFNE PRVFCSQNSGLPYNLTYPEGINSTSAVFRCTYNVLKAHGHAVKV YRDLVASGTIAAGEIGFKSDDNYPIPARPGNADDEESAKRHEAFRI |

TABLE 5-continued

Sequences.

| SEQ ID NO: | Name | Sequence |
|---|---|---|
| | | GIFAQPVYGNGDYPDVVKETVGDMLPALTDEDKGYIKGSGDIFAI<br>DGYRTDISHAALNGIANCIRNQSDPNWPVCEEGSDPFAHVYPSGF<br>AIGQSADPLSSWLVNSAPFIRDQLKFLTQTYPAKGGIYFSEFGWA<br>EDAEYDRQLLYQITWDGLRTQYLTDYLSQLLLAVHKDGINLRGA<br>LTWSFVDNWEWGLGMQQKFGFQFVNQSDPDLTRTFKLSAHAYA<br>QFGRNHL |
| 10 | Synthetic ß-hexosyl transferase (57-594) | gcagaattagatgcgctgtggaacttagtcgaagctcagtacccagttcaaactgctgcagtgacaacttt<br>ggtgacagtgcccgatgattataagtttgaggcagatccaccgagttatgcattagcagggtatgaaaca<br>agcgagattgccggactgaagtttccaaaggggtttaagtttggtgttgcggggggcagccattcaagttg<br>aaggtgcagcaaaagccgaagggcggggcccaagtacctgggattatctgtgtcatcactatgccagc<br>acgcagtgtaacaattatgatcccgatattacaaccaaccattactacctgtacccattggactttgcgcgc<br>ctgcaacacctaggcattaacacttactcgttttcaatttcatggacgcgtatttatccattgggcgcaggct<br>atgttaatgaagcagggttagcccactatgatgccgtaatccatagtgccaagaagtatggtctggaacc<br>agtgggcaccgttttttcactgggatacgccactgtctctgatgctgaaatacggtgcctggcaagatactg<br>gtgaccaaattgttaaggactttgttacctatgccacaactgtgtttaagcgttatggtaatgaagtcaagac<br>gtggtttacttttcaatgaaccacgggttttctgttcacaaaatagtggtctgccatacaatctgacgtatcca<br>gaaggtattaacagcacctccgctgtatttcgttgcacctacaatgttctgaaagctcatggtcatgctgtta<br>aagtgtatcgggatctagttgcctccgggaccattgcggcaggtgaaatcggctttaaatccgatgataa<br>ctacccaatcccggcccgtccagggaacgccgatgacgaggaatcagccaagcgtcacgaggctttc<br>gcattgggattttttgcgcaaccggtttatggtaatggcgattatccagatgttgttaaagaaactgttggag<br>atatgctgccggccctgacggatgaagataaaggatacattaaaggtagcggagatattttttgcgattga<br>cgggtatcgtaccgatatttcccatgcggctctgaacgggatcgcgaattgtattcgcaaccaaagtgac<br>ccgaattggccagtgtgtgaagaagggtcagatccttttgctcatgtttacccatccgggtttgctattggtc<br>aatcagccgatccactgtcttcatggttagtcaactcagccccgtttatccgcgatcaactgaagtttctga<br>cacaaaacctaccctgctaagggtggtattatttctcggaatttggttgggctgaagacgccgaatatgatc<br>gtcaactgctgtatcaaattacctgggatggtctgcgtacgcaataacctgacggactatctgagccagctg<br>ctgttggctgtgcacaaagacgggattaatctgcgaggcgcgctgacgtggagtttttgtcgataattggg<br>agtgggg tttagggatgcaacagaaattcggatttcagtttgttaatcaatcagatcccgatctgacacgc<br>acgtttaaactgagcgctcacgcttacgcccaatttgggcgtaatcatctg |
| 11 | Synthetic ß-hexosyl transferase (82-594) | TVPDDYKFEADPPSYALAGYETSEIAGLKFPKGFKFGVAGAAIQV<br>EGAAKAEGRGPSTWDYLCHHYASTQCNNYDPDITTNHYYLYPL<br>DFARLQHLGINTYSFSISWTRIYPLGAGYVNEAGLAHYDAVIHSA<br>KKYGLEPVGTVFHWDTPLSLMLKYGAWQDTGDQIVKDFVTYAT<br>TVFKRYGNEVKTWFTFNEPRVFCSQNSGLPYNLTYPEGINSTSAV<br>FRCTYNVLKAHGHAVKVYRDLVASGTIAAGEIGFKSDDNYPIPA<br>RPGNADDEESAKRHEAFRIGIFAQPVYGNGDYPDVVKETVGDML<br>PALTDEDKGYIKGSGDIFAIDGYRTDISHAALNGIANCIRNQSDPN<br>WPVCEEGSDPFAHVYPSGFAIGQSADPLSSWLVNSAPFIRDQLKF<br>LTQTYPAKGGIYFSEFGWAEDAEYDRQLLYQITWDGLRTQYLTD<br>YLSQLLLAVHKDGINLRGALTWSFVDNWEWGLGMQQKFGFQFV<br>NQSDPDLTRTFKLSAHAYAQFGRNHL |
| 12 | Synthetic ß-hexosyl transferase (82-594) | acagtgcccgatgattataagtttgaggcagatccaccgagttatgcattagcagggtatgaaacaagcg<br>agattgccggactgaagtttccaaaggggtttaagtttggtgttgcggggggcagccattcaagttgaagg<br>tgcagcaaaagccgaagggggggcccaagtacctgggattatctgtgtcatcactatgccagcacgc<br>agtgtaacaattatgatcccgatattacaaccaaccattactacctgtacccattggactttgcgcgcctgc<br>aacacctaggcattaacacttactcgttttcaatttcatggacgcgtatttatccattgggcgcaggctatgtt<br>aatgaagcagggttagcccactatgatgccgtaatccatagtgccaagaagtatggtctggaaccagtg<br>ggcaccgttttttcactgggatacgccactgtctctgatgctgaaatacggtgcctggcaagatactggtga<br>ccaaattgttaaggactttgttacctatgccacaactgtgtttaagcgttatggtaatgaagtcaagacgtgg<br>tttacttttcaatgaaccacgggttttctgttcacaaaatagtggtctgccatacaatctgacgtatcagaag<br>gtattaacagcacctccgctgtatttcgttgcacctacaatgttctgaaagctcatggtcatgctgttaaagt<br>gtatcgggatctagttgcctccgggaccattgcggcaggtgaaatcggctttaaatccgatgataactac<br>ccaatcccggcccgtccagggaacgccgatgacgaggaatcagccaagcgtcacgaggcttttcgca<br>ttgggattttttgcgcaaccggtttatggtaatggcgattatccagatgttgttaaagaaactgttggagatat<br>gctgccggccctgacggatgaagataaaggatacattaaaggtagcggagatattttttgcgattgacgg<br>gtatcgtaccgatatttcccatgcggctctgaacgggatcgcgaattgtattcgcaaccaaagtgacccg<br>aattggccagtgtgtgaagaagggtcagatccttttgctcatgtttacccatccgggtttgctattggtcaat<br>cagccgatccactgtcttcatggttagtcaactcagccccgtttatccgcgatcaactgaagtttctgacac<br>aaaacctaccctgctaagggtggtattatttctcggaatttggttgggctgaagacgccgaatatgatcgtc<br>aactgctgtatcaaattacctgggatggtctgcgtacgcaataacctgacggactatctgagccagctgctgt<br>tggctgtgcacaaagacgggattaatctgcgaggcgcgctgacgtggagtttttgtcgataattgggagt<br>ggggtttagggatgcaacagaaattcggatttcagtttgttaatcaatcagatcccgatctgacacgcacg<br>tttaaactgagcgctcacgcttacgcccaatttgggcgtaatcatctg |
| 13 | Synthetic ß-hexosyl transferase (95-594) | SYALAGYETSEIAGLKFPKGFKFGVAGAAIQVEGAAKAEGRGPST<br>WDYLCHHYASTQCNNYDPDITTNHYYLYPLDFARLQHLGINTYS<br>FSISWTRIYPLGAGYVNEAGLAHYDAVIHSAKKYGLEPVGTVFH<br>WDTPLSLMLKYGAWQDTGDQIVKDFVTYATTVFKRYGNEVKT<br>WFTFNEPRVFCSQNSGLPYNLTYPEGINSTSAVFRCTYNVLKAHG<br>HAVKVYRDLVASGTIAAGEIGFKSDDNYPIPARPGNADDEESAKR<br>HEAFRIGIFAQPVYGNGDYPDVVKETVGDMLPALTDEDKGYIKG<br>SGDIFAIDGYRTDISHAALNGIANCIRNQSDPNWPVCEEGSDPFAH |

TABLE 5-continued

Sequences.

| SEQ ID NO: | Name | Sequence |
|---|---|---|
|  |  | VYPSGFAIGQSADPLSSWLVNSAPFIRDQLKFLTQTYPAKGGIYFS EFGWAEDAEYDRQLLYQITWDGLRTQYLTDYLSQLLLAVHKDGI NLRGALTWSFVDNWEWGLGMQQKFGFQFVNQSDPDLTRTFKLS AHAYAQFGRNHL |
| 14 | Synthetic ß-hexosyl transferase (95-594) | agttatgcattagcagggtatgaaacaagcgagattgccggactgaagtttccaaagggttttaagtttg gtgttgcgggggcagccattcaagttgaaggtgcagcaaaagccgaagggcggggcccaagtacctg ggattatctgtgtcatcactatgccagcacgcagtgtaacaattatgatcccgatattacaaccaaccatta ctacctgtacccattggactttgcgcgcctgcaacacctaggcattaacacttactcgttttcaatttcatgg acgcgtatttatccattgggcgcaggctatgttaatgaagcagggttagcccactatgatgccgtaatcca tagtgccaagaagtatggtctggaaccagtgggcaccgttttttcactgggatacgccactgtctctgatgc tgaaatacggtgcctggcaagatactggtgaccaaattgttaaggactttgttacctatgccacaactgtgt ttaagcgttatggtaatgaagtcaagacgtggtttacttttcaatgaaccacgggtttttctgttcacaaaatag tggtctgccatacaatctgacgtatccagaaggtattaacagcacctccgctgtatttcgttgcacctacaa tgttctgaaagctcatggtcatgctgttaaagtgtatcgggatctagttgcctccgggaccattgcggcag gtgaaatcggctttaaatccgatgataactacccaatcccggcccgtccagggaacgccgatgacgag gaatcagccaagcgtcacgaggcttttcgcattgggattttttgcgcaaccggtttatggtaatggcgattat ccagatgttgttaaagaaactgttggagatatgctgccggccctgacggatgaagataaaggatacatta aggtagcggagatattttttgcgattgacgggtatcgtaccgatatttcccatgcggctctgaacgggatc gcgaattgtattcgcaacaaagtgacccgaattggccagtgtgtgaagaaagggtcagatccttttgctc atgtttacccatccgggtttgctattggtcaatcagccgatccactgtcttcatggttagtcaactcagcccc gtttatccgcgatcaactgaagtttctgacacaaacctaccctgctaagggtggtatttatttctcggaatttg gttgggctgaagacgccgaatatgatcgtcaactgctgtatcaaattacctgggatggtctgcgtacgca ataccctgacggactatctgagccagctgctgttggctgtgcacaaagacgggattaatctgcgaggcgc gctgacgtggagttttgtcgataattgggagtgggggtttagggatgcaacagaaattcggatttcagtttgt taatcaatcagatcccgatctgacacgcacgtttaaactgagcgctcacgcttacgcccaatttgggcgta atcatctg |
| 15 | Synthetic ß-hexosyl transferase (103-594) | TSEIAGLKFPKGFKFGVAGAAIQVEGAAKAEGRGPSTWDYLCHH YASTQCNNYDPDITTNHYYLYPLDFARLQHLGINTYSFSISWTRIY PLGAGYVNEAGLAHYDAVIHSAKKYGLEPVGTVFHWDTPLSLM LKYGAWQDTGDQIVKDFVTYATTVFKRYGNEVKTWFTFNEPRV FCSQNSGLPYNLTYPEGINSTSAVFRCTYNVLKAHGHAVKVYRD LVASGTIAAGEIGFKSDDNYPIPARPGNADDEESAKRHEAFRIGIF AQPVYGNGDYPDVVKETVGDMLPALTDEDKGYIKGSGDIFAIDG YRTDISHAALNGIANCIRNQSDPNWPVCEEGSDPFAHVYPSGFAI GQSADPLSSWLVNSAPFIRDQLKFLTQTYPAKGGIYFSEFGWAED AEYDRQLLYQITWDGLRTQYLTDYLSQLLLAVHKDGINLRGALT WSFVDNWEWGLGMQQKFGFQFVNQSDPDLTRTFKLSAHAYAQF GRNHL |
| 16 | Synthetic ß-hexosyl transferase (103-594) | acaagcgagattgccggactgaagtttccaaagggttttaagtttggtgttgcgggggcagccattcaa gttgaaggtgcagcaaaagccgaagggcggggcccaagtacctgggattatctgtgtcatcactatgcc agcacgcagtgtaacaattatgatcccgatattacaaccaaccattactacctgtacccattggactttgcg cgcctgcaacacctaggcattaacacttactcgttttcaatttcatggacgcgtatttatccattgggcgcag gctatgttaatgaagcagggttagcccactatgatgccgtaatccatagtgccaagaagtatggtctgga accagtgggcaccgttttttcactgggatacgccactgtctctgatgctgaaatacggtgcctggcaagat actggtgaccaaattgttaaggactttgttacctatgccacaactgtgtttaagcgttatggtaatgaagtca gacgtggtttacttttcaatgaaccacgggtttttctgttcacaaaatagtggtctgccatacaatctgacgta tccagaaggtattaacagcacctccgctgtatttcgttgcacctacaatgttctgaaagctcatggtcatgct gttaaagtgtatcgggatctagttgcctccgggaccattgcggcaggtgaaatcggctttaaatccgatga taactacccaatcccggcccgtccagggaacgccgatgacgaggaatcagccaagcgtcacgaggct tttcgcattgggattttttgcgcaaccggtttatggtaatggcgattatccagatgttgttaaagaaactgttgg agatatgctgccggccctgacggatgaagataaaggatacattaaggtagcggagatattttttgcgatt gacgggtatcgtaccgatatttcccatgcggctctgaacgggatcgcgaattgtattcgcaaccaaagtg acccgaattggccagtgtgtgaagaaagggtcagatccttttgctcatgtttacccatccgggtttgctattg gtcaatcagccgatccactgtcttcatggttagtcaactcagccccgtttatccgcgatcaactgaagtttct gacacaaacctaccctgctaagggtggtatttatttctcggaatttggttgggctgaagacgccgaatatg atcgtcaactgctgtatcaaattacctgggatggtctgcgtacgcaataccctgacggactatctgagccag ctgctgttggctgtgcacaaagacgggattaatctgcgaggcgcgctgacgtggagttttgtcgataattg ggagtgggggtttagggatgcaacagaaattcggatttcagtttgttaatcaatcagatcccgatctgacac gcacgtttaaactgagcgctcacgcttacgcccaatttgggcgtaatcatctg |
| 17 | Synthetic ß-hexosyl transferase (111-594) | FPKGFKFGVAGAAIQVEGAAKAEGRGPSTWDYLCHHYASTQCN NYDPDITTNHYYLYPLDFARLQHLGINTYSFSISWTRIYPLGAGYV NEAGLAHYDAVIHSAKKYGLEPVGTVFHWDTPLSLMLKYGAWQ DTGDQIVKDFVTYATTVFKRYGNEVKTWFTFNEPRVFCSQNSGL PYNLTYPEGINSTSAVFRCTYNVLKAHGHAVKVYRDLVASGTIA AGEIGFKSDDNYPIPARPGNADDEESAKRHEAFRIGIFAQPVYGN GDYPDVVKETVGDMLPALTDEDKGYIKGSGDIFAIDGYRTDISHA ALNGIANCIRNQSDPNWPVCEEGSDPFAHVYPSGFAIGQSADPLSS WLVNSAPFIRDQLKFLTQTYPAKGGIYFSEFGWAEDAEYDRQLL YQITWDGLRTQYLTDYLSQLLLAVHKDGINLRGALTWSFVDNW EWGLGMQQKFGFQFVNQSDPDLTRTFKLSAHAYAQFGRNHL |

TABLE 5-continued

<div style="text-align:center">Sequences.</div>

| SEQ ID NO: | Name | Sequence |
|---|---|---|
| 18 | Synthetic ß-hexosyl transferase (111-594) | tttccaaaggggtttaagtttggtgttgcgggggcagccattcaagttgaaggtgcagcaaaagccgaa<br>gggcggggcccaagtacctgggattatctgtgtcatcactatgccagcacgcagtgtaacaattatgatc<br>ccgatattacaaccaaccattactacctgtacccattggactttgcgcgcctgcaacacctaggcattaac<br>acttactcgttttcaatttcatggacgcgtgatttatccattgggcgcaggctatgttaatgaagcagggttag<br>cccactatgatgccgtaatccatagtgccaagaagtatggtctggaaccagtgggcaccgtttttcactgg<br>gatacgccactgtctctgatgctgaaatacggtgcctggcaagatactggtgaccaaattgttaaggactt<br>tgttacctatgccacaactgtgtttaagcgttatggtaatgaagtcaagacgtggtttactttcaatgaacca<br>cgggtttttctgttcacaaaatagtggtctgccatacaatctgacgtatccagaaggtattaacagcacctcc<br>gctgtatttcgttgcacctacaatgttctgaaagctcatggtcatgctgttaaagtgtatcgggatctagttgc<br>ctccgggaccattgcggcaggtgaaatcggctttaaatccgatgataactacccaatcccggcccgtcc<br>agggaacgccgatgacgaggaatcagccaagcgtcacgaggcttttcgcattgggattttgcgcaacc<br>ggtttatggtaatggcgattatccagatgttgttaaagaaactgttggagatatgctgccggccctgacgg<br>atgaagataaaggatacattaaaggtagcggagatattttttgcgattgacgggtatcgtaccgatatttccc<br>atgcggctctgaacgggatcgcgaattgtattcgcaaccaaagtgacccgaattggccagtgtgtgaag<br>aagggtcagatcctttttgctcatgtttacccatccgggtttgctattggtcaatcagccgatccactgtcttca<br>tggttagtcaactcagccccgtttatccgcgatcaactgaagtttctgacacaaacctaccctgctaaggg<br>tggtatttatttctcggaattttggttgggctgaagacgccgaatatgatcgtcaactgctgtatcaaattacct<br>gggatggtctgcgtacgcaatacctgacggactatctgagccagctgctgttggctgtgcacaaagacg<br>ggattaatctgcgaggcgcgctgacgtggagtttgtcgataattgggagtggggtttagggatgcaaca<br>gaaattcggatttcagtttgttaatcaatcagatcccgatctgacacgcacgtttaaactgagcgctcacgc<br>ttacgcccaatttgggcgtaatcatctg |
| 19 | Synthetic ß-hexosyl transferase (23-594) (N289Q) | VTYPGAIPLSLTSNYETPSPTAIPLEPTPTATGTAELDALWNLVEA<br>QYPVQTAAVTTLVTVPDDYKFEADPPSYALAGYETSEIAGLKFPK<br>GFKFGVAGAAIQVEGAAKAEGRGPSTWDYLCHHYASTQCNNYD<br>PDITTNHYYLYPLDFARLQHLGINTYSFSISWTRIYPLGAGYVNEA<br>GLAHYDAVIHSAKKYGLEPVGTVFHWDTPLSLMLKYGAWQDTG<br>DQIVKDFVTYATTVFKRYGNEVKTWFTFNEPRVFCSQNSGLPYQ<br>LTYPEGINSTSAVFRCTYNVLKAHGHAVKVYRDLVASGTIAAGEI<br>GFKSDDNYPIPARPGNADDEESAKRHEAFRIGIFAQPVYGNGDYP<br>DVVKETVGDMLPALTDEDKGYIKGSGDIFAIDGYRTDISHAALNG<br>IANCIRNQSDPNWPVCEEGSDPFAHVYPSGFAIGQSADPLSSWLV<br>NSAPFIRDQLKFLTQTYPAKGGIYFSEFGWAEDAEYDRQLLYQIT<br>WDGLRTQYLTDYLSQLLLAVHKDGINLRGALTWSFVDNWEWGL<br>GMQQKFGFQFVNQSDPDLTRTFKLSAHAYAQFGRNHL |
| 20 | Synthetic ß-hexosyl transferase (23-594) (N289Q) | GTTACTTATCCGGGAGCCATTCCTCTGTCCCTGACGAGCAATT<br>ACGAAACCCCAAGTCCGACAGCAATCCCGCTGGAGCCAACAC<br>CGACGGCTACCGGTACAGCAGAATTAGATGCGCTGTGGAACTT<br>AGTCGAAGCTCAGTACCCAGTTCAAACTGCTGCAGTGACAACT<br>TTGGTGACAGTGCCCGATGATTATAAGTTTGAGGCAGATCCAC<br>CGAGTTATGCATTAGCAGGGTATGAAACAAGCGAGATTGCCG<br>GACTGAAGTTTCCAAAGGGGTTTAAGTTTGGTGTTGCGGGGGC<br>AGCCATTCAAGTTGAAGGTGCAGCAAAAGCCGAAGGGCGGGG<br>CCCAAGTACCTGGGATTATCTGTGTCATCACTATGCCAGCACG<br>CAGTGTAACAATTATGATCCCGATATTACAACCAACCATTACT<br>ACCTGTACCCATTGGACTTTGCGCGCCTGCAACACCTAGGCAT<br>TAACACTTACTCGTTTTCAATTTCATGGACGCGTATTTATCCAT<br>TGGGCGCAGGCTATGTTAATGAAGCAGGGTTAGCCCACTATGA<br>TGCCGTAATCCATAGTGCCAAGAAGTATGGTCTGGAACCAGTG<br>GGCACCGTTTTTCACTGGGATACGCCACTGTCTCTGATGCTGA<br>AATACGGTGCCTGGCAAGATACTGGTGACCAAATTGTTAAGG<br>ACTTTGTTACCTATGCCACAACTGTGTTTAAGCGTTATGGTAAT<br>GAAGTCAAGACGTGGTTTACTTTCAATGAACCACGGGTTTTCT<br>GTTCACAAAATAGTGGTCTGCCATACCAGCTTACGTATCCAGA<br>AGGTATTAACAGCACCTCCGCTGTATTTCGTTGCACCTACAAT<br>GTTCTGAAAGCTCATGGTCATGCTGTTAAAGTGTATCGGGATC<br>TAGTTGCCTCCGGGACCATTGCGGCAGGTGAAATCGGCTTTAA<br>ATCCGATGATAACTACCCAATCCCGGCCCGTCCAGGGAACGCC<br>GATGACGAGGAATCAGCCAAGCGTCACGAGGCTTTTCGCATTG<br>GGATTTTTGCGCAACCGGTTTATGGTAATGGCGATTATCCAGA<br>TGTTGTTAAAGAAACTGTTGGAGATATGCTGCCGGCCCTGACG<br>GATGAAGATAAAGGATACATTAAAGGTAGCGGAGATATTTTTT<br>GCGATTGACGGGTATCGTACCGATATTTCCCATGCGGCTCTGA<br>ACGGGATCGCGAATTGTATTCGCAACCAAAGTGACCCGAATTG<br>GCCAGTGTGTGAAGAAGGGTCAGATCCTTTTTGCTCATGTTTAC<br>CCATCCGGGTTTGCTATTGGTCAATCAGCCGATCCACTGTCTTC<br>ATGGTTAGTCAACTCAGCCCCGTTTATCCGCGATCAACTGAAG<br>TTTCTGACACAAACCTACCCTGCTAAGGGTGGTATTTATTTCTC<br>GGAATTTGGTTGGGCTGAAGACGCCGAATATGATCGTCAACTG<br>CTGTATCAAATTACCTGGGATGGTCTGCGTACGCAATACCTGA<br>CGGACTATCTGAGCCAGCTGCTGTTGGCTGTGCACAAAGACGG |

TABLE 5-continued

Sequences.

| SEQ ID NO: | Name | Sequence |
|---|---|---|
| | | GATTAATCTGCGAGGCGCGCTGACGTGGAGTTTTGTCGATAAT<br>TGGGAGTGGGGTTTAGGGATGCAACAGAAATTCGGATTTCAGT<br>TTGTTAATCAATCAGATCCCGATCTGACACGCACGTTTAAACT<br>GAGCGCTCACGCTTACGCCCAATTTGGGCGTAATCATCTG |
| 21 | Synthetic ß-<br>hexosyl<br>transferase<br>(23-594)<br>(N297Q) | VTYPGAIPLSLTSNYETPSPTAIPLEPTPTATGTAELDALWNLVEA<br>QYPVQTAAVTTLVTVPDDYKFEADPPSYALAGYETSEIAGLKFPK<br>GFKFGVAGAAIQVEGAAKAEGRGPSTWDYLCHHYASTQCNNYD<br>PDITTNHYYLYPLDFARLQHLGINTYSFSISWTRIYPLGAGYVNEA<br>GLAHYDAVIHSAKKYGLEPVGTVFHWDTPLSLMLKYGAWQDTG<br>DQIVKDFVTYATTVFKRYGNEVKTWFTFNEPRVFCSQNSGLPYN<br>LTYPEGIQSTSAVFRCTYNVLKAHGHAVKVYRDLVASGTIAAGEI<br>GFKSDDNYPIPARPGNADDEESAKRHEAFRIGIFAQPVYGNGDYP<br>DVVKETVGDMLPALTDEDKGYIKGSGDIFAIDGYRTDISHAALNG<br>IANCIRNQSDPNWPVCEEGSDPFAHVYPSGFAIGQSADPLSSWLV<br>NSAPFIRDQLKFLTQTYPAKGGIYFSEFGWAEDAEYDRQLLYQIT<br>WDGLRTQYLTDYLSQLLLAVHKDGINLRGALTWSFVDNWEWGL<br>GMQQKFGFQFVNQSDPDLTRTFKLSAHAYAQFGRNHL |
| 22 | Synthetic ß-<br>hexosyl<br>transferase<br>(23-594)<br>(N297Q) | GTTACTTATCCGGGAGCCATTCCTCTGTCCCTGACGAGCAATT<br>ACGAAACCCCAAGTCCGACAGCAATCCCGCTGGAGCCAACAC<br>CGACGGCTACCGGTACAGCAGAATTAGATGCGCTGTGGAACTT<br>AGTCGAAGCTCAGTACCCAGTTCAAACTGCTGCAGTGACAACT<br>TTGGTGACAGTGCCCGATGATTATAAGTTTGAGGCAGATCCAC<br>CGAGTTATGCATTAGCAGGGTATGAAACAAGCGAGATTGCCG<br>GACTGAAGTTTCCAAAGGGGTTTAAGTTTGGTGTTGCGGGGGC<br>AGCCATTCAAGTTGAAGGTGCAGCAAAAGCCGAAGGGCGGGG<br>CCCAAGTACCTGGGATTATCTGTGTCATCACTATGCCAGCACG<br>CAGTGTAACAATTATGATCCCGATATTACAACCAACCATTACT<br>ACCTGTACCCATTGGACTTTGCGCGCCTGCAACACCTAGGCAT<br>TAACACTTACTCGTTTTCAATTTCATGGACGCGTATTTATCCAT<br>TGGGCGCAGGCTATGTTAATGAAGCAGGGTTAGCCCACTATGA<br>TGCCGTAATCCATAGTGCCAAGAAGTATGGTCTGGAACCAGTG<br>GGCACCGTTTTTCACTGGGATACGCCACTGTCTCTGATGCTGA<br>AATACGGTGCCTGGCAAGATACTGGTGACCAAATTGTTAAGG<br>ACTTTGTTACCTATGCCACAACTGTGTTTAAGCGTTATGGTAAT<br>GAAGTCAAGACGTGGTTTACTTTCAATGAACCACGGGTTTTCT<br>GTTCACAAAATAGTGGTCTGCCATACAATCTGACGTATCCAGA<br>AGGGATCCAGAGCACCTCCGCTGTATTTCGTTGCACCTACAAT<br>GTTCTGAAAGCTCATGGTCATGCTGTTAAAGTGTATCGGGATC<br>TAGTTGCCTCCGGGACCATTGCGGCAGGTGAAATCGGCTTTAA<br>ATCCGATGATAACTACCCAATCCCGGCCCGTCCAGGGAACGCC<br>GATGACGAGGAATCAGCCAAGCGTCACGAGGCTTTTCGCATTG<br>GGATTTTTGCGCAACCGGTTTATGGTAATGGCGATTATCCAGA<br>TGTTGTTAAAGAAACTGTTGGAGATATGCTGCCGGCCCTGACG<br>GATGAAGATAAAGGATACATTAAAGGTAGCGGAGATATTTTT<br>GCGATTGACGGGTATCGTACCGATATTTCCCATGCGGCTCTGA<br>ACGGGATCGCGAATTGTATTCGCAACCAAAGTGACCCGAATTG<br>GCCAGTGTGTGAAGAAGGGTCAGATCCTTTTGCTCATGTTTAC<br>CCATCTCGGGTTTGCTATTGGTCAATCAGCCGATCCACTGTCTTC<br>ATGGTTAGTCAACTCAGCCCCGTTTATCCGCGATCAACTGAAG<br>TTTCTGACACAAACCTACCCTGCTAAGGGTGGTATTTATTTCTC<br>GGAATTTGGTTGGGCTGAAGACGCCGAATATGATCGTCAACTG<br>CTGTATCAAATTACCTGGGATGGTCTGCGTACGCAATACCTGA<br>CGGACTATCTGAGCCAGCTGCTGTTGGCTGTGCACAAAGACGG<br>GATTAATCTGCGAGGCGCGCTGACGTGGAGTTTTGTCGATAAT<br>TGGGAGTGGGGTTTAGGGATGCAACAGAAATTCGGATTTCAGT<br>TTGTTAATCAATCAGATCCCGATCTGACACGCACGTTTAAACT<br>GAGCGCTCACGCTTACGCCCAATTTGGGCGTAATCATCTG |
| 23 | Synthetic ß-<br>hexosyl<br>transferase<br>(23-594)<br>(N431Q) | VTYPGAIPLSLTSNYETPSPTAIPLEPTPTATGTAELDALWNLVEA<br>QYPVQTAAVTTLVTVPDDYKFEADPPSYALAGYETSEIAGLKFPK<br>GFKFGVAGAAIQVEGAAKAEGRGPSTWDYLCHHYASTQCNNYD<br>PDITTNHYYLYPLDFARLQHLGINTYSFSISWTRIYPLGAGYVNEA<br>GLAHYDAVIHSAKKYGLEPVGTVFHWDTPLSLMLKYGAWQDTG<br>DQIVKDFVTYATTVFKRYGNEVKTWFTFNEPRVFCSQNSGLPYN<br>LTYPEGINSTSAVFRCTYNVLKAHGHAVKVYRDLVASGTIAAGEI<br>GFKSDDNYPIPARPGNADDEESAKRHEAFRIGIFAQPVYGNGDYP<br>DVVKETVGDMLPALTDEDKGYIKGSGDIFAIDGYRTDISHAAL<br>NGIANCIRQQSDPNWPVCEEGSDPFAHVYPSGFAIGQSADPLSSW<br>LVNSAPFIRDQLKFLTQTYPAKGGIYFSEFGWAEDAEYDRQLLYQ<br>ITWDGLRTQYLTDYLSQLLLAVHKDGINLRGALTWSFVDNWEW<br>GLGMQQKFGFQFVNQSDPDLTRTFKLSAHAYAQFGRNHL |

TABLE 5-continued

Sequences.

| SEQ ID NO: | Name | Sequence |
|---|---|---|
| 24 | Synthetic ß-hexosyl transferase (23-594) (N431Q) | GTTACTTATCCGGGAGCCATTCCTCTGTCCCTGACGAGCAATT ACGAAACCCCAAGTCCGACAGCAATCCCGCTGGAGCCAACAC CGACGGCTACCGGTACAGCAGAATTAGATGCGCTGTGGAACTT AGTCGAAGCTCAGTACCCAGTTCAAACTGCTGCAGTGACAACT TTGGTGACAGTGCCCGATGATTATAAGTTTGAGGCAGATCCAC CGAGTTATGCATTAGCAGGGTATGAAACAAGCGAGATTGCCG GACTGAAGTTTCCAAAGGGGTTTAAGTTTGGTGTTGCGGGGGC AGCCATTCAAGTTGAAGGTGCAGCAAAAGCCGAAGGGCGGGG CCCAAGTACCTGGGATTATCTGTGTCATCACTATGCCAGCACG CAGTGTAACAATTATGATCCCGATATTACAACCAACCATTACT ACCTGTACCCATTGGACTTTGCGCGCCTGCAACACCTAGGCAT TAACACTTACTCGTTTTCAATTTCATGGACGCGTATTTATCCAT TGGGCGCAGGCTATGTTAATGAAGCAGGGTTAGCCCACTATGA TGCCGTAATCCATAGTGCCAAGAAGTATGGTCTGGAACCAGTG GGCACCGTTTTTCACTGGGATACGCCACTGTCTCTGATGCTGA AATACGGTGCCTGGCAAGATACTGGTGACCAAATTGTTAAGG ACTTTGTTACCTATGCCACAACTGTGTTTAAGCGTTATGGTAAT GAAGTCAAGACGTGGTTTACTTTCAATGAACCACGGGTTTTCT GTTCACAAAATAGTGGTCTGCCATACAATCTGACGTATCCAGA AGGTATTAACAGCACCTCCGCTGTATTTCGTTGCACCTACAAT GTTCTGAAAGCTCATGGTCATGCTGTTAAAGTGTATCGGGAT CTAGTTGCCTCCGGGACCATTGCGGCAGGTGAAATCGGCTTTA AATCCGATGATAACTACCCAATCCCGGCCCGTCCAGGGAACGC CGATGACGAGGAATCAGCCAAGCGTCACGAGGCTTTTCGCATT GGGATTTTTGCGCAACCGGTTTATGGTAATGGCGATTATCCAG ATGTTGTTAAAGAAACTGTTGGAGATATGCTGCCGGCCCTGAC GGATGAAGATAAAGGATACATTAAAGGTAGCGGAGATATTTT TGCGATTGACGGGTATCGTACCGATATTTCCCATGCGGCTCTG AACGGGATCGCGAATTGTATTCGCCAGCAATCGGATCCGAATT GGCCAGTGTGTGAAGAAGGGTCAGATCCTTTTGCTCATGTTTA CCCATCCGGGTTTGCTATTGGTCAATCAGCCGATCCACTGTCTT CATGGTTAGTCAACTCAGCCCCGTTTATCCGCGATCAACTGAA GTTTCTGACACAAACCTACCCTGCTAAGGGTGGTATTTATTTCT CGGAATTTGGTTGGGCTGAAGACGCCGAATATGATCGTCAACT GCTGTATCAAATTACCTGGGATGGTCTGCGTACGCAATACCTG ACGGACTATCTGAGCCAGCTGCTGTTGGCTGTGCACAAAGACG GGATTAATCTGCGAGGCGCGCTGACGTGGAGTTTTGTCGATAA TTGGGAGTGGGGTTTAGGGATGCAACAGAAATTCGGATTTCAG TTTGTTAATCAATCAGATCCCGATCTGACACGCACGTTTAAAC TGAGCGCTCACGCTTACGCCCAATTTGGGCGTAATCATCTG |
| 25 | Synthetic ß-hexosyl transferase (23-594) (N569Q) | VTYPGAIPLSLTSNYETPSPTAIPLEPTPTATGTAELDALWNLVEA QYPVQTAAVTTLVTVPDDYKFEADPPSYALAGYETSEIAGLKFPK GFKFGVAGAAIQVEGAAKAEGRGPSTWDYLCHHYASTQCNNYD PDITTNHYYLYPLDFARLQHLGINTYSFSISWTRIYPLGAGYVNEA GLAHYDAVIHSAKKYGLEPVGTVFHWDTPLSLMLKYGAWQDTG DQIVKDFVTYATTVFKRYGNEVKTWFTFNEPRVFCSQNSGLPYN LTYPEGINSTSAVFRCTYNVLKAHGHAVKVYRDLVASGTIAAGEI GFKSDDNYPIPARPGNADDEESAKRHEAFRIGIFAQPVYGNGDYP DVVKETVGDMLPALTDEDKGYIKGSGDIFAIDGYRTDISHAALNG IANCIRNQSDPNWPVCEEGSDPFAHVYPSGFAIGQSADPLSSWLV NSAPFIRDQLKFLTQTYPAKGGIYFSEFGWAEDAEYDRQLLYQIT WDGLRTQYLTDYLSQLLLAVHKDGINLRGALTWSFVDNWEWGL GMQQKFGFQFVQQSDPDLTRTFKLSAHAYAQFGRNHL |
| 26 | Synthetic ß-hexosyl transferase (23-594) (N569Q) | GTTACTTATCCGGGAGCCATTCCTCTGTCCCTGACGAGCAATT ACGAAACCCCAAGTCCGACAGCAATCCCGCTGGAGCCAACAC CGACGGCTACCGGTACAGCAGAATTAGATGCGCTGTGGAACTT AGTCGAAGCTCAGTACCCAGTTCAAACTGCTGCAGTGACAACT TTGGTGACAGTGCCCGATGATTATAAGTTTGAGGCAGATCCAC CGAGTTATGCATTAGCAGGGTATGAAACAAGCGAGATTGCCG GACTGAAGTTTCCAAAGGGGTTTAAGTTTGGTGTTGCGGGGGC AGCCATTCAAGTTGAAGGTGCAGCAAAAGCCGAAGGGCGGGG CCCAAGTACCTGGGATTATCTGTGTCATCACTATGCCAGCACG CAGTGTAACAATTATGATCCCGATATTACAACCAACCATTACT ACCTGTACCCATTGGACTTTGCGCGCCTGCAACACCTAGGCAT TAACACTTACTCGTTTTCAATTTCATGGACGCGTATTTATCCAT TGGGCGCAGGCTATGTTAATGAAGCAGGGTTAGCCCACTATGA TGCCGTAATCCATAGTGCCAAGAAGTATGGTCTGGAACCAGTG GGCACCGTTTTTCACTGGGATACGCCACTGTCTCTGATGCTGA AATACGGTGCCTGGCAAGATACTGGTGACCAAATTGTTAAGG ACTTTGTTACCTATGCCACAACTGTGTTTAAGCGTTATGGTAAT GAAGTCAAGACGTGGTTTACTTTCAATGAACCACGGGTTTTCT GTTCACAAAATAGTGGTCTGCCATACAATCTGACGTATCCAGA AGGTATTAACAGCACCTCCGCTGTATTTCGTTGCACCTACAAT |

TABLE 5-continued

Sequences.

| SEQ ID NO: | Name | Sequence |
|---|---|---|
| | | GTTCTGAAAGCTCATGGTCATGCTGTTAAAGTGTATCGGGATC<br>TAGTTGCCTCCGGGACCATTGCGGCAGGTGAAATCGGCTTTAA<br>ATCCGATGATAACTACCCAATCCCGGCCCGTCCAGGGAACGCC<br>GATGACGAGGAATCAGCCAAGCGTCACGAGGCTTTTCGCATTG<br>GGATTTTTGCGCAACCGGTTTATGGTAATGGCGATTATCCAGA<br>TGTTGTTAAAGAAACTGTTGGAGATATGCTGCCGGCCCTGACG<br>GATGAAGATAAAGGATACATTAAAGGTAGCGGAGATATTTTT<br>GCGATTGACGGGTATCGTACCGATATTTCCCATGCGGCTCTGA<br>ACGGGATCGCGAATTGTATTCGCAACCAAAGTGACCCGAATTG<br>GCCAGTGTGTGAAGAAGGGTCAGATCCTTTTGCTCATGTTTAC<br>CCATCCGGGTTTGCTATTGGTCAATCAGCCGATCCACTGTCTTC<br>ATGGTTAGTCAACTCAGCCCCGTTTATCCGCGATCAACTGAAG<br>TTTCTGACACAAACCTACCCTGCTAAGGGTGGTATTTATTTCTC<br>GGAATTTGGTTGGGCTGAAGACGCCGAATATGATCGTCAACTG<br>CTGTATCAAATTACCTGGGATGGTCTGCGTACGCAATACCTGA<br>CGGACTATCTGAGCCAGCTGCTGTTGGCTGTGCACAAAGACGG<br>GATTAATCTGCGAGGCGCGCTGACGTGGAGTTTTGTCGATAAT<br>TGGGAGTGGGGTTTAGGGATGCAACAGAAATTCGGATTTCAGT<br>TTGTTCAGCAATCGGATCCCGATCTGACACGCACGTTTAAACT<br>GAGCGCTCACGCTTACGCCCAATTTGGGCGTAATCATCTG |
| 27 | α-mating factor signal sequence from *Saccharomyces cerevisiae* (MFα) | MRFPSIFTAVLFAASSALAAPVNTTTEDETAQIPAEAVIGYSDLEG<br>DFDVAVLPFSNSTNNGLLFINTTIASIAAKEEGVSLEKREAEA |
| 28 | α-mating factor signal sequence from *Saccharomyces cerevisiae* (MFα) | atgagatttccttcaattttttactgcagtttttattcgcagcatcctccgcattagctgctccagtcaacactaca<br>acagaagatgaaacggcacaaattccggctgaagctgtcatcggttactcagatttagaaggggatttcg<br>atgttgctgtttttgccattttttccaacagcacaaataacgggttattgtttataaatactactattgccagcattg<br>ctgctaaagaagaaggggtatctctcgagaaaagagaggctgaagct |
| 29 | α-mating factor signal sequence from *Saccharomyces cerevisiae* (MFα) (57-60) | MRFPSIFTAVLFAASSALAAPVNTTTEDETAQIPAEAVIGYSDLEG<br>DFDVAVLPFSASIAAKEEGVS |
| 30 | Invertase (IV) signal sequence | MLLQAFLFLLAGFAAKISA |
| 31 | Glucoamylase (GA) signal sequence | MSFRSLLALSGLVCSGLA |
| 32 | Inulinase (IN) signal sequence | MKLAYSLLLPLAGVSA |
| 33 | MFα-rBht$_{(1-594)}$-HIS (nucleic acid) | atgagatttccttcaattttttactgcagtttttattcgcagcatcctccgcattagctgctccagtcaacactaca<br>acagaagatgaaacggcacaaattccggctgaagctgtcatcggttactcagatttagaaggggatttcg<br>atgttgctgtttttgccattttttccaacagcacaaataacgggttattgtttataaatactactattgccagcattg<br>ctgctaaagaagaaggggtatctctcgagaaaagagaggctgaagct<br>tagtagcgctgccatgtgttgttttggcgcgcccggccggagcggttacttatccgggagccattcctctg<br>tccctgacgagcaattacgaaaccccaagtccgacagcaatcccgctggagccaacaccgacggcta<br>ccggtacagcagaattagatgcgctgtgtgaacttagtcgaagctcagtacccagttcaaactgctgcagt<br>gacaactttggtgacagtgcccgatgattataagtttgaggcagatccaccgagttatgcattagcagggt<br>atgaaacaagcgagattgccggactgaagtttccaaaggggtttaagtttggtgttgcgggggcagcca<br>ttcaagttgaaggtgcagcaaaagccgaagggcggggcccaagtacctgggattatctgtgtcatcact<br>atgccagcacgcagtgtaacaattatgatcccgatattacaaccaaccattactacctgtacccattggact<br>ttgcgcgcctgcaacacctaggcattaacacttactcgttttcaatttcatggacgcgtatttatccattggg<br>cgcaggctatgttaatgaagcagggttagcccactatgatgccgtaatccatagtgccaagaagtatggt<br>ctggaaccagtgggcaccgtttttcactgggatacgccactgtctctgatgctgaaatacggtgcctggc<br>aagatactggtgaccaaattgttaaggactttgttacctatgccacaactgtgtttaagcgttatggtaatga<br>agtcaagatcggtggttcatccgatgcggtttttctgttcacaaaatagtggtctgcgccatacaatctg<br>acgtatccagaaggtattaacagcacctccgctgtatttcgttgcacctacaatgttctgaaagctcatggt<br>catgctgttaaagtgtatcgggatctagttgcctccgggaccattgcggcaggtgaaatcggctttaaatc<br>cgatgataactacccaatcccggcccgtccagggaacgccgatgacgaggaatcagccaagcgtcac<br>gaggcttttcgcattgggattttttgcgcaaccggtttatggtaatggcgattatccagatgttgttaaagaaa<br>ctgttggagatatgctgccggccctgacggatgaagataaaggatacattaaaggtagcggagatattttt |

TABLE 5-continued

Sequences.

| SEQ ID NO: | Name | Sequence |
|---|---|---|
| | | gcgattgacgggtatcgtaccgatatttcccatgcggctctgaacgggatcgcgaattgtattcgcaacc aaagtgacccgaattggccagtgtgtgaagaagggtcagatcctttgtctcatgtttacccatccgggttt gctattggtcaatcagccgatccactgtcttcatggttagtcaactcagccccgtttatccgcgatcaactg aagtttctgacacaaacctaccctgctaagggtggtatttatttctcggaatttggttgggctgaagacgcc gaatatgatcgtcaactgctgtatcaaattacctgggatggtctgcgtacgcaatacctgacggactatct gagccagctgctgttggctgtgcacaaagacgggattaatctgcgaggcgcgctgacgtggagttttgt cgataattgggagtgggggtttagggatgcaacagaaattcggatttcagtttgttaatcaatcagatcccg atctgacacgcacgtttaaactgagcgctcacgcttacgcccaatttgggcgtaatcatctgcaccacca ccaccactaa |
| 34 | MFα-rBht $_{(1-594)}$-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEAMM LHAALLVALPCVVLARPAGAVTYPGAIPLSLTSNYETPSPTAIPLE PTPTATGTAELDALWNLVEAQYPVQTAAVTTLVTVPDDYKFEAD PPSYALAGYETSEIAGLKFPKGFKFGVAGAAIQVEGAAKAEGRGP STWDYLCHHYASTQCNNYDPDITTNHYYLYPLDFARLQHLGINT YSFSISWTRIYPLGAGYVNEAGLAHYDAVIHSAKKYGLEPVGTVF HWDTPLSLMLKYGAWQDTGDQIVKDFVTYATTVFKRYGNEVKT WFTFNEPRVFCSQNSGLPYNLTYPEGINSTSAVFRCTYNVLKAHG HAVKVYRDLVASGTIAAGEIGFKSDDNYPIPARPGNADDEESAKR HEAFRIGIFAQPVYGNGDYPDVVKETVGDMLPALTDEDKGYIKG SGDIFAIDGYRTDISHAALNGIANCIRNQSDPNWPVCEEGSDPFAH VYPSGFAIGQSADPLSSWLVNSAPFIRDQLKFLTQTYPAKGGIYFS EFGWAEDAEYDRQLLYQITWDGLRTQYLTDYLSQLLLAVHKDGI NLRGALTWSFVDNWEWGLGMQQKFGFQFVNQSDPDLTRTFKLS AHAYAQFGRNHLHHHHHH |
| 35 | rBht $_{(1-594)}$-HIS (nucleic acid) | atgatgctgcatgctgcactgctagtagcgctgccatgtgttgttgttttggcgcgcccggccggagcggtta cttatccgggagccattcctcctctgtccctgacgagcaattacgaaaccccaagtccgacagcaatcccgct ggagccaacaccgacggctaccggtacagcagaattagatgcgctgtggaacttagtcgaagctcagt acccagttcaaactgctgcagtgacaactttggtgacagtgcccgatgattataagtttgaggcagatcca ccgagttatgcattagcagggtatgaaacaagcgagattgccggactgaagtttccaaaggggtttaagt ttggtgttgcgggggcagccattcaagttgaaggtgcagcaaaagccgaaggggcccaagtac ctgggattatctgtgtcatcactatgccagcacgcagtgtaacaattatgatcccgatattacaaccaacca ttactacctgtacccattggactttgcgcgcctgcaacacctaggcattaacacttactcgttttcaatttcat ggacgcgtatttatccattgggcgcaggctatgttaatgaagcagggttagcccactatgatgccgtaatc catagtgccaagaagtatggtctggaaccagtgggcaccgttttcactgggatacgccactgtctctgat gctgaaatacggtgcctggcaagatactggtgaccaaattgttaaggactttgttacctatgccacaactg tgtttaagcgttatggtaatgaagtcaagacgtggtttactttcaatgaaccacgggttttctgttcacaaat agtggtctgccatacaatctgacgtatccagaaggtattaacagcacctccgctgtatttcgttgcacctac aatgttctgaaagctcatggtcatgctgttaaagtgtatcgggatctagttgcctccgggaccattgcggc aggtgaaatcggctttaaatccgatgataactacccaatcccggcccgtccagggaacgccgatgacg aggaatcagccaagcgtcacgaggcttttcgcattgggattttttgcgcaaccggttatggtaatggcgat tatccagatgttgttaaagaaactgttggagatatgctgccggccctgacggatgaagataaaggataca ttaaaggtagcggagatatttttgcgattgacgggtatcgtaccgatatttcccatgcggctctgaacggg atcgcgaattgtattcgcaaccaaagtgacccgaattggccagtgtgtgaagaagggtcagatcctttg ctcatgtttacccatccgggtttgctattggtcaatcagccgatccactgtcttcatggttagtcaactcagc cccgtttatccgcgatcaactgaagtttctgacacaaacctaccctgctaagggtggtatttatttctcggaa tttggttgggctgaagacgccgaatatgatcgtcaactgctgtatcaaattacctgggatggtctgcgtac gcaatacctgacggactatctgagccagctgctgttggctgtgcacaaagacgggattaatctgcgagg cgcgctgacgtggagttttgtcgataattgggagtgggggtttagggatgcaacagaaattcggatttcagt ttgttaatcaatcagatcccgatctgacacgcacgtttaaactgagcgctcacgcttacgcccaatttggg cgtaatcatctgcaccaccaccaccac |
| 36 | rBht $_{(1-594)}$-HIS (protein) | MMLHAALLVALPCVVLARPAGAVTYPGAIPLSLTSNYETPSPTAI PLEPTPTATGTAELDALWNLVEAQYPVQTAAVTTLVTVPDDYKF EADPPSYALAGYETSEIAGLKFPKGFKFGVAGAAIQVEGAAKAEG RGPSTWDYLCHHYASTQCNNYDPDITTNHYYLYPLDFARLQHLG INTYSFSISWTRIYPLGAGYVNEAGLAHYDAVIHSAKKYGLEPVG TVFHWDTPLSLMLKYGAWQDTGDQIVKDFVTYATTVFKRYGNE VKTWFTFNEPRVFCSQNSGLPYNLTYPEGINSTSAVFRCTYNVLK AHGHAVKVYRDLVASGTIAAGEIGFKSDDNYPIPARPGNADDEES AKRHEAFRIGIFAQPVYGNGDYPDVVKETVGDMLPALTDEDKGY IKGSGDIFAIDGYRTDISHAALNGIANCIRNQSDPNWPVCEEGSDP FAHVYPSGFAIGQSADPLSSWLVNSAPFIRDQLKFLTQTYPAKGGI YFSEFGWAEDAEYDRQLLYQITWDGLRTQYLTDYLSQLLLAVHK DGINLRGALTWSFVDNWEWGLGMQQKFGFQFVNQSDPDLTRTF KLSAHAYAQFGRNHLHHHHHH |
| 37 | MFα-rBht $_{(23-594)}$-HIS (nucleic acid) | atgagatttccttcaattttttactgcagttttattcgcagcatcctccgcattagctgctccagtcaacactaca acagaagatgaaacggcacaaattccggctgaagctgtcatcggttactcagatttagaaggggatttcg atgttgctgtttttgccattttccaacagcacaaataacgggttattgtttataaatactactattgccagcattg ctctaaagaagaaggggtatctctcgagaaagagaggctgaagctgttacttatccgggagccattc ctctgtccctgacgagcaattacgaaaccccaagtccgacagcaatcccgctggagccaacaccgacg gctaccggtacagcagaattagatgcgctgtggaacttagtcgaagctcagtacccagttcaaactgctg |

TABLE 5-continued

_Sequences._

| SEQ ID NO: | Name | Sequence |
|---|---|---|
| | | cagtgacaactttggtgacagtgcccgatgattataagtttgaggcagatccaccgagttatgcattagca<br>gggtatgaaacaagcgagattgccggactgaagtttccaaaggggtttaagtttggtgttgcgggggca<br>gccattcaagttgaaggtgcagcaaaagccgaagggcggggcccaagtacctgggattatctgtgtcat<br>cactatgccagcacgcagtgtaacaattatgatcccgatattacaaccaaccaattactacctgtacccattg<br>gactttgcgcgcctgcaacacctaggcattaacacttactcgtttcaatttcatggacgcgtatttatccatt<br>gggcgcaggctatgttaatgaagcagggttagcccactatgatgccgtaatccatagtgccaagaagtat<br>ggtctggaaccagtgggcaccgtttttcactgggatacgccactgtctctgatgctgaaatacggtgcctg<br>gcaagatactggtgaccaaattgttaaggactttgttacctatgccacaactgtgtttaagcgttatggtaat<br>gaagtcaagacgtggtttacttttcaatgaaccacgggttttctgttcacaaaatagtggtctgccatacaat<br>ctgacgtatccagaaggtattaacagcacctccgctgtatttcgttgcacctacaatgttctgaaagctcat<br>ggtcatgctgttaaagtgtatcgggatctagttgcctccgggaccattgcggcaggtgaaatcggctttaa<br>atccgatgataactacccaatcccggccgtccagggaacgccgatgacgaggaatcagccaagcgt<br>cacgaggcttttcgcattgggattttttgcgcaaccggtttatggtaatggcgattatccagatgttgttaaag<br>aaactgttggagatatgctgccggccctgacggatgaagataaaggatacattaaaggtagcggagata<br>ttttgcgattgacgggtatcgtaccgatatttcccatgcggctctgaacgggatcgcgaattgtattcgca<br>accaaagtgacccgaattggccagtgtgtgaagaagggtcagatccttttgctcatgtttacccatccggt<br>gtttgctattggtcaatcagccgatccactgtcttcatggttagtcaactcagccccgtttatccgcgatcaa<br>ctgaagtttctgacacaaacctaccctgctaagggtggtatttatttctcggaattggttgggctgaagac<br>gccgaatatgatcgtcaactgctgtatcaaattacctgggatggtctgcgtacgcaatacctgacggacta<br>tctgagccagctgctgttggctgtgcacaaagacgggattaatctgcgaggcgcgctgacgtggagtttt<br>gtcgataattgggagtggggtttagggatgcaacagaaattcggatttcagtttgttaatcaatcagatccc<br>gatctgacacgacgtttaaactgagcgctcacgcttacgcccaatttgggcgtaatcatctgcaccacc<br>accaccac |
| 38 | MFα-<br>rBht (23-594) -<br>HIS<br>(protein) | MRFPSIFTAVLFAASSALAAPVNTTTEDETAQIPAEAVIGYSDLEG<br>DFDVAVLPFSNSTNNGLLFINTTIASIAAKEEGVSLEKREAEAVTY<br>PGAIPLSLTSNYETPSPTAIPLEPTPTATGTAELDALWNLVEAQYP<br>VQTAAVTTLVTVPDDYKFEADPPSYALAGYETSEIAGLKFPKGFK<br>FGVAGAAIQVEGAAKAEGRGPSTWDYLCHHYASTQCNNYDPDI<br>TTNHYYLYPLDFARLQHLGINTYSFSISWTRIYPLGAGYVNEAGL<br>AHYDAVIHSAKKYGLEPVGTVFHWDTPLSLMLKYGAWQDTGD<br>QIVKDFVTYATTVFKRYGNEVKTWFTFNEPRVFCSQNSGLPYNL<br>TYPEGINSTSAVFRCTYNVLKAHGHAVKVYRDLVASGTIAAGEIG<br>FKSDDNYPIPARPGNADDEESAKRHEAFRIGIFAQPVYGNGDYPD<br>VVKETVGDMLPALTDEDKGYIKGSGDIFAIDGYRTDISHAALNGI<br>ANCIRNQSDPNWPVCEEGSDPFAHVYPSGFAIGQSADPLSSWLVN<br>SAPFIRDQLKFLTQTYPAKGGIYFSEFGWAEDAEYDRQLLYQITW<br>DGLRTQYLTDYLSQLLLAVHKDGINLRGALTWSFVDNWEWGLG<br>MQQKFGFQFVNQSDPDLTRTFKLSAHAYAQFGRNHLHHHHHH |
| 39 | MFα-rBht (23-<br>594) (N289Q) -<br>HIS (nucleic<br>acid) | atgagatttccttcaattttttactgcagtttttattcgcagcatcctccgcattagctgctccagtcaacactaca<br>acagaagatgaaacggcacaaattccggctgaagctgtcatcggttactcagatttagaaggggatttcg<br>atgttgctgttttgccattttccaacagcacaaataacgggttattgtttataaatactactattgccagcattg<br>ctgctaaagaagaaggggtatctctcgagaaaagagaggctgaagctgttacttatccgggagccattc<br>ctctgtccctgacgagcaattacgaaaccccaagtccgacagcaatcccgctggagccaacaccgacg<br>gctaccggtacagcagaattagatgcgctgtggaacttagtcgaagctcagtacccagttcaaactgctg<br>cagtgacaactttggtgacagtgcccgatgattataagtttgaggcagatccaccgagttatgcattagca<br>gggtatgaaacaagcgagattgccggactgaagtttccaaaggggtttaagtttggtgttgcgggggca<br>gccattcaagttgaaggtgcagcaaaagccgaagggcggggcccaagtacctgggattatctgtgtcat<br>cactatgccagcacgcagtgtaacaattatgatcccgatattacaaccaaccaattactacctgtacccattg<br>gactttgcgcgcctgcaacacctaggcattaacacttactcgttttcaatttcatggacgcgtatttatccatt<br>gggcgcaggctatgttaatgaagcagggttagcccactatgatgccgtaatccatagtgccaagaagtat<br>ggtctggaaccagtgggcaccgttttttcactgggatacgccactgtctctgatgctgaaatacggtgcctg<br>gcaagatactggtgaccaaattgttaaggactttgttacctatgccacaactgtgtttaagcgttatggtaat<br>gaagtcaagacgtggtttactttcaatgaaccacgggttttctgttcacaaaatagtggtctgccataccag<br>cttacgtatccagaaggtattaacagcacctccgctgtatttcgttgcacctacaatgttctgaaagctcatg<br>gtcatgctgttaaagtgtatcgggatctagttgcctccgggaccattgcggcaggtgaaatcggctttaaa<br>tccgatgataactacccaatcccggccgtccagggaacgccgatgacgaggaatcagccaagcgtc<br>acgaggcttttcgcattgggattttttgcgcaaccggtttatggtaatggcgattatccagatgttgttaaaga<br>aactgttggagatatgctgccggccctgacggatgaagataaaggatacattaaaggtagcggagatat<br>ttttgcgattgacgggtatcgtaccgatatttcccatgcggctctgaacgggatcgcgaattgtattcgcaa<br>ccaaagtgacccgaattggccagtgtgtgaagaagggtcagatccttttgctcatgtttacccatccgggt<br>ttgctattggtcaatcagccgatccactgtcttcatggttagtcaactcagccccgtttatccgcgatcaact<br>gaagtttctgacacaaacctaccctgctaagggtggtatttatttctcggaattggttgggctgaagacgc<br>cgaatatgatcgtcaactgctgtatcaaattacctgggatggtctgcgtacgcaatacctgacggactatct<br>gagccagctgctgttggctgtgcacaaagacgggattaatctgcgaggcgcgctgacgtggagttttgt<br>cgataattgggagtggggtttagggatgcaacagaaattcggatttcagtttgttaatcaatcagatcccg<br>atctgacacgacgtttaaactgagcgctcacgcttacgcccaatttgggcgtaatcatctgcaccacca<br>ccaccaccac |
| 40 | MFα-rBht (23-<br>594) (N289Q) -<br>HIS (protein) | MRFPSIFTAVLFAASSALAAPVNTTTEDETAQIPAEAVIGYSDLEG<br>DFDVAVLPFSNSTNNGLLFINTTIASIAAKEEGVSLEKREAEAVTY<br>PGAIPLSLTSNYETPSPTAIPLEPTPTATGTAELDALWNLVEAQYP<br>VQTAAVTTLVTVPDDYKFEADPPSYALAGYETSEIAGLKFPKGFK<br>FGVAGAAIQVEGAAKAEGRGPSTWDYLCHHYASTQCNNYDPDI |

TABLE 5-continued

Sequences.

| SEQ ID NO: | Name | Sequence |
|---|---|---|

TTNHYYLYPLDFARLQHLGINTYSFSISWTRIYPLGAGYVNEAGL
AHYDAVIHSAKKYGLEPVGTVFHWDTPLSLMLKYGAWQDTGD
QIVKDFVTYATTVFKRYGNEVKTWFTFNEPRVFCSQNSGLPYQL
TYPEGINSTSAVFRCTYNVLKAHGHAVKVYRDLVASGTIAAGEIG
FKSDDNYPIPARPGNADDEESAKRHEAFRIGIFAQPVYGNGDYPD
VVKETVGDMLPALTDEDKGYIKGSGDIFAIDGYRTDISHAALNGI
ANCIRNQSDPNWPVCEEGSDPFAHVYPSGFAIGQSADPLSSWLVN
SAPFIRDQLKFLTQTYPAKGGIYFSEFGWAEDAEYDRQLLYQITW
DGLRTQYLTDYLSQLLLAVHKDGINLRGALTWSFVDNWEWGLG
MQQKFGFQFVNQSDPDLTRTFKLSAHAYAQFGRNHLHHHHHH

| 41 | MFα-rBht (23-594) (N297Q)-HIS (nucleic acid) | atgagatttccttcaattttttactgcgagttttattcgcagcatcctccgcattagctgctccagtcaacactaca acagaagatgaaacggcacaaattccggctgaagctgtcatcggttactcagatttagaaggggatttcg atgttgctgtttttgccattttccaacagcacaaataacgggttattgtttataaatactactattgccagcattg ctgctaaagaagaaggggtatctctcgagaaaagagaggctgaagctgttacttatccgggagccattc ctctgtccctgacgagcaattacgaaaccccaagtccgacagcaatcccgctggagccaacaccgacg gctaccggtacagcagaattagatgcgctgtggaacttagtcgaagctcagtacccagttcaaactgctg cagtgacaactttggtgacagtgcccgatgattataagtttgaggcagatccaccgagttatgcattagca gggtatgaaacaagcgagattgccggactgaagtttccaaaggggtttaagtttggtgttgcgggggca gccattcaagttgaaggtgcagcaaaagccgaagggcggggcccaagtacctgggattatctgtgtcat cactatgccagcacgcagtgtaacaattatgatcccgatattacaaccaaccattactacctgtacccattg gactttgcgcgcctgcaacacctaggcattaacacttactcgttttcaatttcatggacgcgtatttatccatt gggcgcaggctatgttaatgaagcagggttagcccactatgatgccgtaatccatagtgccaagaagtat ggtctggaaccagtgggcaccgttttttcactgggatacgccactgtctctgatgctgaaatacggtgcctg gcaagatactggtgaccaaattgttaaggactttgttacctatgccacaactgtgtttaagcgttatggtaat gaagtcaagacgtggtttacttttcaatgaaccacgggtttttctgttcacaaaatagtggtctgccatacaat ctgacgtatccagaagggatccagagcacctccgctgtattcgttgcacctacaatgttctgaaagctca tggtcatgctgttaaagtgtatcgggatctagttgcctccgggaccattgcggcaggtgaaatcggctta aatccgatgataactacccaatcccggcccgtccaggaacgccgatgacgaggaatcagccaagcg tcacgaggcttttcgcatttgggattttttgcgcaaccggtttatggtaatggcgattatccagatgttgttaaa gaaactgttggagatatgctgccggccctgacggatgaagataaaggatacattaaaggtagcggagat atttttgcgattgacgggtatcgtaccgatatttcccatgcggctctgaacgggatcgcgaattgtattcgc aaccaaagtgacccgaattggccagtgtgtgaagaaagggtcagatccttttgctcatgtttacccatccgg gtttgctattggtcaatcagccgatccactgtcttcatggttagtcaactcagccccgtttatccgcgatcaa ctgaagtttctgacacaaacctaccctgctaagggtggtatttatttctcggaattggttgggctgaagac tctgagccagctgcctgttggctgtgcacaaagacgggattaatctgcgaggcgcgctgacgtggagtttt gtcgataattgggagtggggtttagggatgcaacagaaattcggatttcagtttgttaatcaatcagatccc gatctgacacgcacgtttaaactgagcgctcacgcttacgcccaatttgggcgtaatcatctgcaccacc accaccac |

| 42 | MFα-rBht (23-594) (N297Q)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEAVTY PGAIPLSLTSNYETPSPTAIPLEPTPTATGTAELDALWNLVEAQYP VQTAAVTTLVTVPDDYKFEADPPSYALAGYETSEIAGLKFPKGFK FGVAGAAIQVEGAAKAEGRGPSTWDYLCHHYASTQCNNYDPDI TTNHYYLYPLDFARLQHLGINTYSFSISWTRIYPLGAGYVNEAGL AHYDAVIHSAKKYGLEPVGTVFHWDTPLSLMLKYGAWQDTGD QIVKDFVTYATTVFKRYGNEVKTWFTFNEPRVFCSQNSGLPYNL TYPEGIQSTSAVFRCTYNVLKAHGHAVKVYRDLVASGTIAAGEIG FKSDDNYPIPARPGNADDEESAKRHEAFRIGIFAQPVYGNGDYPD VVKETVGDMLPALTDEDKGYIKGSGDIFAIDGYRTDISHAALNGI ANCIRNQSDPNWPVCEEGSDPFAHVYPSGFAIGQSADPLSSWLVN SAPFIRDQLKFLTQTYPAKGGIYFSEFGWAEDAEYDRQLLYQITW DGLRTQYLTDYLSQLLLAVHKDGINLRGALTWSFVDNWEWGLG MQQKFGFQFVNQSDPDLTRTFKLSAHAYAQFGRNHLHHHHHH |

| 43 | MFα-rBht (23-594) (N431Q)-HIS (nucleic acid) | atgagatttccttcaattttttactgcgagttttattcgcagcatcctccgcattagctgct ccagtcaacactacaacagaagatgaaacggcacaaattccggctgaagctgtcatcggt tactcagatttagaaggggatttcgatgttgctgtttttgccattttccaacagcacaaat aacgggttattgtttataaatactactattgccagcattgctgctaaagaagaaggggta tctctcgagaaaagagaggctgaagctgttacttatccgggagccattcctctgtccctg acgagcaattacgaaaccccaagtccgacagcaatcccgctggagccaacaccgacg accggtacagcagaattagatgcgctgtggaacttagtcgaagctcagtacccagttcaa actgctgcagtgacaactttggtgacagtgcccgatgattataagtttgaggcagatcca ccgagttatgcattagcagggtatgaaacaagcgagattgccggactgaagtttccaaag gggtttaagtttggtgttgcgggggcagccattcaagttgaaggtgcagcaaaagccgaa gggcggggcccaagtacctgggattatctgtgtcatcactatgccagcacgcagtgtaac aattatgatcccgatattacaaccaaccattactacctgtacccattggactttgcgcgc ctgcaacacctaggcattaacacttactcgttttcaatttcatggacgcgtatttatcatgt gggcgcaggctatgttaatgaagcagggttagcccactatgatgccgtaatccatagt gccaagaagtatggtctggaaccagtgggcaccgttttttcactgggatacgccactgtct ctgatgctgaaatacggtgcctggcaagatactggtgaccaaattgttaaggactttgtt acctatgccacaactgtgtttaagcgttatggtaatgaagtcaagacgtggtttactttc aatgaaccacgggtttttctgttcacaaaatagtggtctgccatacaatctgacgtatcca |

TABLE 5-continued

Sequences.

| SEQ ID NO: | Name | Sequence |
|---|---|---|
| | | gaaggtattaacagcacctccgctgtatttcgttgcacctacaatgttctgaaagctcat ggtcatgctgttaaagtgtatcgggatctagttgcctccgggaccattgcggcaggtgaa atcggctttaaatccgatgataactacccaatcccggcccgtccagggaacgccgatgac gaggaatcagccaagcgtcacgaggcttttcgcattgggattttttgcgcaaccggtttat ggtaatggcgattatccagatgttgttaaagaaactgttggagatatgctgccggccctg acggatgaagataaaggatacattaaaggtagcggagatatttttgcgattgacgggtat cgtaccgatatttcccatgcggctctgaacgggatcgcgaattgtattcgcagcaatcg gatccgaattggccagtgtgtgaagaagggtcagatccttttgctcatgtttacccatcc gggtttgctattggtcaatcagccgatccactgtcttcatggttagtcaactcagcccg tttatccgcgatcaactgaagtttctgacacaaacctaccctgctaagggtggtatttat ttctcggaatttggttgggctgaagacgccgaatatgatcgtcaactgctgtatcaaatt acctgggatggtctgcgtacgcaataacctgacggactatctgagccagctgctgttggct gtgcacaaagacgggattaatctgcgaggcgcgctgacgtggagttttgtcgataattgg gagtgggggtttagggatgcaacagaaattcggatttcagtttgttaatcaatcagatccc gatctgacacgcacgtttaaactgagcgctcacgcttacgcccaatttgggcgtaatcat ctgcaccaccaccaccac |
| 44 | MFα-rBht(23-594) (N431Q)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEAVTY PGAIPLSLTSNYETPSPTAIPLEPTPTATGTAELDALWNLVEAQYP VQTAAVTTLVTVPDDYKFEADPPSYALAGYETSEIAGLKFPKGFK FGVAGAAIQVEGAAKAEGRGPSTWDYLCHHYASTQCNNYDPDI TTNHYYLYPLDFARLQHLGINTYSFSISWTRIYPLGAGYVNEAGL AHYDAVIHSAKKYGLEPVGTVFHWDTPLSLMLKYGAWQDTGD QIVKDFVTYATTVFKRYGNEVKTWFTFNEPRVFCSQNSGLPYNL TYPEGINSTSAVFRCTYNVLKAHGHAVKVYRDLVASGTIAAGEIG FKSDDNYPIPARPGNADDEESAKRHEAFRIGIFAQPVYGNGDYPD VVKETVGDMLPALTDEDKGYIKGSGDIFAIDGYRTDISHAALNGI ANCIRQQSDPNWPVCEEGSDPFAHVYPSGFAIGQSADPLSSWLVN SAPFIRDQLKFLTQTYPAKGGIYFSEFGWAEDAEYDRQLLYQITW DGLRTQYLTDYLSQLLLAVHKDGINLRGALTWSFVDNWEWGLG MQQKFGFQFVNQSDPDLTRTFKLSAHAYAQFGRNH LHHHHHH |
| 45 | MFα-rBht(23-594) (N569Q)-HIS (nucleic acid) | atgagatttccttcaattttttactgcagttttattcgcagcatcctccgcattagctgctccagtcaacactaca acagaagatgaaacggcacaaattccggctgaagctgtcatcggttactcagatttagaaggggatttcg atgttgctgttttgccattttccaacagcacaaataacgggttattgtttataaatactactattgccagcattg ctgtcaaagaagaaggggtatctctcgagaaaagagaggctgaagctgttacttatccgggagccattc ctctgtccctgacgagcaattacgaaaccccaagtccgacagcaatcccgctggagccaacaccgacg gctaccggtacagcagaattagatgcgctgtggaacttagtcgaagctcagtacccagttcaaactgctg cagtgacaacctttggtgacagtgcccgatgattataagtttgaggcagatccaccgagttatgcattagca gggtatgaaacaagcgagattgccggactgaagtttccaaaggggtttaagtttggtgttgcgggggca gccattcaagttgaaggtgcagcaaaagccgaagggcgggggcccaagtacctgggattatctgtgtcat cactatgccagcacgcagtgtaacaattatgatcccgatattacaaccaaccattactacctgtacccattg gactttgcgcgcctgcaacacctaggcattaacacttactcgttttcaattcatggacgcgtatttatccatt gggcgcaggctatgttaatgaagcagggttagcccactatgatgccgtaatccatagtgccaagaagtat ggtctggaaccagtgggcaccgttttttcactgggatacgccactgtctctgatgctgaaatacggtgcctg gcaagatactggtgaccaaattgttaaggactttgttacctatgccacaactgtgtttaagcgttatggtaat gaagtcaagacgtggttttactttcaatgaaccacgggttttctgttcacaaaatagtggtctgccatacaat ctgacgtatccagaaggtattaacagcacctccgctgtatttcgttgcacctacaatgttctgaaagctcat ggtcatgctgttaaagtgtatcgggatctagttgcctccgggaccattgcggcaggtgaaatcggctttaa atccgatgataactacccaatcccggcccgtccagggaacgccgatgacgaggaatcagccaagcgt cacgaggcttttcgcattgggattttttgcgcaaccggtttatggtaatggcgattatccagatgttgttaaag aaactgttggagatatgctgccggccctgacggatgaagataaaggatacattaaaggtagcggagata tttttgcgattgacgggtatcgtaccgatatttcccatgcggctctgaacgggatcgcgaattgtattcgca accaaagtgacccgaattggccagtgtgtgaagaagggtcagatcctttttgctcatgtttacccatccgg gtttgctattggtcaatcagccgatccactgtcttcatggttagtcaactcagccccgtttatccgcgatcaa ctgaagtttctgacacaaacctaccctgctaagggtggtatttatttctcggaatttggttgggctgaagac gccgaatatgatcgtcaactgctgtatcaaattacctgggatggtctgcgtacgcaataacctgacggacta tctgagccagctgctgttggctgtgcacaaagacgggattaatctgcgaggcgcgctgacgtggagtttt gtcgataattgggagtgggggtttagggatgcaacagaaattcggatttcagtttgttcagcaatcggatcc cgatctgacacgcacgtttaaactgagcgctcacgcttacgcccaatttgggcgtaatcatctgcaccac caccaccac |
| 46 | MFα-rBht(23-594) (N569Q)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEAVTY PGAIPLSLTSNYETPSPTAIPLEPTPTATGTAELDALWNLVEAQYP VQTAAVTTLVTVPDDYKFEADPPSYALAGYETSEIAGLKFPKGFK FGVAGAAIQVEGAAKAEGRGPSTWDYLCHHYASTQCNNYDPDI TTNHYYLYPLDFARLQHLGINTYSFSISWTRIYPLGAGYVNEAGL AHYDAVIHSAKKYGLEPVGTVFHWDTPLSLMLKYGAWQDTGD QIVKDFVTYATTVFKRYGNEVKTWFTFNEPRVFCSQNSGLPYNL TYPEGINSTSAVFRCTYNVLKAHGHAVKVYRDLVASGTIAAGEIG FKSDDNYPIPARPGNADDEESAKRHEAFRIGIFAQPVYGNGDYPD VVKETVGDMLPALTDEDKGYIKGSGDIFAIDGYRTDISHAALNGI |

TABLE 5-continued

Sequences.

| SEQ ID NO: | Name | Sequence |
|---|---|---|
| | | ANCIRNQSDPNWPVCEEGSDPFAHVYPSGFAIGQSADPLSSWLVN SAPFIRDQLKFLTQTYPAKGGIYFSEFGWAEDAEYDRQLLYQITW DGLRTQYLTDYLSQLLLAVHKDGINLRGALTWSFVDNWEWGLG MQQKFGFQFVQQSDPDLTRTFKLSAHAYAQFGRNHLHHHHHH |
| 47 | MFα-rBht(32-594)-HIS (nucleic acid) | atgagatttccttcaattttttactgcagtttttattcgcagcatcctccgcattagctgctccagtcaacactaca acagaagatgaaacggcacaaattccggctgaagctgtcatcggttactcagatttagaaggggatttcg atgttgctgttttgccatttttccaacagcacaaataacgggttattgtttataaatactactattgccagcattg ctgctaaagaagaaggggtatctctcgagaaaagagaggctgaagcttccctgacgagcaattacgaa accccaagtccgacagcaatcccgctggagccaacaccgacggctaccggtacagcagaattagatg cgctgtggaacttagtcgaagctcagtacccagttcaaactgctgcagtgacaactttggtgacagtgcc cgatgattataagtttgaggcagatccaccgagttatgcattagcagggtatgaaacaagcgagattgcc ggactgaagtttccaaagggggtttaagtttggtgttgcgggggcagccattcaagttgaaggtgcagcaa aagccgaagggggggcccaagtacctgggattatctgtgtcatcactatgccagcacgcagtgtaac aattatgatcccgatattacaaccaaccattactacctgtacccattggactttgcgcgcctgcaacaccta ggcattaacacttactcgtttttcaatttcatggacgcgtatttatccattgggcgcaggctatgttaatgaag cagggttagcccactatgatgccgtaatccatagtgccaagaagtatggtctggaaccagtgggcaccg ttttttcactgggatacgccactgtctctgatgctgaaatacggtgcctggcaagatactggtgaccaaattg ttaaggactttgttacctatgccacaactgtgtttaagcgttatggtaatgaagtcaagacgtggtttactttc aatgaaccacgggttttctgttcacaaaatagtggtctgccatacaatctgacgtatccagaaggtattaac agcacctccgctgtatttcgttgcacctacaatgttctgaaagctcatggtcatgctgttaaagtgtatcggg atctagttgcctccgggaccattgcggcaggtgaaatcggctttaaatccgatgataactacccaatccc ggcccgtccagggaacgccgatgacgaggaatcagccaagcgtcacgaggcttttcgcattgggatttt tgcgcaaccggtttatggtaatggcgattatccagatgttgttaaagaaactgttggagatatgctgccgg ccctgacggatgaagataaaggatacattaaaggtagcggagatattttttgcgattgacgggtatcgtac cgatatttcccatgcggctctgaacgggatcgcgaattgtattcgcaaccaaagtgacccgaattggcca gtgtgtgaagaagggtcagatcctttttgctcatgtttacccatccgggtttgctattggtcaatcagccgatc cactgtcttcatggttagtcaactcagccccgtttatccgcgatcaactgaagtttctgacacaaacctacc ctgctaagggtggtatttatttctcggaatttggttgggctgaagacgccgaatatgatcgtcaactgctgt atcaaattacctgggatggtctgcgtacgcaatacctgacggactatctgagccagctgctgttggctgtg cacaaagacgggattaatctgcgaggcgcgctgacgtggagtttttgtcgataattgggagtggggtttag ggatgcaacagaaattcggatttcagtttgttaatcaatcagatcccgatctgacacgcacgtttaaactga gcgctcacgcttacgcccaatttgggcgtaatcatctgcaccaccaccaccaccac |
| 48 | MFα-rBht(32-594)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEASLTS NYETPSPTAIPLEPTPTATGTAELDALWNLVEAQYPVQTAAVTTL VTVPDDYKFEADPPSYALAGYETSEIAGLKFPKGFKFGVAGAAIQ VEGAAKAEGRGPSTWDYLCHHYASTQCNNYDPDITTNHYYLYP LDFARLQHLGINTYSFSISWTRIYPLGAGYVNEAGLAHYDAVIHS AKKYGLEPVGTVFHWDTPLSLMLKYGAWQDTGDQIVKDFVTYA TTVFKRYGNEVKTWFTFNEPRVFCSQNSGLPYNLTYPEGINSTSA VFRCTYNVLKAHGHAVKVYRDLVASGTIAAGEIGFKSDDNYPIP ARPGNADDEESAKRHEAFRIGIFAQPVYGNGDYPDVVKETVGDM LPALTDEDKGYIKGSGDIFAIDGYRTDISHAALNGIANCIRNQSDP NWPVCEEGSDPFAHVYPSGFAIGQSADPLSSWLVNSAPFIRDQLK FLTQTYPAKGGIYFSEFGWAEDAEYDRQLLYQITWDGLRTQYLT DYLSQLLLAVHKDGINLRGALTWSFVDNWEWGLGMQQKFGFQF VNQSDPDLTRTFKLSAHAYAQFGRNHLHHHHHH |
| 49 | MFα-rBht(54-594)-HIS (nucleic acid) | atgagatttccttcaattttttactgcagtttttattcgcagcatcctccgcattagctgctccagtcaacactaca acagaagatgaaacgcacaaattccggctgaagctgtcatcggttactcagatttagaagggatttcg atgttgctgttttgccatttttccaacagcacaaataacgggttattgtttataaatactactattgccagcattg ctgctaaagaagaaggggtatctctcgagaaaagagaggctgaagcctaccggtacagcagaattagat gcgctgtggaacttagtcgaagctcagtacccagttcaaactgctgcagtgacaactttggtgacagtgc ccgatgattataagtttgaggcagatccaccgagttatgcattagcagggtatgaaacaagcgagattgc cggactgaagtttccaaagggggtttaagtttggtgttgcgggggcagccattcaagttgaaggtgcagca aaagccgaagggggggcccaagtacctgggattatctgtgtcatcactatgccagcacgcagtgtaa caattatgatcccgatattacaaccaaccattactacctgtacccattggactttgcgcgcctgcaacacct aggcattaacacttactcgtttttcaatttcatggacgcgtatttatccattgggcgcaggctatgttaatgaa gcagggttagcccactatgatgccgtaatccatagtgccaagaagtatggtctggaaccagtgggcacc gttttttcactgggatacgccactgtctctgatgctgaaatacggtgcctggcaagatactggtgaccaaatt gttaaggactttgttacctatgccacaactgtgtttaagcgttatggtaatgaagtcaagacgtggtttacttt caatgaaccacgggttttctgttcacaaaatagtggtctgccatacaatctgacgtatccagaaggtattaa cagcacctccgctgtatttcgttgcacctacaatgttctgaaagctcatggtcatgctgttaaagtgtatcgg gatctagttgcctccgggaccattgcggcaggtgaaatcggctttaaatccgatgataactacccaatcc cggcccgtccagggaacgccgatgacgaggaatcagccaagcgtcacgaggcttttcgcattgggatt tttgcgcaaccggtttatggtaatggcgattatccagatgttgttaaagaaactgttggagatatgctgccg gccctgacggatgaagataaaggatacattaaaggtagcggagatattttttgcgattgacgggtatcgta ccgatatttcccatgcggctctgaacgggatcgcgaattgtattcgcaaccaaagtgacccgaattggcc agtgtgtgaagaagggtcagatcctttttgctcatgtttacccatccgggtttgctattggtcaatcagccgat ccactgtcttcatggttagtcaactcagccccgtttatccgcgatcaactgaagtttctgacacaaacctac cctgctaagggtggtatttatttctcggaatttggttgggctgaagacgccgaatatgatcgtcaactgctg tatcaaattacctgggatggtctgcgtacgcaatacctgacggactatctgagccagctgctgttggctgt gcacaaagacgggattaatctgcgaggcgcgctgacgtggagtttttgtcgataattgggagtggggttta |

TABLE 5-continued

Sequences.

| SEQ ID NO: | Name | Sequence |
|---|---|---|
| | | gggatgcaacagaaattcggatttcagtttgttaatcaatcagatcccgatctgacacgcacgtttaaactg |
| | | agcgctcacgcttacgcccaatttgggcgtaatcatctgcaccaccaccaccac |
| 50 | MFα-rBht(54-594)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEATGT AELDALWNLVEAQYPVQTAAVTTLVTVPDDYKFEADPPSYALA GYETSEIAGLKFPKGFKFGVAGAAIQVEGAAKAEGRGPSTWDYL CHHYASTQCNNYDPDITTNHYYLYPLDFARLQHLGINTYSFSISW TRIYPLGAGYVNEAGLAHYDAVIHSAKKYGLEPVGTVFHWDTPL SLMLKYGAWQDTGDQIVKDFVTYATTVFKRYGNEVKTWFTFNE PRVFCSQNSGLPYNLTYPEGINSTSAVFRCTYNVLKAHGHAVKV YRDLVASGTIAAGEIGFKSDDNYPIPARPGNADDEESAKRHEAFRI GIFAQPVYGNGDYPDVVKETVGDMLPALTDEDKGYIKGSGDIFAI DGYRTDISHAALNGIANCIRNQSDPNWPVCEEGSDPFAHVYPSGF AIGQSADPLSSWLVNSAPFIRDQLKFLTQTYPAKGGIYFSEFGWA EDAEYDRQLLYQITWDGLRTQYLTDYLSQLLLAVHKDGINLRGA LTWSFVDNWEWGLGMQQKFGFQFVNQSDPDLTRTFKLSAHAYA QFGRNHLHHHHHH |
| 51 | MFα-rBht(57-594)-HIS (nucleic acid) | atgagatttccttcaattttttactgcagttttattcgcagcatcctccgcattagctgctccagtcaacactaca acagaagatgaaacggcacaaattccggctgaagctgtcatcggttactcagatttagaaggggatttcg atgttgctgtttttgccattttccaacagcacaaataacgggttattgtttataaatactactattgccagcattg ctgctaaagaagaaggggtatctctcgagaaaagagaggctgaagctgcagaattagatgcgctgtgg aacttagtcgaagctcagtacccagttcaaactgctgcagtgacaacttttggtgacagtgcccgatgatta taagtttgaggcagatccaccgagttatgcattagcagggtatgaaacaagcgagattgccggactgaa gtttccaaaggggtttaagtttggtgttgcggggggcagccattcaagttgaaggtgcagcaaaagccga agggcgggggcccaagtacctgggattatctgtgtcatcactatgccagcacgcagtgtaacaattatgat cccgatattacaaccaaccattactacctgtacccattggactttgcgcgcctgcaacacctaggcattaa cacttactcgttttcaatttcatggacgcgtatttatccattgggcgcaggctatgttaatgaagcagggtta gcccactatgatgccgtaatccatagtgccaagaagtatggtctggaaccagtgggcaccgttttttcactg ggatacgccactgtctctgatgctgaaatacggtgcctggcaagatactggtgaccaaattgttaaggac tttgttacctatgccacaactgtgtttaagcgttatggtaatgaagtcaagacgtggtttactttcaatgaacc acgggttttctgttcacaaaatagtggtctgccatacaatcgacgtatccagaaggtattaacagcacctc cgctgtatttcgttgcacctacaatgttctgaaagctcatggtcatgtgttaaagtgtatcgggatctagttg cctccgggaccattgcggcaggtgaaatcggctttaaatccgatgataactacccaatcccggcccgtc cagggaacgccgatgacgaggaatcagccaagcgtcacgaggcttttcgcattgggattttttgcgcaac cggttatggtaatggcgattatccagatgttgttaaagaaacttgttggagatatgctgccgggccctgacg gatgaagataaaggatacattaaaggtagcggagatattttttgcgattgacgggtatcgtaccgatatttcc catgcggctctgaacgggatcgcgaattgtattcgcaaccaaagtgacccgaattggccagtgtgtgaa gaagggtcagatcctttttgctcatgtttacccatccgggtttgctattggtcaatcagccgatccactgtctt catggttagtcaactcagccccgtttatccgcgatcaactgaagtttctgacacaaacctaccctgctaag ggtggtatttatttctcggaatttggttgggctgaagacgccgaatatgatcgtcaactgctgtatcaaatta cctgggatggtctgcgtacgcaatacctgacggactatctgagccagctgctgttggctgtgcacaaag acgggattaatctgcgaggcgcgctgacgtggagttttgtcgataattgggagtggggtttagggatgca acagaaattcggatttcagtttgttaatcaatcagatcccgatctgacacgcacgtttaaactgagcgctca cgcttacgcccaatttgggcgtaatcatctgcaccaccaccaccac |
| 52 | MFα-rBht(57-594)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEAAEL DALWNLVEAQYPVQTAAVTTLVTVPDDYKFEADPPSYALAGYE TSEIAGLKFPKGFKFGVAGAAIQVEGAAKAEGRGPSTWDYLCHH YASTQCNNYDPDITTNHYYLYPLDFARLQHLGINTYSFSISWTRIY PLGAGYVNEAGLAHYDAVIHSAKKYGLEPVGTVFHWDTPLSLM LKYGAWQDTGDQIVKDFVTYATTVFKRYGNEVKTWFTFNEPRV FCSQNSGLPYNLTYPEGINSTSAVFRCTYNVLKAHGHAVKVYRD LVASGTIAAGEIGFKSDDNYPIPARPGNADDEESAKRHEAFRIGIF AQPVYGNGDYPDVVKETVGDMLPALTDEDKGYIKGSGDIFAIDG YRTDISHAALNGIANCIRNQSDPNWPVCEEGSDPFAHVYPSGFAI GQSADPLSSWLVNSAPFIRDQLKFLTQTYPAKGGIYFSEFGWAED AEYDRQLLYQITWDGLRTQYLTDYLSQLLLAVHKDGINLRGALT WSFVDNWEWGLGMQQKFGFQFVNQSDPDLTRTFKLSAHAYAQF GRNHLHHHHHH |
| 53 | MFα-rBht(82-594)-HIS (nucleic acid) | atgagatttccttcaattttttactgcagttttattcgcagcatcctccgcattagctgctccagtcaacactaca acagaagatgaaacggcacaaattccggctgaagctgtcatcggttactcagatttagaaggggatttcg atgttgctgtttttgccattttccaacagcacaaataacgggttattgtttataaatactactattgccagcattg ctgctaaagaagaaggggtatctctcgagaaaagagaggctgaagctacagtgcgcccgatgattataagt tgaggcagatccaccgagttatgcattagcagggtatgaaacaagcgagattgccggactgaagtttcc aaaggggtttaagtttggtgttgcggggggcagccattcaagttgaaggtgcagcaaaagccgaagggc gggggcccaagtacctgggattatctgtgtcatcactatgccagcacgcagtgtaacaattatgatcccgat attacaaccaaccattactacctgtacccattggactttgcgcgcctgcaacacctaggcattaacacttac tcgttttcaatttcatggacgcgtatttatccattgggcgcaggctatgttaatgaagcagggttagcccact atgatgccgtaatccatagtgccaagaagtatggtctggaaccagtgggcaccgttttttcactgggatac gccactgtctctgatgctgaaatacggtgcctggcaagatactggtgaccaaattgttaaggactttgttac ctatgccacaactgtgtttaagcgttatggtaatgaagtcaagacgtggtttactttcaatgaaccacgggtt |

TABLE 5-continued

Sequences.

| SEQ ID NO: | Name | Sequence |
|---|---|---|
| | | ttctgttcacaaaatagtggtctgccatacaatctgacgtatccagaaggtattaacagcacctccgctgta ttttcgttgcacctacaatgttctgaaagctcatggtcatgctgttaaagtgtatcgggatctagttgcctccg ggaccattgcggcaggtgaaatcggcttttaaatccgatgataactacccaatcccggcccgtccaggga acgccgatgacgaggaatcagccaagcgtcacgaggcttttcgcattgggattttttgcgcaaccggttta tggtaatggcgattatccagatgttgttaaagaaactgttggagatatgctgccggccctgacggatgaa gataaaggatacattaaaggtagcggagatattttttgcgattgacgggtatcgtaccgatatttcccatgcg gctctgaacgggatcgcgaattgtattcgcaaccaaagtgacccgaattggccagtgtgtgaagaaggg tcagatccttttgctcatgtttacccatccgggtttgctcattggtcaatcagccgatccactgtcttcatggtta gtcaactcagccccgtttatccgcgatcaactgaagtttctgacacaaacctaccctgctaagggtggtat ttatttctcggaatttggttgggctgaagacgccgaatatgatcgtcaactgctgtatcaaattacctgggat ggtctgcgtacgcaatacctgacggactatctgagccagctgctgttggctgtgcacaaagacgggatt aatctgcgaggcgcgctgacgtggagtttttgtcgataattgggagtggggtttagggatgcaacagaaat tcggatttcagtttgttaatcaatcagatcccgatctgacacgcacgtttaaactgagcgctcacgcttacg cccaatttgggcgtaatcatctgcaccaccaccaccac |
| 54 | MFα-rBht (82-594) -HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEATVP DDYKFEADPPSYALAGYETSEIAGLKFPKGFKFGVAGAAIQVEGA AKAEGRGPSTWDYLCHHYASTQCNNYDPDITTNHYYLYPLDFAR LQHLGINTYSFSISWTRIYPLGAGYVNEAGLAHYDAVIHSAKKYG LEPVGTVFHWDTPLSLMLKYGAWQDTGDQIVKDFVTYATTVFK RYGNEVKTWFTFNEPRVFCSQNSGLPYNLTYPEGINSTSAVFRCT YNVLKAHGHAVKVYRDLVASGTIAAGEIGFKSDDNYPIPARPGN ADDEESAKRHEAFRIGIFAQPVYGNGDYPDVVKETVGDMLPALT DEDKGYIKGSGDIFAIDGYRTDISHAALNGIANCIRNQSDPNWPV CEEGSDPFAHVYPSGFAIGQSADPLSSWLVNSAPFIRDQLKFLTQT YPAKGGIYFSEFGWAEDAEYDRQLLYQITWDGLRTQYLTDYLSQ LLLAVHKDGINLRGALTWSFVDNWEWGLGMQQKFGFQFVNQS DPDLTRTFKLSAHAYAQFGRNHLHHHHHH |
| 55 | MFα-rBht (95-594) -HIS (nucleic acid) | atgagatttccttcaattttttactgcagtttttattcgcagcatcctccgcattagctgctccagtcaacactaca acagaagatgaaacggcacaaattccggctgaagctgtcatcggttactcagatttagaaggggatttcg atgttgctgtttttgccattttccaacagcacaaataacgggttattgttttataaatactactattgccagcattg ctgctaaagaagaaggggtatctctcgagaaaagagaggctgaagctagttatgcattagcagggtatg aaacaagcgagattgccggactgaagtttccaaaggggtttaagttggtgttgcgggggcagccattca agttgaaggtgcagcaaaagccgaagggcgggccccaagtacctgggattatctgtgtcatcactatgc cagcacgcagtgtaacaattatgatcccgatattacaaccaaccattactacctgtacccattggactttgc gcgcctgcaacacctaggcattaacacttactcgttttcaatttcatggacgcgtatttatccattgggcgca ggctatgttaatgaagcagggttagcccactatgatgccgtaatccatagtgccaagaagtatggtctgg aaccagtgggcaccgttttttcactgggatacgccactgtctctgatgctgaaatacggtgcctggcaaga tactggtgaccaaattgttaaggactttgttaccatggccacaacctgtgtttaagcgttatggtaatgaagtc aagacgtggtttacttttcaatgaaccacgggttttctgttcacaaaatagtggtctgccatacaatctgacgt atccagaaggtattaacagcacctccgctgtatttcgttgcacctacaatgttctgaaagctcatggtcatg ctgttaaagtgtatcgggatctagttgcctccgggaccattgcggcaggtgaaatcggctttaaatccgat gataactacccaatcccggcccgtccagggaacgccgatgacgaggaatcagccaagcgtcacgag gcttttcgcattgggattttttgcgcaaccggtttatggtaatggcgattatccagatgttgttaaagaaactgt tggagatatgctgccggccctgacggatgaagataaaggatacattaaaggtagcggagatattttttgcg attgacgggtatcgtaccgatatttcccatgcggctctgaacgggatcgcgaattgtattcgcaaccaaag tgacccgaattggccagtgtgtgaagaagggtcagatccttttgctcatgtttacccatccgggtttgctatt ggtcaatcagccgatccactgtcttcatggttagtcaactcagccccgtttatccgcgatcaactgaagttt ctgacacaaacctaccctgctaagggtggtatttatttctcggaatttggttgggctgaagacgccgaatat gatcgtcaactgctgtatcaaattacctgggatggtctgcgtacgcaatacctgacggactatctgagcca gctgctgttggctgtgcacaaagacgggattaatctgcgaggcgcgctgacgtggagtttttgtcgataatt gggagtggggtttagggatgcaacagaaattcggatttcagtttgttaatcaatcagatcccgatctgaca cgcacgtttaaactgagcgctcacgcttacgcccaatttgggcgtaatcatctgcaccaccaccaccac ac |
| 56 | MFα-rBht (95-594) -HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEASYA LAGYETSEIAGLKFPKGFKFGVAGAAIQVEGAAKAEGRGPSTWD YLCHHYASTQCNNYDPDITTNHYYLYPLDFARLQHLGINTYSFSI SWTRIYPLGAGYVNEAGLAHYDAVIHSAKKYGLEPVGTVFHWD TPLSLMLKYGAWQDTGDQIVKDFVTYATTVFKRYGNEVKTWFT FNEPRVFCSQNSGLPYNLTYPEGINSTSAVFRCTYNVLKAHGHAV KVYRDLVASGTIAAGEIGFKSDDNYPIPARPGNADDEESAKRHEA FRIGIFAQPVYGNGDYPDVVKETVGDMLPALTDEDKGYIKGSGDI FAIDGYRTDISHAALNGIANCIRNQSDPNWPVCEEGSDPFAHVYP SGFAIGQSADPLSSWLVNSAPFIRDQLKFLTQTYPAKGGIYFSEFG WAEDAEYDRQLLYQITWDGLRTQYLTDYLSQLLLAVHKDGINL RGALTWSFVDNWEWGLGMQQKFGFQFVNQSDPDLTRTFKLSAH AYAQFGRNHLHHHHHH |
| 57 | MFα-rBht (103-594) -HIS (nucleic acid) | atgagatttccttcaattttttactgcagtttttattcgcagcatcctccgcattagctgctccagtcaacactaca acagaagatgaaacggcacaaattccggctgaagctgtcatcggttactcagatttagaaggggatttcg atgttgctgtttttgccattttccaacagcacaaataacgggttattgttttataaatactactattgccagcattg |

TABLE 5-continued

Sequences.

| SEQ ID NO: | Name | Sequence |
|---|---|---|
|  |  | ctgctaaagaagaaggggtatctctcgagaaaagagaggctgaagctacaagcgagattgccggact gaagtttccaaaggggtttaagtttggtgttgcgggggcagccattcaagttgaaggtgcagcaaaagc cgaagggcggggcccaagtacctgggattatctgtgtcatcactatgccagcacgcagtgtaacaattat gatcccgatattacaaccaaccattactacctgtaacccattggactttgcgcgcctgcaacacctaggcat taacacttactcgttttcaatttcatggacgcgtatttatccattgggcgcaggctatgttaatgaagcaggg ttagcccactatgatgccgtaatccatagtgccaagaagtatggtctgaaccagtgggcaccgttttttca ctgggatacgccactgtctctgatgctgaaatacggtgcctggcaagatactggtgaccaaattgttaag gactttgttacctatgccacaactgtgtttaagcgttatggtaatgaagtcaagacgtggtttacttttcaatga accacgggttttctgttcacaaaatagtggtctgccatacaatctgacgtatccagaaggtattaacagca cctccgctgtatttcgttgcacctacaatgttctgaaagctcatggtcatgctgttaaagtgtatcgggatct agttgcctccgggaccattgcggcaggtgaaatcggctttaaatccgatgataactacccaatcccggcc cgtccagggaacgccgatgacgaggaatcagccaagcgtcacgaggcttttcgcattgggattttttgcg caaccggtttatggtaatggcgattatccagatgttgttaaagaaactgttggagatatgctgccggccct gacggatgaagataaaggatacattaaaggtagcggagatattttttgcgattgacgggtatcgtaccgat atttcccatgcggctctgaacgggatcgcgaattgtattcgcaaccaaagtgacccgaattggccagtgt gtgaagaagggtcagatcctttttgctcatgtttacccatccgggtttgctattggtcaatcagccgatcccact gtcttcatggttagtcaactcagccccgtttatccgcgatcaactgaagtttctgacacaaacctaccctgc taagggtggtatttatttctcggaatttggttgggctgaagacgccgaatatgatcgtcaactgctgtatcaa attacctgggatggtctgcgtacgcaatacctgacggactatctgagccagctgctgttggctgtgcaca aagacgggattaatctgcgaggcgcgctgacgtggagtttttgtcgataattgggagtggggtttagggat gcaacagaaattcggatttcagtttgttaatcaatcagatcccgatctgacacgcacgtttaaactgagcg ctcacgcttacgcccaatttgggcgtaatcatctgcaccaccaccaccac |
| 58 | MFα-rBht(103-594)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEATSEI AGLKFPKGFKFGVAGAAIQVEGAAKAEGRGPSTWDYLCHHYAS TQCNNYDPDITTNHYYLYPLDFARLQHLGINTYSFSISWTRIYPLG AGYVNEAGLAHYDAVIHSAKKYGLEPVGTVFHWDTPLSLMLKY GAWQDTGDQIVKDFVTYATTVFKRYGNEVKTWFTFNEPRVFCS QNSGLPYNLTYPEGINSTSAVFRCTYNVLKAHGHAVKVYRDLVA SGTIAAGEIGFKSDDNYPIPARPGNADDEESAKRHEAFRIGIFAQP VYGNGDYPDVVKETVGDMLPALTDEDKGYIKGSGDIFAIDGYRT DISHAALNGIANCIRNQSDPNWPVCEEGSDPFAHVYPSGFAIGQS ADPLSSWLVNSAPFIRDQLKFLTQTYPAKGGIYFSEFGWAEDAEY DRQLLYQITWDGLRTQYLTDYLSQLLLAVHKDGINLRGALTWSF VDNWEWGLGMQQKFGFQFVNQSDPDLTRTFKLSAHAYAQFGR NHLHHHHHH |
| 59 | MFα-rBht(111-594)-HIS (nucleic acid) | atgagatttccttcaatttttactgcagtttattcgcagcatcctccgcattagctgctccagtcaacactaca acagaagatgaaacggcacaaattccggctgaagctgtcatcggttactcagatttagaaggggatttcg atgttgctgttttgccattttccaacagcacaaataacgggtttattgtttataaatactactattgccagcattg ctctaaagaagaaggggtatctctcgagaaaagagaggctgaagctacgtagaattcatgtttccaaa ggggtttaagtttggtgttgcggggcagccattcaagttgaaggtgcagcaaaagccgaagggcggg gcccaagtacctgggattatctgtgtcatcactatgccagcacgcagtgtaacaattatgatcccgatatta caaccaaccattactacctgtaacccattggactttgcgcgcctgcaacacctaggcattaacacttactcgt tttcaatttcatggacgcgtatttatccattgggcgcaggctatgttaatgaagcagggttagcccactatg atgccgtaatccatagtgccaagaagtatggtctgaaccagtgggcaccgttttttcactgggatacgcc actgtctctgatgctgaaatacggtgcctggcaagatactggtgaccaaattgttaaggactttgttacctat gccacaactgtgtttaagcgttatggtaatgaagtcaagacgtggtttacttttcaatgaaccacgggtttct gttcacaaaatagtggtctgccatacaatctgacgtatccagaaggtattaacagcacctccgctgtatttc gttgcacctacaatgttctgaaagctcatggtcatgctgttaaagtgtatcgggatctagttgcctccggga ccattgcggcaggtgaaatcggctttaaatccgatgataactacccaatcccggcccgtccagggaacg ccgatgacgaggaatcagccaagcgtcacgaggcttttcgcattgggattttttgcgcaaccggtttatggt aatggcgattatccagatgttgttaaagaaactgttggagatatgctgccggccctgacggatgaagata aaggatacattaaaggtagcggagatattttttgcgattgacgggtatcgtaccgatatttcccatgcggctc tgaacgggatcgcgaattgtattcgcaaccaaagtgacccgaattggccagtgtgtgaagaagggtcag atcctttttgctcatgtttacccatccgggtttgctattggtcaatcagccgatcccactgtcttcatggttagtca actcagccccgtttatccgcgatcaactgaagtttctgacacaaacctaccctgctaagggtggtatttattt ctcggaatttggttgggctgaagacgccgaatatgatcgtcaactgctgtatcaaattacctgggatggtc tgcgtacgcaatacctgacggactatctgagccagctgctgttggctgtgcacaaagacgggattaatct gcgaggcgcgctgacgtggagtttttgtcgataattgggagtggggtttagggatgcaacagaaattcgg atttcagtttgttaatcaatcagatcccgatctgacacgcacgtttaaactgagcgctcacgcttacgccca atttgggcgtaatcatctgcaccaccaccaccac |
| 60 | MFα-rBht(111-594)-HIS (protein) | MRFPSIFTAVLFAASSALAAPVNTTTEDETAQIPAEAVIGYSDLEG DFDVAVLPFSNSTNNGLLFINTTIASIAAKEEGVSLEKREAEAYVE FMFPKGFKFGVAGAAIQVEGAAKAEGRGPSTWDYLCHHYASTQ CNNYDPDITTNHYYLYPLDFARLQHLGINTYSFSISWTRIYPLGAG YVNEAGLAHYDAVIHSAKKYGLEPVGTVFHWDTPLSLMLKYGA WQDTGDQIVKDFVTYATTVFKRYGNEVKTWFTFNEPRVFCSQNS GLPYNLTYPEGINSTSAVFRCTYNVLKAHGHAVKVYRDLVASGT IAAGEIGFKSDDNYPIPARPGNADDEESAKRHEAFRIGIFAQPVYG NGDYPDVVKETVGDMLPALTDEDKGYIKGSGDIFAIDGYRTDISH AALNGIANCIRNQSDPNWPVCEEGSDPFAHVYPSGFAIGQSADPL SSWLVNSAPFIRDQLKFLTQTYPAKGGIYFSEFGWAEDAEYDRQL |

TABLE 5-continued

Sequences.

| SEQ ID NO: | Name | Sequence |
|---|---|---|
| | | LYQITWDGLRTQYLTDYLSQLLLAVHKDGINLRGALTWSFVDN<br>WEWGLGMQQKFGFQFVNQSDPDLTRTFKLSAHAYAQFGRNHLH<br>HHHHH |
| 61 | IV-<br>rBht $_{(54-594)}$-<br>HIS (nucleic<br>acid) | atgcttttgcaagctttccttttcctttggctggttttgcagccaagatatctgcaaccggtacagcagaatt<br>agatgcgctgtggaacttagtcgaagctcagtacccagttcaaactgctgcagtgacaactttggtgaca<br>gtgcccgatgattataagtttgaggcagatccaccgagttatgcattagcagggtatgaaacaagcgaga<br>ttgccggactgaagtttccaaaggggtttaagtttggtgttgcggggggcagccattcaagttgaaggtgc<br>agcaaaagccgaagggggggcccaagtacctgggattatctgtgtcatcactatgccagcacgcagt<br>gtaacaattatgatcccgatattacaaccaaccattactacctgtacccattggactttgcgcgcctgcaac<br>acctaggcattaacacttactcgttttcaatttcatggacgcgtatttatccattgggcgcaggctatgttaat<br>gaagcagggttagcccactatgatgccgtaatccatagtgccaagaagtatggtctggaaccagtgggc<br>accgttttttcactgggatacgccactgtctctgatgctgaaatacggtgcctggcaagatactggtgacca<br>aattgttaaggactttgttacctatgccacaactgtgtttaagcgttatggtaatgaagtcaagacgtggttta<br>cttttcaatgaaccacgggttttctgttcacaaaatagtggtctgccatacaatctgacgtatccagaaggtat<br>taacagcacctccgctgtatttcgttgcacctacaatgttctgaaagctcatggtcatgctgttaaagtgtat<br>cgggatctagttgcctccgggaccattgcggcaggtgaaatcggctttaaatccgatgataactacccaa<br>tcccggcccgtccagggaacgccgatgacgaggaatcagccaagcgtcacgaggcttttcgcattgg<br>gattttgcgcaaccggtttatggtaatggcgattatccagatgttgttaaagaaactgttggagatatgctg<br>ccggccctgacggatgaagataaaggatacattaaaggtagcggagatattttttgcgattgacgggtatc<br>gtaccgatatttcccatgcggctctgaacgggatcgcgaattgtattcgcaaccaaagtgacccgaattg<br>gccagtgtgtgaagaaggtcagatcctttttgctcatgtttacccatccgggtttgctattggtcaatcagc<br>cgatccactgtcttcatggttagtcaactcagccccgtttatccgcgatcaactgaagtttctgacacaaac<br>ctaccctgctaagggtggtatttatttctcggaatttggttgggctgaagacgccgaatatgatcgtcaact<br>gctgtatcaaattacctgggatggtctgcgtacgcaataccctgacggactatctgagccagctgctgttgg<br>ctgtgcacaaagacgggattaatctgcgaggcgcgctgacgtggagtttttgtcgataattgggagtggg<br>gtttagggatgcaacagaaattcggatttcagtttgttaatcaatcagatcccgatctgacacgcacgttta<br>aactgagcgctcacgcttacgcccaatttgggcgtaatcatctgcaccaccaccaccac |
| 62 | IV-<br>rBht $_{(54-594)}$-<br>HIS (protein) | MLLQAFLFLLAGFAAKISATGTAELDALWNLVEAQYPVQTAAVT<br>TLVTVPDDYKFEADPPSYALAGYETSEIAGLKFPKGFKFGVAGAA<br>IQVEGAAKAEGRGPSTWDYLCHHYASTQCNNYDPDITTNHYYLY<br>PLDFARLQHLGINTYSFSISWTRIYPLGAGYVNEAGLAHYDAVIH<br>SAKKYGLEPVGTVFHWDTPLSLMLKYGAWQDTGDQIVKDFVTY<br>ATTVFKRYGNEVKTWFTFNEPRVFCSQNSGLPYNLTYPEGINSTS<br>AVFRCTYNVLKAHGHAVKVYRDLVASGTIAAGEIGFKSDDNYPI<br>PARPGNADDEESAKRHEAFRIGIFAQPVYGNGDYPDVVKETVGD<br>MLPALTDEDKGYIKGSGDIFAIDGYRTDISHAALNGIANCIRNQSD<br>PNWPVCEEGSDPFAHVYPSGFAIGQSADPLSSWLVNSAPFIRDQL<br>KFLTQTYPAKGGIYFSEFGWAEDAEYDRQLLYQITWDGLRTQYL<br>TDYLSQLLLAVHKDGINLRGALTWSFVDNWEWGLGMQQKFGFQ<br>FVNQSDPDLTRTFKLSAHAYAQFGRNHLHHHHHH |
| 63 | GA-<br>rBht $_{(54-594)}$-<br>HIS (nucleic<br>acid) | atgtcttttagatccttgctagctttgtctggtttggtttgttctggtttggctaccggtacagcagaattagatg<br>cgctgtggaacttagtcgaagctcagtacccagttcaaactgctgcagtgacaactttggtgacagtgcc<br>cgatgattataagtttgaggcagatccaccgagttatgcattagcagggtatgaaacaagcgagattgcc<br>ggactgaagtttccaaaggggtttaagtttggtgttgcggggggcagccattcaagttgaaggtgcagcaa<br>aagccgaagggggggcccaagtacctgggattatctgtgtcatcactatgccagcacgcagtgtaac<br>aattatgatcccgatattacaaccaaccattactacctgtacccattggactttgcgcgcctgcaacaccta<br>ggcattaacacttactcgttttcaatttcatggacgcgtatttatccattgggcgcaggctatgttaatgaag<br>cagggttagcccactatgatgccgtaatccatagtgccaagaagtatggtctggaaccagtgggcaccg<br>ttttttcactgggatacgccactgtctctgatgctgaaatacggtgcctggcaagatactggtgaccaaattg<br>ttaaggactttgttacctatgccacaactgtgtttaagcgttatggtaatgaagtcaagacgtggtttactttc<br>aatgaaccacgggttttctgttcacaaaatagtggtctgccatacaatctgacgtatccagaaggtattaac<br>agcacctccgctgtatttcgttgcacctacaatgttctgaaagctcatggtcatgctgttaaagtgtatcggg<br>atctagttgcctccgggaccattgcggcaggtgaaatcggctttaaatccgatgataactacccaatccc<br>ggcccgtccagggaacgccgatgacgaggaatcagccaagcgtcacgaggcttttcgcattgggatttt<br>tgcgcaaccggtttatggtaatggcgattatccagatgttgttaaagaaactgttggagatatgctgccgg<br>ccctgacggatgaagataaaggatacattaaaggtagcggagatattttttgcgattgacgggtatcgtac<br>cgatatttcccatgcggctctgaacgggatcgcgaattgtattcgcaaccaaagtgacccgaattggcca<br>gtgtgtgaagaaggtcagatcctttttgctcatgtttacccatccgggtttgctattggtcaatcagccgatc<br>cactgtcttcatggttagtcaactcagccccgtttatccgcgatcaactgaagtttctgacacaaacctacc<br>ctgctaagggtggtatttatttctcggaatttggttgggctgaagacgccgaatatgatcgtcaactgctgt<br>atcaaattacctgggatggtctgcgtacgcaataccctgacggactatctgagccagctgctgttggctgtg<br>cacaaagacgggattaatctgcgaggcgcgctgacgtggagtttttgtcgataattgggagtggggtttag<br>ggatgcaacagaaattcggatttcagtttgttaatcaatcagatcccgatctgacacgcacgtttaaactga<br>gcgctcacgcttacgcccaatttgggcgtaatcatctgcaccaccaccaccac |
| 64 | GA-<br>rBht $_{(54-594)}$-<br>HIS (protein) | MSFRSLLALSGLVCSGLATGTAELDALWNLVEAQYPVQTAAVTT<br>LVTVPDDYKFEADPPSYALAGYETSEIAGLKFPKGFKFGVAGAAI<br>QVEGAAKAEGRGPSTWDYLCHHYASTQCNNYDPDITTNHYYLY<br>PLDFARLQHLGINTYSFSISWTRIYPLGAGYVNEAGLAHYDAVIH<br>SAKKYGLEPVGTVFHWDTPLSLMLKYGAWQDTGDQIVKDFVTY<br>ATTVFKRYGNEVKTWFTFNEPRVFCSQNSGLPYNLTYPEGINSTS<br>AVFRCTYNVLKAHGHAVKVYRDLVASGTIAAGEIGFKSDDNYPI |

TABLE 5-continued

Sequences.

| SEQ ID NO: | Name | Sequence |
|---|---|---|
| | | PARPGNADDEESAKRHEAFRIGIFAQPVYGNGDYPDVVKETVGD MLPALTDEDKGYIKGSGDIFAIDGYRTDISHAALNGIANCIRNQSD PNWPVCEEGSDPFAHVYPSGFAIGQSADPLSSWLVNSAPFIRDQL KFLTQTYPAKGGIYFSEFGWAEDAEYDRQLLYQITWDGLRTQYL TDYLSQLLLAVHKDGINLRGALTWSFVDNWEWGLGMQQKFGFQ FVNQSDPDLTRTFKLSAHAYAQFGRNHLHHHHHH |
| 65 | IN-rBht (54-594)-HIS (nucleic acid) | atgaagttagcatactccttgttgcttccgctagcaggagtcagtgctaccggtacagcagaattagatgc gctgtggaacttagtcgaagctcagtacccagttcaaactgctgcagtgacaactttggtgacagtgccc gatgattataagtttgaggcagatccaccgagttatgcattagcagggtatgaaacaagcgagattgccg gactgaagtttccaaaggggtttaagtttggtgttgcggggggcagccattcaagttgaaggtgcagcaaa agccgaagggcggggcccaagtacctggattatctgtgtcatcactatgccagcacgcagtgtaaca attatgatcccgatattacaaccaaccattactacctgtacccattggactttgcgcgcctgcaacacctag gcattaacacttactcgttttcaatttcatggacgcgtatttatccattgggcgcaggctatgttaatgaagca gggttagcccactatgatgccgtaatccatagtgccaagaagtatggtctggaaccagtgggcaccgttt ttcactgggatacgccactgtctctgatgctgaaatacggtgcctggcaagatactggtgaccaaattgtt aaggactttgttacctatgccacaactgtgtttaagcgttatggtaatgaagtcaagacgtggtttactttca atgaaccacgggtttctgttcacaaaatagtggtctgccatacaatctgacgtatccagaaggtattaaca gcacctccgctgtatttcgttgcacctacaatgttctgaaagctcatggtcatgctgttaaagtgtatcggga tctagttgcctccgggaccattgcggcaggtgaaatcggctttaaatccgatgataactacccaatcccg gcccgtccaggaaacgccgatgacgaggaatcagccaagcgtcacgaggcttttcgcattgggattttt gcgcaaccggtttatggtaatggcgattatccagatgttgttaaagaaactgttggagatatgctgccggc cctgacggatgaagataaaggatacattaaaggtagcggagatatttttgcgattgacgggtatcgtacc gatatttcccatgcgcgtctgaacgggatcgcgaattgtattcgcaaccaaagtgaccgaattggccag tgtgtgaagaagggtcagatcctttttgctcatgtttacccatccgggtttgctattggtcaatcagccgatcc actgtcttcatggttagtcaactcagccccgtttatccgcgatcaactgaagtttctgacacaaacctaccct gctaagggtggtatttatttctcggaatttggttgggctgaagacgccgaatatgatcgtcaactgctgtat caaattacctgggatggtctgcgtacgcaatacctgacggactatctgagccagctgctgttggctgtgc acaaagacgggattaatctgcgaggcgcgctgacgtggagtttttgtcgataattgggagtggggtttag ggatgcaacagaaattcggatttcagtttgttaatcaatcagatcccgatctgacacgcacgtttaaactga gcgctcacgcttacgccaattgggcgtaatcatctcaccaccaccaccaccac |
| 66 | IN-rBht (54-594)-HIS (protein) | MKLAYSLLLPLAGVSATGTAELDALWNLVEAQYPVQTAAVTTL VTVPDDYKFEADPPSYALAGYETSEIAGLKFPKGFKFGVAGAAIQ VEGAAKAEGRGPSTWDYLCHHYASTQCNNYDPDITTNHYYLYP LDFARLQHLGINTYSFSISWTRIYPLGAGYVNEAGLAHYDAVIHS AKKYGLEPVGTVFHWDTPLSLMLKYGAWQDTGDQIVKDFVTYA TTVFKRYGNEVKTWFTFNEPRVFCSQNSGLPYNLTYPEGINSTSA VFRCTYNVLKAHGHAVKVYRDLVASGTIAAGEIGFKSDDNYPIP ARPGNADDEESAKRHEAFRIGIFAQPVYGNGDYPDVVKETVGDM LPALTDEDKGYIKGSGDIFAIDGYRTDISHAALNGIANCIRNQSDP NWPVCEEGSDPFAHVYPSGFAIGQSADPLSSWLVNSAPFIRDQLK FLTQTYPAKGGIYFSEFGWAEDAEYDRQLLYQITWDGLRTQYLT DYLSQLLLAVHKDGINLRGALTWSFVDNWEWGLGMQQKFGFQF VNQSDPDLTRTFKLSAHAYAQFGRNHLHHHHHH |
| 67 | MFα (Δ57-70)-rBht (23-594)-HIS (nucleic acid) | atgagatttccttcaattttttactgcagttttattcgcagcatcctccgcattagctgctccagtcaacactaca acagaagatgaaacggcacaaattccggctgaagctgtcatcggttactcagatttagaaggggatttcg atgttgctgttttgccattttccgccagcattgctgctaaagaagaaggggtatctctcgagaaaagagag gctgaagctgttacttatccgggagccattcctctgtccctgacgagcaattacgaaaccccaagtccga cagcaatcccgctggagccaacaccgacggctaccggtacagcagaattagatgcgctgtggaactta gtcgaagctcagtacccagttcaaactgctgcagtgacaactttggtgacagtgcccgatgattataagtt tgaggcagatccaccgagttatgcattagcagggtatgaaacaagcgagattgccggactgaagtttcc aaaggggtttaagtttggtgttgcggggggcagccattcaagttgaaggtgcagcaaaagccgaagggc ggggcccaagtacctgggattatctgtgtcatcactatgccagcacgcagtgtaacaattatgatcccgat attacaaccaaccattactacctgtacccattggactttgcgcgcctgcaacacctaggcattaacacttac tcgttttcaatttcatggacgcgtatttatccattgggcgcaggctatgttaatgaagcagggttagcccact atgatgccgtaatccatagtgccaagaagtatggtctggaaccagtgggcaccgtttttcactgggatac gccactgtctctgatgctgaaatacggtgcctggcaagatactggtgaccaaattgttaaggactttgttac ctatgccacaactgtgtttaagcgttatggtaatgaagtcaagacgtggtttactttcaatgaaccacgggtt ttctgttcacaaaatagtggtctgccatacaatctgacgtatccagaaggtattaacagcacctccgctgta tttcgttgcacctacaatgttctgaaagctcatggtcatgctgttaaagtgtatcgggatctagttgcctccg ggaccattgcggcaggtgaaatcggctttaaatccgatgataactacccaatcccggcccgtccaggga acgccgatgacgaggaatcagccaagcgtcacgaggcttttcgcattgggattttttgcgcaaccggttta tggtaatggcgattatccagatgttgttaaagaaactgttggagatatgctgccggccctgacggatgaa gataaaggatacattaaaggtagcggagatatttttgcgattgacgggtatcgtaccgatatttcccatgcg gctctgaacgggatcgcgaattgtattcgcaaccaaagtgaccgaattggccagtgtgtgaagaaggg tcagatcctttttgctcatgtttacccatccgggtttgctattggtcaatcagccgatccactgtcttcatggtta gtcaactcagccccgtttatccgcgatcaactgaagtttctgacacaaacctaccctgctaagggtggtat ttatttctcggaatttggttgggctgaagacgccgaatatgatcgtcaactgctgtatcaaattacctgggat ggtctgcgtacgcaatacctgacggactatctgagccagctgctgttggctgtgcacaaagacgggatt aatctgcgaggcgcgctgacgtggagtttttgtcgataattgggagtggggtttagggatgcaacagaaat tcggatttcagtttgttaatcaatcagatcccgatctgacacgcacgtttaaactgagcgctcacgcttacg cccaatttgggcgtaatcatctgcaccaccaccaccac |

TABLE 5-continued

Sequences.

| SEQ ID NO: | Name | Sequence |
|---|---|---|
| 68 | MFα(Δ57-70)-rBht(23-594)-HIS (protein) | MRFPSIFTAVLFAASSALAAPVNTTTEDETAQIPAEAVIGYSDLEG DFDVAVLPFSASIAAKEEGVSLEKREAEAVTYPGAIPLSLTSNYET PSPTAIPLEPTPTATGTAELDALWNLVEAQYPVQTAAVTLVTVP DDYKFEADPPSYALAGYETSEIAGLKFPKGFKFGVAGAAIQVEGA AKAEGRGPSTWDYLCHHYASTQCNNYDPDITTNHYYLYPLDFAR LQHLGINTYSFSISWTRIYPLGAGYVNEAGLAHYDAVIHSAKKYG LEPVGTVFHWDTPLSLMLKYGAWQDTGDQIVKDFVTYATTVFK RYGNEVKTWFTFNEPRVFCSQNSGLPYNLTYPEGINSTSAVFRCT YNVLKAHGHAVKVYRDLVASGTIAAGEIGFKSDDNYPIPARPGN ADDEESAKRHEAFRIGIFAQPVYGNGDYPDVVKETVGDMLPALT DEDKGYIKGSGDIFAIDGYRTDISHAALNGIANCIRNQSDPNWPV CEEGSDPFAHVYPSGFAIGQSADPLSSWLVNSAPFIRDQLKFLTQT YPAKGGIYFSEFGWAEDAEYDRQLLYQITWDGLRTQYLTDYLSQ LLLAVHKDGINLRGALTWSFVDNWEWGLGMQQKFGFQFVNQS DPDLTRTFKLSAHAYAQFGRNHLHHHHHH |
| 69 | MFα(Δ57-70)-rBht(23-594)-HIS (nucleic acid) | atgagatttccttcaattttttactgcagtttttattcgcagcatcctccgcattagctgctccagtcaacactaca acagaagatgaaacggcacaaattccggctgaagctgtcatcggttactcagatttagaaggggatttcg atgttgctgtttttgccattttccgccagcattgctgctaaagaagaaggggtatctctcgagaaaagagag gctgaagctgcagaattagatgcgctgtggaacttagtcgaagctcagtacccagttcaaactgctgcag tgacaactttggtgacagtgcccgatgattataagtttgaggcagatccaccgagttatgcattagcaggg tatgaaacaagcgagattgccggactgaagtttccaaaggggtttaagtttggtgttgcggggggcagcc attcaagttgaaggtgcagcaaaagccgaagggcggggcccaagtacctgggattatctgtgtcatcac tatgccagcacgcagtgtaacaattatgatcccgatattacaaccaaccattactacctgtacccattggac tttgcgcgcctgcaacacctaggcattaacacttactcgttttcaatttcatggacgcgtatttatccattggg cgcaggctatgttaatgaagcagggttagcccactatgatgccgtaatccatagtgccaagaagtatggt ctggaaccagtgggcaccgttttcactgggatacgccactgtctctgatgctgaaatacggtgcctggc aagatactggtgacccaaattgttaaggactttgttacctatgccacaactgtgtttaagcgttatggtaatga agtcaagacgtggtttactttcaatgaaccacggttttctgttcacaaaatagtggtctgccatacaatctg acgtatccagaaggtattaacagcacctccgctgtatttcgttgcacctacaatgttctgaaagctcatggt catgctgttaaagtgtatcgggatctagttgcctccgggaccattgcggcaggtgaaatcggctttaaatc cgatgataactacccaatcccggcccgtccagggaacgccgatgacgaggaatcagccaagcgtcac gaggctttcgcattgggaattttgcgcaaccggtttatggtaatggcgattatccagatgtttgttaaagaaa ctgttggagatatgctgccggccctgacggatgaagataaaggatacattaaaggtagcggagatatttttt gcgattgacgggtatcgtaccgatatttcccatgcggctctgaacgggatcgcgaattgtattcgcaacc aaagtgacccgaattggccagtgtgtgaagaagggtcagatcctttgctcatgtttacccatccgggtttt gctattggtcaatcagccgatccactgtcttcatggttagtcaactcagccccgtttatccgcgatcaactg aagtttctgacacaaacctaccctgctaagggtggtatttatttctcggaatttggttgggctgaagacgcc gaatatgatcgtcaactgctgtatcaaattacctgggatggtctgcgtacgcaatacctgacggactatct gagccagctgctgttggctgtgcacaaagacgggattaatctgcgaggcgcgctgacgtggagttttgt cgataattgggagtggggtttagggatgcaacagaaattcggatttcagtttgttaatcaatcagatcccg atctgacacgcacgtttaaactgagcgctcacgcttacgcccaatttgggcgtaatcatctgcaccacca ccaccac |
| 70 | MFα(Δ57-70)-rBht(23-594)-HIS (protein) | MRFPSIFTAVLFAASSALAAPVNTTTEDETAQIPAEAVIGYSDLEG DFDVAVLPFSASIAAKEEGVSLEKREAEAAELDALWNLVEAQYP VQTAAVTTLVTVPDDYKFEADPPSYALAGYETSEIAGLKFPKGFK FGVAGAAIQVEGAAKAEGRGPSTWDYLCHHYASTQCNNYDPDI TTNHYYLYPLDFARLQHLGINTYSFSISWTRIYPLGAGYVNEAGL AHYDAVIHSAKKYGLEPVGTVFHWDTPLSLMLKYGAWQDTGD QIVKDFVTYATTVFKRYGNEVKTWFTFNEPRVFCSQNSGLPYNL TYPEGINSTSAVFRCTYNVLKAHGHAVKVYRDLVASGTIAAGEIG FKSDDNYPIPARPGNADDEESAKRHEAFRIGIFAQPVYGNGDYPD VVKETVGDMLPALTDEDKGYIKGSGDIFAIDGYRTDISHAALNGI ANCIRNQSDPNWPVCEEGSDPFAHVYPSGFAIGQSADPLSSWLVN SAPFIRDQLKFLTQTYPAKGGIYFSEFGWAEDAEYDRQLLYQITW DGLRTQYLTDYLSQLLLAVHKDGINLRGALTWSFVDNWEWGLG MQQKFGFQFVNQSDPDLTRTFKLSAHAYAQFGRNHLHHHHHH |
| 71 (JBB5) | NotI-rBht-6XHIS Reverse | 5'-aaggaaaaaaGCGGCCGCTTAGTGGTGGTGGTGGTG CAGATGATTACGCCCAAATTG-3' |
| 72 (JBB21) | XhoI-MFα-rBht(32-594) Forward | 5'- GAAGAAGGGGTATCTCTCGAGAAAAGAGAGGCTGAAGCTTCC CTGACGAGCAATTACG-3' |
| 73 (JBB22) | XhoI-MFα-rBht(54-594) Forward | 5'- GAAGAAGGGGTATCTCTCGAGAAAAGAGAGGCTGAAGCTACC GGTACAGCAGAATTAG -3 |
| 74 (JBB23) | XhoI-MFα-rBht(57-594) Forward | 5'-GAAGAAGGGGTATCTCTCGAG AAAAGAGAGGCTGAAGCTGCA GAA TTAGATGCGCTGTG-3' |

TABLE 5-continued

Sequences.

| SEQ ID NO: | Name | Sequence |
|---|---|---|
| 75 (JBB24) | XhoI-MFα-rBht$_{(82-594)}$ Forward | 5'-GAAGAAGGGGTATCTCTCGAGAAAAGAGAGGCTGAAGCTACA GTGCCCGATGATTATAAG -3' |
| 76 (JBB25) | XhoI-MFα-rBht$_{(95-594)}$ Forward | 5'-GAAGAAGGGGTATCTCTCGAGAAAAGAGAGGCTGAAGCTAGT TATGCATTAGCAGGGTATG -3' |
| 77 (JBB26) | XhoI-MFα-rBht$_{(103-594)}$ Forward | 5'-GAAGAAGGGGTATCTCTCGAGAAAAGAGAGGCTGAAGCTACA AGCGAGATTGCCGGAC -3' |
| 78 (JBB27) | XhoI-MFα-rBht$_{(23-594)}$ $_{(N289Q)}$ Forward | 5'-TCACAAAATAGTGGTCTGCCATACCAG*CTTACGT*ATCCAGAAG GTATTAACAG-3' |
| 79 (JBB28) | XhoI-MFα-rBht$_{(23-594)}$ $_{(N289Q)}$ Reverse | 5'-CTGTTAATACCTTCTGGATA*CGTAAG*CTGGTATGGCAGACCAC TATTTTGTGA-3' |
| 80 (JBB29) | XhoI-MFα-rBht$_{(23-594)}$ $_{(N297Q)}$ Forward | 5'-CAATCTGACGTATCCAGAAGG*GATCCAG*AGCACCTCCGCTG-3' |
| 81 (JBB30) | XhoI-MFα-rBht$_{(23-594)}$ $_{(N297Q)}$ Reverse | 5'-CAGCGGAGGTGCT*CTGGATC**C*CTTCTGGATACGTCAGATTG-3' |
| 82 (JBB31) | XhoI-MFα-rBht$_{(23-594)}$ $_{(N569Q)}$ Forward | 5'-GAAATTCGGATTTCAGTTTGTT*CAG*CAATC*GG*ATCCCGATCTG ACAC-3' |
| 83 (JBB32) | XhoI-MFα-rBht$_{(23-594)}$ $_{(N569Q)}$ Reverse | 5'-GTGTCAGATCGG*GATCC*GATTG*CT**G*AACAAACTGAAATCCGA ATTTC-3' |
| 84 (JBB33) | XhoI-MFα-rBht (23-594) (N569Q) Forward | 5'-GAAATTCGGATTTCAGTTTGTTCAGCAATCGGATCCCGATCTG ACAC-3' |
| 85 (JBB34) | XhoI-MFα-rBht (23-594) (N569Q) Reverse | 5'-GTGTCAGATCGGGATCCGATTGCTGAACAAACTGAAATCCGA ATTTC-3' |
| 86 (JBB35) | MFα$_{(Δ57-70)}$ Forward | 5'-TTAGCAGCAATGCTGGCGGAAAATGGCAAAACAGC-3' |
| 87 (JBB36) | MFα$_{(Δ57-70)}$ Reverse | 5'-GCTGTTTTGCCATTTTCCGCCAGCATTGCTGCTAA-3' |
| 88 (JBB37) | BamHI-IV-rBht$_{(54-594)}$ Forward | 5'-CGCGGATCCAAACGATGCTTTTGC AAGCTTTCCTTTTCCTTTTGGCTG GTTTTGCAGCCAAGATATCTGCAACCGGTACAGCAGAATTAG-3' |
| 89 (JBB38) | BamHI-GA-rBht$_{(54-594)}$ Forward | 5'-CGCGGATCCAAACGATGTCTTTTA GATCCTTGCTAGCTTTGTCTGGTT TGGTTTGTTCTGGTTTGGCTACCG GTACAGCAGAATTAGATG-3' |
| 90 (JBB39) | BamHI-IN-rBht$_{(54-594)}$ Forward | 5'-CGCGGATCCAAACGATGAAGT TAGCATACTCCTTGTTGCTTCCGC TAGCAGGAGTCAGTGCTACCGGTA CAGCAGAATTAGATG C-3' |
| 91 (JBB3) | rBht Forward internal sequencing | 5'-ATCACTATGCCAGCACGCAGTGTA-3' |

TABLE 5-continued

Sequences.

| SEQ ID NO: | Name | Sequence |
|---|---|---|
| 92 (JBB4) | rBht Reverse internal sequencing | 5'-TTTAAAGCCGATTTCACCTGCCGC-3' |
| 93 (5' AOX1) | AOX1 | 5'-GACTGGTTCCAATTGACAAGC-3' |
| 94 (3' AOX1) | AOX1 | 5'-GCAAATGGCATTCTGACATCC-3' |
| 95 (α-factor) | MFα | 5'-TACTATTGCCAGCATTGCTGC-3' |
| 96 | 2E3Z-A | LALMSAAKLPKSFVWGYATAAYQIEGSPDKDGREPSIWDTFCKA PGKIADGSSGDVATDSYNRWREDVQLLKSYGVKAYRFSLSWSRII PKGGRSDPVNGAGIKHYRTLIEELVKEGITPFVTLYHWDLPQALD DRYGGWLNKEEAIQDFTNYAKLCFESFGDLVQNWITFNEPWVIS VMGYGNGIFAPGHVSNTEPWIVSHHIILAHAHAVKLYRDEFKEK QGGQIGITLDSHWLIPYDDTDASKEATLRAMEFKLGRFANPIYKG EYPPRIKKILGDRLPEFTPEEIELVKGSSDFFGLNTYTTHLVQDGGS DELAGFVKTGHTRADGTQLGTQSDMGWLQTYGPGFRWLLNYL WKAYDKPVYVTENGFPVKGENDLPVEQAVDDTDRQAYYRDYT EALLQAVTEDGADVRGYFGWSLLDNFEWAEGYKVRFGVTHVD YETQKRTPKKSAEFLSRWFKEHIEE |
| 97 | 3AHY-A | MHHHHHHMLPKDFQWGFATAAYQIEGAVDQDGRGPSIWDTFCA QPGKIADGSSGVTACDSYNRTAEDIALLKSLGAKSYRFSISWSRIIP EGGRGDAVNQAGIDHYVKFVDDLLDAGITPFITLFHWDLPEGLH QRYGGLLNRTEFPLDFENYARVMFRALPKVRNWITFNEPLCSAIP GYGSGTFAPGRQSTSEPWTVGHNILVAHGRAVKAYRDDFKPASG DGQIGIVLNGDFTYPWDAADPADKEAAERRLEFFTAWFADPIYL GDYPASMRKQLGDRLPTFTPEERALVHGSNDFYGMNHYTSNYIR HRSSPASADDTVGNVDVLFTNKQGNCIGPETQSPWLRPCAAGFR DFLVWISKRYGYPPIYVTENGTSIKGESDLPKEKILEDDFRVKYYN EYIRAMVTAVELDGVNVKGYFAWSLMDNFEWADGYVTRFGVT YVDYENGQKRFPKKSAKSLKPLFDELI |
| 98 | 5BWF-A | MGSSHHHHHHSSGLVPRGSHMLPKDFQWGFATAAYQIEGAIDK DGRGPSIWDTFCAIPGKIADGTSGVTACDSYNRTAEDIALLKSLG AKSYRFSISWSRIIPKGGRDDPVNQLGIDHYAQFVDDLLEAGITPFI TLFHWDLPEELHQRYGGLLNRTEFPLDFENYARVMFKALPKVRN WITFNEPLCSAIPGYGSGTFAPGRQSTTEPWIVGHNLLVAHGRAV KVYRDEFKDLNDGQIGIVLNGDFTYPWDSSDPLDREAAERRLEFF TAWYADPIYLGDYPASMRKQLGDRLPEFTPEEKAFVLGSNDFYG MNHYTSNYIRHRTSPATADDTVGNVDVLFYNKEGQCIGPETESS WLRPCPAGFRDFLVWISKRYNYPKIYVTENGTSLKGENDLPKEKI LEDDFRVNYYNEYIRAMFTAATLDGVNVKGYFAWSLMDNFEW ADGYVTRFGVTYVDYENGQQRFPKKSAKSLKPLFDELI |
| 99 | 4MDO-A | MGSSHHHHHHSSGLVPRGSHMASMSLPPDFKWGFATAAYQIEGSV NEDGRGPSIWDTFCAIPGKIADGSSGAVACDSYKRTKEDIALLKE LGANSYRFSISWSRIIPLGGRNDPINQKGIDHYVKFVDDLIEAGITP FITLFHWDLPDALDKRYGGFLNKEEFAADFENYARIMFKAIPKCK HWITFNEPWCSAILGYNTGYFAPGHTSDRSKSPVGDSAREPWIVG HNILIAHARAVKAYREDFKPTQGGEIGITLNGDATLPWDPEDPAD IEACDRKIEFAISWFADPIYFGKYPDSMRKQLGDRLPEFTPEEVAL VKGSNDFYGMNHYTANYIKHKTGVPPEDDFLGNLETLFYNKYG DCIGPETQSFWLRPHAQGFRDLLNWLSKRYGYPKIYVTENGTSLK GENDMPLEQVLEDDERVKYFNDYVRAMAAAVAEDGCNVRGYL AWSLLDNFEWAEGYETRFGVTYVDYANDQKRYPKKSAKSLKPL FDSLI |
| 100 | 5JBO-A | MMSESLSLPKDFEWGFATAAYQIEGAVKEGGRGPSIWDTYCHLE PSRTNGANGDVACDHYHRYDEDFDLLTKYGAKAYRFSLSWSRII PLGGRLDPINEEGIQFYSNLIDALLKRGVTPWVTLYHWDLPQALH DRYGGWLNVKEVQLDFERYARLCFERFGDRVKNWITINEPWIQS IYGYATGSNAPGRSSINKHSTEGDTTTEPWLAGKAQIMSHARAV AVYSKDFRASQKGQIGISLNGDYYEPWDSSDPRDKEAAERRMEF |

TABLE 5-continued

| | | |
|---|---|---|
| | | Sequences. |

| SEQ ID NO: | Name | Sequence |
|---|---|---|
| | | HIGWYANPIFLKKDYPASMRKQLGDRLPALTPADFAILNAGETDF |
| | | YGMNYYTSQFARHYEGPVPKTDFLGAIHEHQENKDGSPVGEESG |
| | | IFWLRSCPDMFRKHLARVHGLYGKPIYITENGCPCPGEDKMTCEE |
| | | AINDPFRIQYFDSHLDSISKAISQDGVVVKGYFAWALLDNLEWSD |
| | | GYGPRFGVTYTDYTTLKRTPKKSALVLKDMFADRQ |

$^{a}$, Coding regions are capitalized, restriction sites have been underlined; mutated nucleotides are bold and italicized;
MFα, alpha-factor pre-pro sequence;
IN, Inulinase leader (*Kluyveromyces maxianus*);
GA, Glucoamylase leader (*Aspergillus awamori*);
IV, Invertase leader (*S. cerevisiae*).

Strains and plasmids relevant to the embodiments of the present disclosure are provided in the table below.

TABLE 4B

| | | |
|---|---|---|
| | Stains and Plasmids. | |

| Strains/ Plasmids | $^{a}$Description or genotype | Source or Reference |
|---|---|---|
| *E. coli* | | |
| XL1-Blue | recA1 endA1 gyrA96 thi-1 hsdR17 supE44 relA1 lac [F' proAB lacI$^{q}$ZΔM15 Tn10 (Tet$^{R}$)] | Agilent |
| *K. pastoris* | | |
| GS115 | his4 (his⁻ mut⁺) | Invitrogen |
| JB210 | GS115::MFα-rBht$_{(1-594)}$-HIS (his⁺ mut⁺) | (Dagher and Bruno-Bárcena 2016) |
| JB212 | GS115:MFα-rBht$_{(23-594)}$-HIS (his⁺ mut⁺) | (Dagher and Bruno-Bárcena 2016) |
| JB216 | GS115::MFα-rBht$_{(111-594)}$-HIS (his⁺ mut⁺) | (Dagher and Bruno-Bárcena 2016) |
| JB223 | GS115::MFα-rBht$_{(32-594)}$-HIS (his⁺ mut⁺) | Present disclosure |
| JB224 | GS115::MFα-rBht$_{(54-594)}$-HIS (his⁺ mut⁺) | Present disclosure |
| JB225 | GS115::MFα-rBht$_{(57-594)}$-HIS (his⁺ mut⁺) | Present disclosure |
| JB226 | GS115::MFα-rBht$_{(82-594)}$-HIS (his⁺ mut⁺) | Present disclosure |
| JB227 | GS115::MFα-rBht$_{(95-594)}$-HIS (his⁺ mut⁺) | Present disclosure |
| JB228 | GS115::MFα-rBht$_{(103-594)}$-HIS (his⁺ mut⁺) | Present disclosure |
| JB229 | GS115::MFα-rBht$_{(23-594)(N289Q)}$-HIS (his⁺ mut⁺) | Present disclosure |
| JB230 | GS115::MFα-rBht$_{(23-594)(N297Q)}$-HIS (his⁺ mut⁺) | Present disclosure |
| JB231 | GS115::MFα-rBht$_{(23-594)(N431Q)}$-HIS (his⁺ mut⁺) | Present disclosure |
| JB232 | GS115::MFα-rBht$_{(23-594)(N569Q)}$-HIS (his⁺ mut⁺) | Present disclosure |
| JB233 | GS115::MFα$_{(Δ57-70)}$-rBht$_{(23-594)}$-HIS (his⁺ mut⁺) | Present disclosure |
| JB234 | GS115::IV-rBht$_{(54-594)}$-HIS (his⁺ mut⁺) | Present disclosure |
| JB235 | GS115::GA-rBht$_{(54-594)}$-HIS (his⁺ mut⁺) | Present disclosure |
| JB236 | GS115::IN-rBht$_{(54-594)}$-HIS (his⁺ mut⁺) | Present disclosure |
| JB237 | GS115::pPIC9 (his⁺ mut⁺) control | Present disclosure |
| JB240 | GS115::MFα$_{(Δ57-70)}$-rBht$_{(57-594)}$-HIS (his⁺ mut⁺) | Present disclosure |
| Plasmids *K. pastoris* | | |
| pPIC9 | *K. pastoris* integrative vector carrying AOX1 promoter and transcription terminator, HIS4, Amp$^{r}$ in *E. coli*, pBR322 ori, alpha factor pre-pro leader from *S. cerevisiae* (MFα) | Invitrogen |
| pJB110 | pPIC9-MFα-rBht$_{(1-594)}$-HIS | (Dagher and Bruno-Bárcena 2016) |
| pJB112 | pPIC9-MFα-rBht$_{(23-594)}$-HIS | (Dagher and Bruno-Bárcena 2016) |
| pJB116 | pPIC9-MFα-rBht$_{(111-594)}$-HIS | (Dagher and Bruno-Bárcena 2016) |
| pJB123 | pPIC9-MFα-rBht$_{(32-594)}$-HIS | Present disclosure |
| pJB124 | pPIC9-MFα-rBht$_{(54-594)}$-HIS | Present disclosure |
| pJB125 | pPIC9-MFα-rBht$_{(57-594)}$-HIS | Present disclosure |
| pJB126 | pPIC9-MFα-rBht$_{(82-594)}$-HIS | Present disclosure |
| PJB127 | pPIC9-MFα-rBht$_{(95-594)}$-HIS | Present disclosure |
| PJB128 | pPIC9-MFα-rBht$_{(103-594)}$-HIS | Present disclosure |
| PJB129 | pPIC9-MFα-rBht$_{(23-594)(N2890)}$-HIS | Present disclosure |
| pJB130 | pPIC9-MFα-rBht$_{(23-594)(N297Q)}$-HIS | Present disclosure |
| pJB131 | pPIC9-MFα-rBht$_{(23-594)(N4310)}$-HIS | Present disclosure |

TABLE 4B-continued

Stains and Plasmids.

| Strains/ Plasmids | ªDescription or genotype | Source or Reference |
|---|---|---|
| pJB132 | pPIC9-MFα-rBht(23-594)(N569Q)-HIS | Present disclosure |
| pJB133 | pPIC9-MFα(Δ57-70)-rBht(23-594)-HIS | Present disclosure |
| pJB134 | pPIC9-IV-rBht(54-594)-HIS | Present disclosure |
| pJB135 | pPIC9-GA-rBht(54-594)-HIS | Present disclosure |
| pJB136 | pPIC9-IN-rBht(54-594)-HIS | Present disclosure |
| pJB137 | pPIC9-MFα(Δ57-70)-rBht(57-594)-HIS | Present disclosure |

ªMFα, *S. cerevisiae* alpha factor pre-pro secretion leader found in pPIC9 vector is indicated in constructions to help differentiate between alternative signal sequences; IN, Inulinase leader (*Kluyveromyces maxianus*); GA, Glucoamylase leader (*Aspergillus awamori*); IV, Invertase leader (*S. cerevisiae*).

It is understood that the foregoing detailed description and accompanying examples are merely illustrative and are not to be taken as limitations upon the scope of the disclosure, which is defined solely by the appended claims and their equivalents.

All publications and patents mentioned in the above specification are herein incorporated by reference as if expressly set forth herein. Various changes and modifications to the disclosed embodiments will be apparent to those skilled in the art and may be made without departing from the spirit and scope thereof.

SEQUENCE LISTING

```
<160> NUMBER OF SEQ ID NOS: 100

<210> SEQ ID NO 1
<211> LENGTH: 594
<212> TYPE: PRT
<213> ORGANISM: Artificial sequence
<220> FEATURE:
<223> OTHER INFORMATION: Synthetic

<400> SEQUENCE: 1

Met Met Leu His Ala Ala Leu Leu Val Ala Leu Pro Cys Val Val Leu
1               5                   10                  15

Ala Arg Pro Ala Gly Ala Val Thr Tyr Pro Gly Ala Ile Pro Leu Ser
            20                  25                  30

Leu Thr Ser Asn Tyr Glu Thr Pro Ser Pro Thr Ala Ile Pro Leu Glu
        35                  40                  45

Pro Thr Pro Thr Ala Thr Gly Thr Ala Glu Leu Asp Ala Leu Trp Asn
    50                  55                  60

Leu Val Glu Ala Gln Tyr Pro Val Gln Thr Ala Ala Val Thr Thr Leu
65                  70                  75                  80

Val Thr Val Pro Asp Asp Tyr Lys Phe Glu Ala Asp Pro Pro Ser Tyr
                85                  90                  95

Ala Leu Ala Gly Tyr Glu Thr Ser Glu Ile Ala Gly Leu Lys Phe Pro
                100                 105                 110

Lys Gly Phe Lys Phe Gly Val Ala Gly Ala Ala Ile Gln Val Glu Gly
            115                 120                 125

Ala Ala Lys Ala Glu Gly Arg Gly Pro Ser Thr Trp Asp Tyr Leu Cys
    130                 135                 140

His His Tyr Ala Ser Thr Gln Cys Asn Asn Tyr Asp Pro Asp Ile Thr
145                 150                 155                 160

Thr Asn His Tyr Tyr Leu Tyr Pro Leu Asp Phe Ala Arg Leu Gln His
                165                 170                 175

Leu Gly Ile Asn Thr Tyr Ser Phe Ser Ile Ser Trp Thr Arg Ile Tyr
```

-continued

```
                180                 185                 190
Pro Leu Gly Ala Gly Tyr Val Asn Glu Ala Gly Leu Ala His Tyr Asp
        195                 200                 205
Ala Val Ile His Ser Ala Lys Lys Tyr Gly Leu Glu Pro Val Gly Thr
        210                 215                 220
Val Phe His Trp Asp Thr Pro Leu Ser Leu Met Leu Lys Tyr Gly Ala
225                 230                 235                 240
Trp Gln Asp Thr Gly Asp Gln Ile Val Lys Asp Phe Val Thr Tyr Ala
                245                 250                 255
Thr Thr Val Phe Lys Arg Tyr Gly Asn Glu Val Lys Thr Trp Phe Thr
                260                 265                 270
Phe Asn Glu Pro Arg Val Phe Cys Ser Gln Asn Ser Gly Leu Pro Tyr
        275                 280                 285
Asn Leu Thr Tyr Pro Glu Gly Ile Asn Ser Thr Ser Ala Val Phe Arg
        290                 295                 300
Cys Thr Tyr Asn Val Leu Lys Ala His Gly His Ala Val Lys Val Tyr
305                 310                 315                 320
Arg Asp Leu Val Ala Ser Gly Thr Ile Ala Ala Gly Glu Ile Gly Phe
                325                 330                 335
Lys Ser Asp Asp Asn Tyr Pro Ile Pro Ala Arg Pro Gly Asn Ala Asp
                340                 345                 350
Asp Glu Glu Ser Ala Lys Arg His Glu Ala Phe Arg Ile Gly Ile Phe
                355                 360                 365
Ala Gln Pro Val Tyr Gly Asn Gly Asp Tyr Pro Asp Val Val Lys Glu
        370                 375                 380
Thr Val Gly Asp Met Leu Pro Ala Leu Thr Asp Glu Asp Lys Gly Tyr
385                 390                 395                 400
Ile Lys Gly Ser Gly Asp Ile Phe Ala Ile Asp Gly Tyr Arg Thr Asp
                405                 410                 415
Ile Ser His Ala Ala Leu Asn Gly Ile Ala Asn Cys Ile Arg Asn Gln
                420                 425                 430
Ser Asp Pro Asn Trp Pro Val Cys Glu Glu Gly Ser Asp Pro Phe Ala
                435                 440                 445
His Val Tyr Pro Ser Gly Phe Ala Ile Gly Gln Ser Ala Asp Pro Leu
        450                 455                 460
Ser Ser Trp Leu Val Asn Ser Ala Pro Phe Ile Arg Asp Gln Leu Lys
465                 470                 475                 480
Phe Leu Thr Gln Thr Tyr Pro Ala Lys Gly Gly Ile Tyr Phe Ser Glu
                485                 490                 495
Phe Gly Trp Ala Glu Asp Ala Glu Tyr Asp Arg Gln Leu Leu Tyr Gln
                500                 505                 510
Ile Thr Trp Asp Gly Leu Arg Thr Gln Tyr Leu Thr Asp Tyr Leu Ser
                515                 520                 525
Gln Leu Leu Leu Ala Val His Lys Asp Gly Ile Asn Leu Arg Gly Ala
        530                 535                 540
Leu Thr Trp Ser Phe Val Asp Asn Trp Glu Trp Gly Leu Gly Met Gln
545                 550                 555                 560
Gln Lys Phe Gly Phe Gln Phe Val Asn Gln Ser Asp Pro Asp Leu Thr
                565                 570                 575
Arg Thr Phe Lys Leu Ser Ala His Ala Tyr Ala Gln Phe Gly Arg Asn
                580                 585                 590
His Leu
```

-continued

<210> SEQ ID NO 2
<211> LENGTH: 1782
<212> TYPE: DNA
<213> ORGANISM: Artificial sequence
<220> FEATURE:
<223> OTHER INFORMATION: Synthetic

<400> SEQUENCE: 2

```
atgatgctgc atgctgcact gctagtagcg ctgccatgtg ttgttttggc gcgcccggcc      60
ggagcggtta cttatccggg agccattcct ctgtccctga cgagcaatta cgaaacccca     120
agtccgacag caatcccgct ggagccaaca ccgacggcta ccggtacagc agaattagat     180
gcgctgtgga acttagtcga agctcagtac ccagttcaaa ctgctgcagt gacaactttg     240
gtgacagtgc ccgatgatta taagtttgag gcagatccac cgagttatgc attagcaggg     300
tatgaaacaa gcgagattgc cggactgaag tttccaaagg ggtttaagtt tggtgttgcg     360
ggggcagcca ttcaagttga aggtgcagca aaagccgaag ggcggggccc aagtacctgg     420
gattatctgt gtcatcacta tgccagcacg cagtgtaaca attatgatcc cgatattaca     480
accaaccatt actacctgta cccattggac tttgcgcgcc tgcaacacct aggcattaac     540
acttactcgt tttcaatttc atggacgcgt atttatccat tgggcgcagg ctatgttaat     600
gaagcagggt tagcccacta tgatgccgta atccatagtg ccaagaagta tggtctggaa     660
ccagtgggca ccgttttca ctgggatacg ccactgtctc tgatgctgaa atacggtgcc     720
tggcaagata ctggtgacca aattgttaag gactttgtta cctatgccac aactgtgttt     780
aagcgttatg gtaatgaagt caagacgtgg tttactttca atgaaccacg ggttttctgt     840
tcacaaaata gtggtctgcc atacaatctg acgtatccag aaggtattaa cagcacctcc     900
gctgtatttc gttgcaccta caatgttctg aaagctcatg gtcatgctgt taaagtgtat     960
cgggatctag ttgcctccgg gaccattgcg gcaggtgaaa tcggctttaa atccgatgat    1020
aactacccaa tcccggcccg tccagggaac gccgatgacg aggaatcagc caagcgtcac    1080 gaggctttc gcattgggat ttttgcgcaa ccggtttatg gtaatggcga ttatccagat    1140
gttgttaaag aaactgttgg agatatgctg ccggccctga cggatgaaga taaaggatac    1200
attaaaggta gcggagatat ttttgcgatt gacgggtatc gtaccgatat ttcccatgcg    1260
gctctgaacg ggatcgcgaa ttgtattcgc aaccaaagtg acccgaattg gccagtgtgt    1320
gaagaagggt cagatccttt tgctcatgtt tacccatccg ggtttgctat tggtcaatca    1380
gccgatccac tgtcttcatg gttagtcaac tcagccccgt ttatccgcga tcaactgaag    1440
tttctgacac aaacctaccc tgctaagggt ggtatttatt tctcggaatt tggttgggct    1500
gaagacgccg aatatgatcg tcaactgctg tatcaaatta cctgggatgg tctgcgtacg    1560
caatacctga cggactatct gagccagctg ctgttggctg tgcacaaaga cgggattaat    1620
ctgcgaggcg cgctgacgtg gagttttgtc gataattggg agtggggttt agggatgcaa    1680
cagaaattcg gatttcagtt tgttaatcaa tcagatcccg atctgacacg cacgtttaaa    1740
ctgagcgctc acgcttacgc ccaatttggg cgtaatcatc tg                       1782
```

<210> SEQ ID NO 3
<211> LENGTH: 572
<212> TYPE: PRT
<213> ORGANISM: Artificial sequence
<220> FEATURE:
<223> OTHER INFORMATION: Synthetic

<400> SEQUENCE: 3

-continued

```
Val Thr Tyr Pro Gly Ala Ile Pro Leu Ser Leu Thr Ser Asn Tyr Glu
1               5                   10                  15

Thr Pro Ser Pro Thr Ala Ile Pro Leu Glu Pro Thr Pro Thr Ala Thr
            20                  25                  30

Gly Thr Ala Glu Leu Asp Ala Leu Trp Asn Leu Val Glu Ala Gln Tyr
            35                  40                  45

Pro Val Gln Thr Ala Ala Val Thr Thr Leu Val Thr Val Pro Asp Asp
    50                  55                  60

Tyr Lys Phe Glu Ala Asp Pro Pro Ser Tyr Ala Leu Ala Gly Tyr Glu
65                  70                  75                  80

Thr Ser Glu Ile Ala Gly Leu Lys Phe Pro Lys Gly Phe Lys Phe Gly
                85                  90                  95

Val Ala Gly Ala Ala Ile Gln Val Glu Gly Ala Ala Lys Ala Glu Gly
            100                 105                 110

Arg Gly Pro Ser Thr Trp Asp Tyr Leu Cys His His Tyr Ala Ser Thr
            115                 120                 125

Gln Cys Asn Asn Tyr Asp Pro Asp Ile Thr Thr Asn His Tyr Tyr Leu
    130                 135                 140

Tyr Pro Leu Asp Phe Ala Arg Leu Gln His Leu Gly Ile Asn Thr Tyr
145                 150                 155                 160

Ser Phe Ser Ile Ser Trp Thr Arg Ile Tyr Pro Leu Gly Ala Gly Tyr
                165                 170                 175

Val Asn Glu Ala Gly Leu Ala His Tyr Asp Ala Val Ile His Ser Ala
            180                 185                 190

Lys Lys Tyr Gly Leu Glu Pro Val Gly Thr Val Phe His Trp Asp Thr
            195                 200                 205

Pro Leu Ser Leu Met Leu Lys Tyr Gly Ala Trp Gln Asp Thr Gly Asp
    210                 215                 220

Gln Ile Val Lys Asp Phe Val Thr Tyr Ala Thr Thr Val Phe Lys Arg
225                 230                 235                 240

Tyr Gly Asn Glu Val Lys Thr Trp Phe Thr Phe Asn Glu Pro Arg Val
                245                 250                 255

Phe Cys Ser Gln Asn Ser Gly Leu Pro Tyr Asn Leu Thr Tyr Pro Glu
            260                 265                 270

Gly Ile Asn Ser Thr Ser Ala Val Phe Arg Cys Thr Tyr Asn Val Leu
            275                 280                 285

Lys Ala His Gly His Ala Val Lys Val Tyr Arg Asp Leu Val Ala Ser
    290                 295                 300

Gly Thr Ile Ala Ala Gly Glu Ile Gly Phe Lys Ser Asp Asp Asn Tyr
305                 310                 315                 320

Pro Ile Pro Ala Arg Pro Gly Asn Ala Asp Asp Glu Glu Ser Ala Lys
            325                 330                 335

Arg His Glu Ala Phe Arg Ile Gly Ile Phe Ala Gln Pro Val Tyr Gly
            340                 345                 350

Asn Gly Asp Tyr Pro Asp Val Val Lys Glu Thr Val Gly Asp Met Leu
            355                 360                 365

Pro Ala Leu Thr Asp Glu Asp Lys Gly Tyr Ile Lys Gly Ser Gly Asp
    370                 375                 380

Ile Phe Ala Ile Asp Gly Tyr Arg Thr Asp Ile Ser His Ala Ala Leu
385                 390                 395                 400

Asn Gly Ile Ala Asn Cys Ile Arg Asn Gln Ser Asp Pro Asn Trp Pro
            405                 410                 415
```

```
Val Cys Glu Glu Gly Ser Asp Pro Phe Ala His Val Tyr Pro Ser Gly
            420                 425                 430

Phe Ala Ile Gly Gln Ser Ala Asp Pro Leu Ser Ser Trp Leu Val Asn
            435                 440                 445

Ser Ala Pro Phe Ile Arg Asp Gln Leu Lys Phe Leu Thr Gln Thr Tyr
            450                 455                 460

Pro Ala Lys Gly Gly Ile Tyr Phe Ser Glu Phe Gly Trp Ala Glu Asp
465                 470                 475                 480

Ala Glu Tyr Asp Arg Gln Leu Leu Tyr Gln Ile Thr Trp Asp Gly Leu
                485                 490                 495

Arg Thr Gln Tyr Leu Thr Asp Tyr Leu Ser Gln Leu Leu Leu Ala Val
            500                 505                 510

His Lys Asp Gly Ile Asn Leu Arg Gly Ala Leu Thr Trp Ser Phe Val
            515                 520                 525

Asp Asn Trp Glu Trp Gly Leu Gly Met Gln Gln Lys Phe Gly Phe Gln
            530                 535                 540

Phe Val Asn Gln Ser Asp Pro Asp Leu Thr Arg Thr Phe Lys Leu Ser
545                 550                 555                 560

Ala His Ala Tyr Ala Gln Phe Gly Arg Asn His Leu
                565                 570
```

<210> SEQ ID NO 4
<211> LENGTH: 1716
<212> TYPE: DNA
<213> ORGANISM: Artificial sequence
<220> FEATURE:
<223> OTHER INFORMATION: Synthetic

<400> SEQUENCE: 4

```
gttacttatc cgggagccat tcctctgtcc ctgacgagca attacgaaac cccaagtccg      60
acagcaatcc cgctggagcc aacaccgacg gctaccggta cagcagaatt agatgcgctg     120
tggaacttag tcgaagctca gtacccagtt caaactgctg cagtgacaac tttggtgaca     180
gtgcccgatg attataagtt tgaggcagat ccaccgagtt atgcattagc agggtatgaa     240
acaagcgaga ttgccggact gaagtttcca aaggggttta agtttggtgt tgcggggca     300 gccattcaag ttgaaggtgc agcaaaagcc gaagggcggg gcccaagtac ctgggattat     360
ctgtgtcatc actatgccag cacgcagtgt aacaattatg atcccgatat tacaaccaac     420
cattactacc tgtacccatt ggactttgcg cgcctgcaac acctaggcat taacacttac     480 tcgtttcaa tttcatggac gcgtatttat ccattgggcg caggctatgt taatgaagca     540 gggttagcc actatgatgc cgtaatccat agtgccaaga agtatggtct ggaaccagtg     600
ggcaccgttt ttcactggga tacgccactg tctctgatgc tgaaatacgg tgcctggcaa     660
gatactggtg accaaattgt taaggacttt gttacctatg ccacaactgt gtttaagcgt     720
tatggtaatg aagtcaagac gtggtttact ttcaatgaac cacgggtttt ctgttcacaa     780
aatagtggtc tgccatacaa tctgacgtat ccagaaggta ttaacagcac ctccgctgta     840
tttcgttgca cctacaatgt tctgaaagct catggtcatg ctgttaaagt gtatcgggat     900
ctagttgcct ccgggaccat tgcggcaggt gaaatcggct ttaaatccga tgataactac     960
ccaatcccgg cccgtccagg gaacgccgat gacgaggaat cagccaagcg tcacgaggct    1020
tttcgcattg ggatttttgc gcaaccggtt tatggtaatg cgattatcc agatgttgtt    1080 aaagaaactg ttggagatat gctgccggcc ctgacggatg aagataaagg atacattaaa    1140
ggtagcggag atattttttgc gattgacggg tatcgtaccg atatttccca tgcggctctg    1200
```

-continued

```
aacgggatcg cgaattgtat tcgcaaccaa agtgacccga attggccagt gtgtgaagaa    1260
gggtcagatc cttttgctca tgtttaccca tccgggtttg ctattggtca atcagccgat    1320
ccactgtctt catggttagt caactcagcc ccgtttatcc gcgatcaact gaagtttctg    1380
acacaaacct accctgctaa gggtggtatt tatttctcgg aatttggttg ggctgaagac    1440
gccgaatatg atcgtcaact gctgtatcaa attacctggg atggtctgcg tacgcaatac    1500
ctgacggact atctgagcca gctgctgttg gctgtgcaca aagacgggat taatctgcga    1560
ggcgcgctga cgtggagttt tgtcgataat tgggagtggg gtttagggat gcaacagaaa    1620
ttcggatttc agtttgttaa tcaatcagat cccgatctga cacgcacgtt taaactgagc    1680
gctcacgctt acgcccaatt tgggcgtaat catctg                             1716
```

<210> SEQ ID NO 5
<211> LENGTH: 563
<212> TYPE: PRT
<213> ORGANISM: Artificial sequence
<220> FEATURE:
<223> OTHER INFORMATION: Synthetic

<400> SEQUENCE: 5

```
Ser Leu Thr Ser Asn Tyr Glu Thr Pro Ser Pro Thr Ala Ile Pro Leu
1               5                   10                  15

Glu Pro Thr Pro Thr Ala Thr Gly Thr Ala Glu Leu Asp Ala Leu Trp
            20                  25                  30

Asn Leu Val Glu Ala Gln Tyr Pro Val Gln Thr Ala Ala Val Thr Thr
        35                  40                  45

Leu Val Thr Val Pro Asp Asp Tyr Lys Phe Glu Ala Asp Pro Pro Ser
    50                  55                  60

Tyr Ala Leu Ala Gly Tyr Glu Thr Ser Glu Ile Ala Gly Leu Lys Phe
65                  70                  75                  80

Pro Lys Gly Phe Lys Phe Gly Val Ala Gly Ala Ala Ile Gln Val Glu
                85                  90                  95

Gly Ala Ala Lys Ala Glu Gly Arg Gly Pro Ser Thr Trp Asp Tyr Leu
            100                 105                 110

Cys His His Tyr Ala Ser Thr Gln Cys Asn Asn Tyr Asp Pro Asp Ile
        115                 120                 125

Thr Thr Asn His Tyr Tyr Leu Tyr Pro Leu Asp Phe Ala Arg Leu Gln
    130                 135                 140

His Leu Gly Ile Asn Thr Tyr Ser Phe Ser Ile Ser Trp Thr Arg Ile
145                 150                 155                 160

Tyr Pro Leu Gly Ala Gly Tyr Val Asn Glu Ala Gly Leu Ala His Tyr
                165                 170                 175

Asp Ala Val Ile His Ser Ala Lys Lys Tyr Gly Leu Glu Pro Val Gly
            180                 185                 190

Thr Val Phe His Trp Asp Thr Pro Leu Ser Leu Met Leu Lys Tyr Gly
            195                 200                 205

Ala Trp Gln Asp Thr Gly Asp Gln Ile Val Lys Asp Phe Val Thr Tyr
    210                 215                 220

Ala Thr Thr Val Phe Lys Arg Tyr Gly Asn Glu Val Lys Thr Trp Phe
225                 230                 235                 240

Thr Phe Asn Glu Pro Arg Val Phe Cys Ser Gln Asn Ser Gly Leu Pro
                245                 250                 255

Tyr Asn Leu Thr Tyr Pro Glu Gly Ile Asn Ser Thr Ser Ala Val Phe
            260                 265                 270
```

-continued

```
Arg Cys Thr Tyr Asn Val Leu Lys Ala His Gly His Ala Val Lys Val
        275                 280                 285

Tyr Arg Asp Leu Val Ala Ser Gly Thr Ile Ala Ala Gly Glu Ile Gly
    290                 295                 300

Phe Lys Ser Asp Asp Asn Tyr Pro Ile Pro Ala Arg Pro Gly Asn Ala
305                 310                 315                 320

Asp Asp Glu Glu Ser Ala Lys Arg His Glu Ala Phe Arg Ile Gly Ile
                325                 330                 335

Phe Ala Gln Pro Val Tyr Gly Asn Gly Asp Tyr Pro Asp Val Val Lys
                340                 345                 350

Glu Thr Val Gly Asp Met Leu Pro Ala Leu Thr Asp Glu Asp Lys Gly
                355                 360                 365

Tyr Ile Lys Gly Ser Gly Asp Ile Phe Ala Ile Asp Gly Tyr Arg Thr
    370                 375                 380

Asp Ile Ser His Ala Ala Leu Asn Gly Ile Ala Asn Cys Ile Arg Asn
385                 390                 395                 400

Gln Ser Asp Pro Asn Trp Pro Val Cys Glu Glu Gly Ser Asp Pro Phe
                405                 410                 415

Ala His Val Tyr Pro Ser Gly Phe Ala Ile Gly Gln Ser Ala Asp Pro
                420                 425                 430

Leu Ser Ser Trp Leu Val Asn Ser Ala Pro Phe Ile Arg Asp Gln Leu
                435                 440                 445

Lys Phe Leu Thr Gln Thr Tyr Pro Ala Lys Gly Gly Ile Tyr Phe Ser
    450                 455                 460

Glu Phe Gly Trp Ala Glu Asp Ala Glu Tyr Asp Arg Gln Leu Leu Tyr
465                 470                 475                 480

Gln Ile Thr Trp Asp Gly Leu Arg Thr Gln Tyr Leu Thr Asp Tyr Leu
                485                 490                 495

Ser Gln Leu Leu Leu Ala Val His Lys Asp Gly Ile Asn Leu Arg Gly
                500                 505                 510

Ala Leu Thr Trp Ser Phe Val Asp Asn Trp Glu Trp Gly Leu Gly Met
                515                 520                 525

Gln Gln Lys Phe Gly Phe Gln Phe Val Asn Gln Ser Asp Pro Asp Leu
    530                 535                 540

Thr Arg Thr Phe Lys Leu Ser Ala His Ala Tyr Ala Gln Phe Gly Arg
545                 550                 555                 560

Asn His Leu
```

```
<210> SEQ ID NO 6
<211> LENGTH: 1689
<212> TYPE: DNA
<213> ORGANISM: Artificial sequence
<220> FEATURE:
<223> OTHER INFORMATION: Synthetic

<400> SEQUENCE: 6
tccctgacga gcaattacga aaccccaagt ccgacagcaa tcccgctgga gccaacaccg      60
acggctaccg gtacagcaga attagatgcg ctgtggaact tagtcgaagc tcagtaccca     120
gttcaaactg ctgcagtgac aactttggtg acagtgcccg atgattataa gtttgaggca     180
gatccaccga gttatgcatt agcagggtat gaaacaagcg agattgccgg actgaagttt     240 ccaaagggt ttaagtttgg tgttgcgggg gcagccattc aagttgaagg tgcagcaaaa     300
gccgaagggc ggggcccaag tacctgggat tatctgtgtc atcactatgc cagcacgcag     360
```

-continued

```
tgtaacaatt atgatcccga tattacaacc aaccattact acctgtaccc attggacttt      420
gcgcgcctgc aacacctagg cattaacact tactcgtttt caatttcatg gacgcgtatt      480
tatccattgg gcgcaggcta tgttaatgaa gcagggttag cccactatga tgccgtaatc      540
catagtgcca agaagtatgg tctggaacca gtgggcaccg tttttcactg ggatacgcca      600
ctgtctctga tgctgaaata cggtgcctgg caagatactg gtgaccaaat tgttaaggac      660
tttgttacct atgccacaac tgtgtttaag cgttatggta atgaagtcaa gacgtggttt      720
actttcaatg aaccacgggt tttctgttca caaaatagtg tctgccata caatctgacg      780 tatccagaag gtattaacag cacctccgct gtatttcgtt gcacctacaa tgttctgaaa      840
gctcatggtc atgctgttaa agtgtatcgg gatctagttg cctccgggac cattgcggca      900
ggtgaaatcg gctttaaatc cgatgataac tacccaatcc cggcccgtcc agggaacgcc      960
gatgacgagg aatcagccaa gcgtcacgag gctttccgca ttgggatttt tgcgcaaccg     1020
gtttatggta atggcgatta tccagatgtt gttaaagaaa ctgttggaga tatgctgccg     1080
gccctgacgg atgaagataa aggatacatt aaaggtagcg gagatatttt tgcgattgac     1140
gggtatcgta ccgatatttc ccatgcggct ctgaacggga tcgcgaattg tattcgcaac     1200
caaagtgacc cgaattggcc agtgtgtgaa gaagggtcag atcctttgc tcatgtttac      1260 ccatccgggt ttgctattgg tcaatcagcc gatccactgt cttcatggtt agtcaactca     1320 gccccgtta tccgcgatca actgaagttt ctgacacaaa cctaccctgc taagggtggt      1380
atttatttct cggaatttgg ttgggctgaa gacgccgaat atgatcgtca actgctgtat     1440
caaattacct gggatggtct gcgtacgcaa tacctgacgg actatctgag ccagctgctg     1500
ttggctgtgc acaaagacgg gattaatctg cgaggcgcgc tgacgtggag ttttgtcgat     1560
aattgggagt ggggtttagg gatgcaacag aaattcggat ttcagtttgt taatcaatca     1620
gatcccgatc tgacacgcac gtttaaactg agcgctcacg cttacgccca atttgggcgt     1680
aatcatctg                                                            1689
```

```
<210> SEQ ID NO 7
<211> LENGTH: 541
<212> TYPE: PRT
<213> ORGANISM: Artificial sequence
<220> FEATURE:
<223> OTHER INFORMATION: Synthetic

<400> SEQUENCE: 7

Thr Gly Thr Ala Glu Leu Asp Ala Leu Trp Asn Leu Val Glu Ala Gln
1               5                   10                  15

Tyr Pro Val Gln Thr Ala Ala Val Thr Thr Leu Val Thr Val Pro Asp
                20                  25                  30

Asp Tyr Lys Phe Glu Ala Asp Pro Pro Ser Tyr Ala Leu Ala Gly Tyr
            35                  40                  45

Glu Thr Ser Glu Ile Ala Gly Leu Lys Phe Pro Lys Gly Phe Lys Phe
        50                  55                  60

Gly Val Ala Gly Ala Ala Ile Gln Val Glu Gly Ala Ala Lys Ala Glu
65                  70                  75                  80

Gly Arg Gly Pro Ser Thr Trp Asp Tyr Leu Cys His His Tyr Ala Ser
                85                  90                  95

Thr Gln Cys Asn Asn Tyr Asp Pro Asp Ile Thr Thr Asn His Tyr Tyr
            100                 105                 110

Leu Tyr Pro Leu Asp Phe Ala Arg Leu Gln His Leu Gly Ile Asn Thr
            115                 120                 125
```

-continued

```
Tyr Ser Phe Ser Ile Ser Trp Thr Arg Ile Tyr Pro Leu Gly Ala Gly
    130             135             140

Tyr Val Asn Glu Ala Gly Leu Ala His Tyr Asp Ala Val Ile His Ser
145             150             155             160

Ala Lys Lys Tyr Gly Leu Glu Pro Val Gly Thr Val Phe His Trp Asp
            165             170             175

Thr Pro Leu Ser Leu Met Leu Lys Tyr Gly Ala Trp Gln Asp Thr Gly
            180             185             190

Asp Gln Ile Val Lys Asp Phe Val Thr Tyr Ala Thr Thr Val Phe Lys
            195             200             205

Arg Tyr Gly Asn Glu Val Lys Thr Trp Phe Thr Phe Asn Glu Pro Arg
    210             215             220

Val Phe Cys Ser Gln Asn Ser Gly Leu Pro Tyr Asn Leu Thr Tyr Pro
225             230             235             240

Glu Gly Ile Asn Ser Thr Ser Ala Val Phe Arg Cys Thr Tyr Asn Val
            245             250             255

Leu Lys Ala His Gly His Ala Val Lys Val Tyr Arg Asp Leu Val Ala
            260             265             270

Ser Gly Thr Ile Ala Ala Gly Glu Ile Gly Phe Lys Ser Asp Asp Asn
            275             280             285

Tyr Pro Ile Pro Ala Arg Pro Gly Asn Ala Asp Asp Glu Glu Ser Ala
    290             295             300

Lys Arg His Glu Ala Phe Arg Ile Gly Ile Phe Ala Gln Pro Val Tyr
305             310             315             320

Gly Asn Gly Asp Tyr Pro Asp Val Val Lys Glu Thr Val Gly Asp Met
            325             330             335

Leu Pro Ala Leu Thr Asp Glu Asp Lys Gly Tyr Ile Lys Gly Ser Gly
            340             345             350

Asp Ile Phe Ala Ile Asp Gly Tyr Arg Thr Asp Ile Ser His Ala Ala
            355             360             365

Leu Asn Gly Ile Ala Asn Cys Ile Arg Asn Gln Ser Asp Pro Asn Trp
    370             375             380

Pro Val Cys Glu Glu Gly Ser Asp Pro Phe Ala His Val Tyr Pro Ser
385             390             395             400

Gly Phe Ala Ile Gly Gln Ser Ala Asp Pro Leu Ser Ser Trp Leu Val
            405             410             415

Asn Ser Ala Pro Phe Ile Arg Asp Gln Leu Lys Phe Leu Thr Gln Thr
            420             425             430

Tyr Pro Ala Lys Gly Gly Ile Tyr Phe Ser Glu Phe Gly Trp Ala Glu
            435             440             445

Asp Ala Glu Tyr Asp Arg Gln Leu Leu Tyr Gln Ile Thr Trp Asp Gly
    450             455             460

Leu Arg Thr Gln Tyr Leu Thr Asp Tyr Leu Ser Gln Leu Leu Leu Ala
465             470             475             480

Val His Lys Asp Gly Ile Asn Leu Arg Gly Ala Leu Thr Trp Ser Phe
            485             490             495

Val Asp Asn Trp Glu Trp Gly Leu Gly Met Gln Gln Lys Phe Gly Phe
            500             505             510

Gln Phe Val Asn Gln Ser Asp Pro Asp Leu Thr Arg Thr Phe Lys Leu
            515             520             525

Ser Ala His Ala Tyr Ala Gln Phe Gly Arg Asn His Leu
    530             535             540
```

<210> SEQ ID NO 8
<211> LENGTH: 1623
<212> TYPE: DNA
<213> ORGANISM: Artificial sequence
<220> FEATURE:
<223> OTHER INFORMATION: Synthetic

<400> SEQUENCE: 8
accggtacag cagaattaga tgcgctgtgg aacttagtcg aagctcagta cccagttcaa     60
actgctgcag tgacaacttt ggtgacagtg cccgatgatt ataagtttga ggcagatcca    120
ccgagttatg cattagcagg gtatgaaaca agcgagattg ccggactgaa gtttccaaag    180
gggtttaagt ttggtgttgc gggggcagcc attcaagttg aaggtgcagc aaaagccgaa    240
gggcggggcc caagtacctg ggattatctg tgtcatcact atgccagcac gcagtgtaac    300
aattatgatc ccgatattac aaccaaccat tactacctgt acccattgga ctttgcgcgc    360
ctgcaacacc taggcattaa cacttactcg ttttcaattt catggacgcg tatttatcca    420
ttgggcgcag gctatgttaa tgaagcaggg ttagcccact atgatgccgt aatccatagt    480
gccaagaagt atggtctgga accagtgggc accgtttttc actgggatac gccactgtct    540
ctgatgctga atacggtgc ctggcaagat actggtgacc aaattgttaa ggactttgtt    600
acctatgcca caactgtgtt taagcgttat ggtaatgaag tcaagacgtg gtttactttc    660
aatgaaccac gggttttctg ttcacaaaat agtggtctgc catacaatct gacgtatcca    720
gaaggtatta acagcacctc cgctgtattt cgttgcacct acaatgttct gaaagctcat    780
ggtcatgctg ttaaagtgta tcgggatcta gttgcctccg ggaccattgc ggcaggtgaa    840
atcggcttta aatccgatga taactaccca atcccggccc gtccagggaa cgccgatgac    900
gaggaatcag ccaagcgtca cgaggctttt cgcattggga tttttgcgca accggtttat    960
ggtaatggcg attatccaga tgttgttaaa gaaactgttg gagatatgct gccggccctg   1020
acggatgaag ataaaggata cattaaaggt agcggagata tttttgcgat tgacgggtat   1080
cgtaccgata tttcccatgc ggctctgaac gggatcgcga attgtattcg caaccaaagt   1140
gacccgaatt ggccagtgtg tgaagaaggg tcagatcctt ttgctcatgt ttacccatcc   1200
gggtttgcta ttggtcaatc agccgatcca ctgtcttcat ggttagtcaa ctcagccccg   1260
tttatccgcg atcaactgaa gtttctgaca caaacctacc ctgctaaggg tggtatttat   1320
ttctcggaat ttggttgggc tgaagacgcc gaatatgatc gtcaactgct gtatcaaatt   1380
acctgggatg gtctgcgtac gcaataccctg acggactatc tgagccagct gctgttggct   1440
gtgcacaaag acgggattaa tctgcgaggc gcgctgacgt ggagttttgt cgataattgg   1500 gagtgggggtt tagggatgca acagaaattc ggatttcagt ttgttaatca atcagatccc   1560
gatctgacac gcacgtttaa actgagcgct cacgcttacg cccaatttgg gcgtaatcat   1620
ctg                                                                 1623

<210> SEQ ID NO 9
<211> LENGTH: 538
<212> TYPE: PRT
<213> ORGANISM: Artificial sequence
<220> FEATURE:
<223> OTHER INFORMATION: Synthetic

<400> SEQUENCE: 9

Ala Glu Leu Asp Ala Leu Trp Asn Leu Val Glu Ala Gln Tyr Pro Val
1               5                   10                  15

-continued

```
Gln Thr Ala Ala Val Thr Thr Leu Val Thr Val Pro Asp Asp Tyr Lys
            20                  25                  30

Phe Glu Ala Asp Pro Pro Ser Tyr Ala Leu Ala Gly Tyr Glu Thr Ser
            35                  40                  45

Glu Ile Ala Gly Leu Lys Phe Pro Lys Gly Phe Lys Phe Gly Val Ala
            50                  55                  60

Gly Ala Ala Ile Gln Val Glu Gly Ala Ala Lys Ala Glu Gly Arg Gly
65                  70                  75                  80

Pro Ser Thr Trp Asp Tyr Leu Cys His His Tyr Ala Ser Thr Gln Cys
            85                  90                  95

Asn Asn Tyr Asp Pro Asp Ile Thr Thr Asn His Tyr Tyr Leu Tyr Pro
            100                 105                 110

Leu Asp Phe Ala Arg Leu Gln His Leu Gly Ile Asn Thr Tyr Ser Phe
            115                 120                 125

Ser Ile Ser Trp Thr Arg Ile Tyr Pro Leu Gly Ala Gly Tyr Val Asn
            130                 135                 140

Glu Ala Gly Leu Ala His Tyr Asp Ala Val Ile His Ser Ala Lys Lys
145                 150                 155                 160

Tyr Gly Leu Glu Pro Val Gly Thr Val Phe His Trp Asp Thr Pro Leu
            165                 170                 175

Ser Leu Met Leu Lys Tyr Gly Ala Trp Gln Asp Thr Gly Asp Gln Ile
            180                 185                 190

Val Lys Asp Phe Val Thr Tyr Ala Thr Thr Val Phe Lys Arg Tyr Gly
            195                 200                 205

Asn Glu Val Lys Thr Trp Phe Thr Phe Asn Glu Pro Arg Val Phe Cys
            210                 215                 220

Ser Gln Asn Ser Gly Leu Pro Tyr Asn Leu Thr Tyr Pro Glu Gly Ile
225                 230                 235                 240

Asn Ser Thr Ser Ala Val Phe Arg Cys Thr Tyr Asn Val Leu Lys Ala
            245                 250                 255

His Gly His Ala Val Lys Val Tyr Arg Asp Leu Val Ala Ser Gly Thr
            260                 265                 270

Ile Ala Ala Gly Glu Ile Gly Phe Lys Ser Asp Asp Asn Tyr Pro Ile
            275                 280                 285

Pro Ala Arg Pro Gly Asn Ala Asp Asp Glu Glu Ser Ala Lys Arg His
            290                 295                 300

Glu Ala Phe Arg Ile Gly Ile Phe Ala Gln Pro Val Tyr Gly Asn Gly
305                 310                 315                 320

Asp Tyr Pro Asp Val Val Lys Glu Thr Val Gly Asp Met Leu Pro Ala
            325                 330                 335

Leu Thr Asp Glu Asp Lys Gly Tyr Ile Lys Gly Ser Gly Asp Ile Phe
            340                 345                 350

Ala Ile Asp Gly Tyr Arg Thr Asp Ile Ser His Ala Ala Leu Asn Gly
            355                 360                 365

Ile Ala Asn Cys Ile Arg Asn Gln Ser Asp Pro Asn Trp Pro Val Cys
            370                 375                 380

Glu Glu Gly Ser Asp Pro Phe Ala His Val Tyr Pro Ser Gly Phe Ala
385                 390                 395                 400

Ile Gly Gln Ser Ala Asp Pro Leu Ser Ser Trp Leu Val Asn Ser Ala
            405                 410                 415

Pro Phe Ile Arg Asp Gln Leu Lys Phe Leu Thr Gln Thr Tyr Pro Ala
            420                 425                 430

Lys Gly Gly Ile Tyr Phe Ser Glu Phe Gly Trp Ala Glu Asp Ala Glu
```

-continued

```
           435                440                445
Tyr Asp Arg Gln Leu Leu Tyr Gln Ile Thr Trp Asp Gly Leu Arg Thr
    450                455                460
Gln Tyr Leu Thr Asp Tyr Leu Ser Gln Leu Leu Leu Ala Val His Lys
465                470                475                480
Asp Gly Ile Asn Leu Arg Gly Ala Leu Thr Trp Ser Phe Val Asp Asn
                485                490                495
Trp Glu Trp Gly Leu Gly Met Gln Gln Lys Phe Gly Phe Gln Phe Val
                500                505                510
Asn Gln Ser Asp Pro Asp Leu Thr Arg Thr Phe Lys Leu Ser Ala His
            515                520                525
Ala Tyr Ala Gln Phe Gly Arg Asn His Leu
    530                535
```

```
<210> SEQ ID NO 10
<211> LENGTH: 1614
<212> TYPE: DNA
<213> ORGANISM: Artificial sequence
<220> FEATURE:
<223> OTHER INFORMATION: Synthetic

<400> SEQUENCE: 10
gcagaattag atgcgctgtg gaacttagtc gaagctcagt acccagttca aactgctgca        60
gtgacaactt tggtgacagt gcccgatgat tataagtttg aggcagatcc accgagttat       120
gcattagcag ggtatgaaac aagcgagatt gccggactga agtttccaaa ggggtttaag       180
tttggtgttg cggggggcagc cattcaagtt gaaggtgcag caaaagccga agggcggggc      240
ccaagtacct gggattatct gtgtcatcac tatgccagca cgcagtgtaa caattatgat       300
cccgatatta caaccaacca ttactacctg tacccattgg actttgcgcg cctgcaacac       360
ctaggcatta acacttactc gttttcaatt tcatggacgc gtatttatcc attgggcgca       420
ggctatgtta atgaagcagg gttagcccac tatgatgccg taatccatag tgccaagaag       480
tatggtctgg aaccagtggg caccgttttt cactgggata cgccactgtc tctgatgctg       540
aaatacggtg cctggcaaga tactggtgac caaattgtta aggactttgt tacctatgcc       600
acaactgtgt ttaagcgtta tggtaatgaa gtcaagacgt ggtttacttt caatgaacca       660
cgggttttct gttcacaaaa tagtggtctg ccatacaatc tgacgtatcc agaaggtatt       720
aacagcacct ccgctgtatt tcgttgcacc tacaatgttc tgaaagctca tggtcatgct       780
gttaaagtgt atcgggatct agttgcctcc gggaccattg cggcaggtga aatcggcttt       840
aaatccgatg ataactaccc aatcccggcc cgtccaggga acgccgatga cgaggaatca       900
gccaagcgtc acgaggcttt tcgcattggg atttttgcgc aaccggttta tggtaatggc       960
gattatccag atgttgttaa agaaactgtt ggagatatgc tgccggccct gacggatgaa      1020
gataaaggat acattaaagg tagcggagat attttttgcga ttgacgggta tcgtaccgat     1080
atttcccatg cggctctgaa cgggatcgcg aattgtattc gcaaccaaag tgacccgaat      1140
tggccagtgt gtgaagaagg gtcagatcct tttgctcatg tttacccatc cgggtttgct      1200
attggtcaat cagccgatcc actgtcttca tggttagtca actcagcccc gtttatccgc      1260
gatcaactga agtttctgac acaaacctac cctgctaagg gtggtattta tttctcggaa      1320
tttggttggg ctgaagacgc cgaatatgat cgtcaactgc tgtatcaaat tacctgggat     1380
ggtctgcgta cgcaatacct gacggactat ctgagccagc tgctgttggc gtgtgcacaa     1440
gacgggatta atctgcgagg cgcgctgacg tggagttttg tcgataattg ggagtggggt     1500
```

-continued ttagggatgc aacagaaatt cggatttcag tttgttaatc aatcagatcc cgatctgaca 1560
cgcacgttta aactgagcgc tcacgcttac gcccaatttg ggcgtaatca tctg 1614

```
<210> SEQ ID NO 11
<211> LENGTH: 513
<212> TYPE: PRT
<213> ORGANISM: Artificial sequence
<220> FEATURE:
<223> OTHER INFORMATION: Synthetic

<400> SEQUENCE: 11

Thr Val Pro Asp Asp Tyr Lys Phe Glu Ala Asp Pro Pro Ser Tyr Ala
1               5                   10                  15

Leu Ala Gly Tyr Glu Thr Ser Glu Ile Ala Gly Leu Lys Phe Pro Lys
            20                  25                  30

Gly Phe Lys Phe Gly Val Ala Gly Ala Ala Ile Gln Val Glu Gly Ala
        35                  40                  45

Ala Lys Ala Glu Gly Arg Gly Pro Ser Thr Trp Asp Tyr Leu Cys His
    50                  55                  60

His Tyr Ala Ser Thr Gln Cys Asn Asn Tyr Asp Pro Asp Ile Thr Thr
65                  70                  75                  80

Asn His Tyr Tyr Leu Tyr Pro Leu Asp Phe Ala Arg Leu Gln His Leu
                85                  90                  95

Gly Ile Asn Thr Tyr Ser Phe Ser Ile Ser Trp Thr Arg Ile Tyr Pro
            100                 105                 110

Leu Gly Ala Gly Tyr Val Asn Glu Ala Gly Leu Ala His Tyr Asp Ala
            115                 120                 125

Val Ile His Ser Ala Lys Lys Tyr Gly Leu Glu Pro Val Gly Thr Val
    130                 135                 140

Phe His Trp Asp Thr Pro Leu Ser Leu Met Leu Lys Tyr Gly Ala Trp
145                 150                 155                 160

Gln Asp Thr Gly Asp Gln Ile Val Lys Asp Phe Val Thr Tyr Ala Thr
                165                 170                 175

Thr Val Phe Lys Arg Tyr Gly Asn Glu Val Lys Thr Trp Phe Thr Phe
            180                 185                 190

Asn Glu Pro Arg Val Phe Cys Ser Gln Asn Ser Gly Leu Pro Tyr Asn
            195                 200                 205

Leu Thr Tyr Pro Glu Gly Ile Asn Ser Thr Ser Ala Val Phe Arg Cys
    210                 215                 220

Thr Tyr Asn Val Leu Lys Ala His Gly His Ala Val Lys Val Tyr Arg
225                 230                 235                 240

Asp Leu Val Ala Ser Gly Thr Ile Ala Ala Gly Glu Ile Gly Phe Lys
                245                 250                 255

Ser Asp Asp Asn Tyr Pro Ile Pro Ala Arg Pro Gly Asn Ala Asp Asp
            260                 265                 270

Glu Glu Ser Ala Lys Arg His Glu Ala Phe Arg Ile Gly Ile Phe Ala
            275                 280                 285

Gln Pro Val Tyr Gly Asn Gly Asp Tyr Pro Asp Val Val Lys Glu Thr
    290                 295                 300

Val Gly Asp Met Leu Pro Ala Leu Thr Asp Glu Asp Lys Gly Tyr Ile
305                 310                 315                 320

Lys Gly Ser Gly Asp Ile Phe Ala Ile Asp Gly Tyr Arg Thr Asp Ile
            325                 330                 335

Ser His Ala Ala Leu Asn Gly Ile Ala Asn Cys Ile Arg Asn Gln Ser
```

-continued

```
            340             345             350

Asp Pro Asn Trp Pro Val Cys Glu Glu Gly Ser Asp Pro Phe Ala His
        355             360             365

Val Tyr Pro Ser Gly Phe Ala Ile Gly Gln Ser Ala Asp Pro Leu Ser
    370             375             380

Ser Trp Leu Val Asn Ser Ala Pro Phe Ile Arg Asp Gln Leu Lys Phe
385             390             395             400

Leu Thr Gln Thr Tyr Pro Ala Lys Gly Gly Ile Tyr Phe Ser Glu Phe
            405             410             415

Gly Trp Ala Glu Asp Ala Glu Tyr Asp Arg Gln Leu Leu Tyr Gln Ile
            420             425             430

Thr Trp Asp Gly Leu Arg Thr Gln Tyr Leu Thr Asp Tyr Leu Ser Gln
            435             440             445

Leu Leu Leu Ala Val His Lys Asp Gly Ile Asn Leu Arg Gly Ala Leu
    450             455             460

Thr Trp Ser Phe Val Asp Asn Trp Glu Trp Gly Leu Gly Met Gln Gln
465             470             475             480

Lys Phe Gly Phe Gln Phe Val Asn Gln Ser Asp Pro Asp Leu Thr Arg
            485             490             495

Thr Phe Lys Leu Ser Ala His Ala Tyr Ala Gln Phe Gly Arg Asn His
            500             505             510

Leu
```

```
<210> SEQ ID NO 12
<211> LENGTH: 1539
<212> TYPE: DNA
<213> ORGANISM: Artificial sequence
<220> FEATURE:
<223> OTHER INFORMATION: Synthetic

<400> SEQUENCE: 12
acagtgcccg atgattataa gtttgaggca gatccaccga gttatgcatt agcagggtat      60
gaaacaagcg agattgccgg actgaagttt ccaaaggggt ttaagtttgg tgttgcgggg     120
gcagccattc aagttgaagg tgcagcaaaa gccgaagggc ggggcccaag tacctgggat     180
tatctgtgtc atcactatgc cagcacgcag tgtaacaatt atgatcccga tattacaacc     240
aaccattact acctgtaccc attggacttt gcgcgcctgc aacacctagg cattaacact     300
tactcgtttt caatttcatg gacgcgtatt tatccattgg gcgcaggcta tgttaatgaa     360
gcagggttag cccactatga tgccgtaatc catagtgcca gaagtatgg tctggaacca     420 gtgggcaccg tttttcactg ggatacgcca ctgtctctga tgctgaaata cggtgcctgg     480
caagatactg gtgaccaaat tgttaaggac tttgttacct atgccacaac tgtgtttaag     540
cgttatggta atgaagtcaa gacgtggttt actttcaatg aaccacgggt tttctgttca     600
caaaatagtg gtctgccata caatctgacg tatccagaag gtattaacag cacctccgct     660
gtatttcgtt gcacctacaa tgttctgaaa gctcatggtc atgctgttaa agtgtatcgg     720
gatctagttg cctccgggac cattgcggca ggtgaaatcg ctttaaatc cgatgataac     780 tacccaatcc cggcccgtcc agggaacgcc gatgacgagg aatcagccaa gcgtcacgag     840
gcttttcgca ttgggatttt tgcgcaaccg gtttatggta atggcgatta tccagatgtt     900
gttaaagaaa ctgttggaga tatgctgccg gccctgacgg atgaagataa aggatacatt     960
aaaggtagcg gagatatttt tgcgattgac gggtatcgta ccgatatttc ccatgcggct    1020
ctgaacggga tcgcgaattg tattcgcaac caaagtgacc cgaattggcc agtgtgtgaa    1080
```

-continued

```
gaagggtcag atcctttgc tcatgtttac ccatccgggt ttgctattgg tcaatcagcc     1140
gatccactgt cttcatggtt agtcaactca gccccgttta ccgcgatca actgaagttt     1200 ctgacacaaa cctaccctgc taagggtggt atttatttct cggaatttgg ttgggctgaa     1260
gacgccgaat atgatcgtca actgctgtat caaattacct gggatggtct gcgtacgcaa     1320
tacctgacgg actatctgag ccagctgctg ttggctgtgc acaaagacgg gattaatctg     1380
cgaggcgcgc tgacgtggag ttttgtcgat aattgggagt ggggtttagg gatgcaacag     1440
aaattcggat ttcagtttgt taatcaatca gatcccgatc tgacacgcac gtttaaactg     1500
agcgctcacg cttacgccca atttgggcgt aatcatctg                           1539
```

<210> SEQ ID NO 13
<211> LENGTH: 500
<212> TYPE: PRT
<213> ORGANISM: Artificial sequence
<220> FEATURE:
<223> OTHER INFORMATION: Synthetic

<400> SEQUENCE: 13

```
Ser Tyr Ala Leu Ala Gly Tyr Glu Thr Ser Glu Ile Ala Gly Leu Lys
1               5                   10                  15

Phe Pro Lys Gly Phe Lys Phe Gly Val Ala Gly Ala Ala Ile Gln Val
                20                  25                  30

Glu Gly Ala Ala Lys Ala Glu Gly Arg Gly Pro Ser Thr Trp Asp Tyr
            35                  40                  45

Leu Cys His His Tyr Ala Ser Thr Gln Cys Asn Asn Tyr Asp Pro Asp
        50                  55                  60

Ile Thr Thr Asn His Tyr Tyr Leu Tyr Pro Leu Asp Phe Ala Arg Leu
65                  70                  75                  80

Gln His Leu Gly Ile Asn Thr Tyr Ser Phe Ser Ile Ser Trp Thr Arg
                85                  90                  95

Ile Tyr Pro Leu Gly Ala Gly Tyr Val Asn Glu Ala Gly Leu Ala His
                100                 105                 110

Tyr Asp Ala Val Ile His Ser Ala Lys Lys Tyr Gly Leu Glu Pro Val
            115                 120                 125

Gly Thr Val Phe His Trp Asp Thr Pro Leu Ser Leu Met Leu Lys Tyr
        130                 135                 140

Gly Ala Trp Gln Asp Thr Gly Asp Gln Ile Val Lys Asp Phe Val Thr
145                 150                 155                 160

Tyr Ala Thr Thr Val Phe Lys Arg Tyr Gly Asn Glu Val Lys Thr Trp
                165                 170                 175

Phe Thr Phe Asn Glu Pro Arg Val Phe Cys Ser Gln Asn Ser Gly Leu
                180                 185                 190

Pro Tyr Asn Leu Thr Tyr Pro Glu Gly Ile Asn Ser Thr Ser Ala Val
            195                 200                 205

Phe Arg Cys Thr Tyr Asn Val Leu Lys Ala His Gly His Ala Val Lys
        210                 215                 220

Val Tyr Arg Asp Leu Val Ala Ser Gly Thr Ile Ala Ala Gly Glu Ile
225                 230                 235                 240

Gly Phe Lys Ser Asp Asp Asn Tyr Pro Ile Pro Ala Arg Pro Gly Asn
                245                 250                 255

Ala Asp Asp Glu Glu Ser Ala Lys Arg His Glu Ala Phe Arg Ile Gly
            260                 265                 270

Ile Phe Ala Gln Pro Val Tyr Gly Asn Gly Asp Tyr Pro Asp Val Val
```

-continued

```
              275                 280                 285
Lys Glu Thr Val Gly Asp Met Leu Pro Ala Leu Thr Asp Glu Asp Lys
    290                 295                 300

Gly Tyr Ile Lys Gly Ser Gly Asp Ile Phe Ala Ile Asp Gly Tyr Arg
305                 310                 315                 320

Thr Asp Ile Ser His Ala Ala Leu Asn Gly Ile Ala Asn Cys Ile Arg
                325                 330                 335

Asn Gln Ser Asp Pro Asn Trp Pro Val Cys Glu Glu Gly Ser Asp Pro
                340                 345                 350

Phe Ala His Val Tyr Pro Ser Gly Phe Ala Ile Gly Gln Ser Ala Asp
                355                 360                 365

Pro Leu Ser Ser Trp Leu Val Asn Ser Ala Pro Phe Ile Arg Asp Gln
    370                 375                 380

Leu Lys Phe Leu Thr Gln Thr Tyr Pro Ala Lys Gly Gly Ile Tyr Phe
385                 390                 395                 400

Ser Glu Phe Gly Trp Ala Glu Asp Ala Glu Tyr Asp Arg Gln Leu Leu
                405                 410                 415

Tyr Gln Ile Thr Trp Asp Gly Leu Arg Thr Gln Tyr Leu Thr Asp Tyr
                420                 425                 430

Leu Ser Gln Leu Leu Leu Ala Val His Lys Asp Gly Ile Asn Leu Arg
                435                 440                 445

Gly Ala Leu Thr Trp Ser Phe Val Asp Asn Trp Glu Trp Gly Leu Gly
    450                 455                 460

Met Gln Gln Lys Phe Gly Phe Gln Phe Val Asn Gln Ser Asp Pro Asp
465                 470                 475                 480

Leu Thr Arg Thr Phe Lys Leu Ser Ala His Ala Tyr Ala Gln Phe Gly
                485                 490                 495

Arg Asn His Leu
            500
```

```
<210> SEQ ID NO 14
<211> LENGTH: 1500
<212> TYPE: DNA
<213> ORGANISM: Artificial sequence
<220> FEATURE:
<223> OTHER INFORMATION: Synthetic

<400> SEQUENCE: 14
agttatgcat tagcagggta tgaaacaagc gagattgccg gactgaagtt tccaaagggg      60
tttaagtttg gtgttgcggg ggcagccatt caagttgaag gtgcagcaaa agccgaaggg     120
cggggcccaa gtacctggga ttatctgtgt catcactatg ccagcacgca gtgtaacaat     180
tatgatcccg atattacaac caaccattac tacctgtacc cattggactt tgcgcgcctg     240
caacacctag gcattaacac ttactcgttt tcaatttcat ggacgcgtat ttatccattg     300
ggcgcaggct atgttaatga agcagggtta gcccactatg atgccgtaat ccatagtgcc     360
aagaagtatg gtctggaacc agtgggcacc gtttttcact gggatacgcc actgtctctg     420
atgctgaaat acggtgcctg gcaagatact ggtgaccaaa ttgttaagga ctttgttacc     480
tatgccacaa ctgtgtttaa gcgttatggt aatgaagtca gacgtggtt tactttcaat     540 gaaccacggg ttttctgttc acaaaatagt ggtctgccat acaatctgac gtatccagaa     600
ggtattaaca gcacctccgc tgtatttcgt tgcacctaca atgttctgaa agctcatggt     660
catgctgtta aagtgtatcg ggatctagtt gcctccggga ccattgcggc aggtgaaatc     720
ggctttaaat ccgatgataa ctacccaatc ccggcccgtc cagggaacgc cgatgacgag     780
```

-continued

```
gaatcagcca agcgtcacga ggctttcgc attgggattt ttgcgcaacc ggtttatggt      840
aatggcgatt atccagatgt tgttaaagaa actgttggag atatgctgcc ggccctgacg      900
gatgaagata aaggatacat taaaggtagc ggagatattt ttgcgattga cgggtatcgt      960
accgatattt cccatgcggc tctgaacggg atcgcgaatt gtattcgcaa ccaaagtgac     1020
ccgaattggc cagtgtgtga agaagggtca gatccttttg ctcatgttta cccatccggg     1080
tttgctattg gtcaatcagc cgatccactg tcttcatggt tagtcaactc agccccgttt     1140
atccgcgatc aactgaagtt tctgacacaa acctaccctg ctaagggtgg tatttatttc     1200
tcggaatttg gttgggctga agacgccgaa tatgatcgtc aactgctgta tcaaattacc     1260
tgggatggtc tgcgtacgca atacctgacg gactatctga gccagctgct gttggctgtg     1320
cacaaagacg ggattaatct gcgaggcgcg ctgacgtgga gttttgtcga taattgggag     1380
tggggtttag ggatgcaaca gaaattcgga tttcagtttg ttaatcaatc agatcccgat     1440
ctgacacgca cgtttaaact gagcgctcac gcttacgccc aatttgggcg taatcatctg     1500
```

<210> SEQ ID NO 15
<211> LENGTH: 492
<212> TYPE: PRT
<213> ORGANISM: Artificial sequence
<220> FEATURE:
<223> OTHER INFORMATION: Synthetic

<400> SEQUENCE: 15

```
Thr Ser Glu Ile Ala Gly Leu Lys Phe Pro Lys Gly Phe Lys Phe Gly
1               5                   10                  15

Val Ala Gly Ala Ala Ile Gln Val Glu Gly Ala Ala Lys Ala Glu Gly
            20                  25                  30

Arg Gly Pro Ser Thr Trp Asp Tyr Leu Cys His His Tyr Ala Ser Thr
        35                  40                  45

Gln Cys Asn Asn Tyr Asp Pro Asp Ile Thr Thr Asn His Tyr Tyr Leu
    50                  55                  60

Tyr Pro Leu Asp Phe Ala Arg Leu Gln His Leu Gly Ile Asn Thr Tyr
65                  70                  75                  80

Ser Phe Ser Ile Ser Trp Thr Arg Ile Tyr Pro Leu Gly Ala Gly Tyr
                85                  90                  95

Val Asn Glu Ala Gly Leu Ala His Tyr Asp Ala Val Ile His Ser Ala
            100                 105                 110

Lys Lys Tyr Gly Leu Glu Pro Val Gly Thr Val Phe His Trp Asp Thr
            115                 120                 125

Pro Leu Ser Leu Met Leu Lys Tyr Gly Ala Trp Gln Asp Thr Gly Asp
        130                 135                 140

Gln Ile Val Lys Asp Phe Val Thr Tyr Ala Thr Thr Val Phe Lys Arg
145                 150                 155                 160

Tyr Gly Asn Glu Val Lys Thr Trp Phe Thr Phe Asn Glu Pro Arg Val
                165                 170                 175

Phe Cys Ser Gln Asn Ser Gly Leu Pro Tyr Asn Leu Thr Tyr Pro Glu
            180                 185                 190

Gly Ile Asn Ser Thr Ser Ala Val Phe Arg Cys Thr Tyr Asn Val Leu
            195                 200                 205

Lys Ala His Gly His Ala Val Lys Val Tyr Arg Asp Leu Val Ala Ser
    210                 215                 220

Gly Thr Ile Ala Ala Gly Glu Ile Gly Phe Lys Ser Asp Asp Asn Tyr
225                 230                 235                 240
```

-continued

```
Pro Ile Pro Ala Arg Pro Gly Asn Ala Asp Asp Glu Glu Ser Ala Lys
            245                 250                 255

Arg His Glu Ala Phe Arg Ile Gly Ile Phe Ala Gln Pro Val Tyr Gly
            260                 265                 270

Asn Gly Asp Tyr Pro Asp Val Val Lys Glu Thr Val Gly Asp Met Leu
            275                 280                 285

Pro Ala Leu Thr Asp Glu Asp Lys Gly Tyr Ile Lys Gly Ser Gly Asp
    290                 295                 300

Ile Phe Ala Ile Asp Gly Tyr Arg Thr Asp Ile Ser His Ala Ala Leu
305                 310                 315                 320

Asn Gly Ile Ala Asn Cys Ile Arg Asn Gln Ser Asp Pro Asn Trp Pro
            325                 330                 335

Val Cys Glu Glu Gly Ser Asp Pro Phe Ala His Val Tyr Pro Ser Gly
            340                 345                 350

Phe Ala Ile Gly Gln Ser Ala Asp Pro Leu Ser Ser Trp Leu Val Asn
            355                 360                 365

Ser Ala Pro Phe Ile Arg Asp Gln Leu Lys Phe Leu Thr Gln Thr Tyr
    370                 375                 380

Pro Ala Lys Gly Gly Ile Tyr Phe Ser Glu Phe Gly Trp Ala Glu Asp
385                 390                 395                 400

Ala Glu Tyr Asp Arg Gln Leu Leu Tyr Gln Ile Thr Trp Asp Gly Leu
            405                 410                 415

Arg Thr Gln Tyr Leu Thr Asp Tyr Leu Ser Gln Leu Leu Leu Ala Val
            420                 425                 430

His Lys Asp Gly Ile Asn Leu Arg Gly Ala Leu Thr Trp Ser Phe Val
            435                 440                 445

Asp Asn Trp Glu Trp Gly Leu Gly Met Gln Gln Lys Phe Gly Phe Gln
    450                 455                 460

Phe Val Asn Gln Ser Asp Pro Asp Leu Thr Arg Thr Phe Lys Leu Ser
465                 470                 475                 480

Ala His Ala Tyr Ala Gln Phe Gly Arg Asn His Leu
            485                 490
```

<210> SEQ ID NO 16
<211> LENGTH: 1476
<212> TYPE: DNA
<213> ORGANISM: Artificial sequence
<220> FEATURE:
<223> OTHER INFORMATION: Synthetic

<400> SEQUENCE: 16

```
acaagcgaga ttgccggact gaagtttcca aaggggttta agtttggtgt tgcggggca        60 gccattcaag ttgaaggtgc agcaaaagcc gaagggcggg gcccaagtac ctgggattat      120
ctgtgtcatc actatgccag cacgcagtgt aacaattatg atcccgatat tacaaccaac      180
cattactacc tgtacccatt ggactttgcg cgcctgcaac acctaggcat taacacttac      240 tcgtttttcaa tttcatggac gcgtatttat ccattgggcg caggctatgt taatgaagca      300
gggttagccc actatgatgc cgtaatccat agtgccaaga agtatggtct ggaaccagtg      360
ggcaccgttt ttcactggga tacgccactg tctctgatgc tgaaatacgg tgcctggcaa      420
gatactggtg accaaattgt taaggacttt gttacctatg ccacaactgt gtttaagcgt      480
tatggtaatg aagtcaagac gtggtttact ttcaatgaac cacgggtttt ctgttcacaa      540
aatagtggtc tgccatacaa tctgacgtat ccagaaggta ttaacagcac ctccgctgta      600
```

```
tttcgttgca cctacaatgt tctgaaagct catggtcatg ctgttaaagt gtatcgggat      660
ctagttgcct ccgggaccat tgcggcaggt gaaatcggct ttaaatccga tgataactac      720
ccaatcccgg cccgtccagg gaacgccgat gacgaggaat cagccaagcg tcacgaggct      780
tttcgcattg ggattttttgc gcaaccggtt tatggtaatg cgattatcc agatgttgtt      840 aaagaaactg ttggagatat gctgccggcc ctgacggatg aagataaagg atacattaaa      900
ggtagcggag atattttttgc gattgacggg tatcgtaccg atatttccca tgcggctctg      960
aacgggatcg cgaattgtat tcgcaaccaa agtgacccga attggccagt gtgtgaagaa     1020
gggtcagatc cttttgctca tgtttaccca tccgggtttg ctattggtca atcagccgat     1080
ccactgtctt catggttagt caactcagcc ccgtttatcc gcgatcaact gaagtttctg     1140
acacaaacct accctgctaa gggtggtatt tatttctcgg aatttggttg ggctgaagac     1200
gccgaatatg atcgtcaact gctgtatcaa attacctggg atggtctgcg tacgcaatac     1260
ctgacggact atctgagcca gctgctgttg gctgtgcaca aagacgggat taatctgcga     1320
ggcgcgctga cgtggagttt tgtcgataat tgggagtggg gtttagggat gcaacagaaa     1380
ttcggatttc agtttgttaa tcaatcagat cccgatctga cacgcacgtt taaactgagc     1440
gctcacgctt acgcccaatt tgggcgtaat catctg                               1476
```

<210> SEQ ID NO 17
<211> LENGTH: 484
<212> TYPE: PRT
<213> ORGANISM: Artificial sequence
<220> FEATURE:
<223> OTHER INFORMATION: Synthetic

<400> SEQUENCE: 17

```
Phe Pro Lys Gly Phe Lys Phe Gly Val Ala Gly Ala Ala Ile Gln Val
1               5                   10                  15

Glu Gly Ala Ala Lys Ala Glu Gly Arg Gly Pro Ser Thr Trp Asp Tyr
            20                  25                  30

Leu Cys His His Tyr Ala Ser Thr Gln Cys Asn Asn Tyr Asp Pro Asp
        35                  40                  45

Ile Thr Thr Asn His Tyr Tyr Leu Tyr Pro Leu Asp Phe Ala Arg Leu
    50                  55                  60

Gln His Leu Gly Ile Asn Thr Tyr Ser Phe Ser Ile Ser Trp Thr Arg
65                  70                  75                  80

Ile Tyr Pro Leu Gly Ala Gly Tyr Val Asn Glu Ala Gly Leu Ala His
                85                  90                  95

Tyr Asp Ala Val Ile His Ser Ala Lys Lys Tyr Gly Leu Glu Pro Val
            100                 105                 110

Gly Thr Val Phe His Trp Asp Thr Pro Leu Ser Leu Met Leu Lys Tyr
        115                 120                 125

Gly Ala Trp Gln Asp Thr Gly Asp Gln Ile Val Lys Asp Phe Val Thr
    130                 135                 140

Tyr Ala Thr Thr Val Phe Lys Arg Tyr Gly Asn Glu Val Lys Thr Trp
145                 150                 155                 160

Phe Thr Phe Asn Glu Pro Arg Val Phe Cys Ser Gln Asn Ser Gly Leu
                165                 170                 175

Pro Tyr Asn Leu Thr Tyr Pro Glu Gly Ile Asn Ser Thr Ser Ala Val
            180                 185                 190

Phe Arg Cys Thr Tyr Asn Val Leu Lys Ala His Gly His Ala Val Lys
        195                 200                 205
```

```
Val Tyr Arg Asp Leu Val Ala Ser Gly Thr Ile Ala Ala Gly Glu Ile
210             215             220

Gly Phe Lys Ser Asp Asp Asn Tyr Pro Ile Pro Ala Arg Pro Gly Asn
225             230             235             240

Ala Asp Asp Glu Glu Ser Ala Lys Arg His Glu Ala Phe Arg Ile Gly
            245             250             255

Ile Phe Ala Gln Pro Val Tyr Gly Asn Gly Asp Tyr Pro Asp Val Val
            260             265             270

Lys Glu Thr Val Gly Asp Met Leu Pro Ala Leu Thr Asp Glu Asp Lys
            275             280             285

Gly Tyr Ile Lys Gly Ser Gly Asp Ile Phe Ala Ile Asp Gly Tyr Arg
    290             295             300

Thr Asp Ile Ser His Ala Ala Leu Asn Gly Ile Ala Asn Cys Ile Arg
305             310             315             320

Asn Gln Ser Asp Pro Asn Trp Pro Val Cys Glu Glu Gly Ser Asp Pro
            325             330             335

Phe Ala His Val Tyr Pro Ser Gly Phe Ala Ile Gly Gln Ser Ala Asp
            340             345             350

Pro Leu Ser Ser Trp Leu Val Asn Ser Ala Pro Phe Ile Arg Asp Gln
            355             360             365

Leu Lys Phe Leu Thr Gln Thr Tyr Pro Ala Lys Gly Gly Ile Tyr Phe
    370             375             380

Ser Glu Phe Gly Trp Ala Glu Asp Ala Glu Tyr Asp Arg Gln Leu Leu
385             390             395             400

Tyr Gln Ile Thr Trp Asp Gly Leu Arg Thr Gln Tyr Leu Thr Asp Tyr
            405             410             415

Leu Ser Gln Leu Leu Leu Ala Val His Lys Asp Gly Ile Asn Leu Arg
            420             425             430

Gly Ala Leu Thr Trp Ser Phe Val Asp Asn Trp Glu Trp Gly Leu Gly
            435             440             445

Met Gln Gln Lys Phe Gly Phe Gln Phe Val Asn Gln Ser Asp Pro Asp
    450             455             460

Leu Thr Arg Thr Phe Lys Leu Ser Ala His Ala Tyr Ala Gln Phe Gly
465             470             475             480

Arg Asn His Leu
```

```
<210> SEQ ID NO 18
<211> LENGTH: 1452
<212> TYPE: DNA
<213> ORGANISM: Artificial sequence
<220> FEATURE:
<223> OTHER INFORMATION: Synthetic

<400> SEQUENCE: 18
tttccaaagg ggtttaagtt tggtgttgcg ggggcagcca ttcaagttga aggtgcagca      60
aaagccgaag ggcggggccc aagtacctgg gattatctgt gtcatcacta tgccagcacg     120
cagtgtaaca attatgatcc cgatattaca accaaccatt actacctgta cccattggac     180
tttgcgcgcc tgcaacacct aggcattaac acttactcgt tttcaatttc atggacgcgt     240
atttatccat tgggcgcagg ctatgttaat gaagcagggt tagcccacta tgatgccgta     300
atccatagtg ccaagaagta tggtctggaa ccagtgggca ccgttttttca ctgggatacg     360 ccactgtctc tgatgctgaa atacggtgcc tggcaagata ctggtgacca aattgttaag     420
gactttgtta cctatgccac aactgtgttt aagcgttatg gtaatgaagt caagacgtgg     480
```

-continued

```
tttactttca atgaaccacg ggttttctgt tcacaaaata gtggtctgcc atacaatctg      540
acgtatccag aaggtattaa cagcacctcc gctgtatttc gttgcaccta caatgttctg      600
aaagctcatg gtcatgctgt taaagtgtat cgggatctag ttgcctccgg gaccattgcg      660
gcaggtgaaa tcggctttaa atccgatgat aactacccaa tcccggcccg tccagggaac      720
gccgatgacg aggaatcagc caagcgtcac gaggctttc gcattgggat ttttgcgcaa       780
ccggtttatg gtaatggcga ttatccagat gttgttaaag aaactgttgg agatatgctg      840
ccggccctga cggatgaaga taaaggatac attaaaggta gcggagatat ttttgcgatt      900
gacgggtatc gtaccgatat ttcccatgcg gctctgaacg ggatcgcgaa ttgtattcgc      960
aaccaaagtg acccgaattg gccagtgtgt gaagaagggt cagatccttt tgctcatgtt     1020
tacccatccg ggtttgctat tggtcaatca gccgatccac tgtcttcatg gttagtcaac     1080
tcagccccgt ttatccgcga tcaactgaag tttctgacac aaacctaccc tgctaagggt     1140
ggtatttatt tctcggaatt tggttgggct gaagacgccg aatatgatcg tcaactgctg     1200
tatcaaatta cctgggatgg tctgcgtacg caatacctga cggactatct gagccagctg     1260
ctgttggctg tgcacaaaga cgggattaat ctgcgaggcg cgctgacgtg gagttttgtc     1320
gataattggg agtggggttt agggatgcaa cagaaattcg gatttcagtt tgttaatcaa     1380
tcagatcccg atctgacacg cacgtttaaa ctgagcgctc acgcttacgc ccaatttggg     1440
cgtaatcatc tg                                                         1452
```

<210> SEQ ID NO 19
<211> LENGTH: 572
<212> TYPE: PRT
<213> ORGANISM: Artificial sequence
<220> FEATURE:
<223> OTHER INFORMATION: Synthetic

<400> SEQUENCE: 19

```
Val Thr Tyr Pro Gly Ala Ile Pro Leu Ser Leu Thr Ser Asn Tyr Glu
1               5                   10                  15

Thr Pro Ser Pro Thr Ala Ile Pro Leu Glu Pro Thr Pro Thr Ala Thr
            20                  25                  30

Gly Thr Ala Glu Leu Asp Ala Leu Trp Asn Leu Val Glu Ala Gln Tyr
        35                  40                  45

Pro Val Gln Thr Ala Ala Val Thr Thr Leu Val Thr Val Pro Asp Asp
    50                  55                  60

Tyr Lys Phe Glu Ala Asp Pro Pro Ser Tyr Ala Leu Ala Gly Tyr Glu
65                  70                  75                  80

Thr Ser Glu Ile Ala Gly Leu Lys Phe Pro Lys Gly Phe Lys Phe Gly
                85                  90                  95

Val Ala Gly Ala Ala Ile Gln Val Glu Gly Ala Ala Lys Ala Glu Gly
            100                 105                 110

Arg Gly Pro Ser Thr Trp Asp Tyr Leu Cys His His Tyr Ala Ser Thr
        115                 120                 125

Gln Cys Asn Asn Tyr Asp Pro Asp Ile Thr Thr Asn His Tyr Tyr Leu
    130                 135                 140

Tyr Pro Leu Asp Phe Ala Arg Leu Gln His Leu Gly Ile Asn Thr Tyr
145                 150                 155                 160

Ser Phe Ser Ile Ser Trp Thr Arg Ile Tyr Pro Leu Gly Ala Gly Tyr
                165                 170                 175

Val Asn Glu Ala Gly Leu Ala His Tyr Asp Ala Val Ile His Ser Ala
            180                 185                 190
```

-continued

```
Lys Lys Tyr Gly Leu Glu Pro Val Gly Thr Val Phe His Trp Asp Thr
        195                 200                 205

Pro Leu Ser Leu Met Leu Lys Tyr Gly Ala Trp Gln Asp Thr Gly Asp
        210                 215                 220

Gln Ile Val Lys Asp Phe Val Thr Tyr Ala Thr Thr Val Phe Lys Arg
225                 230                 235                 240

Tyr Gly Asn Glu Val Lys Thr Trp Phe Thr Phe Asn Glu Pro Arg Val
                245                 250                 255

Phe Cys Ser Gln Asn Ser Gly Leu Pro Tyr Gln Leu Thr Tyr Pro Glu
                260                 265                 270

Gly Ile Asn Ser Thr Ser Ala Val Phe Arg Cys Thr Tyr Asn Val Leu
                275                 280                 285

Lys Ala His Gly His Ala Val Lys Val Tyr Arg Asp Leu Val Ala Ser
        290                 295                 300

Gly Thr Ile Ala Ala Gly Glu Ile Gly Phe Lys Ser Asp Asp Asn Tyr
305                 310                 315                 320

Pro Ile Pro Ala Arg Pro Gly Asn Ala Asp Asp Glu Glu Ser Ala Lys
                325                 330                 335

Arg His Glu Ala Phe Arg Ile Gly Ile Phe Ala Gln Pro Val Tyr Gly
                340                 345                 350

Asn Gly Asp Tyr Pro Asp Val Val Lys Glu Thr Val Gly Asp Met Leu
                355                 360                 365

Pro Ala Leu Thr Asp Glu Asp Lys Gly Tyr Ile Lys Gly Ser Gly Asp
        370                 375                 380

Ile Phe Ala Ile Asp Gly Tyr Arg Thr Asp Ile Ser His Ala Ala Leu
385                 390                 395                 400

Asn Gly Ile Ala Asn Cys Ile Arg Asn Gln Ser Asp Pro Asn Trp Pro
                405                 410                 415

Val Cys Glu Glu Gly Ser Asp Pro Phe Ala His Val Tyr Pro Ser Gly
                420                 425                 430

Phe Ala Ile Gly Gln Ser Ala Asp Pro Leu Ser Ser Trp Leu Val Asn
        435                 440                 445

Ser Ala Pro Phe Ile Arg Asp Gln Leu Lys Phe Leu Thr Gln Thr Tyr
        450                 455                 460

Pro Ala Lys Gly Gly Ile Tyr Phe Ser Glu Phe Gly Trp Ala Glu Asp
465                 470                 475                 480

Ala Glu Tyr Asp Arg Gln Leu Leu Tyr Gln Ile Thr Trp Asp Gly Leu
                485                 490                 495

Arg Thr Gln Tyr Leu Thr Asp Tyr Leu Ser Gln Leu Leu Leu Ala Val
                500                 505                 510

His Lys Asp Gly Ile Asn Leu Arg Gly Ala Leu Thr Trp Ser Phe Val
        515                 520                 525

Asp Asn Trp Glu Trp Gly Leu Gly Met Gln Gln Lys Phe Gly Phe Gln
        530                 535                 540

Phe Val Asn Gln Ser Asp Pro Asp Leu Thr Arg Thr Phe Lys Leu Ser
545                 550                 555                 560

Ala His Ala Tyr Ala Gln Phe Gly Arg Asn His Leu
                565                 570
```

```
<210> SEQ ID NO 20
<211> LENGTH: 1716
<212> TYPE: DNA
<213> ORGANISM: Artificial sequence
<220> FEATURE:
```

<223> OTHER INFORMATION: Synthetic

<400> SEQUENCE: 20

```
gttacttatc cgggagccat tcctctgtcc ctgacgagca attacgaaac cccaagtccg        60
acagcaatcc cgctggagcc aacaccgacg gctaccggta cagcagaatt agatgcgctg       120
tggaacttag tcgaagctca gtacccagtt caaactgctg cagtgacaac tttggtgaca       180
gtgcccgatg attataagtt tgaggcagat ccaccgagtt atgcattagc agggtatgaa       240
acaagcgaga ttgccggact gaagtttcca aaggggttta gtttggtgt tgcgggggca        300 gccattcaag ttgaaggtgc agcaaaagcc gaagggcggg gcccaagtac ctgggattat       360
ctgtgtcatc actatgccag cacgcagtgt aacaattatg atcccgatat tacaaccaac       420
cattactacc tgtacccatt ggactttgcg cgcctgcaac acctaggcat taacacttac       480
tcgttttcaa tttcatggac gcgtattta ccattgggcg caggctatgt taatgaagca        540
gggttagccc actatgatgc cgtaatccat agtgccaaga agtatggtct ggaaccagtg       600
ggcaccgttt ttcactggga tacgccactg tctctgatgc tgaaatacgg tgcctggcaa       660
gatactggtg accaaattgt taaggacttt gttacctatg ccacaactgt gtttaagcgt       720
tatggtaatg aagtcaagac gtggtttact ttcaatgaac cacgggtttt ctgttcacaa       780
aatagtggtc tgccatacca gcttacgtat ccagaaggta ttaacagcac ctccgctgta       840
tttcgttgca cctacaatgt tctgaaagct catggtcatg ctgttaaagt gtatcgggat       900
ctagttgcct ccgggaccat tgcggcaggt gaaatcggct ttaaatccga tgataactac       960
ccaatcccgg cccgtccagg aacgccgat gacgaggaat cagccaagcg tcacgaggct       1020
tttcgcattg ggattttgc gcaaccggtt tatggtaatg gcgattatcc agatgttgtt      1080
aaagaaactg ttggagatat gctgccggcc ctgacggatg aagataaagg atacattaa       1140 ggtagcggag atattttgc gattgacggg tatcgtaccg atatttccca tgcggctctg      1200
aacgggatcg cgaattgtat tcgcaaccaa agtgacccga attggccagt gtgtgaagaa      1260
gggtcagatc cttttgctca tgtttaccca tccgggtttg ctattggtca atcagccgat      1320
ccactgtctt catggttagt caactcagcc ccgtttatcc gcgatcaact gaagtttctg      1380
acacaaacct accctgctaa gggtggtatt tatttctcgg aatttggttg ggctgaagac      1440
gccgaatatg atcgtcaact gctgtatcaa attacctggg atggtctgcg tacgcaatac      1500
ctgacggact atctgagcca gctgctgttg gctgtgcaca aagacgggat taatctgcga      1560
ggcgcgctga cgtggagttt tgtcgataat tgggagtggg gtttagggat gcaacagaaa      1620
ttcggatttc agtttgttaa tcaatcagat cccgatctga cacgcacgtt taaactgagc      1680
gctcacgctt acgcccaatt tgggcgtaat catctg                               1716
```

<210> SEQ ID NO 21
<211> LENGTH: 572
<212> TYPE: PRT
<213> ORGANISM: Artificial sequence
<220> FEATURE:
<223> OTHER INFORMATION: Synthetic

<400> SEQUENCE: 21

```
Val Thr Tyr Pro Gly Ala Ile Pro Leu Ser Leu Thr Ser Asn Tyr Glu
1               5                   10                  15

Thr Pro Ser Pro Thr Ala Ile Pro Leu Glu Pro Thr Pro Thr Ala Thr
            20                  25                  30

Gly Thr Ala Glu Leu Asp Ala Leu Trp Asn Leu Val Glu Ala Gln Tyr
```

```
            35                  40                  45
Pro Val Gln Thr Ala Ala Val Thr Thr Leu Val Thr Val Pro Asp Asp
    50                  55                  60

Tyr Lys Phe Glu Ala Asp Pro Pro Ser Tyr Ala Leu Ala Gly Tyr Glu
65                  70                  75                  80

Thr Ser Glu Ile Ala Gly Leu Lys Phe Pro Lys Gly Phe Lys Phe Gly
                85                  90                  95

Val Ala Gly Ala Ala Ile Gln Val Glu Gly Ala Ala Lys Ala Glu Gly
                100                 105                 110

Arg Gly Pro Ser Thr Trp Asp Tyr Leu Cys His His Tyr Ala Ser Thr
                115                 120                 125

Gln Cys Asn Asn Tyr Asp Pro Asp Ile Thr Thr Asn His Tyr Tyr Leu
    130                 135                 140

Tyr Pro Leu Asp Phe Ala Arg Leu Gln His Leu Gly Ile Asn Thr Tyr
145                 150                 155                 160

Ser Phe Ser Ile Ser Trp Thr Arg Ile Tyr Pro Leu Gly Ala Gly Tyr
                165                 170                 175

Val Asn Glu Ala Gly Leu Ala His Tyr Asp Ala Val Ile His Ser Ala
                180                 185                 190

Lys Lys Tyr Gly Leu Glu Pro Val Gly Thr Val Phe His Trp Asp Thr
                195                 200                 205

Pro Leu Ser Leu Met Leu Lys Tyr Gly Ala Trp Gln Asp Thr Gly Asp
    210                 215                 220

Gln Ile Val Lys Asp Phe Val Thr Tyr Ala Thr Thr Val Phe Lys Arg
225                 230                 235                 240

Tyr Gly Asn Glu Val Lys Thr Trp Phe Thr Phe Asn Glu Pro Arg Val
                245                 250                 255

Phe Cys Ser Gln Asn Ser Gly Leu Pro Tyr Asn Leu Thr Tyr Pro Glu
                260                 265                 270

Gly Ile Gln Ser Thr Ser Ala Val Phe Arg Cys Thr Tyr Asn Val Leu
                275                 280                 285

Lys Ala His Gly His Ala Val Lys Val Tyr Arg Asp Leu Val Ala Ser
    290                 295                 300

Gly Thr Ile Ala Ala Gly Glu Ile Gly Phe Lys Ser Asp Asp Asn Tyr
305                 310                 315                 320

Pro Ile Pro Ala Arg Pro Gly Asn Ala Asp Asp Glu Glu Ser Ala Lys
                325                 330                 335

Arg His Glu Ala Phe Arg Ile Gly Ile Phe Ala Gln Pro Val Tyr Gly
                340                 345                 350

Asn Gly Asp Tyr Pro Asp Val Val Lys Glu Thr Val Gly Asp Met Leu
                355                 360                 365

Pro Ala Leu Thr Asp Glu Asp Lys Gly Tyr Ile Lys Gly Ser Gly Asp
    370                 375                 380

Ile Phe Ala Ile Asp Gly Tyr Arg Thr Asp Ile Ser His Ala Ala Leu
385                 390                 395                 400

Asn Gly Ile Ala Asn Cys Ile Arg Asn Gln Ser Asp Pro Asn Trp Pro
                405                 410                 415

Val Cys Glu Glu Gly Ser Asp Pro Phe Ala His Val Tyr Pro Ser Gly
                420                 425                 430

Phe Ala Ile Gly Gln Ser Ala Asp Pro Leu Ser Ser Trp Leu Val Asn
                435                 440                 445

Ser Ala Pro Phe Ile Arg Asp Gln Leu Lys Phe Leu Thr Gln Thr Tyr
    450                 455                 460
```

-continued

```
Pro Ala Lys Gly Gly Ile Tyr Phe Ser Glu Phe Gly Trp Ala Glu Asp
465                 470                 475                 480

Ala Glu Tyr Asp Arg Gln Leu Leu Tyr Gln Ile Thr Trp Asp Gly Leu
                485                 490                 495

Arg Thr Gln Tyr Leu Thr Asp Tyr Leu Ser Gln Leu Leu Leu Ala Val
                500                 505                 510

His Lys Asp Gly Ile Asn Leu Arg Gly Ala Leu Thr Trp Ser Phe Val
            515                 520                 525

Asp Asn Trp Glu Trp Gly Leu Gly Met Gln Gln Lys Phe Gly Phe Gln
        530                 535                 540

Phe Val Asn Gln Ser Asp Pro Asp Leu Thr Arg Thr Phe Lys Leu Ser
545                 550                 555                 560

Ala His Ala Tyr Ala Gln Phe Gly Arg Asn His Leu
                565                 570
```

```
<210> SEQ ID NO 22
<211> LENGTH: 1716
<212> TYPE: DNA
<213> ORGANISM: Artificial sequence
<220> FEATURE:
<223> OTHER INFORMATION: Synthetic

<400> SEQUENCE: 22
gttacttatc cgggagccat tcctctgtcc ctgacgagca attacgaaac cccaagtccg      60
acagcaatcc cgctggagcc aacaccgacg gctaccggta cagcagaatt agatgcgctg     120
tggaacttag tcgaagctca gtacccagtt caaactgctg cagtgacaac tttggtgaca     180
gtgcccgatg attataagtt tgaggcagat ccaccgagtt atgcattagc agggtatgaa     240
acaagcgaga ttgccggact gaagtttcca aaggggttta agtttggtgt tgcgggggca     300
gccattcaag ttgaaggtgc agcaaaagcc gaagggcggg gcccaagtac ctgggattat     360
ctgtgtcatc actatgccag cacgcagtgt aacaattatg atcccgatat tacaaccaac     420
cattactacc tgtacccatt ggactttgcg cgcctgcaac acctaggcat taacacttac     480 tcgtttt caa tttcatggac gcgtatttat ccattgggcg caggctatgt taatgaagca     540
gggttagccc actatgatgc cgtaatccat agtgccaaga gtatggtct ggaaccagtg      600 ggcaccgttt ttcactggga tacgccactg tctctgatgc tgaaatacgg tgcctggcaa     660
gatactggtg accaaattgt taaggacttt gttacctatg ccacaactgt gtttaagcgt     720
tatggtaatg aagtcaagac gtggtttact ttcaatgaac cacgggtttt ctgttcacaa     780
aatagtggtc tgccatacaa tctgacgtat ccagaaggga tccagagcac ctccgctgta     840
tttcgttgca cctacaatgt tctgaaagct catggtcatg ctgttaaagt gtatcgggat     900
ctagttgcct ccgggaccat tgcggcaggt gaaatcggct ttaaatccga tgataactac     960
ccaatcccgg cccgtccagg gaacgccgat gacgaggaat cagccaagcg tcacgaggct    1020
tttcgcattg ggattttttgc gcaaccggtt tatggtaatg cgattatcc agatgttgtt    1080 aaagaaactg ttggagatat gctgccggcc ctgacggatg aagataaagg atacattaaa    1140
ggtagcggag atattttgc gattgacggg tatcgtaccg atatttccca tgcggctctg     1200
aacgggatcg cgaattgtat tcgcaaccaa agtgacccga attggccagt gtgtgaagaa    1260
gggtcagatc cttttgctca tgtttaccca tccgggtttg ctattggtca atcagccgat    1320
ccactgtctt catggttagt caactcagcc ccgtttatcc gcgatcaact gaagtttctg    1380
acacaaacct accctgctaa gggtggtatt tatttctcgg aatttggttg ggctgaagac    1440
```

-continued

```
gccgaatatg atcgtcaact gctgtatcaa attacctggg atggtctgcg tacgcaatac     1500
ctgacggact atctgagcca gctgctgttg gctgtgcaca aagacgggat taatctgcga     1560
ggcgcgctga cgtggagttt tgtcgataat tgggagtggg gtttagggat gcaacagaaa     1620
ttcggatttc agtttgttaa tcaatcagat cccgatctga cacgcacgtt taaactgagc     1680
gctcacgctt acgcccaatt tgggcgtaat catctg                              1716
```

<210> SEQ ID NO 23
<211> LENGTH: 572
<212> TYPE: PRT
<213> ORGANISM: Artificial sequence
<220> FEATURE:
<223> OTHER INFORMATION: Synthetic

<400> SEQUENCE: 23

```
Val Thr Tyr Pro Gly Ala Ile Pro Leu Ser Leu Thr Ser Asn Tyr Glu
1               5                   10                  15

Thr Pro Ser Pro Thr Ala Ile Pro Leu Glu Pro Thr Pro Thr Ala Thr
            20                  25                  30

Gly Thr Ala Glu Leu Asp Ala Leu Trp Asn Leu Val Glu Ala Gln Tyr
        35                  40                  45

Pro Val Gln Thr Ala Ala Val Thr Thr Leu Val Thr Val Pro Asp Asp
    50                  55                  60

Tyr Lys Phe Glu Ala Asp Pro Pro Ser Tyr Ala Leu Ala Gly Tyr Glu
65                  70                  75                  80

Thr Ser Glu Ile Ala Gly Leu Lys Phe Pro Lys Gly Phe Lys Phe Gly
                85                  90                  95

Val Ala Gly Ala Ala Ile Gln Val Glu Gly Ala Ala Lys Ala Glu Gly
            100                 105                 110

Arg Gly Pro Ser Thr Trp Asp Tyr Leu Cys His His Tyr Ala Ser Thr
        115                 120                 125

Gln Cys Asn Asn Tyr Asp Pro Asp Ile Thr Thr Asn His Tyr Tyr Leu
    130                 135                 140

Tyr Pro Leu Asp Phe Ala Arg Leu Gln His Leu Gly Ile Asn Thr Tyr
145                 150                 155                 160

Ser Phe Ser Ile Ser Trp Thr Arg Ile Tyr Pro Leu Gly Ala Gly Tyr
                165                 170                 175

Val Asn Glu Ala Gly Leu Ala His Tyr Asp Ala Val Ile His Ser Ala
            180                 185                 190

Lys Lys Tyr Gly Leu Glu Pro Val Gly Thr Val Phe His Trp Asp Thr
        195                 200                 205

Pro Leu Ser Leu Met Leu Lys Tyr Gly Ala Trp Gln Asp Thr Gly Asp
    210                 215                 220

Gln Ile Val Lys Asp Phe Val Thr Tyr Ala Thr Thr Val Phe Lys Arg
225                 230                 235                 240

Tyr Gly Asn Glu Val Lys Thr Trp Phe Thr Phe Asn Glu Pro Arg Val
                245                 250                 255

Phe Cys Ser Gln Asn Ser Gly Leu Pro Tyr Asn Leu Thr Tyr Pro Glu
            260                 265                 270

Gly Ile Asn Ser Thr Ser Ala Val Phe Arg Cys Thr Tyr Asn Val Leu
        275                 280                 285

Lys Ala His Gly His Ala Val Lys Val Tyr Arg Asp Leu Val Ala Ser
    290                 295                 300

Gly Thr Ile Ala Ala Gly Glu Ile Gly Phe Lys Ser Asp Asp Asn Tyr
```

```
305              310              315              320

Pro Ile Pro Ala Arg Pro Gly Asn Ala Asp Asp Glu Glu Ser Ala Lys
            325              330              335

Arg His Glu Ala Phe Arg Ile Gly Ile Phe Ala Gln Pro Val Tyr Gly
            340              345              350

Asn Gly Asp Tyr Pro Asp Val Val Lys Glu Thr Val Gly Asp Met Leu
            355              360              365

Pro Ala Leu Thr Asp Glu Asp Lys Gly Tyr Ile Lys Gly Ser Gly Asp
            370              375              380

Ile Phe Ala Ile Asp Gly Tyr Arg Thr Asp Ile Ser His Ala Ala Leu
385              390              395              400

Asn Gly Ile Ala Asn Cys Ile Arg Gln Gln Ser Asp Pro Asn Trp Pro
            405              410              415

Val Cys Glu Glu Gly Ser Asp Pro Phe Ala His Val Tyr Pro Ser Gly
            420              425              430

Phe Ala Ile Gly Gln Ser Ala Asp Pro Leu Ser Ser Trp Leu Val Asn
            435              440              445

Ser Ala Pro Phe Ile Arg Asp Gln Leu Lys Phe Leu Thr Gln Thr Tyr
            450              455              460

Pro Ala Lys Gly Gly Ile Tyr Phe Ser Glu Phe Gly Trp Ala Glu Asp
465              470              475              480

Ala Glu Tyr Asp Arg Gln Leu Leu Tyr Gln Ile Thr Trp Asp Gly Leu
            485              490              495

Arg Thr Gln Tyr Leu Thr Asp Tyr Leu Ser Gln Leu Leu Leu Ala Val
            500              505              510

His Lys Asp Gly Ile Asn Leu Arg Gly Ala Leu Thr Trp Ser Phe Val
            515              520              525

Asp Asn Trp Glu Trp Gly Leu Gly Met Gln Gln Lys Phe Gly Phe Gln
            530              535              540

Phe Val Asn Gln Ser Asp Pro Asp Leu Thr Arg Thr Phe Lys Leu Ser
545              550              555              560

Ala His Ala Tyr Ala Gln Phe Gly Arg Asn His Leu
            565              570
```

```
<210> SEQ ID NO 24
<211> LENGTH: 1716
<212> TYPE: DNA
<213> ORGANISM: Artificial sequence
<220> FEATURE:
<223> OTHER INFORMATION: Synthetic

<400> SEQUENCE: 24
gttacttatc cgggagccat tcctctgtcc ctgacgagca attacgaaac cccaagtccg      60
acagcaatcc cgctggagcc aacaccgacg gctaccggta cagcagaatt agatgcgctg     120
tggaacttag tcgaagctca gtacccagtt caaactgctg cagtgacaac tttggtgaca     180
gtgcccgatg attataagtt tgaggcagat ccaccgagtt atgcattagc agggtatgaa     240
acaagcgaga ttgccggact gaagtttcca aaggggttta agtttggtgt tgcggggca     300 gccattcaag ttgaaggtgc agcaaaagcc gaagggcggg gcccaagtac ctgggattat     360
ctgtgtcatc actatgccag cacgcagtgt aacaattatg atcccgatat tacaaccaac     420
cattactacc tgtacccatt ggactttgcg cgcctgcaac acctaggcat taacacttac     480
tcgttttcaa tttcatggac gcgtatttat ccattgggcg caggctatgt taatgaagca     540
gggttagccc actatgatgc cgtaatccat agtgccaaga agtatggtct ggaaccagtg     600
```

-continued

```
ggcaccgttt ttcactggga tacgccactg tctctgatgc tgaaatacgg tgcctggcaa      660
gatactggtg accaaattgt taaggacttt gttacctatg ccacaactgt gtttaagcgt      720
tatggtaatg aagtcaagac gtggtttact ttcaatgaac cacgggtttt ctgttcacaa      780
aatagtggtc tgccatacaa tctgacgtat ccagaaggta ttaacagcac ctccgctgta      840
tttcgttgca cctacaatgt tctgaaagct catggtcatg ctgttaaagt gtatcgggat      900
ctagttgcct ccgggaccat tgcggcaggt gaaatcggct ttaaatccga tgataactac      960
ccaatcccgg cccgtccagg gaacgccgat gacgaggaat cagccaagcg tcacgaggct     1020
tttcgcattg ggattttttgc gcaaccggtt tatggtaatg gcgattatcc agatgttgtt    1080
aaagaaactg ttggagatat gctgccggcc ctgacggatg aagataaagg atacattaaa     1140
ggtagcggag atattttttgc gattgacggg tatcgtaccg atatttccca tgcggctctg     1200
aacgggatcg cgaattgtat tcgccagcaa tcggatccga attggccagt gtgtgaagaa     1260
gggtcagatc cttttgctca tgtttaccca tccgggtttg ctattggtca atcagccgat     1320
ccactgtctt catggttagt caactcagcc ccgtttatcc gcgatcaact gaagtttctg     1380
acacaaacct accctgctaa gggtggtatt tatttctcgg aatttggttg ggctgaagac     1440
gccgaatatg atcgtcaact gctgtatcaa attacctggg atggtctgcg tacgcaatac     1500
ctgacggact atctgagcca gctgctgttg gctgtgcaca aagacgggat taatctgcga     1560
ggcgcgctga cgtggagttt tgtcgataat tgggagtggg gtttagggat gcaacagaaa     1620
ttcggatttc agtttgttaa tcaatcagat cccgatctga cacgcacgtt taaactgagc     1680
gctcacgctt acgcccaatt tgggcgtaat catctg                               1716
```

```
<210> SEQ ID NO 25
<211> LENGTH: 572
<212> TYPE: PRT
<213> ORGANISM: Artificial sequence
<220> FEATURE:
<223> OTHER INFORMATION: Synthetic

<400> SEQUENCE: 25

Val Thr Tyr Pro Gly Ala Ile Pro Leu Ser Leu Thr Ser Asn Tyr Glu
1               5                   10                  15

Thr Pro Ser Pro Thr Ala Ile Pro Leu Glu Pro Thr Pro Thr Ala Thr
            20                  25                  30

Gly Thr Ala Glu Leu Asp Ala Leu Trp Asn Leu Val Glu Ala Gln Tyr
        35                  40                  45

Pro Val Gln Thr Ala Ala Val Thr Thr Leu Val Thr Val Pro Asp Asp
    50                  55                  60

Tyr Lys Phe Glu Ala Asp Pro Pro Ser Tyr Ala Leu Ala Gly Tyr Glu
65                  70                  75                  80

Thr Ser Glu Ile Ala Gly Leu Lys Phe Pro Lys Gly Phe Lys Phe Gly
                85                  90                  95

Val Ala Gly Ala Ala Ile Gln Val Glu Gly Ala Ala Lys Ala Glu Gly
            100                 105                 110

Arg Gly Pro Ser Thr Trp Asp Tyr Leu Cys His His Tyr Ala Ser Thr
        115                 120                 125

Gln Cys Asn Asn Tyr Asp Pro Asp Ile Thr Thr Asn His Tyr Tyr Leu
    130                 135                 140

Tyr Pro Leu Asp Phe Ala Arg Leu Gln His Leu Gly Ile Asn Thr Tyr
145                 150                 155                 160
```

-continued

```
Ser Phe Ser Ile Ser Trp Thr Arg Ile Tyr Pro Leu Gly Ala Gly Tyr
            165                 170                 175

Val Asn Glu Ala Gly Leu Ala His Tyr Asp Ala Val Ile His Ser Ala
            180                 185                 190

Lys Lys Tyr Gly Leu Glu Pro Val Gly Thr Val Phe His Trp Asp Thr
            195                 200                 205

Pro Leu Ser Leu Met Leu Lys Tyr Gly Ala Trp Gln Asp Thr Gly Asp
    210                 215                 220

Gln Ile Val Lys Asp Phe Val Thr Tyr Ala Thr Thr Val Phe Lys Arg
225                 230                 235                 240

Tyr Gly Asn Glu Val Lys Thr Trp Phe Thr Phe Asn Glu Pro Arg Val
            245                 250                 255

Phe Cys Ser Gln Asn Ser Gly Leu Pro Tyr Asn Leu Thr Tyr Pro Glu
            260                 265                 270

Gly Ile Asn Ser Thr Ser Ala Val Phe Arg Cys Thr Tyr Asn Val Leu
            275                 280                 285

Lys Ala His Gly His Ala Val Lys Val Tyr Arg Asp Leu Val Ala Ser
    290                 295                 300

Gly Thr Ile Ala Ala Gly Glu Ile Gly Phe Lys Ser Asp Asp Asn Tyr
305                 310                 315                 320

Pro Ile Pro Ala Arg Pro Gly Asn Ala Asp Asp Glu Glu Ser Ala Lys
            325                 330                 335

Arg His Glu Ala Phe Arg Ile Gly Ile Phe Ala Gln Pro Val Tyr Gly
            340                 345                 350

Asn Gly Asp Tyr Pro Asp Val Val Lys Glu Thr Val Gly Asp Met Leu
            355                 360                 365

Pro Ala Leu Thr Asp Glu Asp Lys Gly Tyr Ile Lys Gly Ser Gly Asp
    370                 375                 380

Ile Phe Ala Ile Asp Gly Tyr Arg Thr Asp Ile Ser His Ala Ala Leu
385                 390                 395                 400

Asn Gly Ile Ala Asn Cys Ile Arg Asn Gln Ser Asp Pro Asn Trp Pro
            405                 410                 415

Val Cys Glu Glu Gly Ser Asp Pro Phe Ala His Val Tyr Pro Ser Gly
            420                 425                 430

Phe Ala Ile Gly Gln Ser Ala Asp Pro Leu Ser Ser Trp Leu Val Asn
            435                 440                 445

Ser Ala Pro Phe Ile Arg Asp Gln Leu Lys Phe Leu Thr Gln Thr Tyr
    450                 455                 460

Pro Ala Lys Gly Gly Ile Tyr Phe Ser Glu Phe Gly Trp Ala Glu Asp
465                 470                 475                 480

Ala Glu Tyr Asp Arg Gln Leu Leu Tyr Gln Ile Thr Trp Asp Gly Leu
            485                 490                 495

Arg Thr Gln Tyr Leu Thr Asp Tyr Leu Ser Gln Leu Leu Leu Ala Val
            500                 505                 510

His Lys Asp Gly Ile Asn Leu Arg Gly Ala Leu Thr Trp Ser Phe Val
            515                 520                 525

Asp Asn Trp Glu Trp Gly Leu Gly Met Gln Gln Lys Phe Gly Phe Gln
    530                 535                 540

Phe Val Gln Gln Ser Asp Pro Asp Leu Thr Arg Thr Phe Lys Leu Ser
545                 550                 555                 560

Ala His Ala Tyr Ala Gln Phe Gly Arg Asn His Leu
            565                 570
```

-continued

```
<210> SEQ ID NO 26
<211> LENGTH: 1716
<212> TYPE: DNA
<213> ORGANISM: Artificial sequence
<220> FEATURE:
<223> OTHER INFORMATION: Synthetic

<400> SEQUENCE: 26
gttacttatc cgggagccat tcctctgtcc ctgacgagca attacgaaac cccaagtccg      60
acagcaatcc cgctggagcc aacaccgacg gctaccggta cagcagaatt agatgcgctg     120
tggaacttag tcgaagctca gtacccagtt caaactgctg cagtgacaac tttggtgaca     180
gtgcccgatg attataagtt tgaggcagat ccaccgagtt atgcattagc agggtatgaa     240
acaagcgaga ttgccggact gaagtttcca aaggggttta agtttggtgt tgcggggggca     300 gccattcaag ttgaaggtgc agcaaaagcc gaagggcggg gcccaagtac ctgggattat     360
ctgtgtcatc actatgccag cacgcagtgt aacaattatg atcccgatat tacaaccaac     420
cattactacc tgtacccatt ggactttgcg cgcctgcaac acctaggcat taacacttac     480 tcgtttttcaa tttcatggac gcgtatttat ccattgggcg caggctatgt taatgaagca     540
gggttagccc actatgatgc cgtaatccat agtgccaaga agtatggtct ggaaccagtg     600
ggcaccgttt ttcactggga tacgccactg tctctgatgc tgaaatacgg tgcctggcaa     660
gatactggtg accaaattgt taaggactttt gttacctatg ccacaactgt gtttaagcgt     720
tatggtaatg aagtcaagac gtggtttact ttcaatgaac cacgggtttt ctgttcacaa     780
aatagtggtc tgccatacaa tctgacgtat ccagaaggta ttaacagcac ctccgctgta     840
tttcgttgca cctacaatgt tctgaaagct catggtcatg ctgttaaagt gtatcgggat     900
ctagttgcct ccgggaccat tgcggcaggt gaaatcggct ttaaatccga tgataactac     960
ccaatcccgg cccgtccagg gaacgccgat gacgaggaat cagccaagcg tcacgaggct    1020
tttcgcattg ggatttttgc gcaaccggtt tatggtaatg gcgattatcc agatgttgtt    1080
aaagaaactg ttggagatat gctgccggcc ctgacggatg aagataaagg atacattaaa    1140
ggtagcggag atatttttgc gattgacggg tatcgtaccg atatttccca tgcggctctg    1200
aacgggatcg cgaattgtat tcgcaaccaa agtgacccga attggccagt gtgtgaagaa    1260
gggtcagatc cttttgctca tgtttacccca tccgggtttg ctattggtca atcagccgat    1320
ccactgtctt catggttagt caactcagcc ccgtttatcc gcgatcaact gaagtttctg    1380
acacaaacct accctgctaa gggtggtatt tatttctcgg aatttggttg ggctgaagac    1440
gccgaatatg atcgtcaact gctgtatcaa attacctggg atggtctgcg tacgcaatac    1500
ctgacggact atctgagcca gctgctgttg gctgtgcaca agacgggat taatctgcga    1560 ggcgcgctga cgtggagttt tgtcgataat tgggagtggg gtttagggat gcaacagaaa    1620
ttcggatttc agtttgttca gcaatcggat cccgatctga cacgcacgtt taaactgagc    1680
gctcacgctt acgcccaatt tgggcgtaat catctg                              1716

<210> SEQ ID NO 27
<211> LENGTH: 89
<212> TYPE: PRT
<213> ORGANISM: Saccharomyces cerevisiae

<400> SEQUENCE: 27

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
```

```
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala
                85

<210> SEQ ID NO 28
<211> LENGTH: 267
<212> TYPE: PRT
<213> ORGANISM: Saccharomyces cerevisiae

<400> SEQUENCE: 28

Ala Thr Gly Ala Gly Ala Thr Thr Thr Cys Cys Thr Thr Cys Ala Ala
1               5                   10                  15

Thr Thr Thr Thr Thr Ala Cys Thr Gly Cys Ala Gly Thr Thr Thr Thr
            20                  25                  30

Ala Thr Thr Cys Gly Cys Ala Gly Cys Ala Thr Cys Cys Thr Cys Cys
        35                  40                  45

Gly Cys Ala Thr Thr Ala Gly Cys Thr Gly Cys Thr Cys Cys Ala Gly
    50                  55                  60

Thr Cys Ala Ala Cys Ala Cys Thr Ala Cys Ala Ala Cys Ala Gly Ala
65              70                  75                  80

Ala Gly Ala Thr Gly Ala Ala Ala Cys Gly Gly Cys Ala Cys Ala Ala
                85                  90                  95

Ala Thr Thr Cys Cys Gly Gly Cys Thr Gly Ala Ala Gly Cys Thr Gly
            100                 105                 110

Thr Cys Ala Thr Cys Gly Gly Thr Thr Ala Cys Thr Cys Ala Gly Ala
            115                 120                 125

Thr Thr Thr Ala Gly Ala Ala Gly Gly Gly Gly Ala Thr Thr Thr Cys
        130                 135                 140

Gly Ala Thr Gly Thr Thr Gly Cys Thr Gly Thr Thr Thr Thr Gly Cys
145                 150                 155                 160

Cys Ala Thr Thr Thr Thr Cys Cys Ala Ala Cys Ala Gly Cys Ala Cys
                165                 170                 175

Ala Ala Ala Thr Ala Ala Cys Gly Gly Gly Thr Thr Ala Thr Thr Gly
            180                 185                 190

Thr Thr Thr Ala Thr Ala Ala Ala Thr Ala Cys Thr Ala Cys Thr Ala
            195                 200                 205

Thr Thr Gly Cys Cys Ala Gly Cys Ala Thr Thr Gly Cys Thr Gly Cys
        210                 215                 220

Thr Ala Ala Ala Gly Ala Ala Gly Ala Ala Gly Gly Gly Gly Thr Ala
225                 230                 235                 240

Thr Cys Thr Cys Thr Cys Gly Ala Gly Ala Ala Ala Ala Gly Ala Gly
                245                 250                 255

Ala Gly Gly Cys Thr Gly Ala Ala Gly Cys Thr
            260                 265

<210> SEQ ID NO 29
<211> LENGTH: 67
<212> TYPE: PRT
<213> ORGANISM: Saccharomyces cerevisiae
```

```
<400> SEQUENCE: 29

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Ala Ser Ile Ala Ala Lys Glu Glu
    50                  55                  60

Gly Val Ser
65

<210> SEQ ID NO 30
<211> LENGTH: 19
<212> TYPE: PRT
<213> ORGANISM: Artificial sequence
<220> FEATURE:
<223> OTHER INFORMATION: Synthetic

<400> SEQUENCE: 30

Met Leu Leu Gln Ala Phe Leu Phe Leu Leu Ala Gly Phe Ala Ala Lys
1               5                   10                  15

Ile Ser Ala

<210> SEQ ID NO 31
<211> LENGTH: 18
<212> TYPE: PRT
<213> ORGANISM: Artificial sequence
<220> FEATURE:
<223> OTHER INFORMATION: Synthetic

<400> SEQUENCE: 31

Met Ser Phe Arg Ser Leu Leu Ala Leu Ser Gly Leu Val Cys Ser Gly
1               5                   10                  15

Leu Ala

<210> SEQ ID NO 32
<211> LENGTH: 16
<212> TYPE: PRT
<213> ORGANISM: Artificial sequence
<220> FEATURE:
<223> OTHER INFORMATION: Synthetic

<400> SEQUENCE: 32

Met Lys Leu Ala Tyr Ser Leu Leu Leu Pro Leu Ala Gly Val Ser Ala
1               5                   10                  15

<210> SEQ ID NO 33
<211> LENGTH: 2070
<212> TYPE: DNA
<213> ORGANISM: Pichia pastori

<400> SEQUENCE: 33
atgagatttc cttcaatttt tactgcagtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgtttttgc catttttccaa cagcacaaat       180 aacgggttat tgtttataaa tactactatt gccagcattg ctgctaaaga agaaggggta       240
tctctcgaga aaagagaggc tgaagctatg atgctgcatg ctgcactgct agtagcgctg       300
ccatgtgttg ttttggcgcg cccggccgga gcggttactt atccgggagc cattcctctg       360
```

-continued

```
tccctgacga gcaattacga aaccccaagt ccgacagcaa tcccgctgga gccaacaccg      420
acggctaccg gtacagcaga attagatgcg ctgtggaact tagtcgaagc tcagtaccca      480
gttcaaactg ctgcagtgac aactttggtg acagtgcccg atgattataa gtttgaggca      540
gatccaccga gttatgcatt agcagggtat gaaacaagcg agattgccgg actgaagttt      600
ccaaaggggt ttaagtttgg tgttgcgggg gcagccattc aagttgaagg tgcagcaaaa      660
gccgaagggc ggggcccaag tacctgggat tatctgtgtc atcactatgc cagcacgcag      720
tgtaacaatt atgatcccga tattacaacc aaccattact acctgtaccc attggacttt      780
gcgcgcctgc aacacctagg cattaacact tactcgtttt caatttcatg gacgcgtatt      840
tatccattgg gcgcaggcta tgttaatgaa gcagggttag cccactatga tgccgtaatc      900
catagtgcca agaagtatgg tctggaacca gtgggcaccg tttttcactg ggatacgcca      960
ctgtctctga tgctgaaata cggtgcctgg caagatactg gtgaccaaat tgttaaggac     1020
tttgttacct atgccacaac tgtgtttaag cgttatggta atgaagtcaa gacgtggttt     1080
actttcaatg aaccacgggt tttctgttca caaaatagtg gtctgccata caatctgacg     1140
tatccagaag gtattaacag cacctccgct gtatttcgtt gcacctacaa tgttctgaaa     1200
gctcatggtc atgctgttaa agtgtatcgg gatctagttg cctccgggac cattgcggca     1260
ggtgaaatcg gctttaaatc cgatgataac tacccaatcc cggcccgtcc agggaacgcc     1320
gatgacgagg aatcagccaa gcgtcacgag gcttttcgca ttgggatttt tgcgcaaccg     1380
gtttatggta atggcgatta tccagatgtt gttaaagaaa ctgttggaga tatgctgccg     1440
gccctgacgg atgaagataa aggatacatt aaaggtagcg gagatatttt tgcgattgac     1500
gggtatcgta ccgatatttc ccatgcggct ctgaacggga tcgcgaattg tattcgcaac     1560
caaagtgacc cgaattggcc agtgtgtgaa gaagggtcag atcctttttgc tcatgtttac     1620 ccatccgggt ttgctattgg tcaatcagcc gatccactgt cttcatggtt agtcaactca     1680 gccccgtttta tccgcgatca actgaagttt ctgacacaaa cctaccctgc taagggtggt     1740
atttatttct cggaatttgg ttgggctgaa gacgccgaat atgatcgtca actgctgtat     1800
caaattacct gggatggtct gcgtacgcaa tacctgacgg actatctgag ccagctgctg     1860
ttggctgtgc acaaagacgg gattaatctg cgaggcgcgc tgacgtggag ttttgtcgat     1920
aattgggagt ggggtttagg gatgcaacag aaattcggat ttcagtttgt taatcaatca     1980
gatcccgatc tgacacgcac gtttaaactg agcgctcacg cttacgccca atttgggcgt     2040
aatcatctgc accaccacca ccaccactaa                                     2070
```

```
<210> SEQ ID NO 34
<211> LENGTH: 689
<212> TYPE: PRT
<213> ORGANISM: Pichia pastori

<400> SEQUENCE: 34

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60
```

-continued

```
Phe Ile Asn Thr Thr Ile Ala Ser Ile Ala Ala Lys Glu Glu Gly Val
65              70              75              80

Ser Leu Glu Lys Arg Glu Ala Glu Ala Met Met Leu His Ala Ala Leu
            85              90              95

Leu Val Ala Leu Pro Cys Val Val Leu Ala Arg Pro Ala Gly Ala Val
            100             105             110

Thr Tyr Pro Gly Ala Ile Pro Leu Ser Leu Thr Ser Asn Tyr Glu Thr
        115             120             125

Pro Ser Pro Thr Ala Ile Pro Leu Glu Pro Thr Pro Thr Ala Thr Gly
    130             135             140

Thr Ala Glu Leu Asp Ala Leu Trp Asn Leu Val Glu Ala Gln Tyr Pro
145             150             155             160

Val Gln Thr Ala Ala Val Thr Thr Leu Val Thr Val Pro Asp Asp Tyr
            165             170             175

Lys Phe Glu Ala Asp Pro Pro Ser Tyr Ala Leu Ala Gly Tyr Glu Thr
            180             185             190

Ser Glu Ile Ala Gly Leu Lys Phe Pro Lys Gly Phe Lys Phe Gly Val
        195             200             205

Ala Gly Ala Ala Ile Gln Val Glu Gly Ala Ala Lys Ala Glu Gly Arg
    210             215             220

Gly Pro Ser Thr Trp Asp Tyr Leu Cys His His Tyr Ala Ser Thr Gln
225             230             235             240

Cys Asn Asn Tyr Asp Pro Asp Ile Thr Thr Asn His Tyr Tyr Leu Tyr
            245             250             255

Pro Leu Asp Phe Ala Arg Leu Gln His Leu Gly Ile Asn Thr Tyr Ser
            260             265             270

Phe Ser Ile Ser Trp Thr Arg Ile Tyr Pro Leu Gly Ala Gly Tyr Val
        275             280             285

Asn Glu Ala Gly Leu Ala His Tyr Asp Ala Val Ile His Ser Ala Lys
    290             295             300

Lys Tyr Gly Leu Glu Pro Val Gly Thr Val Phe His Trp Asp Thr Pro
305             310             315             320

Leu Ser Leu Met Leu Lys Tyr Gly Ala Trp Gln Asp Thr Gly Asp Gln
            325             330             335

Ile Val Lys Asp Phe Val Thr Tyr Ala Thr Thr Val Phe Lys Arg Tyr
            340             345             350

Gly Asn Glu Val Lys Thr Trp Phe Thr Phe Asn Glu Pro Arg Val Phe
        355             360             365

Cys Ser Gln Asn Ser Gly Leu Pro Tyr Asn Leu Thr Tyr Pro Glu Gly
    370             375             380

Ile Asn Ser Thr Ser Ala Val Phe Arg Cys Thr Tyr Asn Val Leu Lys
385             390             395             400

Ala His Gly His Ala Val Lys Val Tyr Arg Asp Leu Val Ala Ser Gly
            405             410             415

Thr Ile Ala Ala Gly Glu Ile Gly Phe Lys Ser Asp Asp Asn Tyr Pro
            420             425             430

Ile Pro Ala Arg Pro Gly Asn Ala Asp Asp Glu Glu Ser Ala Lys Arg
        435             440             445

His Glu Ala Phe Arg Ile Gly Ile Phe Ala Gln Pro Val Tyr Gly Asn
    450             455             460

Gly Asp Tyr Pro Asp Val Val Lys Glu Thr Val Gly Asp Met Leu Pro
465             470             475             480

Ala Leu Thr Asp Glu Asp Lys Gly Tyr Ile Lys Gly Ser Gly Asp Ile
```

-continued

```
              485                  490                  495
Phe Ala Ile Asp Gly Tyr Arg Thr Asp Ile Ser His Ala Ala Leu Asn
              500                  505                  510

Gly Ile Ala Asn Cys Ile Arg Asn Gln Ser Asp Pro Asn Trp Pro Val
              515                  520                  525

Cys Glu Glu Gly Ser Asp Pro Phe Ala His Val Tyr Pro Ser Gly Phe
          530                  535                  540

Ala Ile Gly Gln Ser Ala Asp Pro Leu Ser Ser Trp Leu Val Asn Ser
550                  550                  555                  560

Ala Pro Phe Ile Arg Asp Gln Leu Lys Phe Leu Thr Gln Thr Tyr Pro
                  565                  570                  575

Ala Lys Gly Gly Ile Tyr Phe Ser Glu Phe Gly Trp Ala Glu Asp Ala
              580                  585                  590

Glu Tyr Asp Arg Gln Leu Leu Tyr Gln Ile Thr Trp Asp Gly Leu Arg
              595                  600                  605

Thr Gln Tyr Leu Thr Asp Tyr Leu Ser Gln Leu Leu Leu Ala Val His
          610                  615                  620

Lys Asp Gly Ile Asn Leu Arg Gly Ala Leu Thr Trp Ser Phe Val Asp
625                  630                  635                  640

Asn Trp Glu Trp Gly Leu Gly Met Gln Gln Lys Phe Gly Phe Gln Phe
                  645                  650                  655

Val Asn Gln Ser Asp Pro Asp Leu Thr Arg Thr Phe Lys Leu Ser Ala
              660                  665                  670

His Ala Tyr Ala Gln Phe Gly Arg Asn His Leu His His His His His
          675                  680                  685

His
```

```
<210> SEQ ID NO 35
<211> LENGTH: 1800
<212> TYPE: DNA
<213> ORGANISM: Pichia pastori

<400> SEQUENCE: 35
atgatgctgc atgctgcact gctagtagcg ctgccatgtg ttgttttggc gcgcccggcc    60
ggagcggtta cttatccggg agccattcct ctgtccctga cgagcaatta cgaaacccca   120
agtccgacag caatcccgct ggagccaaca ccgacggcta ccggtacagc agaattagat   180
gcgctgtgga acttagtcga agctcagtac ccagttcaaa ctgctgcagt gacaactttg   240
gtgacagtgc ccgatgatta taagtttgag gcagatccac cgagttatgc attagcaggg   300
tatgaaacaa gcgagattgc cggactgaag tttccaaagg ggtttaagtt tggtgttgcg   360
ggggcagcca ttcaagttga aggtgcagca aaagccgaag gcgggggccc aagtacctgg   420
gattatctgt gtcatcacta tgccagcacg cagtgtaaca attatgatcc cgatattaca   480
accaaccatt actacctgta cccattggac tttgcgcgcc tgcaacacct aggcattaac   540
acttactcgt tttcaatttc atggacgcgt atttatccat tgggcgcagg ctatgttaat   600
gaagcagggt tagcccacta tgatgccgta atccatagtg ccaagaagta tggtctggaa   660
ccagtgggca ccgttttttca ctgggatacg ccactgtctc tgatgctgaa atacggtgcc   720
tggcaagata ctggtgacca aattgttaag actttgttta cctatgccac aactgtgttt   780
aagcgttatg gtaatgaagt caagacgtgg tttacttttca atgaaccacg ggttttctgt   840
tcacaaaata tgggtctgcc atacaatctg acgtatccag aaggtattaa cagcacctcc   900
gctgtatttc gttgcaccta caatgttctg aaagctcatg gtcatgctgt taaagtgtat   960
```

```
cgggatctag ttgcctccgg gaccattgcg gcaggtgaaa tcggctttaa atccgatgat     1020
aactacccaa tcccggcccg tccagggaac gccgatgacg aggaatcagc caagcgtcac     1080
gaggcttttc gcattgggat ttttgcgcaa ccggtttatg gtaatggcga ttatccagat     1140
gttgttaaag aaactgttgg agatatgctg ccggccctga cggatgaaga taaaggatac     1200
attaaaggta gcggagatat ttttgcgatt gacgggtatc gtaccgatat ttcccatgcg     1260
gctctgaacg ggatcgcgaa ttgtattcgc aaccaaagtg acccgaattg gccagtgtgt     1320
gaagaagggt cagatccttt tgctcatgtt tacccatccg ggtttgctat tggtcaatca     1380
gccgatccac tgtcttcatg gttagtcaac tcagccccgt ttatccgcga tcaactgaag     1440
tttctgacac aaacctaccc tgctaagggt ggtatttatt tctcggaatt tggttgggct     1500
gaagacgccg aatatgatcg tcaactgctg tatcaaatta cctgggatgg tctgcgtacg     1560
caatacctga cggactatct gagccagctg ctgttggctg tgcacaaaga cgggattaat     1620
ctgcgaggcg cgctgacgtg gagttttgtc gataattggg agtggggttt agggatgcaa     1680
cagaaattcg gatttcagtt tgttaatcaa tcagatcccg atctgacacg cacgtttaaa     1740
ctgagcgctc acgcttacgc ccaatttggg cgtaatcatc tgcaccacca ccaccaccac     1800
```

```
<210> SEQ ID NO 36
<211> LENGTH: 600
<212> TYPE: PRT
<213> ORGANISM: Pichia pastori

<400> SEQUENCE: 36

Met Met Leu His Ala Ala Leu Leu Val Ala Leu Pro Cys Val Val Leu
1               5                   10                  15

Ala Arg Pro Ala Gly Ala Val Thr Tyr Pro Gly Ala Ile Pro Leu Ser
            20                  25                  30

Leu Thr Ser Asn Tyr Glu Thr Pro Ser Pro Thr Ala Ile Pro Leu Glu
        35                  40                  45

Pro Thr Pro Thr Ala Thr Gly Thr Ala Glu Leu Asp Ala Leu Trp Asn
    50                  55                  60

Leu Val Glu Ala Gln Tyr Pro Val Gln Thr Ala Ala Val Thr Thr Leu
65                  70                  75                  80

Val Thr Val Pro Asp Asp Tyr Lys Phe Glu Ala Asp Pro Pro Ser Tyr
                85                  90                  95

Ala Leu Ala Gly Tyr Glu Thr Ser Glu Ile Ala Gly Leu Lys Phe Pro
            100                 105                 110

Lys Gly Phe Lys Phe Gly Val Ala Gly Ala Ala Ile Gln Val Glu Gly
        115                 120                 125

Ala Ala Lys Ala Glu Gly Arg Gly Pro Ser Thr Trp Asp Tyr Leu Cys
    130                 135                 140

His His Tyr Ala Ser Thr Gln Cys Asn Asn Tyr Asp Pro Asp Ile Thr
145                 150                 155                 160

Thr Asn His Tyr Tyr Leu Tyr Pro Leu Asp Phe Ala Arg Leu Gln His
                165                 170                 175

Leu Gly Ile Asn Thr Tyr Ser Phe Ser Ile Ser Trp Thr Arg Ile Tyr
            180                 185                 190

Pro Leu Gly Ala Gly Tyr Val Asn Glu Ala Gly Leu Ala His Tyr Asp
        195                 200                 205

Ala Val Ile His Ser Ala Lys Lys Tyr Gly Leu Glu Pro Val Gly Thr
    210                 215                 220
```

```
Val Phe His Trp Asp Thr Pro Leu Ser Leu Met Leu Lys Tyr Gly Ala
225             230             235             240

Trp Gln Asp Thr Gly Asp Gln Ile Val Lys Asp Phe Val Thr Tyr Ala
            245             250             255

Thr Thr Val Phe Lys Arg Tyr Gly Asn Glu Val Lys Thr Trp Phe Thr
            260             265             270

Phe Asn Glu Pro Arg Val Phe Cys Ser Gln Asn Ser Gly Leu Pro Tyr
            275             280             285

Asn Leu Thr Tyr Pro Glu Gly Ile Asn Ser Thr Ser Ala Val Phe Arg
            290             295             300

Cys Thr Tyr Asn Val Leu Lys Ala His Gly His Ala Val Lys Val Tyr
305             310             315             320

Arg Asp Leu Val Ala Ser Gly Thr Ile Ala Ala Gly Glu Ile Gly Phe
            325             330             335

Lys Ser Asp Asp Asn Tyr Pro Ile Pro Ala Arg Pro Gly Asn Ala Asp
            340             345             350

Asp Glu Glu Ser Ala Lys Arg His Glu Ala Phe Arg Ile Gly Ile Phe
            355             360             365

Ala Gln Pro Val Tyr Gly Asn Gly Asp Tyr Pro Asp Val Val Lys Glu
370             375             380

Thr Val Gly Asp Met Leu Pro Ala Leu Thr Asp Glu Asp Lys Gly Tyr
385             390             395             400

Ile Lys Gly Ser Gly Asp Ile Phe Ala Ile Asp Gly Tyr Arg Thr Asp
            405             410             415

Ile Ser His Ala Ala Leu Asn Gly Ile Ala Asn Cys Ile Arg Asn Gln
            420             425             430

Ser Asp Pro Asn Trp Pro Val Cys Glu Glu Gly Ser Asp Pro Phe Ala
            435             440             445

His Val Tyr Pro Ser Gly Phe Ala Ile Gly Gln Ser Ala Asp Pro Leu
            450             455             460

Ser Ser Trp Leu Val Asn Ser Ala Pro Phe Ile Arg Asp Gln Leu Lys
465             470             475             480

Phe Leu Thr Gln Thr Tyr Pro Ala Lys Gly Gly Ile Tyr Phe Ser Glu
            485             490             495

Phe Gly Trp Ala Glu Asp Ala Glu Tyr Asp Arg Gln Leu Leu Tyr Gln
            500             505             510

Ile Thr Trp Asp Gly Leu Arg Thr Gln Tyr Leu Thr Asp Tyr Leu Ser
            515             520             525

Gln Leu Leu Leu Ala Val His Lys Asp Gly Ile Asn Leu Arg Gly Ala
            530             535             540

Leu Thr Trp Ser Phe Val Asp Asn Trp Glu Trp Gly Leu Gly Met Gln
545             550             555             560

Gln Lys Phe Gly Phe Gln Phe Val Asn Gln Ser Asp Pro Asp Leu Thr
            565             570             575

Arg Thr Phe Lys Leu Ser Ala His Ala Tyr Ala Gln Phe Gly Arg Asn
            580             585             590

His Leu His His His His His His
            595             600
```

<210> SEQ ID NO 37
<211> LENGTH: 2001
<212> TYPE: DNA
<213> ORGANISM: Pichia pastori

<400> SEQUENCE: 37

```
atgagatttc cttcaatttt tactgcagtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgttttgc cattttccaa cagcacaaat       180
aacgggttat tgtttataaa tactactatt gccagcattc tgctaaaga agaaggggta       240 tctctcgaga aaagagaggc tgaagctgtt acttatccgg gagccattcc tctgtccctg       300
acgagcaatt acgaaacccc aagtccgaca gcaatcccgc tggagccaac accgacggct       360
accggtacag cagaattaga tgcgctgtgg aacttagtcg aagctcagta cccagttcaa       420
actgctgcag tgacaacttt ggtgacagtg cccgatgatt ataagtttga ggcagatcca       480
ccgagttatg cattagcagg gtatgaaaca agcgagattg ccggactgaa gtttccaaag       540
gggtttaagt ttggtgttgc gggggcagcc attcaagttg aaggtgcagc aaaagccgaa       600
gggcggggcc caagtacctg ggattatctg tgtcatcact atgccagcac gcagtgtaac       660
aattatgatc ccgatattac aaccaaccat tactacctgt acccattgga ctttgcgcgc       720
ctgcaacacc taggcattaa cacttactcg ttttcaattt catggacgcg tatttatcca       780
ttgggcgcag gctatgttaa tgaagcaggg ttagcccact atgatgccgt aatccatagt       840
gccaagaagt atggtctgga accagtgggc accgtttttc actgggatac gccactgtct       900
ctgatgctga aataccggtgc ctggcaagat actggtgacc aaattgttaa ggactttgtt       960
acctatgcca caactgtgtt taagcgttat ggtaatgaag tcaagacgtg gtttactttc      1020
aatgaaccac gggttttctg ttcacaaaat agtggtctgc catacaatct gacgtatcca      1080
gaaggtatta acagcacctc cgctgtattt cgttgcacct acaatgttct gaaagctcat      1140
ggtcatgctg ttaaagtgta tcgggatcta gttgcctccg ggaccattgc ggcaggtgaa      1200 atcggctttta aatccgatga taactacccca atcccggccc gtccagggaa cgccgatgac      1260
gaggaatcag ccaagcgtca cgaggctttt cgcattggga tttttgcgca accggtttat      1320
ggtaatggcg attatccaga tgttgttaaa gaaactgttg gagatatgct gccggccctg      1380
acggatgaag ataaaggata cattaaaggt agcggagata tttttgcgat tgacgggtat      1440
cgtaccgata tttcccatgc ggctctgaac gggatcgcga attgtattcg caaccaaagt      1500 gaccgaatt ggccagtgtg tgaagaaggg tcagatcctt ttgctcatgt ttacccatcc       1560
gggtttgcta ttggtcaatc agccgatcca ctgtcttcat ggttagtcaa ctcagccccg      1620
tttatccgcg atcaactgaa gtttctgaca caaacctacc ctgctaaggg tggtatttat      1680
ttctcggaat ttggttgggc tgaagacgcc gaatatgatc gtcaactgct gtatcaaatt      1740
acctgggatg gtctgcgtac gcaatacctg acggactatc tgagccagct gctgttggct      1800
gtgcacaaag acgggattaa tctgcgaggc gcgctgacgt ggagtttttgt cgataattgg      1860 gagtggggtt tagggatgca acagaaattc ggatttcagt ttgttaatca atcagatccc      1920
gatctgacac gcacgtttaa actgagcgct cacgcttacg cccaatttgg gcgtaatcat      1980
ctgcaccacc accaccacca c                                               2001
```

```
<210> SEQ ID NO 38
<211> LENGTH: 667
<212> TYPE: PRT
<213> ORGANISM: Pichia pastori

<400> SEQUENCE: 38

Met Arg Phe Pro Ser Ile Phe Thr Ala Val Leu Phe Ala Ala Ser Ser
1               5                   10                  15
```

-continued

```
Ala Leu Ala Ala Pro Val Asn Thr Thr Thr Glu Asp Glu Thr Ala Gln
         20              25              30

Ile Pro Ala Glu Ala Val Ile Gly Tyr Ser Asp Leu Glu Gly Asp Phe
         35              40              45

Asp Val Ala Val Leu Pro Phe Ser Asn Ser Thr Asn Asn Gly Leu Leu
         50              55              60

Phe Ile Asn Thr Thr Ile Ala Ser Ile Ala Ala Lys Glu Glu Gly Val
65              70              75              80

Ser Leu Glu Lys Arg Glu Ala Glu Ala Val Thr Tyr Pro Gly Ala Ile
             85              90              95

Pro Leu Ser Leu Thr Ser Asn Tyr Glu Thr Pro Ser Pro Thr Ala Ile
         100             105             110

Pro Leu Glu Pro Thr Pro Thr Ala Thr Gly Thr Ala Glu Leu Asp Ala
         115             120             125

Leu Trp Asn Leu Val Glu Ala Gln Tyr Pro Val Gln Thr Ala Ala Val
     130             135             140

Thr Thr Leu Val Thr Val Pro Asp Asp Tyr Lys Phe Glu Ala Asp Pro
145             150             155             160

Pro Ser Tyr Ala Leu Ala Gly Tyr Glu Thr Ser Glu Ile Ala Gly Leu
             165             170             175

Lys Phe Pro Lys Gly Phe Lys Phe Gly Val Ala Gly Ala Ala Ile Gln
         180             185             190

Val Glu Gly Ala Ala Lys Ala Glu Gly Arg Gly Pro Ser Thr Trp Asp
         195             200             205

Tyr Leu Cys His His Tyr Ala Ser Thr Gln Cys Asn Asn Tyr Asp Pro
     210             215             220

Asp Ile Thr Thr Asn His Tyr Tyr Leu Tyr Pro Leu Asp Phe Ala Arg
225             230             235             240

Leu Gln His Leu Gly Ile Asn Thr Tyr Ser Phe Ser Ile Ser Trp Thr
             245             250             255

Arg Ile Tyr Pro Leu Gly Ala Gly Tyr Val Asn Glu Ala Gly Leu Ala
             260             265             270

His Tyr Asp Ala Val Ile His Ser Ala Lys Lys Tyr Gly Leu Glu Pro
     275             280             285

Val Gly Thr Val Phe His Trp Asp Thr Pro Leu Ser Leu Met Leu Lys
     290             295             300

Tyr Gly Ala Trp Gln Asp Thr Gly Asp Gln Ile Val Lys Asp Phe Val
305             310             315             320

Thr Tyr Ala Thr Thr Val Phe Lys Arg Tyr Gly Asn Glu Val Lys Thr
             325             330             335

Trp Phe Thr Phe Asn Glu Pro Arg Val Phe Cys Ser Gln Asn Ser Gly
         340             345             350

Leu Pro Tyr Asn Leu Thr Tyr Pro Glu Gly Ile Asn Ser Thr Ser Ala
         355             360             365

Val Phe Arg Cys Thr Tyr Asn Val Leu Lys Ala His Gly His Ala Val
     370             375             380

Lys Val Tyr Arg Asp Leu Val Ala Ser Gly Thr Ile Ala Ala Gly Glu
385             390             395             400

Ile Gly Phe Lys Ser Asp Asp Asn Tyr Pro Ile Pro Ala Arg Pro Gly
             405             410             415

Asn Ala Asp Asp Glu Glu Ser Ala Lys Arg His Glu Ala Phe Arg Ile
         420             425             430
```

-continued

```
Gly Ile Phe Ala Gln Pro Val Tyr Gly Asn Gly Asp Tyr Pro Asp Val
        435             440             445

Val Lys Glu Thr Val Gly Asp Met Leu Pro Ala Leu Thr Asp Glu Asp
    450             455             460

Lys Gly Tyr Ile Lys Gly Ser Gly Asp Ile Phe Ala Ile Asp Gly Tyr
465             470             475             480

Arg Thr Asp Ile Ser His Ala Ala Leu Asn Gly Ile Ala Asn Cys Ile
            485             490             495

Arg Asn Gln Ser Asp Pro Asn Trp Pro Val Cys Glu Glu Gly Ser Asp
            500             505             510

Pro Phe Ala His Val Tyr Pro Ser Gly Phe Ala Ile Gly Gln Ser Ala
            515             520             525

Asp Pro Leu Ser Ser Trp Leu Val Asn Ser Ala Pro Phe Ile Arg Asp
        530             535             540

Gln Leu Lys Phe Leu Thr Gln Thr Tyr Pro Ala Lys Gly Gly Ile Tyr
545             550             555             560

Phe Ser Glu Phe Gly Trp Ala Glu Asp Ala Glu Tyr Asp Arg Gln Leu
            565             570             575

Leu Tyr Gln Ile Thr Trp Asp Gly Leu Arg Thr Gln Tyr Leu Thr Asp
            580             585             590

Tyr Leu Ser Gln Leu Leu Leu Ala Val His Lys Asp Gly Ile Asn Leu
            595             600             605

Arg Gly Ala Leu Thr Trp Ser Phe Val Asp Asn Trp Glu Trp Gly Leu
        610             615             620

Gly Met Gln Gln Lys Phe Gly Phe Gln Phe Val Asn Gln Ser Asp Pro
625             630             635             640

Asp Leu Thr Arg Thr Phe Lys Leu Ser Ala His Ala Tyr Ala Gln Phe
            645             650             655

Gly Arg Asn His Leu His His His His His His
            660             665
```

<210> SEQ ID NO 39
<211> LENGTH: 2001
<212> TYPE: DNA
<213> ORGANISM: Pichia pastori

<400> SEQUENCE: 39

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta     240 tctctcgaga aaagagaggc tgaagctgtt acttatccgg gagccattcc tctgtccctg     300
acgagcaatt acgaaacccc aagtccgaca gcaatcccgc tggagccaac accgacggct     360
accggtacag cagaattaga tgcgctgtgg aacttagtcg aagctcagta cccagttcaa     420
actgctgcag tgacaacttt ggtgacagtg cccgatgatt ataagtttga ggcagatcca     480
ccgagttatg cattagcagg gtatgaaaca agcgagattg ccggactgaa gtttccaaag     540
gggtttaagt ttggtgttgc gggggcagcc attcaagttg aaggtgcagc aaaagccgaa     600
gggcggggcc caagtacctg ggattatctg tgtcatcact atgccagcac gcagtgtaac     660
aattatgatc ccgatattac aaccaaccat tactacctgt acccattgga ctttgcgcgc     720
ctgcaacacc taggcattaa cacttactcg ttttcaattt catggacgcg tatttatcca     780
```

-continued

```
ttgggcgcag gctatgttaa tgaagcaggg ttagcccact atgatgccgt aatccatagt   840
gccaagaagt atggtctgga accagtgggc accgttttc actgggatac gccactgtct   900
ctgatgctga aatacggtgc ctggcaagat actggtgacc aaattgttaa ggactttgtt   960
acctatgcca caactgtgtt taagcgttat ggtaatgaag tcaagacgtg gtttactttc  1020
aatgaaccac gggttttctg ttcacaaaat agtggtctgc ataccagct tacgtatcca  1080 gaaggtatta acagcacctc cgctgtattt cgttgcacct acaatgttct gaaagctcat  1140
ggtcatgctg ttaaagtgta tcgggatcta gttgcctccg ggaccattgc ggcaggtgaa  1200
atcggcttta aatccgatga taactaccca atcccggccc gtccagggaa cgccgatgac  1260
gaggaatcag ccaagcgtca cgaggctttt cgcattggga tttttgcgca accggtttat  1320
ggtaatggcg attatccaga tgttgttaaa gaaactgttg gagatatgct gccggccctg  1380
acggatgaag ataaaggata cattaaaggt agcggagata tttttgcgat tgacgggtat  1440
cgtaccgata tttcccatgc ggctctgaac gggatcgcga attgtattcg caaccaaagt  1500
gacccgaatt ggccagtgtg tgaagaaggg tcagatcctt ttgctcatgt ttacccatcc  1560
gggtttgcta ttggtcaatc agccgatcca ctgtcttcat ggttagtcaa ctcagccccg  1620
tttatccgcg atcaactgaa gtttctgaca caaacctacc ctgctaaggg tggtatttat  1680
ttctcggaat ttggttgggc tgaagacgcc gaatatgatc gtcaactgct gtatcaaatt  1740
acctgggatg gtctgcgtac gcaatacctg acggactatc tgagccagct gctgttggct  1800
gtgcacaaag acgggattaa tctgcgaggc gcgctgacgt ggagttttgt cgataattgg  1860 gagtgggggtt tagggatgca acagaaattc ggatttcagt ttgttaatca atcagatccc  1920
gatctgacac gcacgtttaa actgagcgct cacgcttacg cccaatttgg gcgtaatcat  1980
ctgcaccacc accaccacca c                                             2001
```

<210> SEQ ID NO 40
<211> LENGTH: 667
<212> TYPE: PRT
<213> ORGANISM: Pichia pastori

<400> SEQUENCE: 40

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Val Thr Tyr Pro Gly Ala Ile
                85                  90                  95

Pro Leu Ser Leu Thr Ser Asn Tyr Glu Thr Pro Ser Pro Thr Ala Ile
            100                 105                 110

Pro Leu Glu Pro Thr Pro Thr Ala Thr Gly Thr Ala Glu Leu Asp Ala
        115                 120                 125

Leu Trp Asn Leu Val Glu Ala Gln Tyr Pro Val Gln Thr Ala Ala Val
    130                 135                 140

Thr Thr Leu Val Thr Val Pro Asp Asp Tyr Lys Phe Glu Ala Asp Pro
145                 150                 155                 160
```

-continued

Pro Ser Tyr Ala Leu Ala Gly Tyr Glu Thr Ser Glu Ile Ala Gly Leu
            165                 170                 175

Lys Phe Pro Lys Gly Phe Lys Phe Gly Val Ala Gly Ala Ala Ile Gln
            180                 185                 190

Val Glu Gly Ala Ala Lys Ala Glu Gly Arg Gly Pro Ser Thr Trp Asp
            195                 200                 205

Tyr Leu Cys His His Tyr Ala Ser Thr Gln Cys Asn Asn Tyr Asp Pro
            210                 215                 220

Asp Ile Thr Thr Asn His Tyr Tyr Leu Tyr Pro Leu Asp Phe Ala Arg
225                 230                 235                 240

Leu Gln His Leu Gly Ile Asn Thr Tyr Ser Phe Ser Ile Ser Trp Thr
            245                 250                 255

Arg Ile Tyr Pro Leu Gly Ala Gly Tyr Val Asn Glu Ala Gly Leu Ala
            260                 265                 270

His Tyr Asp Ala Val Ile His Ser Ala Lys Lys Tyr Gly Leu Glu Pro
            275                 280                 285

Val Gly Thr Val Phe His Trp Asp Thr Pro Leu Ser Leu Met Leu Lys
            290                 295                 300

Tyr Gly Ala Trp Gln Asp Thr Gly Asp Gln Ile Val Lys Asp Phe Val
305                 310                 315                 320

Thr Tyr Ala Thr Thr Val Phe Lys Arg Tyr Gly Asn Glu Val Lys Thr
            325                 330                 335

Trp Phe Thr Phe Asn Glu Pro Arg Val Phe Cys Ser Gln Asn Ser Gly
            340                 345                 350

Leu Pro Tyr Gln Leu Thr Tyr Pro Glu Gly Ile Asn Ser Thr Ser Ala
            355                 360                 365

Val Phe Arg Cys Thr Tyr Asn Val Leu Lys Ala His Gly His Ala Val
            370                 375                 380

Lys Val Tyr Arg Asp Leu Val Ala Ser Gly Thr Ile Ala Ala Gly Glu
385                 390                 395                 400

Ile Gly Phe Lys Ser Asp Asp Asn Tyr Pro Ile Pro Ala Arg Pro Gly
            405                 410                 415

Asn Ala Asp Asp Glu Glu Ser Ala Lys Arg His Glu Ala Phe Arg Ile
            420                 425                 430

Gly Ile Phe Ala Gln Pro Val Tyr Gly Asn Gly Asp Tyr Pro Asp Val
            435                 440                 445

Val Lys Glu Thr Val Gly Asp Met Leu Pro Ala Leu Thr Asp Glu Asp
            450                 455                 460

Lys Gly Tyr Ile Lys Gly Ser Gly Asp Ile Phe Ala Ile Asp Gly Tyr
465                 470                 475                 480

Arg Thr Asp Ile Ser His Ala Ala Leu Asn Gly Ile Ala Asn Cys Ile
            485                 490                 495

Arg Asn Gln Ser Asp Pro Asn Trp Pro Val Cys Glu Glu Gly Ser Asp
            500                 505                 510

Pro Phe Ala His Val Tyr Pro Ser Gly Phe Ala Ile Gly Gln Ser Ala
            515                 520                 525

Asp Pro Leu Ser Ser Trp Leu Val Asn Ser Ala Pro Phe Ile Arg Asp
            530                 535                 540

Gln Leu Lys Phe Leu Thr Gln Thr Tyr Pro Ala Lys Gly Gly Ile Tyr
545                 550                 555                 560

Phe Ser Glu Phe Gly Trp Ala Glu Asp Ala Glu Tyr Asp Arg Gln Leu
            565                 570                 575

-continued

```
Leu Tyr Gln Ile Thr Trp Asp Gly Leu Arg Thr Gln Tyr Leu Thr Asp
          580                 585                 590

Tyr Leu Ser Gln Leu Leu Leu Ala Val His Lys Asp Gly Ile Asn Leu
      595                 600                 605

Arg Gly Ala Leu Thr Trp Ser Phe Val Asp Asn Trp Glu Trp Gly Leu
      610                 615                 620

Gly Met Gln Gln Lys Phe Gly Phe Gln Phe Val Asn Gln Ser Asp Pro
625                 630                 635                 640

Asp Leu Thr Arg Thr Phe Lys Leu Ser Ala His Ala Tyr Ala Gln Phe
              645                 650                 655

Gly Arg Asn His Leu His His His His His His
          660                 665
```

```
<210> SEQ ID NO 41
<211> LENGTH: 2001
<212> TYPE: DNA
<213> ORGANISM: Pichia pastori

<400> SEQUENCE: 41
atgagatttc cttcaatttt tactgcagtt ttattcgcag catcctccgc attagctgct       60
ccagtcaaca ctacaacaga agatgaaacg gcacaaattc cggctgaagc tgtcatcggt      120
tactcagatt tagaaggggga tttcgatgtt gctgttttgc cattttccaa cagcacaaat      180
aacgggttat tgtttataaa tactactatt gccagcattc tgctaaaga agaaggggta       240 tctctcgaga aaagagaggc tgaagctgtt acttatccgg agccattcc tctgtccctg       300 acgagcaatt acgaaacccc aagtccgaca gcaatcccgc tggagccaac accgacggct       360
accggtacag cagaattaga tgcgctgtgg aacttagtcg aagctcagta cccagttcaa       420
actgctgcag tgacaacttt ggtgacagtg cccgatgatt ataagtttga ggcagatcca       480
ccgagttatg cattagcagg gtatgaaaca agcgagattg ccggactgaa gtttccaaag       540
gggtttaagt ttggtgttgc gggggcagcc attcaagttg aaggtgcagc aaaagccgaa       600
gggcggggcc caagtacctg ggattatctg tgtcatcact atgccagcac gcagtgtaac       660
aattatgatc ccgatattac aaccaaccat tactacctgt acccattgga ctttgcgcgc       720
ctgcaacacc taggcattaa cacttactcg ttttcaattt catggacgcg tatttatcca       780
ttgggcgcag gctatgttaa tgaagcaggg ttagcccact atgatgccgt aatccatagt       840
gccaagaagt atggtctgga accagtgggc accgtttttc actgggatac gccactgtct       900
ctgatgctga aataccggtgc ctggcaagat actggtgacc aaattgttaa ggactttgtt       960
acctatgcca caactgtgtt taagcgttat ggtaatgaag tcaagacgtg gtttactttc      1020
aatgaaccac gggttttctg ttcacaaaat agtggtctgc catacaatct gacgtatcca      1080
gaagggatcc agagcacctc cgctgtattt cgttgcacct acaatgttct gaaagctcat      1140
ggtcatgctg ttaaagtgta tcgggatcta gttgcctccg ggaccattgc ggcaggtgaa      1200
atcggcttta aatccgatga taactaccca atcccggccc gtccagggaa cgccgatgac      1260
gaggaatcag ccaagcgtca cgaggctttt cgcattggga ttttttgcgca accggtttat      1320 ggtaatggcg attatccaga tgttgttaaa gaaactgttg gagatatgct gccggccctg      1380
acggatgaag ataaaggata cattaaaggt agcggagata ttttttgcgat tgacgggtat      1440 cgtaccgata tttcccatgc ggctctgaac gggatcgcga attgtattcg caaccaaagt      1500
gacccgaatt ggccagtgtg tgaagaaggg tcagatcctt ttgctcatgt ttacccatcc      1560
gggtttgcta ttggtcaatc agccgatcca ctgtcttcat ggttagtcaa ctcagccccg      1620
```

-continued

```
tttatccgcg atcaactgaa gtttctgaca caaacctacc ctgctaaggg tggtatttat      1680
ttctcggaat ttggttgggc tgaagacgcc gaatatgatc gtcaactgct gtatcaaatt      1740
acctgggatg gtctgcgtac gcaatacctg acggactatc tgagccagct gctgttggct      1800
gtgcacaaag acgggattaa tctgcgaggc gcgctgacgt ggagttttgt cgataattgg      1860 gagtgggggtt tagggatgca acagaaattc ggatttcagt ttgttaatca atcagatccc      1920
gatctgacac gcacgtttaa actgagcgct cacgcttacg cccaatttgg gcgtaatcat      1980
ctgcaccacc accaccacca c                                                 2001
```

<210> SEQ ID NO 42
<211> LENGTH: 667
<212> TYPE: PRT
<213> ORGANISM: Pichia pastori

<400> SEQUENCE: 42

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Val Thr Tyr Pro Gly Ala Ile
                85                  90                  95

Pro Leu Ser Leu Thr Ser Asn Tyr Glu Thr Pro Ser Pro Thr Ala Ile
            100                 105                 110

Pro Leu Glu Pro Thr Pro Thr Ala Thr Gly Thr Ala Glu Leu Asp Ala
            115                 120                 125

Leu Trp Asn Leu Val Glu Ala Gln Tyr Pro Val Gln Thr Ala Ala Val
        130                 135                 140

Thr Thr Leu Val Thr Val Pro Asp Asp Tyr Lys Phe Glu Ala Asp Pro
145                 150                 155                 160

Pro Ser Tyr Ala Leu Ala Gly Tyr Glu Thr Ser Glu Ile Ala Gly Leu
                165                 170                 175

Lys Phe Pro Lys Gly Phe Lys Phe Gly Val Ala Gly Ala Ala Ile Gln
            180                 185                 190

Val Glu Gly Ala Ala Lys Ala Glu Gly Arg Gly Pro Ser Thr Trp Asp
        195                 200                 205

Tyr Leu Cys His His Tyr Ala Ser Thr Gln Cys Asn Asn Tyr Asp Pro
    210                 215                 220

Asp Ile Thr Thr Asn His Tyr Tyr Leu Tyr Pro Leu Asp Phe Ala Arg
225                 230                 235                 240

Leu Gln His Leu Gly Ile Asn Thr Tyr Ser Phe Ser Ile Ser Trp Thr
                245                 250                 255

Arg Ile Tyr Pro Leu Gly Ala Gly Tyr Val Asn Glu Ala Gly Leu Ala
            260                 265                 270

His Tyr Asp Ala Val Ile His Ser Ala Lys Lys Tyr Gly Leu Glu Pro
        275                 280                 285

Val Gly Thr Val Phe His Trp Asp Thr Pro Leu Ser Leu Met Leu Lys
        290                 295                 300
```

```
Tyr Gly Ala Trp Gln Asp Thr Gly Asp Gln Ile Val Lys Asp Phe Val
305             310             315             320

Thr Tyr Ala Thr Thr Val Phe Lys Arg Tyr Gly Asn Glu Val Lys Thr
            325             330             335

Trp Phe Thr Phe Asn Glu Pro Arg Val Phe Cys Ser Gln Asn Ser Gly
            340             345             350

Leu Pro Tyr Asn Leu Thr Tyr Pro Glu Gly Ile Gln Ser Thr Ser Ala
            355             360             365

Val Phe Arg Cys Thr Tyr Asn Val Leu Lys Ala His Gly His Ala Val
            370             375             380

Lys Val Tyr Arg Asp Leu Val Ala Ser Gly Thr Ile Ala Ala Gly Glu
385             390             395             400

Ile Gly Phe Lys Ser Asp Asp Asn Tyr Pro Ile Pro Ala Arg Pro Gly
            405             410             415

Asn Ala Asp Asp Glu Glu Ser Ala Lys Arg His Glu Ala Phe Arg Ile
            420             425             430

Gly Ile Phe Ala Gln Pro Val Tyr Gly Asn Gly Asp Tyr Pro Asp Val
            435             440             445

Val Lys Glu Thr Val Gly Asp Met Leu Pro Ala Leu Thr Asp Glu Asp
            450             455             460

Lys Gly Tyr Ile Lys Gly Ser Gly Asp Ile Phe Ala Ile Asp Gly Tyr
465             470             475             480

Arg Thr Asp Ile Ser His Ala Ala Leu Asn Gly Ile Ala Asn Cys Ile
            485             490             495

Arg Asn Gln Ser Asp Pro Asn Trp Pro Val Cys Glu Glu Gly Ser Asp
            500             505             510

Pro Phe Ala His Val Tyr Pro Ser Gly Phe Ala Ile Gly Gln Ser Ala
            515             520             525

Asp Pro Leu Ser Ser Trp Leu Val Asn Ser Ala Pro Phe Ile Arg Asp
            530             535             540

Gln Leu Lys Phe Leu Thr Gln Thr Tyr Pro Ala Lys Gly Gly Ile Tyr
545             550             555             560

Phe Ser Glu Phe Gly Trp Ala Glu Asp Ala Glu Tyr Asp Arg Gln Leu
            565             570             575

Leu Tyr Gln Ile Thr Trp Asp Gly Leu Arg Thr Gln Tyr Leu Thr Asp
            580             585             590

Tyr Leu Ser Gln Leu Leu Leu Ala Val His Lys Asp Gly Ile Asn Leu
            595             600             605

Arg Gly Ala Leu Thr Trp Ser Phe Val Asp Asn Trp Glu Trp Gly Leu
            610             615             620

Gly Met Gln Gln Lys Phe Gly Phe Gln Phe Val Asn Gln Ser Asp Pro
625             630             635             640

Asp Leu Thr Arg Thr Phe Lys Leu Ser Ala His Ala Tyr Ala Gln Phe
            645             650             655

Gly Arg Asn His Leu His His His His His His
            660             665
```

<210> SEQ ID NO 43
<211> LENGTH: 2001
<212> TYPE: DNA
<213> ORGANISM: Pichia pastori

<400> SEQUENCE: 43
atgagatttc cttcaatttt tactgcagtt ttattcgcag catcctccgc attagctgct      60

-continued

```
ccagtcaaca ctacaacaga agatgaaacg gcacaaattc cggctgaagc tgtcatcggt    120
tactcagatt tagaaggggga tttcgatgtt gctgttttgc cattttccaa cagcacaaat    180
aacgggttat tgtttataaa tactactatt gccagcattg ctgctaaaga agaaggggta    240
tctctcgaga aaagagaggc tgaagctgtt acttatccgg gagccattcc tctgtccctg    300
acgagcaatt acgaaacccc aagtccgaca gcaatcccgc tggagccaac accgacggct    360
accggtacag cagaattaga tgcgctgtgg aacttagtcg aagctcagta cccagttcaa    420
actgctgcag tgacaacttt ggtgacagtg cccgatgatt ataagtttga ggcagatcca    480
ccgagttatg cattagcagg gtatgaaaca agcgagattc ccggactgaa gtttccaaag    540
gggtttaagt ttggtgttgc gggggcagcc attcaagttg aaggtgcagc aaaagccgaa    600 gggcgggggcc caagtacctg ggattatctg tgtcatcact atgccagcac gcagtgtaac    660
aattatgatc ccgatattac aaccaaccat tactacctgt acccattgga ctttgcgcgc    720
ctgcaacacc taggcattaa cacttactcg ttttcaattt catggacgcg tatttatcca    780
ttgggcgcag gctatgttaa tgaagcaggg ttagcccact atgatgccgt aatccatagt    840
gccaagaagt atggtctgga accagtgggc accgttttttc actgggatac gccactgtct    900
ctgatgctga aatacggtgc ctggcaagat actggtgacc aaattgttaa ggactttgtt    960
acctatgcca caactgtgtt taagcgttat ggtaatgaag tcaagacgtg gtttactttc    1020
aatgaaccac gggttttctg ttcacaaaat agtggtctgc catacaatct gacgtatcca    1080
gaaggtatta acagcacctc cgctgtattt cgttgcacct acaatgttct gaaagctcat    1140
ggtcatgctg ttaaagtgta tcgggatcta gttgcctccg ggaccattgc ggcaggtgaa    1200
atcggcttta aatccgatga taactaccca atcccggccc gtccagggaa cgccgatgac    1260
gaggaatcag ccaagcgtca cgaggctttt cgcattggga tttttgcgca accggtttat    1320
ggtaatggcg attatccaga tgttgttaaa gaaactgttg gagatatgct gccggccctg    1380
acggatgaag ataaaggata cattaaaggt agcggagata tttttgcgat tgacgggtat    1440
cgtaccgata tttcccatgc ggctctgaac gggatcgcga attgtattcg ccagcaatcg    1500
gatccgaatt ggccagtgtg tgaagaaggg tcagatcctt ttgctcatgt ttacccatcc    1560
gggtttgcta ttggtcaatc agccgatcca ctgtcttcat ggttagtcaa ctcagccccg    1620
tttatccgcg atcaactgaa gtttctgaca caaacctacc ctgctaaggg tggtatttat    1680
ttctcggaat ttggttgggc tgaagacgcc gaatatgatc gtcaactgct gtatcaaatt    1740
acctgggatg gtctgcgtac gcaataccctg acggactatc tgagccagct gctgttggct    1800
gtgcacaaag acgggattaa tctgcgaggc gcgctgacgt ggagttttgt cgataattgg    1860
gagtgggggt tagggatgca acagaaattc ggatttcagt ttgttaatca atcagatccc    1920
gatctgacac gcacgtttaa actgagcgct cacgcttacg cccaatttgg gcgtaatcat    1980
ctgcaccacc accaccacca c                                              2001
```

<210> SEQ ID NO 44
<211> LENGTH: 667
<212> TYPE: PRT
<213> ORGANISM: Pichia pastori

<400> SEQUENCE: 44

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
```

```
                 20               25               30
Ile Pro Ala Glu Ala Val Ile Gly Tyr Ser Asp Leu Glu Gly Asp Phe
            35               40               45

Asp Val Ala Val Leu Pro Phe Ser Asn Ser Thr Asn Asn Gly Leu Leu
        50               55               60

Phe Ile Asn Thr Thr Ile Ala Ser Ile Ala Ala Lys Glu Glu Gly Val
65               70               75               80

Ser Leu Glu Lys Arg Glu Ala Glu Ala Val Thr Tyr Pro Gly Ala Ile
                85               90               95

Pro Leu Ser Leu Thr Ser Asn Tyr Glu Thr Pro Ser Pro Thr Ala Ile
            100              105              110

Pro Leu Glu Pro Thr Pro Thr Ala Thr Gly Thr Ala Glu Leu Asp Ala
            115              120              125

Leu Trp Asn Leu Val Glu Ala Gln Tyr Pro Val Gln Thr Ala Ala Val
        130              135              140

Thr Thr Leu Val Thr Val Pro Asp Asp Tyr Lys Phe Glu Ala Asp Pro
145              150              155              160

Pro Ser Tyr Ala Leu Ala Gly Tyr Glu Thr Ser Glu Ile Ala Gly Leu
            165              170              175

Lys Phe Pro Lys Gly Phe Lys Phe Gly Val Ala Gly Ala Ala Ile Gln
            180              185              190

Val Glu Gly Ala Ala Lys Ala Glu Gly Arg Gly Pro Ser Thr Trp Asp
            195              200              205

Tyr Leu Cys His His Tyr Ala Ser Thr Gln Cys Asn Asn Tyr Asp Pro
        210              215              220

Asp Ile Thr Thr Asn His Tyr Tyr Leu Tyr Pro Leu Asp Phe Ala Arg
225              230              235              240

Leu Gln His Leu Gly Ile Asn Thr Tyr Ser Phe Ser Ile Ser Trp Thr
            245              250              255

Arg Ile Tyr Pro Leu Gly Ala Gly Tyr Val Asn Glu Ala Gly Leu Ala
            260              265              270

His Tyr Asp Ala Val Ile His Ser Ala Lys Lys Tyr Gly Leu Glu Pro
        275              280              285

Val Gly Thr Val Phe His Trp Asp Thr Pro Leu Ser Leu Met Leu Lys
        290              295              300

Tyr Gly Ala Trp Gln Asp Thr Gly Asp Gln Ile Val Lys Asp Phe Val
305              310              315              320

Thr Tyr Ala Thr Thr Val Phe Lys Arg Tyr Gly Asn Glu Val Lys Thr
            325              330              335

Trp Phe Thr Phe Asn Glu Pro Arg Val Phe Cys Ser Gln Asn Ser Gly
            340              345              350

Leu Pro Tyr Asn Leu Thr Tyr Pro Glu Gly Ile Asn Ser Thr Ser Ala
            355              360              365

Val Phe Arg Cys Thr Tyr Asn Val Leu Lys Ala His Gly His Ala Val
        370              375              380

Lys Val Tyr Arg Asp Leu Val Ala Ser Gly Thr Ile Ala Ala Gly Glu
385              390              395              400

Ile Gly Phe Lys Ser Asp Asp Asn Tyr Pro Ile Pro Ala Arg Pro Gly
            405              410              415

Asn Ala Asp Asp Glu Glu Ser Ala Lys Arg His Glu Ala Phe Arg Ile
            420              425              430

Gly Ile Phe Ala Gln Pro Val Tyr Gly Asn Gly Asp Tyr Pro Asp Val
            435              440              445
```

```
Val Lys Glu Thr Val Gly Asp Met Leu Pro Ala Leu Thr Asp Glu Asp
    450             455         460

Lys Gly Tyr Ile Lys Gly Ser Gly Asp Ile Phe Ala Ile Asp Gly Tyr
465             470             475             480

Arg Thr Asp Ile Ser His Ala Ala Leu Asn Gly Ile Ala Asn Cys Ile
            485             490             495

Arg Gln Gln Ser Asp Pro Asn Trp Pro Val Cys Glu Glu Gly Ser Asp
            500             505             510

Pro Phe Ala His Val Tyr Pro Ser Gly Phe Ala Ile Gly Gln Ser Ala
        515             520             525

Asp Pro Leu Ser Ser Trp Leu Val Asn Ser Ala Pro Phe Ile Arg Asp
    530             535             540

Gln Leu Lys Phe Leu Thr Gln Thr Tyr Pro Ala Lys Gly Gly Ile Tyr
545             550             555             560

Phe Ser Glu Phe Gly Trp Ala Glu Asp Ala Glu Tyr Asp Arg Gln Leu
            565             570             575

Leu Tyr Gln Ile Thr Trp Asp Gly Leu Arg Thr Gln Tyr Leu Thr Asp
            580             585             590

Tyr Leu Ser Gln Leu Leu Leu Ala Val His Lys Asp Gly Ile Asn Leu
        595             600             605

Arg Gly Ala Leu Thr Trp Ser Phe Val Asp Asn Trp Glu Trp Gly Leu
    610             615             620

Gly Met Gln Gln Lys Phe Gly Phe Gln Phe Val Asn Gln Ser Asp Pro
625             630             635             640

Asp Leu Thr Arg Thr Phe Lys Leu Ser Ala His Ala Tyr Ala Gln Phe
            645             650             655

Gly Arg Asn His Leu His His His His His His
            660             665
```

<210> SEQ ID NO 45
<211> LENGTH: 2001
<212> TYPE: DNA
<213> ORGANISM: Pichia pastori

<400> SEQUENCE: 45

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgtttttgc cattttccaa cagcacaaat     180
aacgggttat tgtttataaa tactactatt gccagcattg ctgctaaaga agaaggggta     240
tctctcgaga aaagagaggc tgaagctgtt acttatccgg gagccattcc tctgtccctg     300
acgagcaatt acgaaacccc aagtccgaca gcaatcccgc tggagccaac accgacggct     360
accggtacag cagaattaga tgcgctgtgg aacttagtcg aagctcagta cccagttcaa     420
actgctgcag tgcaactttt ggtgacagtg cccgatgatt ataagtttga ggcagatcca     480
ccgagttatg cattagcagg gtatgaaaca agcgagattg ccggactgaa gtttccaaag     540
gggtttaagt ttggtgttgc gggggcagcc attcaagttg aaggtgcagc aaaagccgaa     600
gggcggggcc caagtacctg ggattatctg tgtcatcact atgccagcac gcagtgtaac     660
aattatgatc ccgatattac aaccaaccat tactacctgt acccattgga ctttgcgcgc     720
ctgcaacacc taggcattaa cacttactcg ttttcaattt catggacgcg tatttatcca     780
ttgggcgcag gctatgttaa tgaagcaggg ttagcccact atgatgccgt aatccatagt     840
```

-continued

```
gccaagaagt atggtctgga accagtgggc accgtttttc actgggatac gccactgtct      900
ctgatgctga aatacggtgc ctggcaagat actggtgacc aaattgttaa ggactttgtt      960
acctatgcca caactgtgtt taagcgttat ggtaatgaag tcaagacgtg gtttactttc     1020
aatgaaccac gggtttcctg ttcacaaaat agtggtctgc catacaatct gacgtatcca     1080
gaaggtatta acagcacctc cgctgtattt cgttgcacct acaatgttct gaaagctcat     1140
ggtcatgctg ttaaagtgta tcgggatcta gttgcctccg ggaccattgc ggcaggtgaa     1200
atcggcttta aatccgatga taactaccca atcccggccc gtccagggaa cgccgatgac     1260
gaggaatcag ccaagcgtca cgaggctttt cgcattggga tttttgcgca accggtttat     1320
ggtaatggcg attatccaga tgttgttaaa gaaactgttg gagatatgct gccggccctg     1380
acggatgaag ataaaggata cattaaaggt agcggagata tttttgcgat tgacgggtat     1440
cgtaccgata tttcccatgc ggctctgaac gggatcgcga attgtattcg caaccaaagt     1500
gacccgaatt ggccagtgtg tgaagaaggg tcagatcctt ttgctcatgt ttacccatcc     1560
gggtttgcta ttggtcaatc agccgatcca ctgtcttcat ggttagtcaa ctcagccccg     1620
tttatccgcg atcaactgaa gtttctgaca caaacctacc ctgctaaggg tggtatttat     1680
ttctcggaat ttggttgggc tgaagacgcc gaatatgatc gtcaactgct gtatcaaatt     1740
acctgggatg gtctgcgtac gcaatacctg acggactatc tgagccagct gctgttggct     1800
gtgcacaaag acgggattaa tctgcgaggc gcgctgacgt ggagttttgt cgataattgg     1860 gagtgggggtt tagggatgca acagaaattc ggatttcagt ttgttcagca atcggatccc     1920
gatctgacac gcacgtttaa actgagcgct cacgcttacg cccaatttgg gcgtaatcat     1980
ctgcaccacc accaccacca c                                                2001
```

```
<210> SEQ ID NO 46
<211> LENGTH: 667
<212> TYPE: PRT
<213> ORGANISM: Pichia pastori

<400> SEQUENCE: 46

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Val Thr Tyr Pro Gly Ala Ile
                85                  90                  95

Pro Leu Ser Leu Thr Ser Asn Tyr Glu Thr Pro Ser Pro Thr Ala Ile
            100                 105                 110

Pro Leu Glu Pro Thr Pro Thr Ala Thr Gly Thr Ala Glu Leu Asp Ala
        115                 120                 125

Leu Trp Asn Leu Val Glu Ala Gln Tyr Pro Val Gln Thr Ala Ala Val
        130                 135                 140

Thr Thr Leu Val Thr Val Pro Asp Asp Tyr Lys Phe Glu Ala Asp Pro
145                 150                 155                 160

Pro Ser Tyr Ala Leu Ala Gly Tyr Glu Thr Ser Glu Ile Ala Gly Leu
```

```
                165              170              175

Lys Phe Pro Lys Gly Phe Lys Phe Gly Val Ala Gly Ala Ala Ile Gln
            180              185              190

Val Glu Gly Ala Ala Lys Ala Glu Gly Arg Gly Pro Ser Thr Trp Asp
            195              200              205

Tyr Leu Cys His His Tyr Ala Ser Thr Gln Cys Asn Asn Tyr Asp Pro
    210              215              220

Asp Ile Thr Thr Asn His Tyr Tyr Leu Tyr Pro Leu Asp Phe Ala Arg
225              230              235              240

Leu Gln His Leu Gly Ile Asn Thr Tyr Ser Phe Ser Ile Ser Trp Thr
            245              250              255

Arg Ile Tyr Pro Leu Gly Ala Gly Tyr Val Asn Glu Ala Gly Leu Ala
            260              265              270

His Tyr Asp Ala Val Ile His Ser Ala Lys Lys Tyr Gly Leu Glu Pro
            275              280              285

Val Gly Thr Val Phe His Trp Asp Thr Pro Leu Ser Leu Met Leu Lys
    290              295              300

Tyr Gly Ala Trp Gln Asp Thr Gly Asp Gln Ile Val Lys Asp Phe Val
305              310              315              320

Thr Tyr Ala Thr Thr Val Phe Lys Arg Tyr Gly Asn Glu Val Lys Thr
            325              330              335

Trp Phe Thr Phe Asn Glu Pro Arg Val Phe Cys Ser Gln Asn Ser Gly
            340              345              350

Leu Pro Tyr Asn Leu Thr Tyr Pro Glu Gly Ile Asn Ser Thr Ser Ala
            355              360              365

Val Phe Arg Cys Thr Tyr Asn Val Leu Lys Ala His Gly His Ala Val
    370              375              380

Lys Val Tyr Arg Asp Leu Val Ala Ser Gly Thr Ile Ala Ala Gly Glu
385              390              395              400

Ile Gly Phe Lys Ser Asp Asp Asn Tyr Pro Ile Pro Ala Arg Pro Gly
            405              410              415

Asn Ala Asp Asp Glu Glu Ser Ala Lys Arg His Glu Ala Phe Arg Ile
            420              425              430

Gly Ile Phe Ala Gln Pro Val Tyr Gly Asn Gly Asp Tyr Pro Asp Val
            435              440              445

Val Lys Glu Thr Val Gly Asp Met Leu Pro Ala Leu Thr Asp Glu Asp
    450              455              460

Lys Gly Tyr Ile Lys Gly Ser Gly Asp Ile Phe Ala Ile Asp Gly Tyr
465              470              475              480

Arg Thr Asp Ile Ser His Ala Ala Leu Asn Gly Ile Ala Asn Cys Ile
            485              490              495

Arg Asn Gln Ser Asp Pro Asn Trp Pro Val Cys Glu Glu Gly Ser Asp
            500              505              510

Pro Phe Ala His Val Tyr Pro Ser Gly Phe Ala Ile Gly Gln Ser Ala
            515              520              525

Asp Pro Leu Ser Ser Trp Leu Val Asn Ser Ala Pro Phe Ile Arg Asp
    530              535              540

Gln Leu Lys Phe Leu Thr Gln Thr Tyr Pro Ala Lys Gly Gly Ile Tyr
545              550              555              560

Phe Ser Glu Phe Gly Trp Ala Glu Asp Ala Glu Tyr Asp Arg Gln Leu
            565              570              575

Leu Tyr Gln Ile Thr Trp Asp Gly Leu Arg Thr Gln Tyr Leu Thr Asp
            580              585              590
```

-continued

```
Tyr Leu Ser Gln Leu Leu Leu Ala Val His Lys Asp Gly Ile Asn Leu
        595                 600                 605

Arg Gly Ala Leu Thr Trp Ser Phe Val Asp Asn Trp Glu Trp Gly Leu
        610                 615                 620

Gly Met Gln Gln Lys Phe Gly Phe Gln Phe Val Gln Gln Ser Asp Pro
625                 630                 635                 640

Asp Leu Thr Arg Thr Phe Lys Leu Ser Ala His Ala Tyr Ala Gln Phe
                645                 650                 655

Gly Arg Asn His Leu His His His His His His
                660                 665

<210> SEQ ID NO 47
<211> LENGTH: 1974
<212> TYPE: DNA
<213> ORGANISM: Pichia pastori

<400> SEQUENCE: 47
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgtttgc cattttccaa cagcacaaat     180
aacgggttat tgtttataaa tactactatt gccagcattg ctgctaaaga agaagggta     240 tctctcgaga aaagagaggc tgaagcttcc ctgacgagca attacgaaac cccaagtccg     300
acagcaatcc cgctggagcc aacaccgacg gctaccggta cagcagaatt agatgcgctg     360
tggaacttag tcgaagctca gtacccagtt caaactgctg cagtgacaac tttggtgaca     420
gtgcccgatg attataagtt tgaggcagat ccaccgagtt atgcattagc agggtatgaa     480
acaagcgaga ttgccggact gaagtttcca aaggggttta agtttggtgt tgcggggca      540 gccattcaag ttgaaggtgc agcaaaagcc gaagggcggg gcccaagtac ctggattat      600 ctgtgtcatc actatgccag cacgcagtgt aacaattatg atcccgatat tacaaccaac     660
cattactacc tgtacccatt ggactttgcg cgcctgcaac acctaggcat taacacttac     720 tcgtttcaa tttcatggac gcgtatttat ccattgggcg caggctatgt taatgaagca     780
gggttagccc actatgatgc cgtaatccat agtgccaaga gtatggtct ggaaccagtg     840 ggcaccgttt ttcactggga tacgccactg tctctgatgc tgaaatacgg tgcctggcaa     900
gatactggtg accaaattgt taaggacttt gttacctatg ccacaactgt gtttaagcgt     960
tatggtaatg aagtcaagac gtggtttact ttcaatgaac cacgggtttt ctgttcacaa    1020
aatagtggtc tgccatacaa tctgacgtat ccagaaggta ttaacagcac ctccgctgta    1080
tttcgttgca cctacaatgt tctgaaagct catggtcatg ctgttaaagt gtatcgggat    1140
ctagttgcct ccgggaccat tgcggcaggt gaaatcggct ttaaatccga tgataactac    1200
ccaatcccgg cccgtccagg aacgccgat gacgaggaat cagccaagcg tcacgaggct    1260
tttcgcattg ggattttgc gcaaccggtt tatggtaatg cgattatcc agatgttgtt    1320 aaagaaactg ttggagatat gctgccggcc ctgacggatg aagataaagg atacattaaa    1380
ggtagcggag atattttgc gattgacggg tatcgtaccg atatttccca tgcggctctg    1440
aacgggatcg cgaattgtat tcgcaaccaa agtgacccga attggccagt gtgtgaagaa    1500
gggtcagatc ctttttgctca tgtttacca tccgggtttg ctattggtca atcagccgat    1560
ccactgtctt catggttagt caactcagcc ccgtttatcc gcgatcaact gaagtttctg    1620
acacaaacct accctgctaa gggtggtatt tatttctcgg aatttggttg ggctgaagac    1680
```

-continued

```
gccgaatatg atcgtcaact gctgtatcaa attacctggg atggtctgcg tacgcaatac    1740
ctgacggact atctgagcca gctgctgttg gctgtgcaca aagacgggat taatctgcga    1800
ggcgcgctga cgtggagttt tgtcgataat tgggagtggg gtttagggat gcaacagaaa    1860
ttcggatttc agtttgttaa tcaatcagat cccgatctga cacgcacgtt taaactgagc    1920
gctcacgctt acgcccaatt tgggcgtaat catctgcacc accaccacca ccac          1974
```

```
<210> SEQ ID NO 48
<211> LENGTH: 658
<212> TYPE: PRT
<213> ORGANISM: Pichia pastori

<400> SEQUENCE: 48

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ser Leu Thr Ser Asn Tyr Glu
                85                  90                  95

Thr Pro Ser Pro Thr Ala Ile Pro Leu Glu Pro Thr Pro Thr Ala Thr
            100                 105                 110

Gly Thr Ala Glu Leu Asp Ala Leu Trp Asn Leu Val Glu Ala Gln Tyr
        115                 120                 125

Pro Val Gln Thr Ala Ala Val Thr Thr Leu Val Thr Val Pro Asp Asp
        130                 135                 140

Tyr Lys Phe Glu Ala Asp Pro Pro Ser Tyr Ala Leu Ala Gly Tyr Glu
145                 150                 155                 160

Thr Ser Glu Ile Ala Gly Leu Lys Phe Pro Lys Gly Phe Lys Phe Gly
                165                 170                 175

Val Ala Gly Ala Ala Ile Gln Val Glu Gly Ala Ala Lys Ala Glu Gly
            180                 185                 190

Arg Gly Pro Ser Thr Trp Asp Tyr Leu Cys His His Tyr Ala Ser Thr
            195                 200                 205

Gln Cys Asn Asn Tyr Asp Pro Asp Ile Thr Thr Asn His Tyr Tyr Leu
        210                 215                 220

Tyr Pro Leu Asp Phe Ala Arg Leu Gln His Leu Gly Ile Asn Thr Tyr
225                 230                 235                 240

Ser Phe Ser Ile Ser Trp Thr Arg Ile Tyr Pro Leu Gly Ala Gly Tyr
                245                 250                 255

Val Asn Glu Ala Gly Leu Ala His Tyr Asp Ala Val Ile His Ser Ala
            260                 265                 270

Lys Lys Tyr Gly Leu Glu Pro Val Gly Thr Val Phe His Trp Asp Thr
            275                 280                 285

Pro Leu Ser Leu Met Leu Lys Tyr Gly Ala Trp Gln Asp Thr Gly Asp
        290                 295                 300

Gln Ile Val Lys Asp Phe Val Thr Tyr Ala Thr Thr Val Phe Lys Arg
305                 310                 315                 320
```

-continued

```
Tyr Gly Asn Glu Val Lys Thr Trp Phe Thr Phe Asn Glu Pro Arg Val
                325                     330                     335

Phe Cys Ser Gln Asn Ser Gly Leu Pro Tyr Asn Leu Thr Tyr Pro Glu
                340                     345                 350

Gly Ile Asn Ser Thr Ser Ala Val Phe Arg Cys Thr Tyr Asn Val Leu
                355                     360             365

Lys Ala His Gly His Ala Val Lys Val Tyr Arg Asp Leu Val Ala Ser
            370                 375                 380

Gly Thr Ile Ala Ala Gly Glu Ile Gly Phe Lys Ser Asp Asp Asn Tyr
385                     390                 395                     400

Pro Ile Pro Ala Arg Pro Gly Asn Ala Asp Asp Glu Glu Ser Ala Lys
                405                 410                     415

Arg His Glu Ala Phe Arg Ile Gly Ile Phe Ala Gln Pro Val Tyr Gly
            420                 425                 430

Asn Gly Asp Tyr Pro Asp Val Val Lys Glu Thr Val Gly Asp Met Leu
            435                 440                 445

Pro Ala Leu Thr Asp Glu Asp Lys Gly Tyr Ile Lys Gly Ser Gly Asp
            450                 455                 460

Ile Phe Ala Ile Asp Gly Tyr Arg Thr Asp Ile Ser His Ala Ala Leu
465                     470                 475                     480

Asn Gly Ile Ala Asn Cys Ile Arg Asn Gln Ser Asp Pro Asn Trp Pro
                485                 490                     495

Val Cys Glu Glu Gly Ser Asp Pro Phe Ala His Val Tyr Pro Ser Gly
                500                 505                 510

Phe Ala Ile Gly Gln Ser Ala Asp Pro Leu Ser Ser Trp Leu Val Asn
                515                 520                 525

Ser Ala Pro Phe Ile Arg Asp Gln Leu Lys Phe Leu Thr Gln Thr Tyr
            530                 535                 540

Pro Ala Lys Gly Gly Ile Tyr Phe Ser Glu Phe Gly Trp Ala Glu Asp
545                     550                 555                     560

Ala Glu Tyr Asp Arg Gln Leu Leu Tyr Gln Ile Thr Trp Asp Gly Leu
                565                 570                 575

Arg Thr Gln Tyr Leu Thr Asp Tyr Leu Ser Gln Leu Leu Leu Ala Val
                580                 585                 590

His Lys Asp Gly Ile Asn Leu Arg Gly Ala Leu Thr Trp Ser Phe Val
            595                 600                 605

Asp Asn Trp Glu Trp Gly Leu Gly Met Gln Gln Lys Phe Gly Phe Gln
            610                 615                 620

Phe Val Asn Gln Ser Asp Pro Asp Leu Thr Arg Thr Phe Lys Leu Ser
625                     630                 635                     640

Ala His Ala Tyr Ala Gln Phe Gly Arg Asn His Leu His His His His
            645                 650                 655

His His
```

```
<210> SEQ ID NO 49
<211> LENGTH: 1908
<212> TYPE: DNA
<213> ORGANISM: Pichia pastori

<400> SEQUENCE: 49
atgagatttc cttcaatttt tactgcagtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgtttttgc cattttccaa cagcacaaat      180
```

-continued

```
aacgggttat tgtttataaa tactactatt gccagcattg ctgctaaaga agaaggggta        240
tctctcgaga aaagagaggc tgaagctacc ggtacagcag aattagatgc gctgtggaac        300
ttagtcgaag ctcagtaccc agttcaaact gctgcagtga caactttggt gacagtgccc        360
gatgattata agtttgaggc agatccaccg agttatgcat tagcagggta tgaaacaagc        420
gagattgccg gactgaagtt tccaaagggg tttaagtttg gtgttgcggg ggcagccatt        480
caagttgaag gtgcagcaaa agccgaaggg cggggcccaa gtacctggga ttatctgtgt        540
catcactatg ccagcacgca gtgtaacaat tatgatcccg atattacaac caaccattac        600
tacctgtacc cattggactt tgcgcgcctg caacacctag gcattaacac ttactcgttt        660
tcaatttcat ggacgcgtat ttatccattg ggcgcaggct atgttaatga agcagggtta        720
gcccactatg atgccgtaat ccatagtgcc aagaagtatg gtctggaacc agtgggcacc        780
gtttttcact gggatacgcc actgtctctg atgctgaaat acggtgcctg gcaagatact        840
ggtgaccaaa ttgttaagga ctttgttacc tatgccacaa ctgtgtttaa gcgttatggt        900
aatgaagtca agacgtggtt tactttcaat gaaccacggg ttttctgttc acaaaatagt        960
ggtctgccat acaatctgac gtatccagaa ggtattaaca gcacctccgc tgtatttcgt       1020
tgcacctaca atgttctgaa agctcatggt catgctgtta agtgtatcg ggatctagtt       1080 gcctccggga ccattgcggc aggtgaaatc ggctttaaat ccgatgataa ctacccaatc       1140
ccggcccgtc agggaacgc cgatgacgag gaatcagcca agcgtcacga gcttttcgc       1200 attgggattt ttgcgcaacc ggtttatggt aatggcgatt atccagatgt tgttaaagaa       1260
actgttggag atatgctgcc ggccctgacg gatgaagata aggatacat aaaggtagc       1320 ggagatattt ttgcgattga cgggtatcgt accgatattt cccatgcggc tctgaacggg       1380
atcgcgaatt gtattcgcaa ccaaagtgac ccgaattggc cagtgtgtga agaaggtca       1440 gatccttttg ctcatgttta cccatccggg tttgctattg gtcaatcagc cgatccactg       1500
tcttcatggt tagtcaactc agccccgttt atccgcgatc aactgaagtt tctgacacaa       1560
acctaccctg ctaagggtgg tatttatttc tcggaatttg gttgggctga agacgccgaa       1620
tatgatcgtc aactgctgta tcaaattacc tgggatggtc tgcgtacgca atacctgacg       1680
gactatctga gccagctgct gttggctgtg cacaaagacg ggattaatct gcgaggcgcg       1740
ctgacgtgga gttttgtcga taattgggag tggggtttag ggatgcaaca gaaattcgga       1800
tttcagtttg ttaatcaatc agatcccgat ctgacacgca cgtttaaact gagcgctcac       1860
gcttacgccc aatttgggcg taatcatctg caccaccacc accaccac                    1908
```

<210> SEQ ID NO 50
<211> LENGTH: 636
<212> TYPE: PRT
<213> ORGANISM: Pichia pastori

<400> SEQUENCE: 50

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
```

```
65              70              75              80

Ser Leu Glu Lys Arg Glu Ala Glu Ala Thr Gly Thr Ala Glu Leu Asp
                85              90              95

Ala Leu Trp Asn Leu Val Glu Ala Gln Tyr Pro Val Gln Thr Ala Ala
            100             105             110

Val Thr Thr Leu Val Thr Val Pro Asp Asp Tyr Lys Phe Glu Ala Asp
            115             120             125

Pro Pro Ser Tyr Ala Leu Ala Gly Tyr Glu Thr Ser Glu Ile Ala Gly
        130             135             140

Leu Lys Phe Pro Lys Gly Phe Lys Phe Gly Val Ala Gly Ala Ala Ile
145             150             155             160

Gln Val Glu Gly Ala Ala Lys Ala Glu Gly Arg Gly Pro Ser Thr Trp
            165             170             175

Asp Tyr Leu Cys His His Tyr Ala Ser Thr Gln Cys Asn Asn Tyr Asp
            180             185             190

Pro Asp Ile Thr Thr Asn His Tyr Tyr Leu Tyr Pro Leu Asp Phe Ala
            195             200             205

Arg Leu Gln His Leu Gly Ile Asn Thr Tyr Ser Phe Ser Ile Ser Trp
        210             215             220

Thr Arg Ile Tyr Pro Leu Gly Ala Gly Tyr Val Asn Glu Ala Gly Leu
225             230             235             240

Ala His Tyr Asp Ala Val Ile His Ser Ala Lys Lys Tyr Gly Leu Glu
            245             250             255

Pro Val Gly Thr Val Phe His Trp Asp Thr Pro Leu Ser Leu Met Leu
            260             265             270

Lys Tyr Gly Ala Trp Gln Asp Thr Gly Asp Gln Ile Val Lys Asp Phe
            275             280             285

Val Thr Tyr Ala Thr Thr Val Phe Lys Arg Tyr Gly Asn Glu Val Lys
        290             295             300

Thr Trp Phe Thr Phe Asn Glu Pro Arg Val Phe Cys Ser Gln Asn Ser
305             310             315             320

Gly Leu Pro Tyr Asn Leu Thr Tyr Pro Glu Gly Ile Asn Ser Thr Ser
            325             330             335

Ala Val Phe Arg Cys Thr Tyr Asn Val Leu Lys Ala His Gly His Ala
            340             345             350

Val Lys Val Tyr Arg Asp Leu Val Ala Ser Gly Thr Ile Ala Ala Gly
        355             360             365

Glu Ile Gly Phe Lys Ser Asp Asp Asn Tyr Pro Ile Pro Ala Arg Pro
        370             375             380

Gly Asn Ala Asp Asp Glu Glu Ser Ala Lys Arg His Glu Ala Phe Arg
385             390             395             400

Ile Gly Ile Phe Ala Gln Pro Val Tyr Gly Asn Gly Asp Tyr Pro Asp
            405             410             415

Val Val Lys Glu Thr Val Gly Asp Met Leu Pro Ala Leu Thr Asp Glu
            420             425             430

Asp Lys Gly Tyr Ile Lys Gly Ser Gly Asp Ile Phe Ala Ile Asp Gly
        435             440             445

Tyr Arg Thr Asp Ile Ser His Ala Ala Leu Asn Gly Ile Ala Asn Cys
        450             455             460

Ile Arg Asn Gln Ser Asp Pro Asn Trp Pro Val Cys Glu Glu Gly Ser
465             470             475             480

Asp Pro Phe Ala His Val Tyr Pro Ser Gly Phe Ala Ile Gly Gln Ser
            485             490             495
```

Ala Asp Pro Leu Ser Ser Trp Leu Val Asn Ser Ala Pro Phe Ile Arg
            500                     505                 510

Asp Gln Leu Lys Phe Leu Thr Gln Thr Tyr Pro Ala Lys Gly Gly Ile
            515                 520                 525

Tyr Phe Ser Glu Phe Gly Trp Ala Glu Asp Ala Glu Tyr Asp Arg Gln
            530                     535                 540

Leu Leu Tyr Gln Ile Thr Trp Asp Gly Leu Arg Thr Gln Tyr Leu Thr
545                 550                     555                 560

Asp Tyr Leu Ser Gln Leu Leu Leu Ala Val His Lys Asp Gly Ile Asn
                565                 570                 575

Leu Arg Gly Ala Leu Thr Trp Ser Phe Val Asp Asn Trp Glu Trp Gly
            580                     585                 590

Leu Gly Met Gln Gln Lys Phe Gly Phe Gln Phe Val Asn Gln Ser Asp
            595                 600                 605

Pro Asp Leu Thr Arg Thr Phe Lys Leu Ser Ala His Ala Tyr Ala Gln
            610                 615                 620

Phe Gly Arg Asn His Leu His His His His His His
625                 630                 635

<210> SEQ ID NO 51
<211> LENGTH: 1899
<212> TYPE: DNA
<213> ORGANISM: Pichia pastori

<400> SEQUENCE: 51
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga aaagagaggc tgaagctgca gaattagatg cgctgtggaa cttagtcgaa     300
gctcagtacc cagttcaaac tgctgcagtg acaactttgg tgacagtgcc cgatgattat     360
aagtttgagg cagatccacc gagttatgca ttagcagggt atgaaacaag cgagattgcc     420
ggactgaagt ttccaaaggg gtttaagttt ggtgttgcgg gggcagccat tcaagttgaa     480
ggtgcagcaa aagccgaagg gcggggccca agtacctggg attatctgtg tcatcactat     540
gccagcacgc agtgtaacaa ttatgatccc gatattacaa ccaaccatta ctacctgtac     600
ccattggact ttgcgcgcct gcaacaccta ggcattaaca cttactcgtt ttcaatttca     660
tggacgcgta tttatccatt gggcgcaggc tatgttaatg aagcagggtt agcccactat     720
gatgccgtaa tccatagtgc caagaagtat ggtctggaac cagtgggcac cgttttttac     780
tgggatacgc cactgtctct gatgctgaaa tacggtgcct ggcaagatac tggtgaccaa     840
attgttaagg actttgttac ctatgccaca actgtgttta agcgttatgg taatgaagtc     900
aagacgtggt ttactttcaa tgaaccacgg gttttctgtt cacaaaatag tggtctgcca     960
tacaatctga cgtatccaga aggtattaac agcacctccg ctgtatttcg ttgcacctac    1020
aatgttctga aagctcatgg tcatgctgtt aaagtgtatc gggatctagt tgcctccggg    1080
accattgcgg caggtgaaat cggctttaaa tccgatgata actacccaat cccggcccgt    1140
ccagggaacg ccgatgacga ggaatcagcc aagcgtcacg aggcttttcg cattgggatt    1200
tttgcgcaac cggtttatgg taatggcgat tatccagatg ttgttaaaga aactgttgga    1260
gatatgctgc cggccctgac ggatgaagat aaaggataca ttaaaggtag cggagatatt    1320

-continued

```
tttgcgattg acgggtatcg taccgatatt tcccatgcgg ctctgaacgg gatcgcgaat     1380
tgtattcgca accaaagtga cccgaattgg ccagtgtgtg aagaagggtc agatcctttt     1440
gctcatgttt acccatccgg gtttgctatt ggtcaatcag ccgatccact gtcttcatgg     1500
ttagtcaact cagccccgtt tatccgcgat caactgaagt ttctgacaca aacctaccct     1560
gctaagggtg gtatttattt ctcggaattt ggttgggctg aagacgccga atatgatcgt     1620
caactgctgt atcaaattac ctgggatggt ctgcgtacgc aatacctgac ggactatctg     1680
agccagctgc tgttggctgt gcacaaagac gggattaatc tgcgaggcgc gctgacgtgg     1740
agttttgtcg ataattggga gtggggttta gggatgcaac agaaattcgg atttcagttt     1800
gttaatcaat cagatcccga tctgacacgc acgtttaaac tgagcgctca cgcttacgcc     1860
caatttgggc gtaatcatct gcaccaccac caccaccac                           1899
```

<210> SEQ ID NO 52
<211> LENGTH: 633
<212> TYPE: PRT
<213> ORGANISM: Pichia pastori

<400> SEQUENCE: 52

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Glu Leu Asp Ala Leu Trp
                85                  90                  95

Asn Leu Val Glu Ala Gln Tyr Pro Val Gln Thr Ala Ala Val Thr Thr
            100                 105                 110

Leu Val Thr Val Pro Asp Asp Tyr Lys Phe Glu Ala Asp Pro Pro Ser
        115                 120                 125

Tyr Ala Leu Ala Gly Tyr Glu Thr Ser Glu Ile Ala Gly Leu Lys Phe
    130                 135                 140

Pro Lys Gly Phe Lys Phe Gly Val Ala Gly Ala Ala Ile Gln Val Glu
145                 150                 155                 160

Gly Ala Ala Lys Ala Glu Gly Arg Gly Pro Ser Thr Trp Asp Tyr Leu
                165                 170                 175

Cys His His Tyr Ala Ser Thr Gln Cys Asn Asn Tyr Asp Pro Asp Ile
            180                 185                 190

Thr Thr Asn His Tyr Tyr Leu Tyr Pro Leu Asp Phe Ala Arg Leu Gln
        195                 200                 205

His Leu Gly Ile Asn Thr Tyr Ser Phe Ser Ile Ser Trp Thr Arg Ile
    210                 215                 220

Tyr Pro Leu Gly Ala Gly Tyr Val Asn Glu Ala Gly Leu Ala His Tyr
225                 230                 235                 240

Asp Ala Val Ile His Ser Ala Lys Lys Tyr Gly Leu Glu Pro Val Gly
                245                 250                 255

Thr Val Phe His Trp Asp Thr Pro Leu Ser Leu Met Leu Lys Tyr Gly
            260                 265                 270
```

-continued

---

```
Ala Trp Gln Asp Thr Gly Asp Gln Ile Val Lys Asp Phe Val Thr Tyr
        275                 280                 285

Ala Thr Thr Val Phe Lys Arg Tyr Gly Asn Glu Val Lys Thr Trp Phe
        290                 295                 300

Thr Phe Asn Glu Pro Arg Val Phe Cys Ser Gln Asn Ser Gly Leu Pro
305                 310                 315                 320

Tyr Asn Leu Thr Tyr Pro Glu Gly Ile Asn Ser Thr Ser Ala Val Phe
                325                 330                 335

Arg Cys Thr Tyr Asn Val Leu Lys Ala His Gly His Ala Val Lys Val
                340                 345                 350

Tyr Arg Asp Leu Val Ala Ser Gly Thr Ile Ala Ala Gly Glu Ile Gly
                355                 360                 365

Phe Lys Ser Asp Asp Asn Tyr Pro Ile Pro Ala Arg Pro Gly Asn Ala
        370                 375                 380

Asp Asp Glu Glu Ser Ala Lys Arg His Glu Ala Phe Arg Ile Gly Ile
385                 390                 395                 400

Phe Ala Gln Pro Val Tyr Gly Asn Gly Asp Tyr Pro Asp Val Val Lys
                405                 410                 415

Glu Thr Val Gly Asp Met Leu Pro Ala Leu Thr Asp Glu Asp Lys Gly
                420                 425                 430

Tyr Ile Lys Gly Ser Gly Asp Ile Phe Ala Ile Asp Gly Tyr Arg Thr
                435                 440                 445

Asp Ile Ser His Ala Ala Leu Asn Gly Ile Ala Asn Cys Ile Arg Asn
        450                 455                 460

Gln Ser Asp Pro Asn Trp Pro Val Cys Glu Glu Gly Ser Asp Pro Phe
465                 470                 475                 480

Ala His Val Tyr Pro Ser Gly Phe Ala Ile Gly Gln Ser Ala Asp Pro
                485                 490                 495

Leu Ser Ser Trp Leu Val Asn Ser Ala Pro Phe Ile Arg Asp Gln Leu
                500                 505                 510

Lys Phe Leu Thr Gln Thr Tyr Pro Ala Lys Gly Gly Ile Tyr Phe Ser
        515                 520                 525

Glu Phe Gly Trp Ala Glu Asp Ala Glu Tyr Asp Arg Gln Leu Leu Tyr
        530                 535                 540

Gln Ile Thr Trp Asp Gly Leu Arg Thr Gln Tyr Leu Thr Asp Tyr Leu
545                 550                 555                 560

Ser Gln Leu Leu Leu Ala Val His Lys Asp Gly Ile Asn Leu Arg Gly
                565                 570                 575

Ala Leu Thr Trp Ser Phe Val Asp Asn Trp Glu Trp Gly Leu Gly Met
        580                 585                 590

Gln Gln Lys Phe Gly Phe Gln Phe Val Asn Gln Ser Asp Pro Asp Leu
        595                 600                 605

Thr Arg Thr Phe Lys Leu Ser Ala His Ala Tyr Ala Gln Phe Gly Arg
        610                 615                 620

Asn His Leu His His His His His His
625                 630
```

<210> SEQ ID NO 53
<211> LENGTH: 1824
<212> TYPE: DNA
<213> ORGANISM: Pichia pastori

<400> SEQUENCE: 53
atgagatttc cttcaatttt tactgcagtt ttattcgcag catcctccgc attagctgct      60

-continued

```
ccagtcaaca ctacaacaga agatgaaacg gcacaaattc cggctgaagc tgtcatcggt      120
tactcagatt tagaagggga tttcgatgtt gctgttttgc cattttccaa cagcacaaat      180
aacgggttat tgtttataaa tactactatt gccagcattg ctgctaaaga agaaggggta      240
tctctcgaga aaagagaggc tgaagctaca gtgcccgatg attataagtt tgaggcagat      300
ccaccgagtt atgcattagc agggtatgaa acaagcgaga ttgccggact gaagtttcca      360
aaggggttta agtttggtgt tgcggggggca gccattcaag ttgaaggtgc agcaaaagcc      420
gaagggcggg gcccaagtac ctgggattat ctgtgtcatc actatgccag cacgcagtgt      480
aacaattatg atcccgatat tacaaccaac cattactacc tgtacccatt ggactttgcg      540
cgcctgcaac acctaggcat taacacttac tcgtttttcaa tttcatggac gcgtatttat      600
ccattgggcg caggctatgt taatgaagca gggttagccc actatgatgc cgtaatccat      660
agtgccaaga agtatggtct ggaaccagtg ggcaccgttt ttcactggga tacgccactg      720
tctctgatgc tgaaatacgg tgcctggcaa gatactggtg accaaattgt taaggacttt      780
gttacctatg ccacaactgt gtttaagcgt tatggtaatg aagtcaagac gtggtttact      840
ttcaatgaac cacgggtttt ctgttcacaa aatagtggtc tgccatacaa tctgacgtat      900
ccagaaggta ttaacagcac ctccgctgta tttcgttgca cctacaatgt tctgaaagct      960
catggtcatg ctgttaaagt gtatcgggat ctagttgcct ccgggaccat tgcggcaggt     1020
gaaatcggct ttaaatccga tgataactac ccaatcccgg cccgtccagg gaacgccgat     1080
gacgaggaat cagccaagcg tcacgaggct tttcgcattg ggattttttgc gcaaccggtt     1140 tatggtaatg gcgattatcc agatgttgtt aaagaaactg ttggagatat gctgccggcc     1200
ctgacggatg aagataaagg atacattaaa ggtagcggag atatttttgc gattgacggg     1260
tatcgtaccg atatttccca tgcggctctg aacgggatcg cgaattgtat tcgcaaccaa     1320
agtgacccga attggccagt gtgtgaagaa gggtcagatc cttttgctca tgtttaccca     1380
tccgggtttg ctattggtca atcagccgat ccactgtctt catggttagt caactcagcc     1440
ccgtttatcc gcgatcaact gaagtttctg acacaaacct accctgctaa gggtggtatt     1500
tatttctcgg aatttggttg ggctgaagac gccgaatatg atcgtcaact gctgtatcaa     1560
attacctggg atggtctgcg tacgcaatac ctgacggact atctgagcca gctgctgttg     1620
gctgtgcaca aagacgggat taatctgcga ggcgcgctga cgtggagttt tgtcgataat     1680
tgggagtggg gtttagggat gcaacagaaa ttcggatttc agtttgttaa tcaatcagat     1740
cccgatctga cacgcacgtt taaactgagc gctcacgctt acgcccaatt tgggcgtaat     1800
catctgcacc accaccacca ccac                                            1824
```

<210> SEQ ID NO 54
<211> LENGTH: 608
<212> TYPE: PRT
<213> ORGANISM: Pichia pastori

<400> SEQUENCE: 54

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
```

-continued

```
            50               55               60
Phe Ile Asn Thr Thr Ile Ala Ser Ile Ala Ala Lys Glu Glu Gly Val
65                  70               75                  80

Ser Leu Glu Lys Arg Glu Ala Glu Ala Thr Val Pro Asp Asp Tyr Lys
                85               90               95

Phe Glu Ala Asp Pro Pro Ser Tyr Ala Leu Ala Gly Tyr Glu Thr Ser
                100              105              110

Glu Ile Ala Gly Leu Lys Phe Pro Lys Gly Phe Lys Phe Gly Val Ala
            115              120              125

Gly Ala Ala Ile Gln Val Glu Gly Ala Ala Lys Ala Glu Gly Arg Gly
            130              135              140

Pro Ser Thr Trp Asp Tyr Leu Cys His His Tyr Ala Ser Thr Gln Cys
145              150              155              160

Asn Asn Tyr Asp Pro Asp Ile Thr Thr Asn His Tyr Tyr Leu Tyr Pro
                165              170              175

Leu Asp Phe Ala Arg Leu Gln His Leu Gly Ile Asn Thr Tyr Ser Phe
                180              185              190

Ser Ile Ser Trp Thr Arg Ile Tyr Pro Leu Gly Ala Gly Tyr Val Asn
            195              200              205

Glu Ala Gly Leu Ala His Tyr Asp Ala Val Ile His Ser Ala Lys Lys
    210              215              220

Tyr Gly Leu Glu Pro Val Gly Thr Val Phe His Trp Asp Thr Pro Leu
225              230              235              240

Ser Leu Met Leu Lys Tyr Gly Ala Trp Gln Asp Thr Gly Asp Gln Ile
            245              250              255

Val Lys Asp Phe Val Thr Tyr Ala Thr Thr Val Phe Lys Arg Tyr Gly
            260              265              270

Asn Glu Val Lys Thr Trp Phe Thr Phe Asn Glu Pro Arg Val Phe Cys
    275              280              285

Ser Gln Asn Ser Gly Leu Pro Tyr Asn Leu Thr Tyr Pro Glu Gly Ile
    290              295              300

Asn Ser Thr Ser Ala Val Phe Arg Cys Thr Tyr Asn Val Leu Lys Ala
305              310              315              320

His Gly His Ala Val Lys Val Tyr Arg Asp Leu Val Ala Ser Gly Thr
            325              330              335

Ile Ala Ala Gly Glu Ile Gly Phe Lys Ser Asp Asp Asn Tyr Pro Ile
            340              345              350

Pro Ala Arg Pro Gly Asn Ala Asp Asp Glu Glu Ser Ala Lys Arg His
            355              360              365

Glu Ala Phe Arg Ile Gly Ile Phe Ala Gln Pro Val Tyr Gly Asn Gly
    370              375              380

Asp Tyr Pro Asp Val Val Lys Glu Thr Val Gly Asp Met Leu Pro Ala
385              390              395              400

Leu Thr Asp Glu Asp Lys Gly Tyr Ile Lys Gly Ser Gly Asp Ile Phe
                405              410              415

Ala Ile Asp Gly Tyr Arg Thr Asp Ile Ser His Ala Ala Leu Asn Gly
            420              425              430

Ile Ala Asn Cys Ile Arg Asn Gln Ser Asp Pro Asn Trp Pro Val Cys
            435              440              445

Glu Glu Gly Ser Asp Pro Phe Ala His Val Tyr Pro Ser Gly Phe Ala
    450              455              460

Ile Gly Gln Ser Ala Asp Pro Leu Ser Ser Trp Leu Val Asn Ser Ala
465              470              475              480
```

-continued

```
Pro Phe Ile Arg Asp Gln Leu Lys Phe Leu Thr Gln Thr Tyr Pro Ala
            485                 490                 495

Lys Gly Gly Ile Tyr Phe Ser Glu Phe Gly Trp Ala Glu Asp Ala Glu
            500                 505                 510

Tyr Asp Arg Gln Leu Leu Tyr Gln Ile Thr Trp Asp Gly Leu Arg Thr
            515                 520                 525

Gln Tyr Leu Thr Asp Tyr Leu Ser Gln Leu Leu Leu Ala Val His Lys
        530                 535                 540

Asp Gly Ile Asn Leu Arg Gly Ala Leu Thr Trp Ser Phe Val Asp Asn
545                 550                 555                 560

Trp Glu Trp Gly Leu Gly Met Gln Gln Lys Phe Gly Phe Gln Phe Val
            565                 570                 575

Asn Gln Ser Asp Pro Asp Leu Thr Arg Thr Phe Lys Leu Ser Ala His
            580                 585                 590

Ala Tyr Ala Gln Phe Gly Arg Asn His Leu His His His His His His
            595                 600                 605
```

<210> SEQ ID NO 55
<211> LENGTH: 1785
<212> TYPE: DNA
<213> ORGANISM: Pichia pastori

<400> SEQUENCE: 55

```
atgagatttc cttcaatttt tactgcagtt ttattcgcag catcctccgc attagctgct       60
ccagtcaaca ctacaacaga agatgaaacg gcacaaattc cggctgaagc tgtcatcggt      120
tactcagatt tagaaggggga tttcgatgtt gctgttttgc cattttccaa cagcacaaat      180
aacgggttat tgtttataaa tactactatt gccagcattg ctgctaaaga agaaggggta      240
tctctcgaga aaagagaggc tgaagctagt tatgcattag cagggtatga aacaagcgag      300
attgccggac tgaagtttcc aaagggggttt aagtttggtg ttgcggggggc agccattcaa      360 gttgaaggtg cagcaaaagc cgaaggggcgg ggcccaagta cctgggatta tctgtgtcat      420
cactatgcca gcacgcagtg taacaattat gatcccgata ttacaaccaa ccattactac      480
ctgtacccat tggactttgc gcgcctgcaa cacctaggca ttaacactta ctcgttttca      540
atttcatgga cgcgtattta tccattgggc gcaggctatg ttaatgaagc agggttagcc      600
cactatgatg ccgtaatcca tagtgccaag aagtatggtc tggaaccagt gggcaccgtt      660
tttcactggg atacgccact gtctctgatg ctgaaatacg gtgcctggca agatactggt      720
gaccaaattg ttaaggactt tgttacctat gccacaactg tgtttaagcg ttatggtaat      780
gaagtcaaga cgtggtttac tttcaatgaa ccacggggttt tctgttcaca aaatagtggt      840
ctgccataca atctgacgta tccagaaggt attaacagca cctccgctgt atttcgttgc      900
acctacaatg ttctgaaagc tcatggtcat gctgttaaag tgtatcggga tctagttgcc      960
tccgggacca ttgcggcagg tgaaatcggc tttaaatccg atgataacta cccaatcccg     1020
gcccgtccag ggaacgccga tgacgaggaa tcagccaagc gtcacgaggc ttttcgcatt     1080 gggattttttg cgcaaccggt ttatggtaat ggcgattatc cagatgttgt taaagaaact     1140
gttggagata tgctgccggc cctgacggat gaagataaag gatacattaa aggtagcgga     1200 gatattttttg cgattgacgg gtatcgtacc gatatttccc atgcggctct gaacgggatc     1260
gcgaattgta ttcgcaacca aagtgacccg aattggccag tgtgtgaaga agggtcagat     1320
ccttttgctc atgtttaccc atccgggttt gctattggtc aatcagccga tccactgtct     1380
```

-continued

```
tcatggttag tcaactcagc cccgtttatc cgcgatcaac tgaagtttct gacacaaacc    1440
taccctgcta agggtggtat ttatttctcg gaatttggtt gggctgaaga cgccgaatat    1500
gatcgtcaac tgctgtatca aattacctgg gatggtctgc gtacgcaata cctgacggac    1560
tatctgagcc agctgctgtt ggctgtgcac aaagacggga ttaatctgcg aggcgcgctg    1620
acgtggagtt ttgtcgataa ttgggagtgg ggtttaggga tgcaacagaa attcggattt    1680
cagtttgtta atcaatcaga tcccgatctg acacgcacgt ttaaactgag cgctcacgct    1740
tacgcccaat ttgggcgtaa tcatctgcac caccaccacc accac           1785
```

<210> SEQ ID NO 56
<211> LENGTH: 595
<212> TYPE: PRT
<213> ORGANISM: Pichia pastori

<400> SEQUENCE: 56

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ser Tyr Ala Leu Ala Gly Tyr
                85                  90                  95

Glu Thr Ser Glu Ile Ala Gly Leu Lys Phe Pro Lys Gly Phe Lys Phe
            100                 105                 110

Gly Val Ala Gly Ala Ala Ile Gln Val Glu Gly Ala Ala Lys Ala Glu
            115                 120                 125

Gly Arg Gly Pro Ser Thr Trp Asp Tyr Leu Cys His His Tyr Ala Ser
        130                 135                 140

Thr Gln Cys Asn Asn Tyr Asp Pro Asp Ile Thr Thr Asn His Tyr Tyr
145                 150                 155                 160

Leu Tyr Pro Leu Asp Phe Ala Arg Leu Gln His Leu Gly Ile Asn Thr
                165                 170                 175

Tyr Ser Phe Ser Ile Ser Trp Thr Arg Ile Tyr Pro Leu Gly Ala Gly
            180                 185                 190

Tyr Val Asn Glu Ala Gly Leu Ala His Tyr Asp Ala Val Ile His Ser
            195                 200                 205

Ala Lys Lys Tyr Gly Leu Glu Pro Val Gly Thr Val Phe His Trp Asp
        210                 215                 220

Thr Pro Leu Ser Leu Met Leu Lys Tyr Gly Ala Trp Gln Asp Thr Gly
225                 230                 235                 240

Asp Gln Ile Val Lys Asp Phe Val Thr Tyr Ala Thr Thr Val Phe Lys
                245                 250                 255

Arg Tyr Gly Asn Glu Val Lys Thr Trp Phe Thr Phe Asn Glu Pro Arg
            260                 265                 270

Val Phe Cys Ser Gln Asn Ser Gly Leu Pro Tyr Asn Leu Thr Tyr Pro
        275                 280                 285

Glu Gly Ile Asn Ser Thr Ser Ala Val Phe Arg Cys Thr Tyr Asn Val
    290                 295                 300
```

```
Leu Lys Ala His Gly His Ala Val Lys Val Tyr Arg Asp Leu Val Ala
305                 310                 315                 320

Ser Gly Thr Ile Ala Ala Gly Glu Ile Gly Phe Lys Ser Asp Asp Asn
                325                 330                 335

Tyr Pro Ile Pro Ala Arg Pro Gly Asn Ala Asp Asp Glu Glu Ser Ala
            340                 345                 350

Lys Arg His Glu Ala Phe Arg Ile Gly Ile Phe Ala Gln Pro Val Tyr
        355                 360                 365

Gly Asn Gly Asp Tyr Pro Asp Val Val Lys Glu Thr Val Gly Asp Met
    370                 375                 380

Leu Pro Ala Leu Thr Asp Glu Asp Lys Gly Tyr Ile Lys Gly Ser Gly
385                 390                 395                 400

Asp Ile Phe Ala Ile Asp Gly Tyr Arg Thr Asp Ile Ser His Ala Ala
                405                 410                 415

Leu Asn Gly Ile Ala Asn Cys Ile Arg Asn Gln Ser Asp Pro Asn Trp
                420                 425                 430

Pro Val Cys Glu Glu Gly Ser Asp Pro Phe Ala His Val Tyr Pro Ser
            435                 440                 445

Gly Phe Ala Ile Gly Gln Ser Ala Asp Pro Leu Ser Ser Trp Leu Val
    450                 455                 460

Asn Ser Ala Pro Phe Ile Arg Asp Gln Leu Lys Phe Leu Thr Gln Thr
465                 470                 475                 480

Tyr Pro Ala Lys Gly Gly Ile Tyr Phe Ser Glu Phe Gly Trp Ala Glu
                485                 490                 495

Asp Ala Glu Tyr Asp Arg Gln Leu Leu Tyr Gln Ile Thr Trp Asp Gly
            500                 505                 510

Leu Arg Thr Gln Tyr Leu Thr Asp Tyr Leu Ser Gln Leu Leu Leu Ala
        515                 520                 525

Val His Lys Asp Gly Ile Asn Leu Arg Gly Ala Leu Thr Trp Ser Phe
    530                 535                 540

Val Asp Asn Trp Glu Trp Gly Leu Gly Met Gln Gln Lys Phe Gly Phe
545                 550                 555                 560

Gln Phe Val Asn Gln Ser Asp Pro Asp Leu Thr Arg Thr Phe Lys Leu
                565                 570                 575

Ser Ala His Ala Tyr Ala Gln Phe Gly Arg Asn His Leu His His His
            580                 585                 590

His His His
        595
```

<210> SEQ ID NO 57
<211> LENGTH: 1761
<212> TYPE: DNA
<213> ORGANISM: Pichia pastori

<400> SEQUENCE: 57

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattc tgctaaaga agaagggta       240 tctctcgaga aaagagaggc tgaagctaca agcgagattg ccggactgaa gtttccaaag     300
gggtttaagt ttggtgttgc gggggcagcc attcaagttg aaggtgcagc aaaagccgaa     360
gggcggggcc caagtacctg ggattatctg tgtcatcact atgccagcac gcagtgtaac     420
```

-continued

```
aattatgatc ccgatattac aaccaaccat tactacctgt acccattgga ctttgcgcgc      480
ctgcaacacc taggcattaa cacttactcg ttttcaattt catggacgcg tatttatcca      540
ttgggcgcag gctatgttaa tgaagcaggg ttagcccact atgatgccgt aatccatagt      600
gccaagaagt atggtctgga accagtgggc accgttttc actgggatac gccactgtct        660
ctgatgctga aatacggtgc ctggcaagat actggtgacc aaattgttaa ggactttgtt      720
acctatgcca caactgtgtt taagcgttat ggtaatgaag tcaagacgtg gtttactttc      780
aatgaaccac gggttttctg ttcacaaaat agtggtctgc catacaatct gacgtatcca      840
gaaggtatta acagcacctc cgctgtattt cgttgcacct acaatgttct gaaagctcat      900
ggtcatgctg ttaaagtgta tcgggatcta gttgcctccg ggaccattgc ggcaggtgaa      960
atcggcttta aatccgatga taactaccca atcccggccc gtccaggaa cgccgatgac       1020 gaggaatcag ccaagcgtca cgaggctttt cgcattggga tttttgcgca accggtttat     1080
ggtaatggcg attatccaga tgttgttaaa gaaactgttg gagatatgct gccggccctg      1140
acggatgaag ataaaggata cattaaaggt agcggagata tttttgcgat tgacgggtat     1200
cgtaccgata tttcccatgc ggctctgaac gggatcgcga attgtattcg caaccaaagt      1260
gacccgaatt ggccagtgtg tgaagaaggg tcagatcctt ttgctcatgt ttacccatcc     1320
gggtttgcta ttggtcaatc agccgatcca ctgtcttcat ggttagtcaa ctcagccccg      1380
tttatccgcg atcaactgaa gtttctgaca caaacctacc ctgctaaggg tggtatttat     1440
ttctcggaat ttggttgggc tgaagacgcc gaatatgatc gtcaactgct gtatcaaatt      1500
acctgggatg gtctgcgtac gcaatacctg acggactatc tgagccagct gctgttggct     1560
gtgcacaaag acgggattaa tctgcgaggc gcgctgacgt ggagttttgt cgataattgg      1620 gagtgggggtt tagggatgca acagaaattc ggatttcagt ttgttaatca atcagatccc     1680
gatctgacac gcacgtttaa actgagcgct cacgcttacg cccaatttgg gcgtaatcat      1740
ctgcaccacc accaccacca c                                                1761
```

<210> SEQ ID NO 58
<211> LENGTH: 587
<212> TYPE: PRT
<213> ORGANISM: Pichia pastori

<400> SEQUENCE: 58

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Thr Ser Glu Ile Ala Gly Leu
                85                  90                  95

Lys Phe Pro Lys Gly Phe Lys Phe Gly Val Ala Gly Ala Ala Ile Gln
            100                 105                 110

Val Glu Gly Ala Ala Lys Ala Glu Gly Arg Gly Pro Ser Thr Trp Asp
        115                 120                 125

Tyr Leu Cys His His Tyr Ala Ser Thr Gln Cys Asn Asn Tyr Asp Pro
```

-continued

```
           130                 135                 140

Asp Ile Thr Thr Asn His Tyr Tyr Leu Tyr Pro Leu Asp Phe Ala Arg
145                 150                 155                 160

Leu Gln His Leu Gly Ile Asn Thr Tyr Ser Phe Ser Ile Ser Trp Thr
                165                 170                 175

Arg Ile Tyr Pro Leu Gly Ala Gly Tyr Val Asn Glu Ala Gly Leu Ala
                180                 185                 190

His Tyr Asp Ala Val Ile His Ser Ala Lys Lys Tyr Gly Leu Glu Pro
                195                 200                 205

Val Gly Thr Val Phe His Trp Asp Thr Pro Leu Ser Leu Met Leu Lys
                210                 215                 220

Tyr Gly Ala Trp Gln Asp Thr Gly Asp Gln Ile Val Lys Asp Phe Val
225                 230                 235                 240

Thr Tyr Ala Thr Thr Val Phe Lys Arg Tyr Gly Asn Glu Val Lys Thr
                245                 250                 255

Trp Phe Thr Phe Asn Glu Pro Arg Val Phe Cys Ser Gln Asn Ser Gly
                260                 265                 270

Leu Pro Tyr Asn Leu Thr Tyr Pro Glu Gly Ile Asn Ser Thr Ser Ala
                275                 280                 285

Val Phe Arg Cys Thr Tyr Asn Val Leu Lys Ala His Gly His Ala Val
                290                 295                 300

Lys Val Tyr Arg Asp Leu Val Ala Ser Gly Thr Ile Ala Ala Gly Glu
305                 310                 315                 320

Ile Gly Phe Lys Ser Asp Asp Asn Tyr Pro Ile Pro Ala Arg Pro Gly
                325                 330                 335

Asn Ala Asp Asp Glu Glu Ser Ala Lys Arg His Glu Ala Phe Arg Ile
                340                 345                 350

Gly Ile Phe Ala Gln Pro Val Tyr Gly Asn Gly Asp Tyr Pro Asp Val
                355                 360                 365

Val Lys Glu Thr Val Gly Asp Met Leu Pro Ala Leu Thr Asp Glu Asp
                370                 375                 380

Lys Gly Tyr Ile Lys Gly Ser Gly Asp Ile Phe Ala Ile Asp Gly Tyr
385                 390                 395                 400

Arg Thr Asp Ile Ser His Ala Ala Leu Asn Gly Ile Ala Asn Cys Ile
                405                 410                 415

Arg Asn Gln Ser Asp Pro Asn Trp Pro Val Cys Glu Glu Gly Ser Asp
                420                 425                 430

Pro Phe Ala His Val Tyr Pro Ser Gly Phe Ala Ile Gly Gln Ser Ala
                435                 440                 445

Asp Pro Leu Ser Ser Trp Leu Val Asn Ser Ala Pro Phe Ile Arg Asp
                450                 455                 460

Gln Leu Lys Phe Leu Thr Gln Thr Tyr Pro Ala Lys Gly Gly Ile Tyr
465                 470                 475                 480

Phe Ser Glu Phe Gly Trp Ala Glu Asp Ala Glu Tyr Asp Arg Gln Leu
                485                 490                 495

Leu Tyr Gln Ile Thr Trp Asp Gly Leu Arg Thr Gln Tyr Leu Thr Asp
                500                 505                 510

Tyr Leu Ser Gln Leu Leu Leu Ala Val His Lys Asp Gly Ile Asn Leu
                515                 520                 525

Arg Gly Ala Leu Thr Trp Ser Phe Val Asp Asn Trp Glu Trp Gly Leu
                530                 535                 540

Gly Met Gln Gln Lys Phe Gly Phe Gln Phe Val Asn Gln Ser Asp Pro
545                 550                 555                 560
```

-continued

```
Asp Leu Thr Arg Thr Phe Lys Leu Ser Ala His Ala Tyr Ala Gln Phe
            565                 570                 575

Gly Arg Asn His Leu His His His His His His
            580                 585

<210> SEQ ID NO 59
<211> LENGTH: 1752
<212> TYPE: DNA
<213> ORGANISM: Pichia pastori

<400> SEQUENCE: 59
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgtttttgc cattttccaa cagcacaaat    180
aacgggttat tgtttataaa tactactatt gccagcattg ctgctaaaga agaaggggta     240
tctctcgaga aaagagaggc tgaagcttac gtagaattca tgtttccaaa ggggtttaag     300
tttggtgttg cggggggcagc cattcaagtt gaaggtgcag caaaagccga agggcggggc    360
ccaagtacct gggattatct gtgtcatcac tatgccagca cgcagtgtaa caattatgat     420
cccgatatta caaccaacca ttactacctg tacccattgg actttgcgcg cctgcaacac     480
ctaggcatta acacttactc gttttcaatt tcatggacgc gtatttatcc attgggcgca     540
ggctatgtta atgaagcagg gttagcccac tatgatgccg taatccatag tgccaagaag     600
tatggtctgg aaccagtggg caccgttttt cactgggata cgccactgtc tctgatgctg     660
aaatacggtg cctggcaaga tactggtgac caaattgtta aggactttgt tacctatgcc     720
acaactgtgt ttaagcgtta tggtaatgaa gtcaagacgt ggtttacttt caatgaacca     780
cgggttttct gttcacaaaa tagtggtctg ccatacaatc tgacgtatcc agaaggtatt     840
aacagcacct ccgctgtatt tcgttgcacc tacaatgttc tgaaagctca tggtcatgct     900
gttaaagtgt atcgggatct agttgcctcc gggaccattg cggcaggtga aatcggcttt     960
aaatccgatg ataactaccc aatcccggcc cgtccaggga acgccgatga cgaggaatca    1020
gccaagcgtc acgaggcttt tcgcattggg attttttgcgc aaccggttta tggtaatggc    1080
gattatccag atgttgttaa agaaactgtt ggagatatgc tgccggccct gacggatgaa    1140
gataaaggat acattaaagg tagcggagat attttttgcga ttgacgggta tcgtaccgat    1200
atttcccatg cggctctgaa cgggatcgcg aattgtattc gcaaccaaag tgacccgaat    1260
tggccagtgt gtgaagaagg tcagatcct tttgctcatg tttacccatc cgggtttgct     1320
attggtcaat cagccgatcc actgtcttca tggttagtca actcagcccc gtttatccgc    1380
gatcaactga gtttctgac acaaacctac cctgctaagg gtggtattta tttctcggaa     1440
tttggttggg ctgaagacgc cgaatatgat cgtcaactgc tgtatcaaat acctgggat    1500 ggtctgcgta cgcaatacct gacggactat ctgagccagc tgctgttggc tgtgcacaaa    1560
gacgggatta atctgcgagg cgcgctgacg tggagtttg tcgataattg ggagtggggt    1620
ttagggatgc aacagaaatt cggatttcag tttgttaatc aatcagatcc cgatctgaca    1680
cgcacgttta aactgagcgc tcacgcttac gcccaatttg ggcgtaatca tctgcaccac    1740
caccaccacc ac                                                       1752

<210> SEQ ID NO 60
<211> LENGTH: 584
<212> TYPE: PRT
```

```
<213> ORGANISM: Pichia pastori

<400> SEQUENCE: 60

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Tyr Val Glu Phe Met Phe Pro
                85                  90                  95

Lys Gly Phe Lys Phe Gly Val Ala Gly Ala Ala Ile Gln Val Glu Gly
            100                 105                 110

Ala Ala Lys Ala Glu Gly Arg Gly Pro Ser Thr Trp Asp Tyr Leu Cys
            115                 120                 125

His His Tyr Ala Ser Thr Gln Cys Asn Asn Tyr Asp Pro Asp Ile Thr
    130                 135                 140

Thr Asn His Tyr Tyr Leu Tyr Pro Leu Asp Phe Ala Arg Leu Gln His
145                 150                 155                 160

Leu Gly Ile Asn Thr Tyr Ser Phe Ser Ile Ser Trp Thr Arg Ile Tyr
                165                 170                 175

Pro Leu Gly Ala Gly Tyr Val Asn Glu Ala Gly Leu Ala His Tyr Asp
            180                 185                 190

Ala Val Ile His Ser Ala Lys Lys Tyr Gly Leu Glu Pro Val Gly Thr
            195                 200                 205

Val Phe His Trp Asp Thr Pro Leu Ser Leu Met Leu Lys Tyr Gly Ala
    210                 215                 220

Trp Gln Asp Thr Gly Asp Gln Ile Val Lys Asp Phe Val Thr Tyr Ala
225                 230                 235                 240

Thr Thr Val Phe Lys Arg Tyr Gly Asn Glu Val Lys Thr Trp Phe Thr
                245                 250                 255

Phe Asn Glu Pro Arg Val Phe Cys Ser Gln Asn Ser Gly Leu Pro Tyr
            260                 265                 270

Asn Leu Thr Tyr Pro Glu Gly Ile Asn Ser Thr Ser Ala Val Phe Arg
            275                 280                 285

Cys Thr Tyr Asn Val Leu Lys Ala His Gly His Ala Val Lys Val Tyr
    290                 295                 300

Arg Asp Leu Val Ala Ser Gly Thr Ile Ala Ala Gly Glu Ile Gly Phe
305                 310                 315                 320

Lys Ser Asp Asp Asn Tyr Pro Ile Pro Ala Arg Pro Gly Asn Ala Asp
            325                 330                 335

Asp Glu Glu Ser Ala Lys Arg His Glu Ala Phe Arg Ile Gly Ile Phe
            340                 345                 350

Ala Gln Pro Val Tyr Gly Asn Gly Asp Tyr Pro Asp Val Val Lys Glu
            355                 360                 365

Thr Val Gly Asp Met Leu Pro Ala Leu Thr Asp Glu Asp Lys Gly Tyr
    370                 375                 380

Ile Lys Gly Ser Gly Asp Ile Phe Ala Ile Asp Gly Tyr Arg Thr Asp
385                 390                 395                 400
```

-continued

```
Ile Ser His Ala Ala Leu Asn Gly Ile Ala Asn Cys Ile Arg Asn Gln
                405                 410                 415

Ser Asp Pro Asn Trp Pro Val Cys Glu Glu Gly Ser Asp Pro Phe Ala
            420                 425                 430

His Val Tyr Pro Ser Gly Phe Ala Ile Gly Gln Ser Ala Asp Pro Leu
            435                 440                 445

Ser Ser Trp Leu Val Asn Ser Ala Pro Phe Ile Arg Asp Gln Leu Lys
        450                 455                 460

Phe Leu Thr Gln Thr Tyr Pro Ala Lys Gly Gly Ile Tyr Phe Ser Glu
465                 470                 475                 480

Phe Gly Trp Ala Glu Asp Ala Glu Tyr Asp Arg Gln Leu Leu Tyr Gln
                485                 490                 495

Ile Thr Trp Asp Gly Leu Arg Thr Gln Tyr Leu Thr Asp Tyr Leu Ser
                500                 505                 510

Gln Leu Leu Leu Ala Val His Lys Asp Gly Ile Asn Leu Arg Gly Ala
            515                 520                 525

Leu Thr Trp Ser Phe Val Asp Asn Trp Glu Trp Gly Leu Gly Met Gln
        530                 535                 540

Gln Lys Phe Gly Phe Gln Phe Val Asn Gln Ser Asp Pro Asp Leu Thr
545                 550                 555                 560

Arg Thr Phe Lys Leu Ser Ala His Ala Tyr Ala Gln Phe Gly Arg Asn
                565                 570                 575

His Leu His His His His His His
            580
```

```
<210> SEQ ID NO 61
<211> LENGTH: 1698
<212> TYPE: DNA
<213> ORGANISM: Artificial sequence
<220> FEATURE:
<223> OTHER INFORMATION: Synthetic

<400> SEQUENCE: 61
atgcttttgc aagctttcct tttcctttg gctggttttg cagccaagat atctgcaacc      60
ggtacagcag aattagatgc gctgtggaac ttagtcgaag ctcagtaccc agttcaaact     120
gctgcagtga caactttggt gacagtgccc gatgattata agtttgaggc agatccaccg     180
agttatgcat tagcagggta tgaaacaagc gagattgccg gactgaagtt tccaaagggg     240
tttaagtttg gtgttgcggg ggcagccatt caagttgaag gtgcagcaaa agccgaaggg     300
cggggcccaa gtacctggga ttatctgtgt catcactatg ccagcacgca gtgtaacaat     360
tatgatcccg atattacaac caaccattac tacctgtacc cattggactt tgcgcgcctg     420
caacacctag gcattaacac ttactcgttt tcaatttcat ggacgcgtat ttatccattg     480
ggcgcaggct atgttaatga agcagggtta gcccactatg atgccgtaat ccatagtgcc     540
aagaagtatg tctctggaacc agtgggcacc gttttcact gggatacgcc actgtctctg     600
atgctgaaat acggtgcctg gcaagatact ggtgaccaaa ttgttaagga ctttgttacc     660
tatgccacaa ctgtgtttaa gcgttatggt aatgaagtca agacgtggtt tactttcaat     720
gaaccacggg ttttctgttc acaaaatagt ggtctgccat acaatctgac gtatccagaa     780
ggtattaaca gcacctccgc tgtatttcgt tgcacctaca atgttctgaa agctcatggt     840
catgctgtta aagtgtatcg ggatctagtt gcctccggga ccattgcggc aggtgaaatc     900
ggctttaaat ccgatgataa ctacccaatc ccggcccgtc cagggaacgc cgatgacgag     960
gaatcagcca agcgtcacga ggcttttcgc attgggattt ttgcgcaacc ggtttatggt    1020
```

-continued

```
aatggcgatt atccagatgt tgttaaagaa actgttggag atatgctgcc ggccctgacg    1080
gatgaagata aaggatacat taaaggtagc ggagatattt ttgcgattga cgggtatcgt    1140
accgatattt cccatgcggc tctgaacggg atcgcgaatt gtattcgcaa ccaaagtgac    1200
ccgaattggc cagtgtgtga agaagggtca gatccttttg ctcatgttta cccatccggg    1260
tttgctattg gtcaatcagc cgatccactg tcttcatggt tagtcaactc agccccgttt    1320
atccgcgatc aactgaagtt tctgacacaa acctaccctg ctaagggtgg tatttatttc    1380
tcggaatttg gttgggctga agacgccgaa tatgatcgtc aactgctgta tcaaattacc    1440
tgggatggtc tgcgtacgca atacctgacg gactatctga gccagctgct gttggctgtg    1500
cacaaagacg ggattaatct gcgaggcgcg ctgacgtgga gttttgtcga taattgggag    1560
tggggtttag ggatgcaaca gaaattcgga tttcagtttg ttaatcaatc agatcccgat    1620
ctgacacgca cgtttaaact gagcgctcac gcttacgccc aatttgggcg taatcatctg    1680
caccaccacc accaccac                                                   1698
```

<210> SEQ ID NO 62
<211> LENGTH: 566
<212> TYPE: PRT
<213> ORGANISM: Artificial sequence
<220> FEATURE:
<223> OTHER INFORMATION: Synthetic

<400> SEQUENCE: 62

```
Met Leu Leu Gln Ala Phe Leu Phe Leu Leu Ala Gly Phe Ala Ala Lys
1               5                   10                  15

Ile Ser Ala Thr Gly Thr Ala Glu Leu Asp Ala Leu Trp Asn Leu Val
            20                  25                  30

Glu Ala Gln Tyr Pro Val Gln Thr Ala Ala Val Thr Thr Leu Val Thr
        35                  40                  45

Val Pro Asp Asp Tyr Lys Phe Glu Ala Asp Pro Pro Ser Tyr Ala Leu
    50                  55                  60

Ala Gly Tyr Glu Thr Ser Glu Ile Ala Gly Leu Lys Phe Pro Lys Gly
65                  70                  75                  80

Phe Lys Phe Gly Val Ala Gly Ala Ala Ile Gln Val Glu Gly Ala Ala
            85                  90                  95

Lys Ala Glu Gly Arg Gly Pro Ser Thr Trp Asp Tyr Leu Cys His His
        100                 105                 110

Tyr Ala Ser Thr Gln Cys Asn Asn Tyr Asp Pro Asp Ile Thr Thr Asn
        115                 120                 125

His Tyr Tyr Leu Tyr Pro Leu Asp Phe Ala Arg Leu Gln His Leu Gly
    130                 135                 140

Ile Asn Thr Tyr Ser Phe Ser Ile Ser Trp Thr Arg Ile Tyr Pro Leu
145                 150                 155                 160

Gly Ala Gly Tyr Val Asn Glu Ala Gly Leu Ala His Tyr Asp Ala Val
            165                 170                 175

Ile His Ser Ala Lys Lys Tyr Gly Leu Glu Pro Val Gly Thr Val Phe
        180                 185                 190

His Trp Asp Thr Pro Leu Ser Leu Met Leu Lys Tyr Gly Ala Trp Gln
        195                 200                 205

Asp Thr Gly Asp Gln Ile Val Lys Asp Phe Val Thr Tyr Ala Thr Thr
    210                 215                 220

Val Phe Lys Arg Tyr Gly Asn Glu Val Lys Thr Trp Phe Thr Phe Asn
225                 230                 235                 240
```

Glu Pro Arg Val Phe Cys Ser Gln Asn Ser Gly Leu Pro Tyr Asn Leu
                245                 250                 255

Thr Tyr Pro Glu Gly Ile Asn Ser Thr Ser Ala Val Phe Arg Cys Thr
            260                 265                 270

Tyr Asn Val Leu Lys Ala His Gly His Ala Val Lys Val Tyr Arg Asp
            275                 280                 285

Leu Val Ala Ser Gly Thr Ile Ala Ala Gly Glu Ile Gly Phe Lys Ser
    290                 295                 300

Asp Asp Asn Tyr Pro Ile Pro Ala Arg Pro Gly Asn Ala Asp Asp Glu
305                 310                 315                 320

Glu Ser Ala Lys Arg His Glu Ala Phe Arg Ile Gly Ile Phe Ala Gln
                325                 330                 335

Pro Val Tyr Gly Asn Gly Asp Tyr Pro Asp Val Val Lys Glu Thr Val
            340                 345                 350

Gly Asp Met Leu Pro Ala Leu Thr Asp Glu Asp Lys Gly Tyr Ile Lys
            355                 360                 365

Gly Ser Gly Asp Ile Phe Ala Ile Asp Gly Tyr Arg Thr Asp Ile Ser
    370                 375                 380

His Ala Ala Leu Asn Gly Ile Ala Asn Cys Ile Arg Asn Gln Ser Asp
385                 390                 395                 400

Pro Asn Trp Pro Val Cys Glu Glu Gly Ser Asp Pro Phe Ala His Val
                405                 410                 415

Tyr Pro Ser Gly Phe Ala Ile Gly Gln Ser Ala Asp Pro Leu Ser Ser
            420                 425                 430

Trp Leu Val Asn Ser Ala Pro Phe Ile Arg Asp Gln Leu Lys Phe Leu
            435                 440                 445

Thr Gln Thr Tyr Pro Ala Lys Gly Gly Ile Tyr Phe Ser Glu Phe Gly
    450                 455                 460

Trp Ala Glu Asp Ala Glu Tyr Asp Arg Gln Leu Leu Tyr Gln Ile Thr
465                 470                 475                 480

Trp Asp Gly Leu Arg Thr Gln Tyr Leu Thr Asp Tyr Leu Ser Gln Leu
            485                 490                 495

Leu Leu Ala Val His Lys Asp Gly Ile Asn Leu Arg Gly Ala Leu Thr
            500                 505                 510

Trp Ser Phe Val Asp Asn Trp Glu Trp Gly Leu Gly Met Gln Gln Lys
            515                 520                 525

Phe Gly Phe Gln Phe Val Asn Gln Ser Asp Pro Asp Leu Thr Arg Thr
    530                 535                 540

Phe Lys Leu Ser Ala His Ala Tyr Ala Gln Phe Gly Arg Asn His Leu
545                 550                 555                 560

His His His His His His
            565

<210> SEQ ID NO 63
<211> LENGTH: 1695
<212> TYPE: DNA
<213> ORGANISM: Artificial sequence
<220> FEATURE:
<223> OTHER INFORMATION: Synthetic

<400> SEQUENCE: 63 atgtcttta gatccttgct agctttgtct ggtttggttt gttctggttt ggctaccggt        60
acagcagaat tagatgcgct gtggaactta gtcgaagctc agtacccagt tcaaactgct        120
gcagtgacaa ctttggtgac agtgcccgat gattataagt ttgaggcaga tccaccgagt        180

-continued

```
tatgcattag cagggtatga aacaagcgag attgccggac tgaagtttcc aaaggggttt      240
aagtttggtg ttgcgggggc agccattcaa gttgaaggtg cagcaaaagc cgaagggcgg      300
ggcccaagta cctgggatta tctgtgtcat cactatgcca gcacgcagtg taacaattat      360
gatcccgata ttacaaccaa ccattactac ctgtacccat tggactttgc gcgcctgcaa      420
cacctaggca ttaacactta ctcgttttca atttcatgga cgcgtattta tccattgggc      480
gcaggctatg ttaatgaagc agggttagcc cactatgatg ccgtaatcca tagtgccaag      540
aagtatggtc tggaaccagt gggcaccgtt tttcactggg atacgccact gtctctgatg      600
ctgaaatacg gtgcctggca agatactggt gaccaaattg ttaaggactt tgttaccctat      660 gccacaactg tgtttaagcg ttatggtaat gaagtcaaga cgtggtttac tttcaatgaa      720
ccacgggttt tctgttcaca aaatagtggt ctgccataca atctgacgta tccagaaggt      780
attaacagca cctccgctgt atttcgttgc acctacaatg ttctgaaagc tcatggtcat      840
gctgttaaag tgtatcggga tctagttgcc tccgggacca ttgcggcagg tgaaatcggc      900
tttaaatccg atgataacta cccaatcccg gcccgtccag ggaacgccga tgacgaggaa      960
tcagccaagc gtcacgaggc ttttcgcatt gggattttttg cgcaaccggt ttatggtaat     1020
ggcgattatc cagatgttgt taaagaaact gttggagata tgctgccggc cctgacggat     1080
gaagataaag gatacattaa aggtagcgga gatattttttg cgattgacgg gtatcgtacc     1140
gatatttccc atgcggctct gaacgggatc gcgaattgta ttcgcaacca aagtgacccg     1200
aattggccag tgtgtgaaga aaggtcagat ccttttgctc atgtttaccc atccgggttt     1260
gctattggtc aatcagccga tccactgtct tcatggttag tcaactcagc cccgtttatc     1320
cgcgatcaac tgaagtttct gacacaaacc taccctgcta agggtggtat ttatttctcg     1380
gaatttggtt gggctgaaga cgccgaatat gatcgtcaac tgctgtatca aattacctgg     1440
gatggtctgc gtacgcaata cctgacggac tatctgagcc agctgctgtt ggctgtgcac     1500
aaagacggga ttaatctgcg aggcgcgctg acgtggagtt ttgtcgataa ttgggagtgg     1560
ggtttaggga tgcaacagaa attcggattt cagtttgtta atcaatcaga tcccgatctg     1620
acacgcacgt ttaaactgag cgctcacgct tacgcccaat ttgggcgtaa tcatctgcac     1680
caccaccacc accac                                                       1695
```

<210> SEQ ID NO 64
<211> LENGTH: 565
<212> TYPE: PRT
<213> ORGANISM: Artificial sequence
<220> FEATURE:
<223> OTHER INFORMATION: Synthetic

<400> SEQUENCE: 64

```
Met Ser Phe Arg Ser Leu Leu Ala Leu Ser Gly Leu Val Cys Ser Gly
1               5                   10                  15

Leu Ala Thr Gly Thr Ala Glu Leu Asp Ala Leu Trp Asn Leu Val Glu
            20                  25                  30

Ala Gln Tyr Pro Val Gln Thr Ala Ala Val Thr Thr Leu Val Thr Val
        35                  40                  45

Pro Asp Asp Tyr Lys Phe Glu Ala Asp Pro Pro Ser Tyr Ala Leu Ala
    50                  55                  60

Gly Tyr Glu Thr Ser Glu Ile Ala Gly Leu Lys Phe Pro Lys Gly Phe
65                  70                  75                  80

Lys Phe Gly Val Ala Gly Ala Ala Ile Gln Val Glu Gly Ala Ala Lys
```

-continued

```
            85                    90                    95

Ala Glu Gly Arg Gly Pro Ser Thr Trp Asp Tyr Leu Cys His His Tyr
            100                   105                   110

Ala Ser Thr Gln Cys Asn Asn Tyr Asp Pro Asp Ile Thr Thr Asn His
            115                   120                   125

Tyr Tyr Leu Tyr Pro Leu Asp Phe Ala Arg Leu Gln His Leu Gly Ile
            130                   135                   140

Asn Thr Tyr Ser Phe Ser Ile Ser Trp Thr Arg Ile Tyr Pro Leu Gly
145                   150                   155                   160

Ala Gly Tyr Val Asn Glu Ala Gly Leu Ala His Tyr Asp Ala Val Ile
                      165                   170                   175

His Ser Ala Lys Lys Tyr Gly Leu Glu Pro Val Gly Thr Val Phe His
                      180                   185                   190

Trp Asp Thr Pro Leu Ser Leu Met Leu Lys Tyr Gly Ala Trp Gln Asp
            195                   200                   205

Thr Gly Asp Gln Ile Val Lys Asp Phe Val Thr Tyr Ala Thr Thr Val
            210                   215                   220

Phe Lys Arg Tyr Gly Asn Glu Val Lys Thr Trp Phe Thr Phe Asn Glu
225                   230                   235                   240

Pro Arg Val Phe Cys Ser Gln Asn Ser Gly Leu Pro Tyr Asn Leu Thr
                      245                   250                   255

Tyr Pro Glu Gly Ile Asn Ser Thr Ser Ala Val Phe Arg Cys Thr Tyr
                      260                   265                   270

Asn Val Leu Lys Ala His Gly His Ala Val Lys Val Tyr Arg Asp Leu
            275                   280                   285

Val Ala Ser Gly Thr Ile Ala Ala Gly Glu Ile Gly Phe Lys Ser Asp
            290                   295                   300

Asp Asn Tyr Pro Ile Pro Ala Arg Pro Gly Asn Ala Asp Asp Glu Glu
305                   310                   315                   320

Ser Ala Lys Arg His Glu Ala Phe Arg Ile Gly Ile Phe Ala Gln Pro
                      325                   330                   335

Val Tyr Gly Asn Gly Asp Tyr Pro Asp Val Val Lys Glu Thr Val Gly
                      340                   345                   350

Asp Met Leu Pro Ala Leu Thr Asp Glu Asp Lys Gly Tyr Ile Lys Gly
            355                   360                   365

Ser Gly Asp Ile Phe Ala Ile Asp Gly Tyr Arg Thr Asp Ile Ser His
            370                   375                   380

Ala Ala Leu Asn Gly Ile Ala Asn Cys Ile Arg Asn Gln Ser Asp Pro
385                   390                   395                   400

Asn Trp Pro Val Cys Glu Glu Gly Ser Asp Pro Phe Ala His Val Tyr
                      405                   410                   415

Pro Ser Gly Phe Ala Ile Gly Gln Ser Ala Asp Pro Leu Ser Ser Trp
                      420                   425                   430

Leu Val Asn Ser Ala Pro Phe Ile Arg Asp Gln Leu Lys Phe Leu Thr
            435                   440                   445

Gln Thr Tyr Pro Ala Lys Gly Gly Ile Tyr Phe Ser Glu Phe Gly Trp
            450                   455                   460

Ala Glu Asp Ala Glu Tyr Asp Arg Gln Leu Leu Tyr Gln Ile Thr Trp
465                   470                   475                   480

Asp Gly Leu Arg Thr Gln Tyr Leu Thr Asp Tyr Leu Ser Gln Leu Leu
                      485                   490                   495

Leu Ala Val His Lys Asp Gly Ile Asn Leu Arg Gly Ala Leu Thr Trp
            500                   505                   510
```

Ser Phe Val Asp Asn Trp Glu Trp Gly Leu Gly Met Gln Gln Lys Phe
        515                 520                 525

Gly Phe Gln Phe Val Asn Gln Ser Asp Pro Asp Leu Thr Arg Thr Phe
        530                 535                 540

Lys Leu Ser Ala His Ala Tyr Ala Gln Phe Gly Arg Asn His Leu His
545                 550                 555                 560

His His His His His
                565

<210> SEQ ID NO 65
<211> LENGTH: 1689
<212> TYPE: DNA
<213> ORGANISM: Artificial sequence
<220> FEATURE:
<223> OTHER INFORMATION: Synthetic

<400> SEQUENCE: 65
atgaagttag catactcctt gttgcttccg ctagcaggag tcagtgctac cggtacagca      60
gaattagatg cgctgtggaa cttagtcgaa gctcagtacc cagttcaaac tgctgcagtg     120
acaactttgg tgacagtgcc cgatgattat aagtttgagg cagatccacc gagttatgca     180
ttagcagggt atgaaacaag cgagattgcc ggactgaagt ttccaaaggg gtttaagttt     240
ggtgttgcgg gggcagccat tcaagttgaa ggtgcagcaa aagccgaagg gcggggccca     300
agtacctggg attatctgtg tcatcactat gccagcacgc agtgtaacaa ttatgatccc     360
gatattacaa ccaaccatta ctacctgtac ccattggact ttgcgcgcct gcaacaccta     420
ggcattaaca cttactcgtt ttcaatttca tggacgcgta tttatccatt gggcgcaggc     480
tatgttaatg aagcagggtt agcccactat gatgccgtaa tccatagtgc caagaagtat     540
ggtctggaac cagtgggcac cgtttttcac tgggatacgc cactgtctct gatgctgaaa     600
tacggtgcct ggcaagatac tggtgaccaa attgttaagg actttgttac ctatgccaca     660
actgtgttta agcgttatgg taatgaagtc aagacgtggt ttactttcaa tgaaccacgg     720
gttttctgtt cacaaaatag tggtctgcca tacaatctga cgtatccaga aggtattaac     780
agcacctccg ctgtatttcg ttgcacctac aatgttctga aagctcatgg tcatgctgtt     840
aaagtgtatc gggatctagt tgcctccggg accattgcgg caggtgaaat cggctttaaa     900
tccgatgata actacccaat cccggcccgt ccagggaacg ccgatgacga ggaatcagcc     960
aagcgtcacg aggcttttcg cattgggatt tttgcgcaac cggtttatgg taatggcgat    1020
tatccagatg ttgttaaaga aactgttgga gatatgctgc cggccctgac ggatgaagat    1080
aaaggataca ttaaaggtag cggagatatt tttgcgattg acgggtatcg taccgatatt    1140
tcccatgcgg ctctgaacgg gatcgcgaat tgtattcgca accaaagtga cccgaattgg    1200
ccagtgtgtg aagaagggtc agatcctttt gctcatgttt acccatccgg gtttgctatt    1260
ggtcaatcag ccgatccact gtcttcatgg ttagtcaact cagccccgtt tatccgcgat    1320
caactgaagt ttctgacaca aacctaccct gctaagggtg gtatttattt ctcggaattt    1380
ggttgggctg aagacgccga atatgatcgt caactgctgt atcaaattac ctgggatggt    1440
ctgcgtacgc aatacctgac ggactatctg agccagctgt gttggctgt gcacaaagac    1500 gggattaatc tgcgaggcgc gctgacgtgg agttttgtcg ataattggga gtggggttta    1560
gggatgcaac agaaattcgg atttcagttt gttaatcaat cagatcccga tctgacacgc    1620
acgtttaaac tgagcgctca cgcttacgcc caatttgggc gtaatcatct gcaccaccac    1680

-continued caccaccac                                                                      1689

<210> SEQ ID NO 66
<211> LENGTH: 563
<212> TYPE: PRT
<213> ORGANISM: Artificial sequence
<220> FEATURE:
<223> OTHER INFORMATION: Synthetic

<400> SEQUENCE: 66

Met Lys Leu Ala Tyr Ser Leu Leu Leu Pro Leu Ala Gly Val Ser Ala
1               5                   10                  15

Thr Gly Thr Ala Glu Leu Asp Ala Leu Trp Asn Leu Val Glu Ala Gln
            20                  25                  30

Tyr Pro Val Gln Thr Ala Ala Val Thr Thr Leu Val Thr Val Pro Asp
        35                  40                  45

Asp Tyr Lys Phe Glu Ala Asp Pro Pro Ser Tyr Ala Leu Ala Gly Tyr
    50                  55                  60

Glu Thr Ser Glu Ile Ala Gly Leu Lys Phe Pro Lys Gly Phe Lys Phe
65                  70                  75                  80

Gly Val Ala Gly Ala Ala Ile Gln Val Glu Gly Ala Ala Lys Ala Glu
                85                  90                  95

Gly Arg Gly Pro Ser Thr Trp Asp Tyr Leu Cys His His Tyr Ala Ser
            100                 105                 110

Thr Gln Cys Asn Asn Tyr Asp Pro Asp Ile Thr Thr Asn His Tyr Tyr
            115                 120                 125

Leu Tyr Pro Leu Asp Phe Ala Arg Leu Gln His Leu Gly Ile Asn Thr
    130                 135                 140

Tyr Ser Phe Ser Ile Ser Trp Thr Arg Ile Tyr Pro Leu Gly Ala Gly
145                 150                 155                 160

Tyr Val Asn Glu Ala Gly Leu Ala His Tyr Asp Ala Val Ile His Ser
                165                 170                 175

Ala Lys Lys Tyr Gly Leu Glu Pro Val Gly Thr Val Phe His Trp Asp
            180                 185                 190

Thr Pro Leu Ser Leu Met Leu Lys Tyr Gly Ala Trp Gln Asp Thr Gly
            195                 200                 205

Asp Gln Ile Val Lys Asp Phe Val Thr Tyr Ala Thr Thr Val Phe Lys
    210                 215                 220

Arg Tyr Gly Asn Glu Val Lys Thr Trp Phe Thr Phe Asn Glu Pro Arg
225                 230                 235                 240

Val Phe Cys Ser Gln Asn Ser Gly Leu Pro Tyr Asn Leu Thr Tyr Pro
                245                 250                 255

Glu Gly Ile Asn Ser Thr Ser Ala Val Phe Arg Cys Thr Tyr Asn Val
            260                 265                 270

Leu Lys Ala His Gly His Ala Val Lys Val Tyr Arg Asp Leu Val Ala
    275                 280                 285

Ser Gly Thr Ile Ala Ala Gly Glu Ile Gly Phe Lys Ser Asp Asp Asn
    290                 295                 300

Tyr Pro Ile Pro Ala Arg Pro Gly Asn Ala Asp Asp Glu Glu Ser Ala
305                 310                 315                 320

Lys Arg His Glu Ala Phe Arg Ile Gly Ile Phe Ala Gln Pro Val Tyr
                325                 330                 335

Gly Asn Gly Asp Tyr Pro Asp Val Val Lys Glu Thr Val Gly Asp Met
            340                 345                 350

Leu Pro Ala Leu Thr Asp Glu Asp Lys Gly Tyr Ile Lys Gly Ser Gly

-continued

```
      355              360              365
```

Asp Ile Phe Ala Ile Asp Gly Tyr Arg Thr Asp Ile Ser His Ala Ala
    370              375              380

Leu Asn Gly Ile Ala Asn Cys Ile Arg Asn Gln Ser Asp Pro Asn Trp
385              390              395              400

Pro Val Cys Glu Glu Gly Ser Asp Pro Phe Ala His Val Tyr Pro Ser
                405              410              415

Gly Phe Ala Ile Gly Gln Ser Ala Asp Pro Leu Ser Ser Trp Leu Val
                420              425              430

Asn Ser Ala Pro Phe Ile Arg Asp Gln Leu Lys Phe Leu Thr Gln Thr
                435              440              445

Tyr Pro Ala Lys Gly Gly Ile Tyr Phe Ser Glu Phe Gly Trp Ala Glu
    450              455              460

Asp Ala Glu Tyr Asp Arg Gln Leu Leu Tyr Gln Ile Thr Trp Asp Gly
465              470              475              480

Leu Arg Thr Gln Tyr Leu Thr Asp Tyr Leu Ser Gln Leu Leu Leu Ala
                485              490              495

Val His Lys Asp Gly Ile Asn Leu Arg Gly Ala Leu Thr Trp Ser Phe
                500              505              510

Val Asp Asn Trp Glu Trp Gly Leu Gly Met Gln Gln Lys Phe Gly Phe
                515              520              525

Gln Phe Val Asn Gln Ser Asp Pro Asp Leu Thr Arg Thr Phe Lys Leu
    530              535              540

Ser Ala His Ala Tyr Ala Gln Phe Gly Arg Asn His Leu His His His
545              550              555              560

His His His

<210> SEQ ID NO 67
<211> LENGTH: 1959
<212> TYPE: DNA
<213> ORGANISM: Artificial sequence
<220> FEATURE:
<223> OTHER INFORMATION: Synthetic

<400> SEQUENCE: 67
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaaggga tttcgatgtt gctgttttgc cattttccgc cagcattgct     180
gctaaagaag aagggtatc tctcgagaaa agagaggctg aagctgttac ttatccggga     240
gccattcctc tgtccctgac gagcaattac gaaaccccaa gtccgacagc aatcccgctg     300
gagccaacac cgacggctac cggtacagca gaattagatg cgctgtggaa cttagtcgaa     360
gctcagtacc cagttcaaac tgctgcagtg acaactttgg tgacagtgcc cgatgattat     420
aagtttgagg cagatccacc gagttatgca ttagcagggt atgaaacaag cgagattgcc     480
ggactgaagt ttccaaaggg gtttaagttt ggtgttgcgg gggcagccat tcaagttgaa     540
ggtgcagcaa aagccgaagg gcggggccca agtacctggg attatctgtg tcatcactat     600
gccagcacgc agtgtaacaa ttatgatccc gatattacaa ccaaccatta ctacctgtac     660
ccattggact ttgcgcgcct gcaacaccta ggcattaaca cttactcgtt ttcaatttca     720
tggacgcgta tttatccatt gggcgcaggc tatgttaatg aagcagggtt agcccactat     780
gatgccgtaa tccatagtgc caagaagtat ggtctggaac cagtgggcac cgttttcac     840 tgggatacgc cactgtctct gatgctgaaa tacggtgcct ggcaagatac tggtgaccaa     900
```

-continued

```
attgttaagg actttgttac ctatgccaca actgtgttta agcgttatgg taatgaagtc    960
aagacgtggt ttactttcaa tgaaccacgg gttttctgtt cacaaaatag tggtctgcca    1020
tacaatctga cgtatccaga aggtattaac agcacctccg ctgtatttcg ttgcacctac    1080
aatgttctga aagctcatgg tcatgctgtt aaagtgtatc gggatctagt tgcctccggg    1140
accattgcgg caggtgaaat cggctttaaa tccgatgata actacccaat cccggcccgt    1200
ccagggaacg ccgatgacga ggaatcagcc aagcgtcacg aggctttcg cattgggatt    1260 tttgcgcaac cggtttatgg taatggcgat tatccagatg ttgttaaaga aactgttgga    1320
gatatgctgc cggccctgac ggatgaagat aaaggataca ttaaaggtag cggagatatt    1380
tttgcgattg acgggtatcg taccgatatt cccatgcggg ctctgaacgg gatcgcgaat    1440
tgtattcgca accaaagtga cccgaattgg ccagtgtgtg aagaagggtc agatcctttt    1500
gctcatgttt acccatccgg gtttgctatt ggtcaatcag ccgatccact gtcttcatgg    1560
ttagtcaact cagccccgtt tatccgcgat caactgaagt ttctgacaca aacctaccct    1620
gctaagggtg gtatttattt ctcggaattt ggttgggctg aagacgccga atatgatcgt    1680
caactgctgt atcaaattac ctgggatggt ctgcgtacgc aatacctgac ggactatctg    1740
agccagctgc tgttggctgt gcacaaagac gggattaatc tgcgaggcgc gctgacgtgg    1800
agttttgtcg ataattggga gtggggttta gggatgcaac agaaattcgg atttcagttt    1860
gttaatcaat cagatcccga tctgacacgc acgtttaaac tgagcgctca cgcttacgcc    1920
caatttgggc gtaatcatct gcaccaccac caccaccac    1959
```

<210> SEQ ID NO 68
<211> LENGTH: 653
<212> TYPE: PRT
<213> ORGANISM: Artificial sequence
<220> FEATURE:
<223> OTHER INFORMATION: Synthetic

<400> SEQUENCE: 68

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Ala Ser Ile Ala Ala Lys Glu Glu
    50                  55                  60

Gly Val Ser Leu Glu Lys Arg Glu Ala Glu Ala Val Thr Tyr Pro Gly
65                  70                  75                  80

Ala Ile Pro Leu Ser Leu Thr Ser Asn Tyr Glu Thr Pro Ser Pro Thr
                85                  90                  95

Ala Ile Pro Leu Glu Pro Thr Pro Thr Ala Thr Gly Thr Ala Glu Leu
            100                 105                 110

Asp Ala Leu Trp Asn Leu Val Glu Ala Gln Tyr Pro Val Gln Thr Ala
        115                 120                 125

Ala Val Thr Thr Leu Val Thr Val Pro Asp Asp Tyr Lys Phe Glu Ala
    130                 135                 140

Asp Pro Pro Ser Tyr Ala Leu Ala Gly Tyr Glu Thr Ser Glu Ile Ala
145                 150                 155                 160

Gly Leu Lys Phe Pro Lys Gly Phe Lys Phe Gly Val Ala Gly Ala Ala
                165                 170                 175
```

-continued

```
Ile Gln Val Glu Gly Ala Ala Lys Ala Glu Gly Arg Gly Pro Ser Thr
            180                 185                 190

Trp Asp Tyr Leu Cys His His Tyr Ala Ser Thr Gln Cys Asn Asn Tyr
            195                 200                 205

Asp Pro Asp Ile Thr Thr Asn His Tyr Tyr Leu Tyr Pro Leu Asp Phe
            210                 215                 220

Ala Arg Leu Gln His Leu Gly Ile Asn Thr Tyr Ser Phe Ser Ile Ser
225                 230                 235                 240

Trp Thr Arg Ile Tyr Pro Leu Gly Ala Gly Tyr Val Asn Glu Ala Gly
                245                 250                 255

Leu Ala His Tyr Asp Ala Val Ile His Ser Ala Lys Lys Tyr Gly Leu
            260                 265                 270

Glu Pro Val Gly Thr Val Phe His Trp Asp Thr Pro Leu Ser Leu Met
            275                 280                 285

Leu Lys Tyr Gly Ala Trp Gln Asp Thr Gly Asp Gln Ile Val Lys Asp
            290                 295                 300

Phe Val Thr Tyr Ala Thr Thr Val Phe Lys Arg Tyr Gly Asn Glu Val
305                 310                 315                 320

Lys Thr Trp Phe Thr Phe Asn Glu Pro Arg Val Phe Cys Ser Gln Asn
                325                 330                 335

Ser Gly Leu Pro Tyr Asn Leu Thr Tyr Pro Glu Gly Ile Asn Ser Thr
                340                 345                 350

Ser Ala Val Phe Arg Cys Thr Tyr Asn Val Leu Lys Ala His Gly His
            355                 360                 365

Ala Val Lys Val Tyr Arg Asp Leu Val Ala Ser Gly Thr Ile Ala Ala
            370                 375                 380

Gly Glu Ile Gly Phe Lys Ser Asp Asp Asn Tyr Pro Ile Pro Ala Arg
385                 390                 395                 400

Pro Gly Asn Ala Asp Asp Glu Glu Ser Ala Lys Arg His Glu Ala Phe
                405                 410                 415

Arg Ile Gly Ile Phe Ala Gln Pro Val Tyr Gly Asn Gly Asp Tyr Pro
                420                 425                 430

Asp Val Val Lys Glu Thr Val Gly Asp Met Leu Pro Ala Leu Thr Asp
            435                 440                 445

Glu Asp Lys Gly Tyr Ile Lys Gly Ser Gly Asp Ile Phe Ala Ile Asp
            450                 455                 460

Gly Tyr Arg Thr Asp Ile Ser His Ala Ala Leu Asn Gly Ile Ala Asn
465                 470                 475                 480

Cys Ile Arg Asn Gln Ser Asp Pro Asn Trp Pro Val Cys Glu Glu Gly
                485                 490                 495

Ser Asp Pro Phe Ala His Val Tyr Pro Ser Gly Phe Ala Ile Gly Gln
            500                 505                 510

Ser Ala Asp Pro Leu Ser Ser Trp Leu Val Asn Ser Ala Pro Phe Ile
            515                 520                 525

Arg Asp Gln Leu Lys Phe Leu Thr Gln Thr Tyr Pro Ala Lys Gly Gly
            530                 535                 540

Ile Tyr Phe Ser Glu Phe Gly Trp Ala Glu Asp Ala Glu Tyr Asp Arg
545                 550                 555                 560

Gln Leu Leu Tyr Gln Ile Thr Trp Asp Gly Leu Arg Thr Gln Tyr Leu
                565                 570                 575

Thr Asp Tyr Leu Ser Gln Leu Leu Leu Ala Val His Lys Asp Gly Ile
            580                 585                 590
```

```
Asn Leu Arg Gly Ala Leu Thr Trp Ser Phe Val Asp Asn Trp Glu Trp
        595                 600                 605

Gly Leu Gly Met Gln Gln Lys Phe Gly Phe Gln Phe Val Asn Gln Ser
        610                 615                 620

Asp Pro Asp Leu Thr Arg Thr Phe Lys Leu Ser Ala His Ala Tyr Ala
625                 630                 635                 640

Gln Phe Gly Arg Asn His Leu His His His His His His
                645                 650
```

```
<210> SEQ ID NO 69
<211> LENGTH: 1857
<212> TYPE: DNA
<213> ORGANISM: Artificial sequence
<220> FEATURE:
<223> OTHER INFORMATION: Synthetic

<400> SEQUENCE: 69
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccgc cagcattgct     180
gctaaagaag aaggggtatc tctcgagaaa agagaggctg aagctgcaga attagatgcg     240
ctgtggaact tagtcgaagc tcagtaccca gttcaaactg ctgcagtgac aactttggtg     300
acagtgcccg atgattataa gtttgaggca gatccaccga gttatgcatt agcagggtat     360
gaaacaagcg agattgccgg actgaagttt ccaaaggggt ttaagtttgg tgttgcgggg     420
gcagccattc aagttgaagg tgcagcaaaa gccgaagggc ggggcccaag tacctgggat     480
tatctgtgtc atcactatgc cagcacgcag tgtaacaatt atgatcccga tattacaacc     540
aaccattact acctgtaccc attggacttt gcgcgcctgc aacacctagg cattaacact     600
tactcgtttt caatttcatg gacgcgtatt tatccattgg gcgcaggcta tgttaatgaa     660
gcagggttag cccactatga tgccgtaatc catagtgcca agaagtatgg tctggaacca     720
gtgggcaccg ttttcactg gatacgcca ctgtctctga tgctgaaata cggtgcctgg     780
caagatactg tgaccaaat tgttaaggac tttgttacct atgccacaac tgtgtttaag     840
cgttatggta atgaagtcaa gacgtggttt actttcaatg aaccacgggt tttctgttca     900
caaaatagtg tctgccata caatctgacg tatccagaag gtattaacag cacctccgct     960
gtatttcgtt gcacctacaa tgttctgaaa gctcatggtc atgctgttaa agtgtatcgg    1020
gatctagttg cctccgggac cattgcggca ggtgaaatcg ctttaaatc cgatgataac    1080 tacccaatcc cggcccgtcc agggaacgcc gatgacgagg aatcagccaa gcgtcacgag    1140
gcttttcgca ttgggatttt tgcgcaaccg gtttatggta atggcgatta tccagatgtt    1200
gttaaagaaa ctgttggaga tatgctgccg gccctgacgg atgaagataa aggatacatt    1260
aaaggtagcg gagatatttt tgcgattgac gggtatcgta ccgatatttc ccatgcggct    1320
ctgaacggga tcgcgaattg tattcgcaac caaagtgacc gaattggcc agtgtgtgaa    1380 gaagggtcag atcctttgc tcatgtttac ccatccgggt ttgctattgg tcaatcagcc    1440
gatccactgt cttcatggtt agtcaactca gccccgttta ccgcgatca actgaagttt    1500 ctgacacaaa cctaccctgc taagggtggt atttatttct cggaatttgg ttgggctgaa    1560
gacgccgaat atgatcgtca actgctgtat caaattacct gggatggtct gcgtacgcaa    1620
tacctgacgg actatctgag ccagctgctg ttggctgtgc acaaagacgg gattaatctg    1680
cgaggcgcgc tgacgtggag ttttgtcgat aattgggagt ggggtttagg gatgcaacag    1740
```

-continued

```
aaattcggat ttcagtttgt taatcaatca gatcccgatc tgacacgcac gtttaaactg    1800
agcgctcacg cttacgccca atttgggcgt aatcatctgc accaccacca ccaccac      1857
```

```
<210> SEQ ID NO 70
<211> LENGTH: 619
<212> TYPE: PRT
<213> ORGANISM: Artificial sequence
<220> FEATURE:
<223> OTHER INFORMATION: Synthetic

<400> SEQUENCE: 70

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Ala Ser Ile Ala Ala Lys Glu Glu
    50                  55                  60

Gly Val Ser Leu Glu Lys Arg Glu Ala Glu Ala Glu Leu Asp Ala
65                  70                  75                  80

Leu Trp Asn Leu Val Glu Ala Gln Tyr Pro Val Gln Thr Ala Ala Val
                85                  90                  95

Thr Thr Leu Val Thr Val Pro Asp Asp Tyr Lys Phe Glu Ala Asp Pro
            100                 105                 110

Pro Ser Tyr Ala Leu Ala Gly Tyr Glu Thr Ser Glu Ile Ala Gly Leu
            115                 120                 125

Lys Phe Pro Lys Gly Phe Lys Phe Gly Val Ala Gly Ala Ala Ile Gln
        130                 135                 140

Val Glu Gly Ala Ala Lys Ala Glu Gly Arg Gly Pro Ser Thr Trp Asp
145                 150                 155                 160

Tyr Leu Cys His His Tyr Ala Ser Thr Gln Cys Asn Asn Tyr Asp Pro
                165                 170                 175

Asp Ile Thr Thr Asn His Tyr Tyr Leu Tyr Pro Leu Asp Phe Ala Arg
            180                 185                 190

Leu Gln His Leu Gly Ile Asn Thr Tyr Ser Phe Ser Ile Ser Trp Thr
            195                 200                 205

Arg Ile Tyr Pro Leu Gly Ala Gly Tyr Val Asn Glu Ala Gly Leu Ala
        210                 215                 220

His Tyr Asp Ala Val Ile His Ser Ala Lys Lys Tyr Gly Leu Glu Pro
225                 230                 235                 240

Val Gly Thr Val Phe His Trp Asp Thr Pro Leu Ser Leu Met Leu Lys
            245                 250                 255

Tyr Gly Ala Trp Gln Asp Thr Gly Asp Gln Ile Val Lys Asp Phe Val
            260                 265                 270

Thr Tyr Ala Thr Thr Val Phe Lys Arg Tyr Gly Asn Glu Val Lys Thr
            275                 280                 285

Trp Phe Thr Phe Asn Glu Pro Arg Val Phe Cys Ser Gln Asn Ser Gly
        290                 295                 300

Leu Pro Tyr Asn Leu Thr Tyr Pro Glu Gly Ile Asn Ser Thr Ser Ala
305                 310                 315                 320

Val Phe Arg Cys Thr Tyr Asn Val Leu Lys Ala His Gly His Ala Val
            325                 330                 335

Lys Val Tyr Arg Asp Leu Val Ala Ser Gly Thr Ile Ala Ala Gly Glu
```

-continued

```
              340                  345                  350

Ile Gly Phe Lys Ser Asp Asp Asn Tyr Pro Ile Pro Ala Arg Pro Gly
         355                  360                  365

Asn Ala Asp Asp Glu Glu Ser Ala Lys Arg His Glu Ala Phe Arg Ile
    370                  375                  380

Gly Ile Phe Ala Gln Pro Val Tyr Gly Asn Gly Asp Tyr Pro Asp Val
385                  390                  395                  400

Val Lys Glu Thr Val Gly Asp Met Leu Pro Ala Leu Thr Asp Glu Asp
              405                  410                  415

Lys Gly Tyr Ile Lys Gly Ser Gly Asp Ile Phe Ala Ile Asp Gly Tyr
         420                  425                  430

Arg Thr Asp Ile Ser His Ala Ala Leu Asn Gly Ile Ala Asn Cys Ile
         435                  440                  445

Arg Asn Gln Ser Asp Pro Asn Trp Pro Val Cys Glu Glu Gly Ser Asp
    450                  455                  460

Pro Phe Ala His Val Tyr Pro Ser Gly Phe Ala Ile Gly Gln Ser Ala
465                  470                  475                  480

Asp Pro Leu Ser Ser Trp Leu Val Asn Ser Ala Pro Phe Ile Arg Asp
              485                  490                  495

Gln Leu Lys Phe Leu Thr Gln Thr Tyr Pro Ala Lys Gly Gly Ile Tyr
         500                  505                  510

Phe Ser Glu Phe Gly Trp Ala Glu Asp Ala Glu Tyr Asp Arg Gln Leu
         515                  520                  525

Leu Tyr Gln Ile Thr Trp Asp Gly Leu Arg Thr Gln Tyr Leu Thr Asp
    530                  535                  540

Tyr Leu Ser Gln Leu Leu Leu Ala Val His Lys Asp Gly Ile Asn Leu
545                  550                  555                  560

Arg Gly Ala Leu Thr Trp Ser Phe Val Asp Asn Trp Glu Trp Gly Leu
              565                  570                  575

Gly Met Gln Gln Lys Phe Gly Phe Gln Phe Val Asn Gln Ser Asp Pro
         580                  585                  590

Asp Leu Thr Arg Thr Phe Lys Leu Ser Ala His Ala Tyr Ala Gln Phe
         595                  600                  605

Gly Arg Asn His Leu His His His His His
    610                  615
```

```
<210> SEQ ID NO 71
<211> LENGTH: 60
<212> TYPE: DNA
<213> ORGANISM: Artificial sequence
<220> FEATURE:
<223> OTHER INFORMATION: Synthetic

<400> SEQUENCE: 71
aaggaaaaaa gcggccgctt agtggtggtg gtggtggtgc agatgattac gcccaaattg      60

<210> SEQ ID NO 72
<211> LENGTH: 58
<212> TYPE: DNA
<213> ORGANISM: Artificial sequence
<220> FEATURE:
<223> OTHER INFORMATION: Synthetic

<400> SEQUENCE: 72
gaagaagggg tatctctcga gaaaagagag gctgaagctt ccctgacgag caattacg      58

<210> SEQ ID NO 73
```

-continued

```
<211> LENGTH: 58
<212> TYPE: DNA
<213> ORGANISM: Artificial sequence
<220> FEATURE:
<223> OTHER INFORMATION: Synthetic

<400> SEQUENCE: 73 gaagaaggggg tatctctcga gaaaagagag gctgaagcta ccggtacagc agaattag          58

<210> SEQ ID NO 74
<211> LENGTH: 59
<212> TYPE: DNA
<213> ORGANISM: Artificial sequence
<220> FEATURE:
<223> OTHER INFORMATION: Synthetic

<400> SEQUENCE: 74 gaagaaggggg tatctctcga gaaaagagag gctgaagctg cagaattaga tgcgctgtg         59

<210> SEQ ID NO 75
<211> LENGTH: 60
<212> TYPE: DNA
<213> ORGANISM: Artificial sequence
<220> FEATURE:
<223> OTHER INFORMATION: Synthetic

<400> SEQUENCE: 75 gaagaaggggg tatctctcga gaaaagagag gctgaagcta cagtgcccga tgattataag        60

<210> SEQ ID NO 76
<211> LENGTH: 61
<212> TYPE: DNA
<213> ORGANISM: Artificial sequence
<220> FEATURE:
<223> OTHER INFORMATION: Synthetic

<400> SEQUENCE: 76 gaagaaggggg tatctctcga gaaaagagag gctgaagcta gttatgcatt agcagggtat        60
g                                                                         61

<210> SEQ ID NO 77
<211> LENGTH: 58
<212> TYPE: DNA
<213> ORGANISM: Artificial sequence
<220> FEATURE:
<223> OTHER INFORMATION: Synthetic

<400> SEQUENCE: 77 gaagaaggggg tatctctcga gaaaagagag gctgaagcta caagcgagat tgccggac          58

<210> SEQ ID NO 78
<211> LENGTH: 53
<212> TYPE: DNA
<213> ORGANISM: Artificial sequence
<220> FEATURE:
<223> OTHER INFORMATION: Synthetic

<400> SEQUENCE: 78
tcacaaaata gtggtctgcc ataccagctt acgtatccag aaggtattaa cag               53

<210> SEQ ID NO 79
<211> LENGTH: 53
<212> TYPE: DNA
<213> ORGANISM: Artificial sequence
<220> FEATURE:
<223> OTHER INFORMATION: Synthetic
```

-continued

```
<400> SEQUENCE: 79
ctgttaatac cttctggata cgtaagctgg tatggcagac cactattttg tga          53

<210> SEQ ID NO 80
<211> LENGTH: 41
<212> TYPE: DNA
<213> ORGANISM: Artificial sequence
<220> FEATURE:
<223> OTHER INFORMATION: Synthetic

<400> SEQUENCE: 80
caatctgacg tatccagaag ggatccagag cacctccgct g                       41

<210> SEQ ID NO 81
<211> LENGTH: 41
<212> TYPE: DNA
<213> ORGANISM: Artificial sequence
<220> FEATURE:
<223> OTHER INFORMATION: Synthetic

<400> SEQUENCE: 81
cagcggaggt gctctggatc ccttctggat acgtcagatt g                       41

<210> SEQ ID NO 82
<211> LENGTH: 47
<212> TYPE: DNA
<213> ORGANISM: Artificial sequence
<220> FEATURE:
<223> OTHER INFORMATION: Synthetic

<400> SEQUENCE: 82
gaaattcgga tttcagtttg ttcagcaatc ggatcccgat ctgacac                 47

<210> SEQ ID NO 83
<211> LENGTH: 47
<212> TYPE: DNA
<213> ORGANISM: Artificial sequence
<220> FEATURE:
<223> OTHER INFORMATION: Synthetic

<400> SEQUENCE: 83
gtgtcagatc gggatccgat tgctgaacaa actgaaatcc gaatttc                 47

<210> SEQ ID NO 84
<211> LENGTH: 47
<212> TYPE: DNA
<213> ORGANISM: Artificial sequence
<220> FEATURE:
<223> OTHER INFORMATION: Synthetic

<400> SEQUENCE: 84
gaaattcgga tttcagtttg ttcagcaatc ggatcccgat ctgacac                 47

<210> SEQ ID NO 85
<211> LENGTH: 47
<212> TYPE: DNA
<213> ORGANISM: Artificial sequence
<220> FEATURE:
<223> OTHER INFORMATION: Synthetic

<400> SEQUENCE: 85
gtgtcagatc gggatccgat tgctgaacaa actgaaatcc gaatttc                 47

<210> SEQ ID NO 86
```

-continued

```
<211> LENGTH: 35
<212> TYPE: DNA
<213> ORGANISM: Artificial sequence
<220> FEATURE:
<223> OTHER INFORMATION: Synthetic

<400> SEQUENCE: 86
ttagcagcaa tgctggcgga aaatggcaaa acagc                               35

<210> SEQ ID NO 87
<211> LENGTH: 35
<212> TYPE: DNA
<213> ORGANISM: Artificial sequence
<220> FEATURE:
<223> OTHER INFORMATION: Synthetic

<400> SEQUENCE: 87
gctgttttgc cattttccgc cagcattgct gctaa                               35

<210> SEQ ID NO 88
<211> LENGTH: 90
<212> TYPE: DNA
<213> ORGANISM: Artificial sequence
<220> FEATURE:
<223> OTHER INFORMATION: Synthetic

<400> SEQUENCE: 88
cgcggatcca aacgatgctt ttgcaagctt tccttttcct tttggctggt tttgcagcca    60
agatatctgc aaccggtaca gcagaattag                                     90

<210> SEQ ID NO 89
<211> LENGTH: 90
<212> TYPE: DNA
<213> ORGANISM: Artificial sequence
<220> FEATURE:
<223> OTHER INFORMATION: Synthetic

<400> SEQUENCE: 89
cgcggatcca aacgatgtct tttagatcct tgctagcttt gtctggtttg gtttgttctg    60
gtttggctac cggtacagca gaattagatg                                     90

<210> SEQ ID NO 90
<211> LENGTH: 85
<212> TYPE: DNA
<213> ORGANISM: Artificial sequence
<220> FEATURE:
<223> OTHER INFORMATION: Synthetic

<400> SEQUENCE: 90
cgcggatcca aacgatgaag ttagcatact ccttgttgct ccgctagca ggagtcagtg     60 ctaccggtac agcagaatta gatgc                                          85

<210> SEQ ID NO 91
<211> LENGTH: 24
<212> TYPE: DNA
<213> ORGANISM: Artificial sequence
<220> FEATURE:
<223> OTHER INFORMATION: Synthetic

<400> SEQUENCE: 91
atcactatgc cagcacgcag tgta                                           24

<210> SEQ ID NO 92
<211> LENGTH: 24
```

-continued

```
<212> TYPE: DNA
<213> ORGANISM: Artificial sequence
<220> FEATURE:
<223> OTHER INFORMATION: Synthetic

<400> SEQUENCE: 92
tttaaagccg atttcacctg ccgc                                          24

<210> SEQ ID NO 93
<211> LENGTH: 21
<212> TYPE: DNA
<213> ORGANISM: Artificial sequence
<220> FEATURE:
<223> OTHER INFORMATION: Synthetic

<400> SEQUENCE: 93
gactggttcc aattgacaag c                                             21

<210> SEQ ID NO 94
<211> LENGTH: 21
<212> TYPE: DNA
<213> ORGANISM: Artificial sequence
<220> FEATURE:
<223> OTHER INFORMATION: Synthetic

<400> SEQUENCE: 94
gcaaatggca ttctgacatc c                                             21

<210> SEQ ID NO 95
<211> LENGTH: 21
<212> TYPE: DNA
<213> ORGANISM: Artificial sequence
<220> FEATURE:
<223> OTHER INFORMATION: Synthetic

<400> SEQUENCE: 95
tactattgcc agcattgctg c                                             21

<210> SEQ ID NO 96
<211> LENGTH: 465
<212> TYPE: PRT
<213> ORGANISM: Artificial sequence
<220> FEATURE:
<223> OTHER INFORMATION: Synthetic

<400> SEQUENCE: 96

Leu Ala Leu Met Ser Ala Ala Lys Leu Pro Lys Ser Phe Val Trp Gly
1               5                   10                  15

Tyr Ala Thr Ala Ala Tyr Gln Ile Glu Gly Ser Pro Asp Lys Asp Gly
            20                  25                  30

Arg Glu Pro Ser Ile Trp Asp Thr Phe Cys Lys Ala Pro Gly Lys Ile
        35                  40                  45

Ala Asp Gly Ser Ser Gly Asp Val Ala Thr Asp Ser Tyr Asn Arg Trp
    50                  55                  60

Arg Glu Asp Val Gln Leu Leu Lys Ser Tyr Gly Val Lys Ala Tyr Arg
65                  70                  75                  80

Phe Ser Leu Ser Trp Ser Arg Ile Ile Pro Lys Gly Gly Arg Ser Asp
                85                  90                  95

Pro Val Asn Gly Ala Gly Ile Lys His Tyr Arg Thr Leu Ile Glu Glu
            100                 105                 110

Leu Val Lys Glu Gly Ile Thr Pro Phe Val Thr Leu Tyr His Trp Asp
        115                 120                 125
```

```
Leu Pro Gln Ala Leu Asp Asp Arg Tyr Gly Gly Trp Leu Asn Lys Glu
    130                 135                 140

Glu Ala Ile Gln Asp Phe Thr Asn Tyr Ala Lys Leu Cys Phe Glu Ser
145                 150                 155                 160

Phe Gly Asp Leu Val Gln Asn Trp Ile Thr Phe Asn Glu Pro Trp Val
                165                 170                 175

Ile Ser Val Met Gly Tyr Gly Asn Gly Ile Phe Ala Pro Gly His Val
                180                 185                 190

Ser Asn Thr Glu Pro Trp Ile Val Ser His His Ile Ile Leu Ala His
        195                 200                 205

Ala His Ala Val Lys Leu Tyr Arg Asp Glu Phe Lys Glu Lys Gln Gly
    210                 215                 220

Gly Gln Ile Gly Ile Thr Leu Asp Ser His Trp Leu Ile Pro Tyr Asp
225                 230                 235                 240

Asp Thr Asp Ala Ser Lys Glu Ala Thr Leu Arg Ala Met Glu Phe Lys
                245                 250                 255

Leu Gly Arg Phe Ala Asn Pro Ile Tyr Lys Gly Glu Tyr Pro Pro Arg
                260                 265                 270

Ile Lys Lys Ile Leu Gly Asp Arg Leu Pro Glu Phe Thr Pro Glu Glu
        275                 280                 285

Ile Glu Leu Val Lys Gly Ser Ser Asp Phe Phe Gly Leu Asn Thr Tyr
    290                 295                 300

Thr Thr His Leu Val Gln Asp Gly Gly Ser Asp Glu Leu Ala Gly Phe
305                 310                 315                 320

Val Lys Thr Gly His Thr Arg Ala Asp Gly Thr Gln Leu Gly Thr Gln
                325                 330                 335

Ser Asp Met Gly Trp Leu Gln Thr Tyr Gly Pro Gly Phe Arg Trp Leu
                340                 345                 350

Leu Asn Tyr Leu Trp Lys Ala Tyr Asp Lys Pro Val Tyr Val Thr Glu
        355                 360                 365

Asn Gly Phe Pro Val Lys Gly Glu Asn Asp Leu Pro Val Glu Gln Ala
    370                 375                 380

Val Asp Asp Thr Asp Arg Gln Ala Tyr Tyr Arg Asp Tyr Thr Glu Ala
385                 390                 395                 400

Leu Leu Gln Ala Val Thr Glu Asp Gly Ala Asp Val Arg Gly Tyr Phe
                405                 410                 415

Gly Trp Ser Leu Leu Asp Asn Phe Glu Trp Ala Glu Gly Tyr Lys Val
                420                 425                 430

Arg Phe Gly Val Thr His Val Asp Tyr Glu Thr Gln Lys Arg Thr Pro
            435                 440                 445

Lys Lys Ser Ala Glu Phe Leu Ser Arg Trp Phe Lys Glu His Ile Glu
    450                 455                 460

Glu
465
```

<210> SEQ ID NO 97
<211> LENGTH: 470
<212> TYPE: PRT
<213> ORGANISM: Artificial sequence
<220> FEATURE:
<223> OTHER INFORMATION: Synthetic

<400> SEQUENCE: 97

```
Met His His His His His His Met Leu Pro Lys Asp Phe Gln Trp Gly
1               5                   10                  15
```

-continued

```
Phe Ala Thr Ala Ala Tyr Gln Ile Glu Gly Ala Val Asp Gln Asp Gly
            20              25              30

Arg Gly Pro Ser Ile Trp Asp Thr Phe Cys Ala Gln Pro Gly Lys Ile
            35              40              45

Ala Asp Gly Ser Ser Gly Val Thr Ala Cys Asp Ser Tyr Asn Arg Thr
    50              55              60

Ala Glu Asp Ile Ala Leu Leu Lys Ser Leu Gly Ala Lys Ser Tyr Arg
65              70              75              80

Phe Ser Ile Ser Trp Ser Arg Ile Ile Pro Glu Gly Gly Arg Gly Asp
                85              90              95

Ala Val Asn Gln Ala Gly Ile Asp His Tyr Val Lys Phe Val Asp Asp
            100             105             110

Leu Leu Asp Ala Gly Ile Thr Pro Phe Ile Thr Leu Phe His Trp Asp
            115             120             125

Leu Pro Glu Gly Leu His Gln Arg Tyr Gly Gly Leu Leu Asn Arg Thr
            130             135             140

Glu Phe Pro Leu Asp Phe Glu Asn Tyr Ala Arg Val Met Phe Arg Ala
145             150             155             160

Leu Pro Lys Val Arg Asn Trp Ile Thr Phe Asn Glu Pro Leu Cys Ser
            165             170             175

Ala Ile Pro Gly Tyr Gly Ser Gly Thr Phe Ala Pro Gly Arg Gln Ser
            180             185             190

Thr Ser Glu Pro Trp Thr Val Gly His Asn Ile Leu Val Ala His Gly
            195             200             205

Arg Ala Val Lys Ala Tyr Arg Asp Asp Phe Lys Pro Ala Ser Gly Asp
    210             215             220

Gly Gln Ile Gly Ile Val Leu Asn Gly Asp Phe Thr Tyr Pro Trp Asp
225             230             235             240

Ala Ala Asp Pro Ala Asp Lys Glu Ala Ala Glu Arg Arg Leu Glu Phe
            245             250             255

Phe Thr Ala Trp Phe Ala Asp Pro Ile Tyr Leu Gly Asp Tyr Pro Ala
            260             265             270

Ser Met Arg Lys Gln Leu Gly Asp Arg Leu Pro Thr Phe Thr Pro Glu
            275             280             285

Glu Arg Ala Leu Val His Gly Ser Asn Asp Phe Tyr Gly Met Asn His
    290             295             300

Tyr Thr Ser Asn Tyr Ile Arg His Arg Ser Ser Pro Ala Ser Ala Asp
305             310             315             320

Asp Thr Val Gly Asn Val Asp Val Leu Phe Thr Asn Lys Gln Gly Asn
            325             330             335

Cys Ile Gly Pro Glu Thr Gln Ser Pro Trp Leu Arg Pro Cys Ala Ala
            340             345             350

Gly Phe Arg Asp Phe Leu Val Trp Ile Ser Lys Arg Tyr Gly Tyr Pro
            355             360             365

Pro Ile Tyr Val Thr Glu Asn Gly Thr Ser Ile Lys Gly Glu Ser Asp
    370             375             380

Leu Pro Lys Glu Lys Ile Leu Glu Asp Asp Phe Arg Val Lys Tyr Tyr
385             390             395             400

Asn Glu Tyr Ile Arg Ala Met Val Thr Ala Val Glu Leu Asp Gly Val
            405             410             415

Asn Val Lys Gly Tyr Phe Ala Trp Ser Leu Met Asp Asn Phe Glu Trp
            420             425             430

Ala Asp Gly Tyr Val Thr Arg Phe Gly Val Thr Tyr Val Asp Tyr Glu
```

-continued

```
            435               440               445

Asn Gly Gln Lys Arg Phe Pro Lys Lys Ser Ala Lys Ser Leu Lys Pro
    450               455               460

Leu Phe Asp Glu Leu Ile
465               470

<210> SEQ ID NO 98
<211> LENGTH: 482
<212> TYPE: PRT
<213> ORGANISM: Artificial sequence
<220> FEATURE:
<223> OTHER INFORMATION: Synthetic

<400> SEQUENCE: 98

Met Gly Ser Ser His His His His His His Ser Ser Gly Leu Val Pro
1               5                   10                  15

Arg Gly Ser His Met Leu Pro Lys Asp Phe Gln Trp Gly Phe Ala Thr
                20                  25                  30

Ala Ala Tyr Gln Ile Glu Gly Ala Ile Asp Lys Asp Gly Arg Gly Pro
            35                  40                  45

Ser Ile Trp Asp Thr Phe Cys Ala Ile Pro Gly Lys Ile Ala Asp Gly
    50                  55                  60

Thr Ser Gly Val Thr Ala Cys Asp Ser Tyr Asn Arg Thr Ala Glu Asp
65                  70                  75                  80

Ile Ala Leu Leu Lys Ser Leu Gly Ala Lys Ser Tyr Arg Phe Ser Ile
                85                  90                  95

Ser Trp Ser Arg Ile Ile Pro Lys Gly Gly Arg Asp Asp Pro Val Asn
            100                 105                 110

Gln Leu Gly Ile Asp His Tyr Ala Gln Phe Val Asp Asp Leu Leu Glu
        115                 120                 125

Ala Gly Ile Thr Pro Phe Ile Thr Leu Phe His Trp Asp Leu Pro Glu
    130                 135                 140

Glu Leu His Gln Arg Tyr Gly Gly Leu Leu Asn Arg Thr Glu Phe Pro
145                 150                 155                 160

Leu Asp Phe Glu Asn Tyr Ala Arg Val Met Phe Lys Ala Leu Pro Lys
                165                 170                 175

Val Arg Asn Trp Ile Thr Phe Asn Glu Pro Leu Cys Ser Ala Ile Pro
            180                 185                 190

Gly Tyr Gly Ser Gly Thr Phe Ala Pro Gly Arg Gln Ser Thr Thr Glu
        195                 200                 205

Pro Trp Ile Val Gly His Asn Leu Leu Val Ala His Gly Arg Ala Val
    210                 215                 220

Lys Val Tyr Arg Asp Glu Phe Lys Asp Leu Asn Asp Gly Gln Ile Gly
225                 230                 235                 240

Ile Val Leu Asn Gly Asp Phe Thr Tyr Pro Trp Asp Ser Ser Asp Pro
                245                 250                 255

Leu Asp Arg Glu Ala Ala Glu Arg Arg Leu Glu Phe Phe Thr Ala Trp
            260                 265                 270

Tyr Ala Asp Pro Ile Tyr Leu Gly Asp Tyr Pro Ala Ser Met Arg Lys
        275                 280                 285

Gln Leu Gly Asp Arg Leu Pro Glu Phe Thr Pro Glu Glu Lys Ala Phe
    290                 295                 300

Val Leu Gly Ser Asn Asp Phe Tyr Gly Met Asn His Tyr Thr Ser Asn
305                 310                 315                 320

Tyr Ile Arg His Arg Thr Ser Pro Ala Thr Ala Asp Asp Thr Val Gly
```

-continued

```
                  325                 330                 335

Asn Val Asp Val Leu Phe Tyr Asn Lys Glu Gly Gln Cys Ile Gly Pro
            340                 345                 350

Glu Thr Glu Ser Ser Trp Leu Arg Pro Cys Pro Ala Gly Phe Arg Asp
            355                 360                 365

Phe Leu Val Trp Ile Ser Lys Arg Tyr Asn Tyr Pro Lys Ile Tyr Val
            370                 375                 380

Thr Glu Asn Gly Thr Ser Leu Lys Gly Glu Asn Asp Leu Pro Lys Glu
385                 390                 395                 400

Lys Ile Leu Glu Asp Asp Phe Arg Val Asn Tyr Tyr Asn Glu Tyr Ile
                  405                 410                 415

Arg Ala Met Phe Thr Ala Ala Thr Leu Asp Gly Val Asn Val Lys Gly
                  420                 425                 430

Tyr Phe Ala Trp Ser Leu Met Asp Asn Phe Glu Trp Ala Asp Gly Tyr
                  435                 440                 445

Val Thr Arg Phe Gly Val Thr Tyr Val Asp Tyr Glu Asn Gly Gln Gln
            450                 455                 460

Arg Phe Pro Lys Lys Ser Ala Lys Ser Leu Lys Pro Leu Phe Asp Glu
465                 470                 475                 480

Leu Ile

<210> SEQ ID NO 99
<211> LENGTH: 496
<212> TYPE: PRT
<213> ORGANISM: Artificial sequence
<220> FEATURE:
<223> OTHER INFORMATION: Synthetic

<400> SEQUENCE: 99

Met Gly Ser Ser His His His His His His Ser Ser Gly Leu Val Pro
1               5                   10                  15

Arg Gly Ser His Met Ala Ser Met Ser Leu Pro Pro Asp Phe Lys Trp
            20                  25                  30

Gly Phe Ala Thr Ala Ala Tyr Gln Ile Glu Gly Ser Val Asn Glu Asp
            35                  40                  45

Gly Arg Gly Pro Ser Ile Trp Asp Thr Phe Cys Ala Ile Pro Gly Lys
      50                  55                  60

Ile Ala Asp Gly Ser Ser Gly Ala Val Ala Cys Asp Ser Tyr Lys Arg
65                  70                  75                  80

Thr Lys Glu Asp Ile Ala Leu Leu Lys Glu Leu Gly Ala Asn Ser Tyr
                  85                  90                  95

Arg Phe Ser Ile Ser Trp Ser Arg Ile Ile Pro Leu Gly Gly Arg Asn
            100                 105                 110

Asp Pro Ile Asn Gln Lys Gly Ile Asp His Tyr Val Lys Phe Val Asp
            115                 120                 125

Asp Leu Ile Glu Ala Gly Ile Thr Pro Phe Ile Thr Leu Phe His Trp
      130                 135                 140

Asp Leu Pro Asp Ala Leu Asp Lys Arg Tyr Gly Gly Phe Leu Asn Lys
145                 150                 155                 160

Glu Glu Phe Ala Ala Asp Phe Glu Asn Tyr Ala Arg Ile Met Phe Lys
                  165                 170                 175

Ala Ile Pro Lys Cys Lys His Trp Ile Thr Phe Asn Glu Pro Trp Cys
            180                 185                 190

Ser Ala Ile Leu Gly Tyr Asn Thr Gly Tyr Phe Ala Pro Gly His Thr
            195                 200                 205
```

-continued

```
Ser Asp Arg Ser Lys Ser Pro Val Gly Asp Ser Ala Arg Glu Pro Trp
    210             215             220
```

```
Ile Val Gly His Asn Ile Leu Ile Ala His Ala Arg Ala Val Lys Ala
225             230             235             240
```

```
Tyr Arg Glu Asp Phe Lys Pro Thr Gln Gly Gly Glu Ile Gly Ile Thr
            245             250             255
```

```
Leu Asn Gly Asp Ala Thr Leu Pro Trp Asp Pro Glu Asp Pro Ala Asp
            260             265             270
```

```
Ile Glu Ala Cys Asp Arg Lys Ile Glu Phe Ala Ile Ser Trp Phe Ala
        275             280             285
```

```
Asp Pro Ile Tyr Phe Gly Lys Tyr Pro Asp Ser Met Arg Lys Gln Leu
    290             295             300
```

```
Gly Asp Arg Leu Pro Glu Phe Thr Pro Glu Glu Val Ala Leu Val Lys
305             310             315             320
```

```
Gly Ser Asn Asp Phe Tyr Gly Met Asn His Tyr Thr Ala Asn Tyr Ile
            325             330             335
```

```
Lys His Lys Thr Gly Val Pro Pro Glu Asp Asp Phe Leu Gly Asn Leu
            340             345             350
```

```
Glu Thr Leu Phe Tyr Asn Lys Tyr Gly Asp Cys Ile Gly Pro Glu Thr
            355             360             365
```

```
Gln Ser Phe Trp Leu Arg Pro His Ala Gln Gly Phe Arg Asp Leu Leu
    370             375             380
```

```
Asn Trp Leu Ser Lys Arg Tyr Gly Tyr Pro Lys Ile Tyr Val Thr Glu
385             390             395             400
```

```
Asn Gly Thr Ser Leu Lys Gly Glu Asn Asp Met Pro Leu Glu Gln Val
            405             410             415
```

```
Leu Glu Asp Asp Phe Arg Val Lys Tyr Phe Asn Asp Tyr Val Arg Ala
            420             425             430
```

```
Met Ala Ala Ala Val Ala Glu Asp Gly Cys Asn Val Arg Gly Tyr Leu
            435             440             445
```

```
Ala Trp Ser Leu Leu Asp Asn Phe Glu Trp Ala Glu Gly Tyr Glu Thr
    450             455             460
```

```
Arg Phe Gly Val Thr Tyr Val Asp Tyr Ala Asn Asp Gln Lys Arg Tyr
465             470             475             480
```

```
Pro Lys Lys Ser Ala Lys Ser Leu Lys Pro Leu Phe Asp Ser Leu Ile
            485             490             495
```

```
<210> SEQ ID NO 100
<211> LENGTH: 479
<212> TYPE: PRT
<213> ORGANISM: Artificial sequence
<220> FEATURE:
<223> OTHER INFORMATION: Synthetic

<400> SEQUENCE: 100
```

```
Met Met Ser Glu Ser Leu Ser Leu Pro Lys Asp Phe Glu Trp Gly Phe
1               5               10              15
```

```
Ala Thr Ala Ala Tyr Gln Ile Glu Gly Ala Val Lys Glu Gly Gly Arg
            20              25              30
```

```
Gly Pro Ser Ile Trp Asp Thr Tyr Cys His Leu Glu Pro Ser Arg Thr
        35              40              45
```

```
Asn Gly Ala Asn Gly Asp Val Ala Cys Asp His Tyr His Arg Tyr Asp
    50              55              60
```

```
Glu Asp Phe Asp Leu Leu Thr Lys Tyr Gly Ala Lys Ala Tyr Arg Phe
65              70              75              80
```

-continued

Ser Leu Ser Trp Ser Arg Ile Ile Pro Leu Gly Gly Arg Leu Asp Pro
            85              90              95

Ile Asn Glu Glu Gly Ile Gln Phe Tyr Ser Asn Leu Ile Asp Ala Leu
            100             105             110

Leu Lys Arg Gly Val Thr Pro Trp Val Thr Leu Tyr His Trp Asp Leu
            115             120             125

Pro Gln Ala Leu His Asp Arg Tyr Gly Gly Trp Leu Asn Val Lys Glu
        130             135             140

Val Gln Leu Asp Phe Glu Arg Tyr Ala Arg Leu Cys Phe Glu Arg Phe
145             150             155             160

Gly Asp Arg Val Lys Asn Trp Ile Thr Ile Asn Glu Pro Trp Ile Gln
                165             170             175

Ser Ile Tyr Gly Tyr Ala Thr Gly Ser Asn Ala Pro Gly Arg Ser Ser
            180             185             190

Ile Asn Lys His Ser Thr Glu Gly Asp Thr Thr Thr Glu Pro Trp Leu
            195             200             205

Ala Gly Lys Ala Gln Ile Met Ser His Ala Arg Ala Val Ala Val Tyr
        210             215             220

Ser Lys Asp Phe Arg Ala Ser Gln Lys Gly Gln Ile Gly Ile Ser Leu
225             230             235             240

Asn Gly Asp Tyr Tyr Glu Pro Trp Asp Ser Ser Asp Pro Arg Asp Lys
            245             250             255

Glu Ala Ala Glu Arg Arg Met Glu Phe His Ile Gly Trp Tyr Ala Asn
            260             265             270

Pro Ile Phe Leu Lys Lys Asp Tyr Pro Ala Ser Met Arg Lys Gln Leu
            275             280             285

Gly Asp Arg Leu Pro Ala Leu Thr Pro Ala Asp Phe Ala Ile Leu Asn
        290             295             300

Ala Gly Glu Thr Asp Phe Tyr Gly Met Asn Tyr Tyr Thr Ser Gln Phe
305             310             315             320

Ala Arg His Tyr Glu Gly Pro Val Pro Lys Thr Asp Phe Leu Gly Ala
            325             330             335

Ile His Glu His Gln Glu Asn Lys Asp Gly Ser Pro Val Gly Glu Glu
            340             345             350

Ser Gly Ile Phe Trp Leu Arg Ser Cys Pro Asp Met Phe Arg Lys His
            355             360             365

Leu Ala Arg Val His Gly Leu Tyr Gly Lys Pro Ile Tyr Ile Thr Glu
        370             375             380

Asn Gly Cys Pro Cys Pro Gly Glu Asp Lys Met Thr Cys Glu Glu Ala
385             390             395             400

Ile Asn Asp Pro Phe Arg Ile Gln Tyr Phe Asp Ser His Leu Asp Ser
            405             410             415

Ile Ser Lys Ala Ile Ser Gln Asp Gly Val Val Val Lys Gly Tyr Phe
            420             425             430

Ala Trp Ala Leu Leu Asp Asn Leu Glu Trp Ser Asp Gly Tyr Gly Pro
            435             440             445

Arg Phe Gly Val Thr Tyr Thr Asp Tyr Thr Thr Leu Lys Arg Thr Pro
        450             455             460

Lys Lys Ser Ala Leu Val Leu Lys Asp Met Phe Ala Asp Arg Gln
465             470             475

What is claimed is:

1. A functional, recombinant β-hexosyl-transferase (rBHT) polypeptide comprising at least 90% sequence identity with SEQ ID NO: 1 and an N-terminal truncation of 56 amino acids to 81 amino acids in length, with reference to SEQ ID NO: 1.

2. The polypeptide of claim 1, wherein the polypeptide comprises at least 95% sequence identity with SEQ ID NO: 1.

3. The polypeptide of claim 1, wherein the polypeptide further comprises at least one additional amino acid substitution.

4. The polypeptide of claim 1, wherein the polypeptide further comprises a signal sequence.

5. The polypeptide of claim 4, wherein the signal sequence comprises an amino acid sequence from a protein from any one of *Komagataella* (*Pichia*) *pastoris, Saccharomyces cerevisiae, Yarrowia lipolytica, Hansenula* (*Ogataea*) *polymorpha*, or *Kluyveromyces lactis*.

6. The polypeptide of claim 4, wherein the signal sequence comprises a polypeptide with at least 90% sequence identity to at least one of α-mating factor signal sequence from *Saccharomyces cerevisiae* (MFα) (SEQ ID NO: 29), Invertase (IV) signal sequence (SEQ ID NO: 30), Glucoamylase (GA) signal sequence (SEQ ID NO: 31), or Inulinase (IN) signal sequence (SEQ ID NO: 32).

7. The polypeptide of claim 4, wherein the polypeptide comprises the amino acid sequence of SEQ ID NO: 50, 52, 54, 56, 58, 60, 68, or 70.

8. The polypeptide of claim 1, wherein the polypeptide comprises at least one asparagine residue at position 289, 297, 431, or 569 with respect to SEQ ID NO: 1.

9. The polypeptide of claim 1, wherein the polypeptide catalyzes the hydrolysis of lactose β-(1-4) glycosidic linkages.

10. A nucleic acid molecule encoding the polypeptide of claim 1.

11. A vector comprising the nucleic acid molecule of claim 10.

12. A method of generating a galactooligosaccharide (GOD) composition from lactose in a host cell using the polypeptide of claim 1.

13. The method of claim 12, wherein the GOS composition comprises LacNAc-enriched GOS or GOS lacking GlcNAc.

14. The method of claim 13, wherein the host cell is one or more of a yeast cell, a fungal cell, a mammalian cell, an insect cell, a plant cell, or an algal cell.

15. The method of claim 14, wherein the host cell comprises one or more cells from *Komagataella* (*Pichia*) *pastoris, Saccharomyces cerevisiae, Yarrowia lipolytica, Hansenula* (*Ogataea*) *polymorpha*, or *Kluyveromyces lactis, Aspergillus* spp., and *Trichoderma reesei.*

16. The method of claim 13, wherein the method produces a LacNAc-enriched GOS yield of at least 10% of initial lactose concentration, and a total GOS concentration of at least 50% of initial lactose concentration.

*   *   *   *   *